United States Patent
So et al.

(10) Patent No.: US 12,193,321 B2
(45) Date of Patent: Jan. 7, 2025

(54) COMPOUND FOR ORGANIC ELECTRIC ELEMENT, ORGANIC ELECTRIC ELEMENT COMPRISING THE SAME, AND ELECTRONIC DEVICE THEREOF

(71) Applicant: DUK SAN NEOLUX CO., LTD., Cheonan-si (KR)

(72) Inventors: Ki Ho So, Cheonan-si (KR); Hyung Dong Lee, Cheonan-si (KR); Dae Hwan Oh, Cheonan-si (KR); Won Sam Kim, Cheonan-si (KR); Byoung Yeop Kang, Cheonan-si (KR)

(73) Assignee: DUK SAN NEOLUX CO., LTD., Cheonan-si (KR)

(*) Notice: Subject to any disclaimer, the term of this patent is extended or adjusted under 35 U.S.C. 154(b) by 591 days.

(21) Appl. No.: 16/946,904

(22) Filed: Jul. 10, 2020

(65) Prior Publication Data
US 2021/0013420 A1 Jan. 14, 2021

(30) Foreign Application Priority Data

Jul. 10, 2019 (KR) .................. 10-2019-0083318
Aug. 20, 2019 (KR) .................. 10-2019-0101535
May 14, 2020 (KR) .................. 10-2020-0057682

(51) Int. Cl.
*H10K 85/60* (2023.01)
*C07D 405/12* (2006.01)
(Continued)

(52) U.S. Cl.
CPC ......... *H10K 85/636* (2023.02); *C07D 405/12* (2013.01); *C07D 409/12* (2013.01);
(Continued)

(58) Field of Classification Search
CPC ............ H01L 51/0061; H01L 51/0071; H01L 51/0072; H01L 51/0073; H01L 51/0074;
(Continued)

(56) References Cited

U.S. PATENT DOCUMENTS

2004/0075382 A1* 4/2004 Stegamat ............ H01L 51/5281
313/506
2012/0097998 A1* 4/2012 Pieh ...................... H01L 51/504
257/E33.012
(Continued)

FOREIGN PATENT DOCUMENTS

CN 106977491 A 7/2017
CN 109867652 A 6/2019
(Continued)

OTHER PUBLICATIONS

Machine translation of WO2020218680A1 (Year: 2020).*
(Continued)

*Primary Examiner* — Jenna N Chandhok
(74) *Attorney, Agent, or Firm* — Vorys, Sater, Seymour and Pease LLP; Mih Suhn Koh

(57) ABSTRACT

Provided are a compound represented by Formula 1, an organic electric element comprising a first electrode, a second electrode, and an organic material layer formed between the first electrode and the second electrode, and an electronic device thereof, wherein by comprising compound represented by Formula 1 in the organic material layer, the driving voltage of the organic electric element can be lowered, and the luminous efficiency and life time, in particular, life time can be improved.

13 Claims, 3 Drawing Sheets

(51) Int. Cl.
| | |
|---|---|
| *C07D 409/12* | (2006.01) |
| *C07D 411/12* | (2006.01) |
| *C07D 411/14* | (2006.01) |
| *C07D 471/06* | (2006.01) |
| *C07D 513/10* | (2006.01) |
| *C09K 11/06* | (2006.01) |
| *H10K 50/15* | (2023.01) |

(52) U.S. Cl.
CPC .......... *C07D 411/12* (2013.01); *C07D 411/14* (2013.01); *C07D 471/06* (2013.01); *C07D 513/10* (2013.01); *C09K 11/06* (2013.01); *C09K 2211/1018* (2013.01); *H10K 50/15* (2023.02); *H10K 85/657* (2023.02); *H10K 85/6572* (2023.02); *H10K 85/6574* (2023.02); *H10K 85/6576* (2023.02)

(58) Field of Classification Search
CPC . H01L 51/006; H01L 51/0058; C07D 405/12; C07D 409/12; C07D 411/12; C07D 411/14; C07D 411/471; C07D 411/06; C07D 513/10; C07D 407/12; C07D 409/14; C07D 413/10; C07D 471/10; C07D 498/10; C09K 2211/1018; C09K 2211/1011; C09K 2211/1014; C09K 2211/1029; C09K 2211/1033; C09K 2211/1037; C09K 2211/1088; C09K 2211/1092; H10K 85/636; H10K 85/657; H10K 85/6572; H10K 85/6574; H10K 85/6576

See application file for complete search history.

(56) References Cited

U.S. PATENT DOCUMENTS

| | | |
|---|---|---|
| 2015/0221873 A1* | 8/2015 | Park .................... H01L 51/0059 548/418 |
| 2017/0237013 A1 | 8/2017 | Park et al. |
| 2019/0088879 A1 | 3/2019 | Haketa et al. |
| 2019/0189927 A1 | 6/2019 | Lee et al. |

FOREIGN PATENT DOCUMENTS

| | | |
|---|---|---|
| EP | 3 385 265 A1 | 10/2018 |
| EP | 3 466 926 A1 | 4/2019 |
| JP | 2016-505518 A | 2/2016 |
| JP | 2018-108939 A | 7/2018 |
| JP | 2019-026556 A | 2/2019 |
| JP | 2019-505475 A | 2/2019 |
| KR | 10-2018-0031874 A | 3/2018 |
| KR | 10-2018-0037695 A | 4/2018 |
| KR | 10-2018-0080603 A | 7/2018 |
| KR | 10-2019-0075798 A | 7/2019 |
| WO | 2014/072017 A1 | 5/2014 |
| WO | 2017/204557 A1 | 11/2017 |
| WO | 2018/056649 A1 | 3/2018 |
| WO | 2019/027040 A1 | 2/2019 |
| WO | 2019/126548 A1 | 6/2019 |
| WO | WO-2020218680 A1 * | 10/2020 |

OTHER PUBLICATIONS

Extended European search report dated Nov. 26, 2020, 5 pages, for corresponding application EP 20185207.6.

Notice of Allowance issued Apr. 19, 2022, for corresponding application JP 2020-119432, two pages.

* cited by examiner

COMPOUND FOR ORGANIC ELECTRIC ELEMENT, ORGANIC ELECTRIC ELEMENT COMPRISING THE SAME, AND ELECTRONIC DEVICE THEREOF

BACKGROUND

Technical Field

The present invention relates to a compound for an organic electric element, an organic electric element comprising the same and an electronic device thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

The most important issues in organic electroluminescent element are life and efficiency, and as the display becomes larger, these efficiency and life problems must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase.

However, efficiency cannot be maximized only by simply improving the organic material layer. This is because long life span and high efficiency can be simultaneously achieved when energy levels and T1 values among the respective layers included in the organic material layer, inherent material properties (mobility, interfacial properties, etc.) and the like are optimal combination.

In addition, an emission-auxiliary layer must be present between the hole transport layer and the light emitting layer in order to solve the problem of luminescence in the hole transport layer of recent organic electroluminescent devices, and material of different emission-auxiliary layers have been developed for each of the light emitting layers (R, G, B).

In general, an electron is transferred from an electron transport layer to a light emitting layer and a hole is transferred from a hole transport layer to the light emitting layer, as a result, an exciton is formed by the recombination of the electron and hole. However, the material used for the hole transport layer has a low HOMO value and therefore has a low T1 value. As a result, the exciton generated in the light emitting layer is transferred to the hole transport layer, resulting in a charge unbalance in the light emitting layer and light is emitted at the interface of the hole transport layer.

When light is emitted at the interface of the hole transport layer, the color purity and efficiency of the organic electric element are lowered and a problem occurs in that the life time is shortened. Therefore, it is necessary to develop the emission-auxiliary layer material having a high T1 value and a HOMO level between the hole transport layer and the light emitting layer.

Object, Technical Solution and Effects of the Invention

The object of the present invention is to provide a compound capable of lowering the driving voltage of an organic electronic element and improving the luminous efficiency and life time, particularly the life time of the element, an organic electric element comprising the compound, and an electronic device thereof.

In an aspect of the present invention, the present invention provides a compound represented by the following formula.

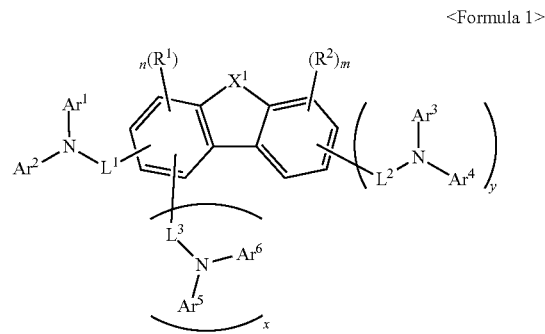

<Formula 1>

In another aspect of the present invention, the present invention provides an organic electric element employing the compound represented by the formula above and an electronic device thereof.

By using the compound according to one embodiment of the present invention, the driving voltage of an organic electric element can be lowered and the luminous efficiency and lifetime of the element can be improved, in particular, the lifetime can be largely improved.

DETAILED DESCRIPTION

Figure 1:
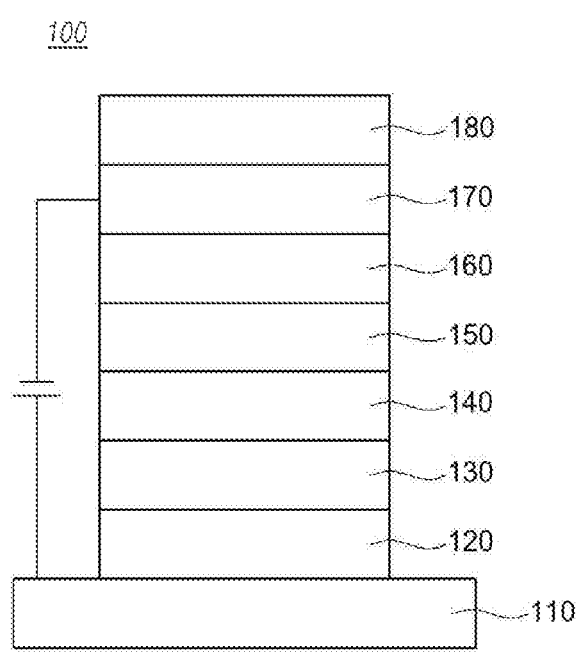
FIGS. 1 to 3 each illustrate an embodiment of an organic electroluminescent element according to the present invention: 100, 200, 300 are an organic electric element, 110 is a first electrode, 120 is a hole injection layer, 130 is a hole transport layer, 140 is a light emitting layer, 150 is an electron transport layer, 160 is an electron injection layer, 170 is a second electrode, 180 is a light efficiency improving layer, 210 is a buffer layer, 220 is an emission-auxiliary layer, 320 is a first hole injection layer, 330 is a first hole transport layer, 340 is a first light emitting layer, 350 is a first electron transport layer, 360 is a first charge generation layer, 361 is a second charge generation layer, 420 is a second hole injection layer, 430 is a second hole transport layer, 440 is a second light emitting layer, 450 is a second electron transport layer, CGL is a charge generation layer, ST1 is a first stack and ST2 is a second stack.

Unless otherwise stated, the term "aryl group" or "arylene group" as used herein has, but not limited to, 6 to 60 carbon atoms. The aryl group or arylene group in the present invention may comprise a monocyclic ring, ring assemblies, a fused polycyclic system, spiro compounds and the like. In addition, unless otherwise stated, a fluorenyl group may be comprised in an aryl group and a fluorenylene group may be comprised in an arylene group.

Unless otherwise stated, the term "fluorenyl group", "fluorenylene group" or "fluorenylenetriyl group" as used herein means univalent, bivalent or trivalent functional group in which R, R' and R" are all hydrogen in the following structure, "substituted fluorenyl group", "substituted fluorenylene group" or "substituted fluorenylenetriyl group" means that at least any one of R, R' and R" is a substituent other than hydrogen, and the case where R and R' are bonded to each other to form the spiro compound together with the carbon bonded to them is comprised. In this specification, a fluorene group, a fluorenylene group, and a fluorenyl group may be referred to as a fluorene group regardless of the valence.

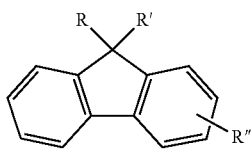

The term "spiro compound" as used herein has a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

The term "heterocyclic group" used in the specification comprises a non-aromatic ring as well as an aromatic ring like "heteroaryl group" or "heteroarylene group". Unless otherwise stated, the term "heterocyclic group" means, but not limited to, a ring containing one or more heteroatoms and having 2 to 60 carbon atoms. Unless otherwise stated, the term "heteroatom" as used herein represents N, O, S, P or Si and the heterocyclic group means a monocyclic, ring assemblies, fused polycyclic system or spiro compound containing a heteroatom. In addition, heterocyclic group comprises the compound comprising the heteroatom group such as $SO_2$, P=O etc. instead of carbon forming a ring such as the following compound.

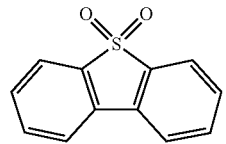 [SMILES: O=S1(=O)c2ccccc2-c2ccccc21]

The term "aliphatic ring group" as used herein refers to a cyclic hydrocarbon except for aromatic hydrocarbons, and comprises a monocyclic ring, ring assemblies, a fused polycyclic system, spiro compounds, and the like, and unless otherwise specified, it means a ring of 3 to 60 carbon atoms, but not limited thereto. For example, a fused ring formed by benzene being an aromatic ring with cyclohexane being a non-aromatic ring corresponds to aliphatic ring group.

In this specification, a 'group name' corresponding to an aryl group, an arylene group, a heterocyclic group, and the like exemplified for each symbol and its substituent may be written in the name of functional group reflecting the valence, and may also be described as the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

In addition, in the present specification, the numbers and alphabets indicating a position may be omitted when describing a compound name or a substituent name. For example, pyrido[4,3-d]pyrimidine, benzopuro[2,3-d]pyrimidine and 9,9-dimethyl-9H-fluorene can be described as pyridopyrimidine, benzofurropyrimidine and dimethylfluorene, respectively. Therefore, both benzo[g]quinoxaline and benzo[f]quinoxaline can be described as benzoquinoxaline.

In addition, unless otherwise expressed, where any formula of the present invention is represented by the following formula, the substituent according to the index may be defined as follows.

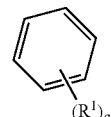

In the above formula, where a is an integer of zero, the substituent $R^1$ is absent, that is, hydrogen atoms are bonded to all the carbon constituting the benzene ring. Here, chemical formulas or compounds may be written without explicitly describing the hydrogen. In addition, one substituent $R^1$ is bonded to any carbon of the carbons forming the benzene ring when "a" is an integer of 1. Similarly, where "a" is an integer of 2 or 3, substituents $R^1 s$ may be bonded to the carbon of the benzene ring, for example, as followings. Also, where "a" is an integer of 4 to 6, substituents $R^1$s are bonded to the carbon of the benzene ring in a similar manner. Further, where "a" is an integer of 2 or more, $R^1$s may be the same or different from each other.

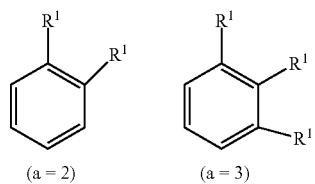

In addition, unless otherwise specified in the present specification, when referring to a condensed/fused ring, the number in the 'number-condensed/fused ring' indicates the number of condensed/fused rings. For example, a condensed ring in which three rings are condensed/fused with each other, such as anthracene, phenanthrene, and benzoquinazoline, may be represented by a '3-condensed/fused ring.'

In addition, unless otherwise described herein, in the case of expressing a ring in the form of a 'number-membered ring,' such as a 5-membered ring or a 6-membered ring, the number in the 'number-membered ring' represents the number of atoms forming the ring. For example, thiophene or furan may be referred to a 5-membered ring, and benzene or pyridine may be referred to a 6-membered ring.

In addition, unless otherwise specified in the present specification, the ring formed by bonding between adjacent groups may be selected from the group consisting of a $C_6$-$C_{60}$ aromatic ring group, a fluorenyl group, a $C_2$-$C_{60}$ heterocyclic group containing at least one heteroatom selected from the group consisting of O, N, S, Si, and P, and a $C_3$-$C_{60}$ aliphatic ring.

Unless otherwise stated, the term "between adjacent groups", for example, in case of the following Formulas, comprises not only "between $R^1$ and $R^2$", "between $R^2$ and $R^3$", "between $R^3$ and $R^4$", "between $R^5$ and $R^6$", but also "between $R^7$ and $R^8$" sharing one carbon, and may comprise "between substituents" attached to the atom (carbon or nitrogen) consisting different rings, such as "between $R^1$ and $R^7$", "between $R^1$ and $R^8$", or "between $R^4$ and $R^5$" and the like. That is, where there are substituents bonded to adjacent elements constituting the same ring, the substituents may be correspond "adjacent groups", and even if there are no adjacent substituents on the same ring, substituents attached to the neighboring ring may be referred to "adjacent groups".

In the following Formula, when the substituents bonded to the same carbon, such as $R^7$ and $R^8$, are linked to each other to form a ring, a compound containing a spiro-moiety may be formed.

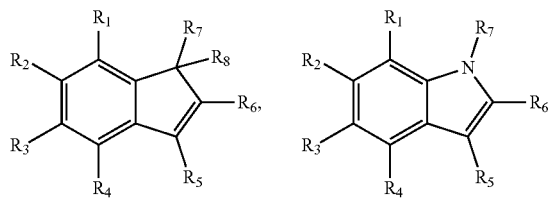

In addition, in the present specification, the expression 'neighboring groups may be linked to each other to form a ring' is used in the same sense as 'neighboring groups are linked selectively to each other to form a ring', and a case where at least one pair of neighboring groups may be bonded to each other to form a ring.

Hereinafter, referring to FIGS. 1 to 3, a lamination structure of an organic electric element including the compound of the present invention will be described.

In designation of reference numerals to components in respective drawings, it should be noted that the same elements will be designated by the same reference numerals although they are shown in different drawings. In addition, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It will be understood that the expression "one component is "connected," "coupled" or "joined" to another component" comprises the case where a third component may be "connected," "coupled," and "joined" between the first and second components as well as the case where the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

Figure 2:
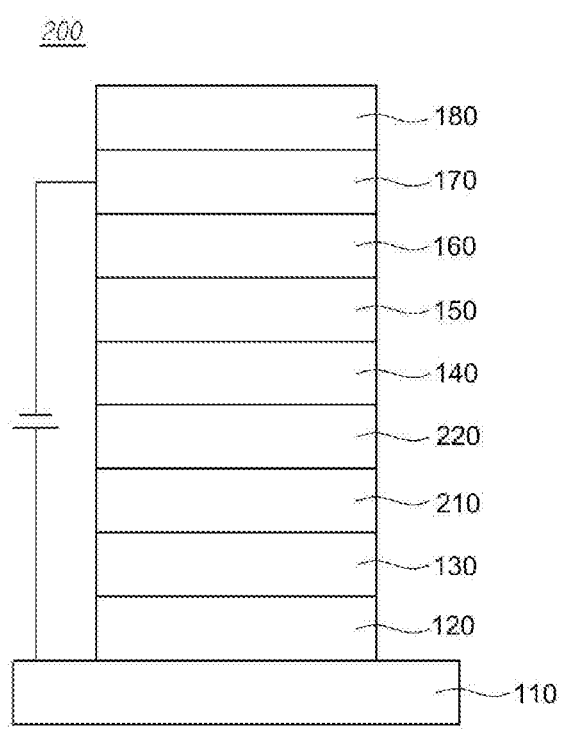
Figure 3:
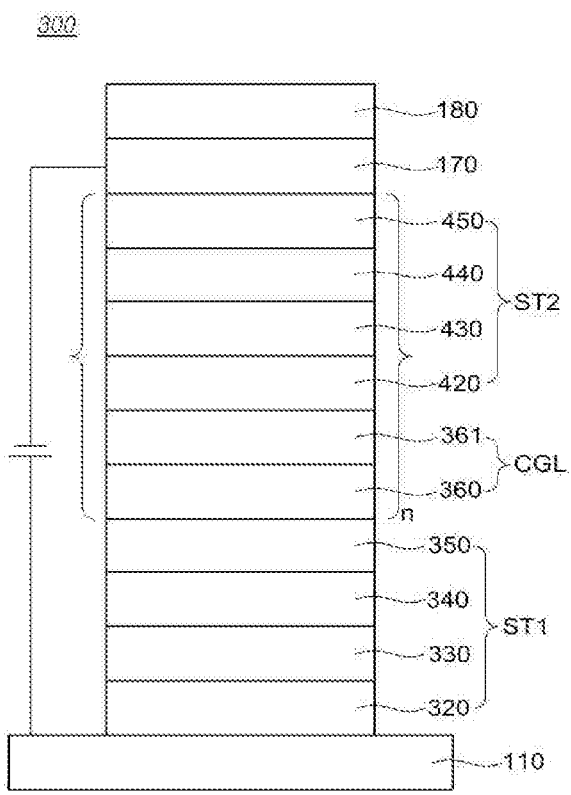

The FIGS. 1 to 3 are laminated structures for showing an example of an organic electric element according to an embodiment of the present invention, respectively.

Referring to the FIG. 1, an organic electric element 100 according to an embodiment of the present invention includes a first electrode 110 formed on a substrate (not shown), a second electrode 170, and an organic material layer formed between the first electrode 110 and the second electrode 170.

The first electrode 110 may be an anode (positive electrode), and the second electrode 170 may be a cathode (negative electrode). In the case of an inverted organic electric element, the first electrode may be a cathode, and the second electrode may be an anode.

The organic material layer may be comprised a hole injection layer 120, a hole transport layer 130, a light emitting layer 140, an electron transport layer 150, and an electron injection layer 160. Specifically, a hole injection layer 120, a hole transport layer 130, a light emitting layer 140, an electron transport layer 150, and an electron injection layer 160 are formed on the first electrode 110 in sequence.

Preferably, a layer for improving the luminous efficiency 180 may be formed one side of sides of the first electrode 110 and the second electrode 170, wherein one side is not facing the organic material layer, as a result the luminous efficiency of an organic electric element can be improved.

For example, the light efficiency improving layer 180 may be formed on the second electrode 170, as a result, in the case of a top emission organic light emitting diode, the optical energy loss due to Surface Plasmon Polaritons (SPPs) at the second electrode 170 may be reduced and in the case of a bottom emission organic light emitting diode, the light efficiency improving layer 180 may serve as a buffer for the second electrode 170.

Meanwhile, a buffer layer 210 or an emission-auxiliary layer 220 may be further formed between the hole transport layer 130 and the light emitting layer 140, which will be described with reference to FIG. 2.

Referring to FIG. 2, the organic electric element 200 according to another embodiment of the present invention may comprise a hole injection layer 120, a hole transport layer 130, a buffer layer 210, an emission-auxiliary layer 220, a light emitting layer 140, the electron transport layer 150, the electron injection layer 160, and a second electrode 170 formed on a first electrode 110 in sequence, and a light efficiency improving layer 180 may be formed on the second electrode 170.

Although not shown in FIG. 2, an electron transport auxiliary layer may be further formed between the light emitting layer 140 and the electron transport layer 150.

In addition, according to another embodiment of the present invention, the organic material layer may be a form consisting of a plurality of stacks, wherein the stacks comprise a hole transport layer, a light emitting layer, and an electron transport layer, respectively. This will be described with reference to FIG. 3.

Referring to FIG. 3, two or more sets of stacks of the organic material layers ST1 and ST2 may be formed between the first electrode 110 and the second electrode 170 in the organic electric element 300 according to another embodiment of the present invention, wherein the organic material layers are consisted of multiple layers, respectively, and the charge generation layer CGL may be formed between the stacks of the organic material layer.

Specifically, the organic electric element according to the embodiment of the present invention may comprise the first electrode 110, the first stack ST1, the charge generation layer CGL, the second stack ST2, and the second electrode 170 and the light efficiency improving layer 180.

The first stack ST1 is an organic layer formed on the first electrode 110, and the first stack ST1 may comprise the first hole injection layer 320, the first hole transport layer 330, the first light emitting layer 340 and the first electron transport layer 350 and the second stack ST2 may comprise a second hole injection layer 420, a second hole transport layer 430, a second light emitting layer 440 and a second electron transport layer 450. As such, the first stack and the second stack may be the organic layers having the same or different stacked structures.

The charge generation layer CGL may be formed between the first stack ST1 and the second stack ST2. The charge generation layer CGL may comprise a first charge generation layer 360 and a second charge generation layer 361. The charge generating layer CGL is formed between the first light emitting layer 340 and the second light emitting layer 440 to increase the current efficiency generated in each light emitting layer and to smoothly distribute charges.

The first light emitting layer 340 may comprise a light emitting material comprising a blue host doped with a blue fluorescent dopant and the second light emitting layer 440 may comprise a light emitting material comprising a green host doped with a greenish yellow dopant and a red dopant together, but the material of the first light emitting layer 340 and the second light emitting layer 440 according to an embodiment of the present invention is not limited thereto.

In FIG. 3, n may be an integer of 1 to 5 and the charge generation layer CGL and the third stack may be further stacked on the second stack ST2 when n is 2.

When a plurality of light emitting layers are formed in a multi-layer stack structure as shown in FIG. 3, it is possible to manufacture an organic electroluminescent element that emits not only white light but also various colors, wherein the white light is emitted by the mixing effect of light emitted from each light emitting layer.

The mixture of the compound represented by Formula 1 can be used as material of a hole injection layer 120, 320, 420, a hole transport layer 130, 330, 430, a buffer layer 210, an emission-auxiliary layer 220, an electron transport layer 150, 350, 450, an electron injection layer 160, a light emitting layer 140, 340, 440, or a layer for improving luminous efficiency 180, preferably as material of an emission-auxiliary layer 220 and/or a layer for improving luminous efficiency 180.

Even if the core is the same core, the band gap, the electrical characteristics, the interface characteristics and the like may be different depending on which substituent is bonded at which position. Therefore, it is necessary to study the selection of the core and the combination of the core and the sub-substituent bonded to the core. In particular, long life span and high efficiency can be simultaneously achieved when the optimal combination of energy levels and T1 values, inherent material properties (mobility, interfacial properties, etc.), and the like among the respective layers of an organic material layer is achieved.

Therefore, energy level and T1 value between the respective layers of the organic material layer, inherent material properties (mobility, interfacial properties, etc.) and the like can be optimized by using the mixture of the compound represented by Formula 1 as an emission-auxiliary layer 220 and/or a layer for improving luminous efficiency 180, and thus it is possible to simultaneously improve the lifetime and efficiency of the organic electric element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 110, forming the organic material layer comprising the hole injection layer 120, the hole transport layer 130, the light emitting layer 140, the electron transport layer 150, and the electron injection layer 160 thereon, and then depositing a material, which can be used as the cathode 170, thereon. Also, an emission-auxiliary layer 220 may be formed between a hole transport layer 130 and a light emitting layer 140, and an electron transport auxiliary layer (not shown) may be further formed between a light emitting layer 140 and an electron transport layer 150 and, as described above, a stack structure may be formed.

Also, the organic material layer may be manufactured in such a manner that the fewer layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

In addition, the organic electric element according to an embodiment of the present invention may be selected from the group consisting of an organic light emitting diode, an organic solar cell, an organic photo conductor, an organic transistor, an element for monochromatic illumination and an element for quantum dot display. Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the compound according to an aspect of the present invention will be described.

The compound according to an aspect of the present invention is represented by formula 1 below.

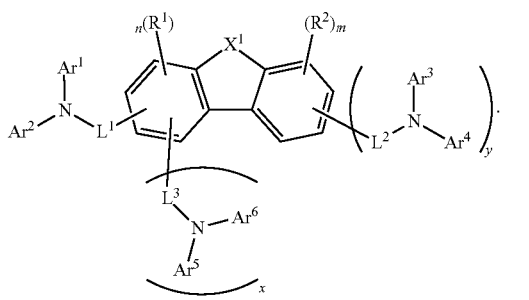

<Formula 1>

In Formula 1, each of symbols may be defined as follows:

x and y are each an integer of 0 to 2, preferably, an integer of 0 or 1, and x+y is an integer greater than or equal to 1. Where x and y are each 2 or more, each of $L^2$s, each of $L^3$s, each of $Ar^3$s, each of $Ar^4$s, each of $Ar^5$s, each of $Ar^6$s is the same or different from each other.

$Ar^1$ to $Ar^6$ are each independently selected from the group consisting of a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring group, -L'-N($R_a$)($R_b$), Formula A-1 and Formula A-2, and at least one of $Ar^1$ to $Ar^6$ is Formula A-1 or Formula A-2,

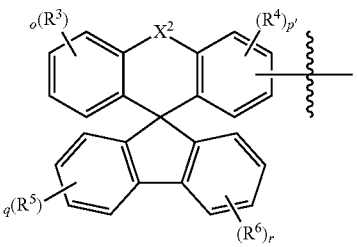

<Formula A-1>

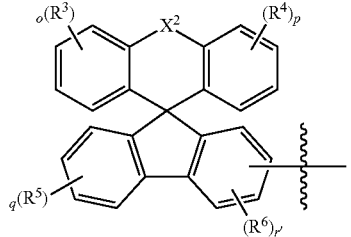

<Formula A-2>

$X^1$ is O or S and $X^2$ is N(R'), O or S.

Where at least one of $Ar^1$ to $Ar^6$ is an aryl group, the aryl group may be preferably a $C_6$-$C_{30}$, more preferably a $C_6$-$C_{18}$ aryl group, for example, phenyl, biphenyl, naphthyl, terphenyl and the like.

Where at least one of $Ar^1$ to $Ar^6$ is a heterocyclic group except for Formula A-1 or Formula A-2, the heterocyclic group may be preferably a $C_2$-$C_{30}$, more preferably a $C_2$-$C_{16}$ heterocyclic group, for example, dibenzofuran, dibenzothiophene, naphthobenzofuran, naphthobenzothiophene and the like.

Where at least one of $Ar^1$ to $Ar^6$ is a fluorenyl group, the fluorenyl group may be 9,9-dimethyl-9H-fluorene, 9,9-diphenyl-9H-fluorene, 9,9'-spirofluorene and the like.

$R^1$ to $R^6$ are each independently selected from the group consisting of hydrogen, deuterium, halogen, cyano group, nitro group, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring group, a $C_1$-$C_{30}$ alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxy group and -L'-N($R_a$)($R_b$), and adjacent groups together may be bonded to each other to form a ring.

Here, the term 'neighboring groups' means neighboring $R^1$s, neighboring $R^2$s, neighboring $R^3$s, neighboring $R^4$s, neighboring $R^5$s, neighboring $R^6$s, neighboring $R^3$ and R', and/or neighboring $R^4$ and R'.

The ring formed by neighboring $R^1$s, neighboring $R^2$s, neighboring $R^3$s, neighboring $R^4$s, neighboring $R^5$s or/and neighboring $R^6$s is/are a $C_6$-$C_{60}$ aromatic ring group, a fluorenyl group, a $C_2$-$C_{60}$ heterocyclic group containing at least one heteroatom of O, N, S, Si and P, or a $C_3$-$C_{60}$ aliphatic ring. For example, where the aromatic ring is formed by bonding between neighboring groups, the aromatic ring may be preferably a $C_6$-$C_{20}$ aromatic ring group, more preferably, a $C_6$-$C_{14}$ aromatic ring group, for example, benzene, naphthalene, phenanthrene or the like.

Where neighboring $R^3$ and R', and/or neighboring $R^4$ and R' are bonded to each other to form a ring, a heterocyclic ring containing N may be formed. The heterocyclic ring may comprise a moiety, such as indole, carbazole, phenothiazine, phenoxazine, acridine, or the like.

n, p' and r' are each an integer of 0 to 3, m, o, p, q and r are each an integer of 0 to 4, where they are each an integer of 2 or more, each of $R^1$s, each of $R^2$s, each of $R^3$s, each of $R^4$s, each of $R^5$s, each of $R^6$s is the same or different from each other.

Where at least one of $R^1$ to $R^6$ is an aryl group, the aryl group may be preferably a $C_6$-$C_{30}$, more preferably a $C_6$-$C_{18}$ aryl group, for example, phenyl, biphenyl, naphthyl, terphenyl and the like.

Where at least one of $R^1$ to $R^6$ is a heterocyclic group, the heterocyclic group may be preferably a $C_2$-$C_{30}$, more preferably a $C_2$-$C_{18}$ heterocyclic group, for example, dibenzothiophene, dibenzofuran, carbazole, phenylcarbazole and the like.

Where at least one of $R^1$ to $R^6$ is an alkyl group, the alkyl group may be preferably a $C_1$-$C_{10}$ alkyl group, for example, methyl, t-butyl and the like.

Where at least one of $R^1$ to $R^6$ is an alkoxyl group, the alkoxyl group may be preferably a $C_1$-$C_{20}$ alkoxy group, more preferably a $C_1$-$C_{10}$ alkoxy group, for example, methoxy, t-butoxy and the like.

$L^1$ to $L^3$ and L' are each independently selected from the group consisting of a single bond, a $C_6$-$C_{60}$ arylene group, a fluorenylene group, a $C_3$-$C_{60}$ aliphatic ring group and a $C_2$-$C_{60}$ heterocyclic group containing at least one heteroatom of O, N, S, Si, and P.

Where at least one of $L^1$ to $L^3$ and L' is an arylene group, the arylene group may be preferably a $C_6$-$C_{30}$, more preferably a $C_6$-$C_{18}$ arylene group, for example, phenylene, naphthalene, biphenyl, terphenyl and the like.

R', $R_a$ and $R_b$ are each independently selected from the group consisting of a $C_6$-$C_{60}$ aryl group, a fluorenyl group, a $C_2$-$C_{60}$ heterocyclic group containing at least one heteroatom of O, N, S, Si, and P and a $C_3$-$C_{60}$ aliphatic ring group.

Where at least one of R', $R_a$ and $R_b$ is an aryl group, the aryl group may be preferably a $C_6$-$C_{30}$, more preferably a $C_6$-$C_{18}$ aryl group, for example, phenyl, biphenyl, naphthyl, terphenyl, phenanthrene and the like.

Where at least one of R', $R_a$ and $R_b$ is a heterocyclic group, the heterocyclic group may be preferably a $C_2$-$C_{30}$, more preferably a $C_2$-$C_{18}$ heterocyclic group, for example, carbazole, phenylcarbazole, dibenzofuran, dibenzothiophene and the like.

Where at least one of R', $R_a$ and $R_b$ is a fluorenyl group, the fluorenyl group may be 9,9-dimethyl-9H-fluorene, 9,9-diphenyl-9H-fluorene, 9,9'-spirofluorene and the like.

$Ar^1$ to $Ar^6$, $R^1$ to $R^6$, $L^1$ to $L^3$, R' and the ring formed by adjacent groups may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_6$-$C_{20}$ arylthio group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group, and $C_8$-$C_{20}$ arylalkenyl group.

Formula 1 may be represented by Formula 2 or Formula 3.

<Formula 2>
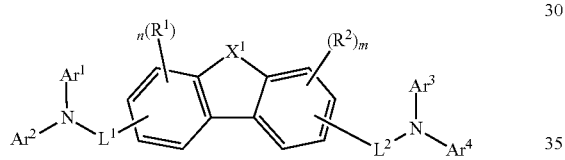

<Formula 3>
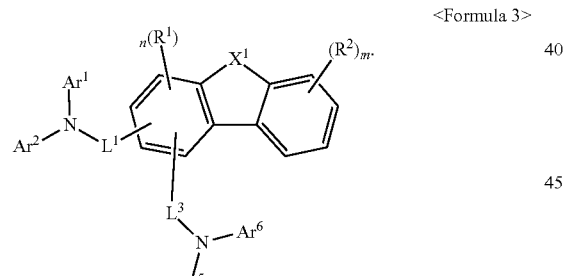

In Formulas 2 and 3, $X^1$, $L^1$-$L^3$, $Ar^1$-$Ar^6$, $R^1$, $R^2$, n, m are the same as defined for Formula 1.

In addition, Formula 1 may be represented by one of Formula 4 to Formula 19.

<Formula 4>
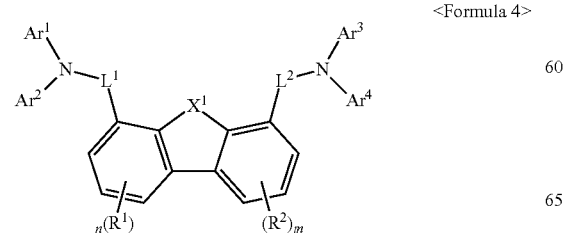

<Formula 5>
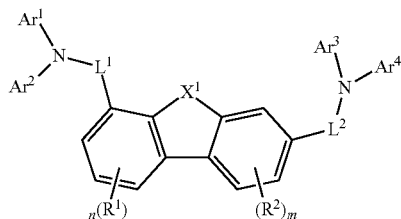

<Formula 6>
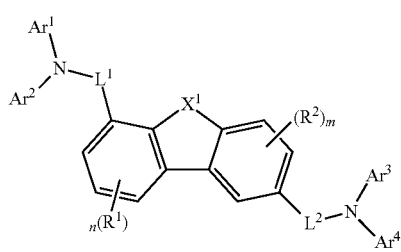

<Formula 7>
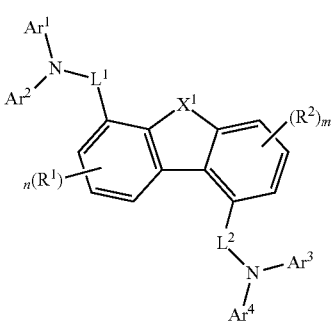

<Formula 8>
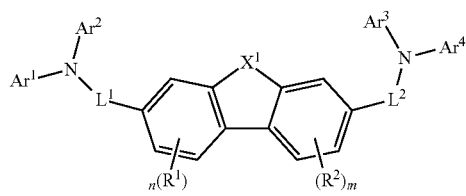

<Formula 9>
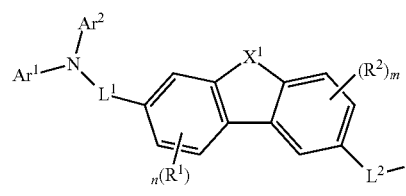

<Formula 10>
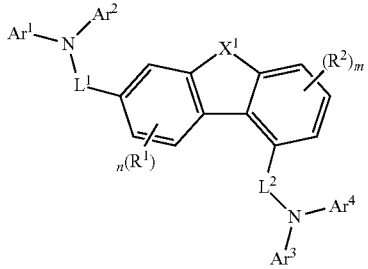

<Formula 11>
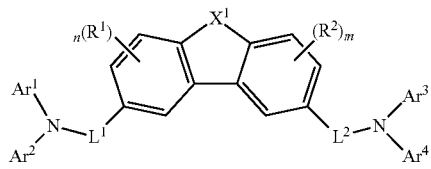
<Formula 12>
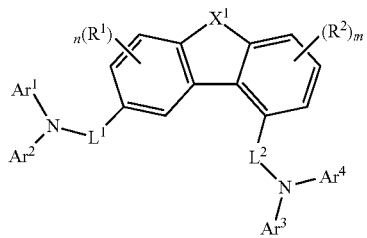
<Formula 13>
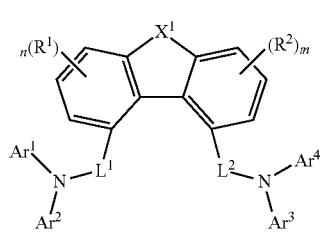
<Formula 14>
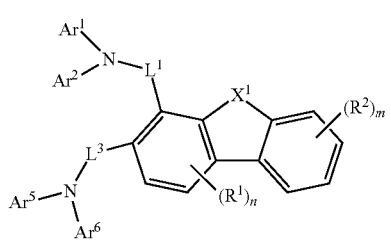
<Formula 15>
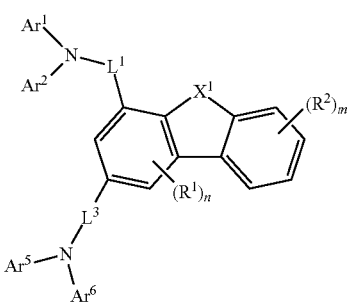
<Formula 16>
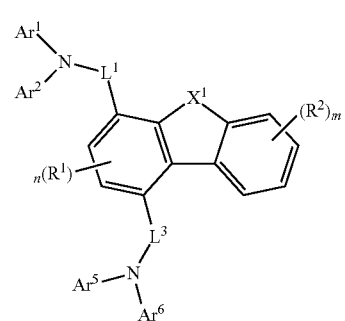
<Formula 17>
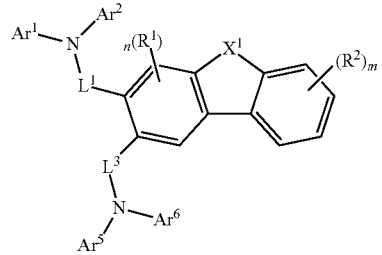
<Formula 18>
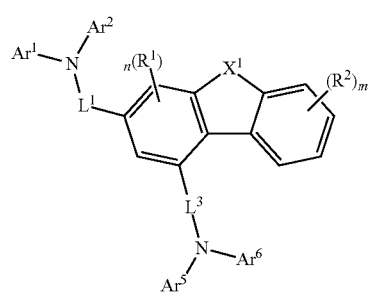
<Formula 19>
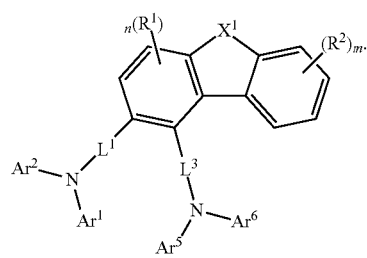
In Formulas 4 to 19, $X^1$, $L^1$-$L^3$, $Ar^1$-$Ar^6$, $R^1$, $R^2$, n, m are the same as defined for Formula 1.
In addition, Formula 1 may be represented by one of Formula 20 to Formula 34.
<Formula 20>
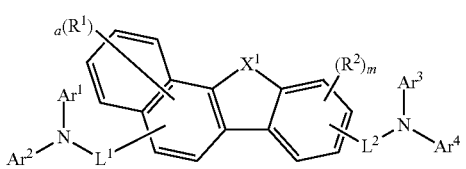
<Formula 21>
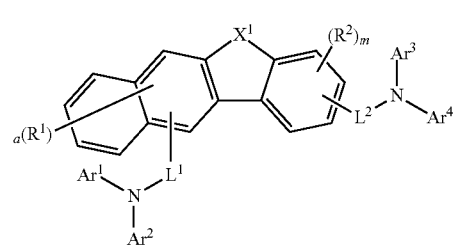

<Formula 22>
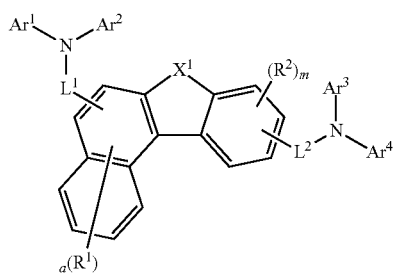
<Formula 23>
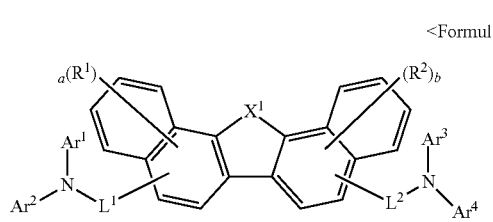
<Formula 24>
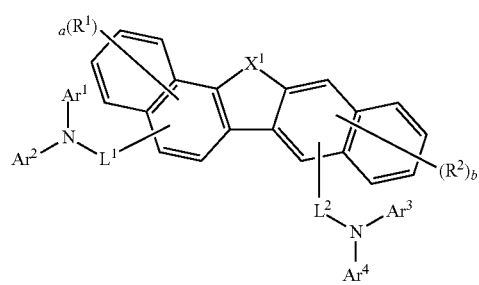
<Formula 25>
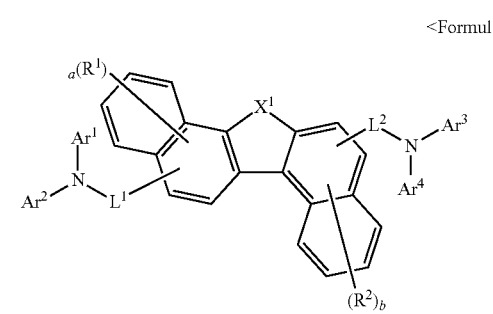
<Formula 26>
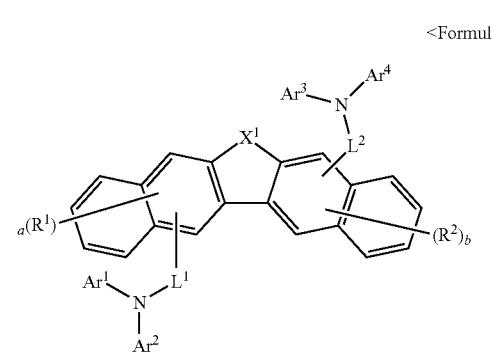
<Formula 27>
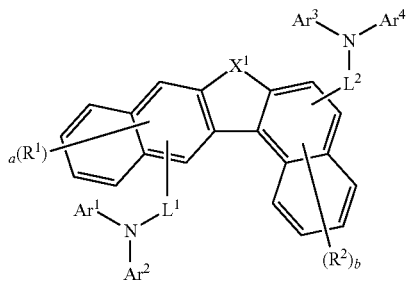
<Formula 28>
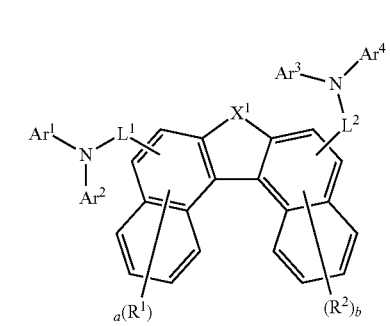
<Formula 29>
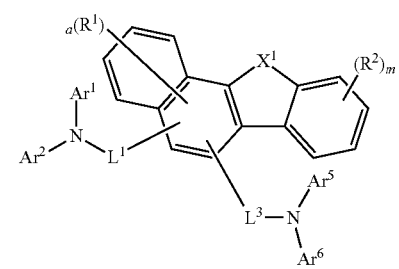
<Formula 30>
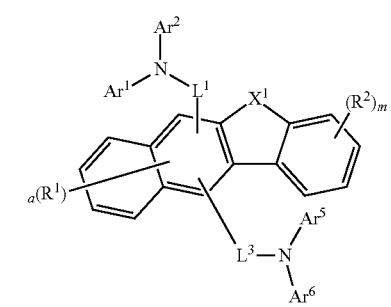
<Formula 31>
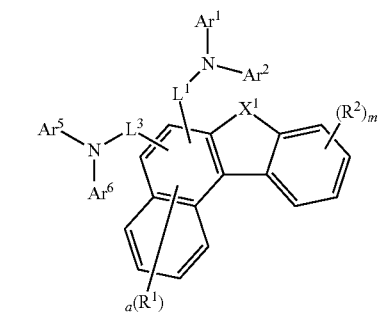

<Formula 32>
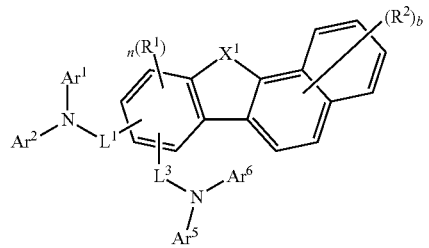
<Formula 33>
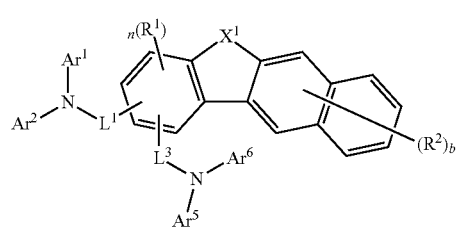
<Formula 34>
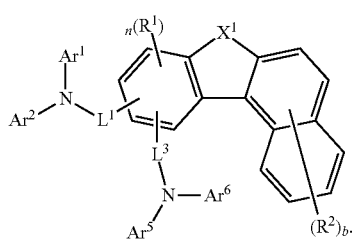
In Formulas 20 to 34, $X^1$, $L^1$-$L^3$, $Ar^1$-$Ar^6$, $R^1$, $R^2$, n, m are the same as defined for Formula 1, and a and b are each an integer of 0 to 6.
Specifically, the compound represented by formula 1 may be one of the following compounds, but there is no limitation thereto.
P-1
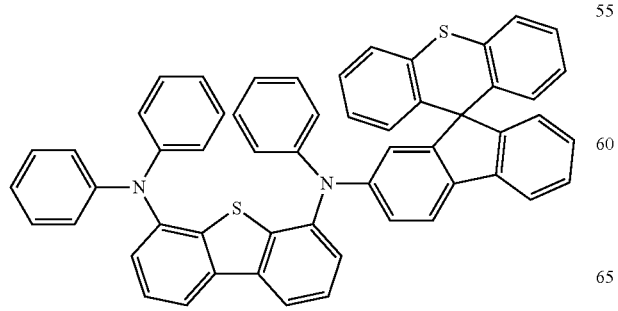
P-2
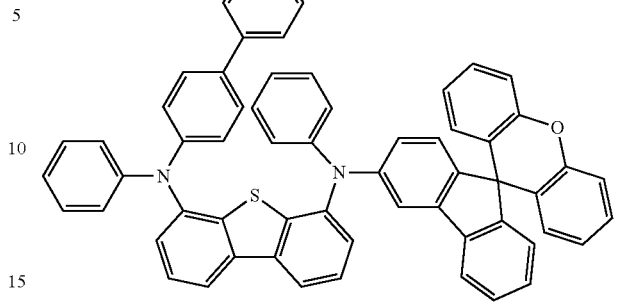
P-3
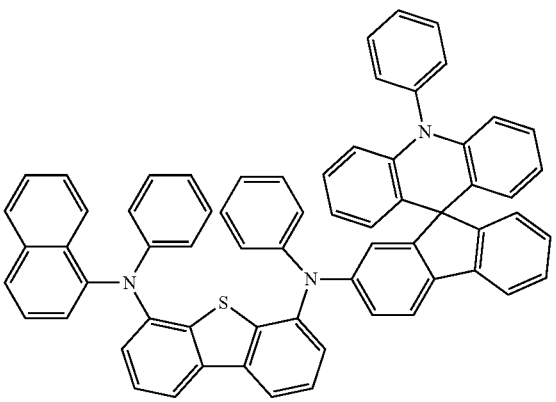
P-4
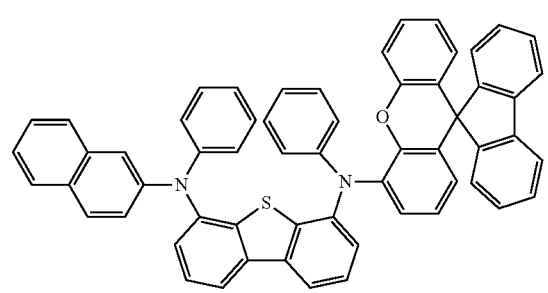
P-5

P-6
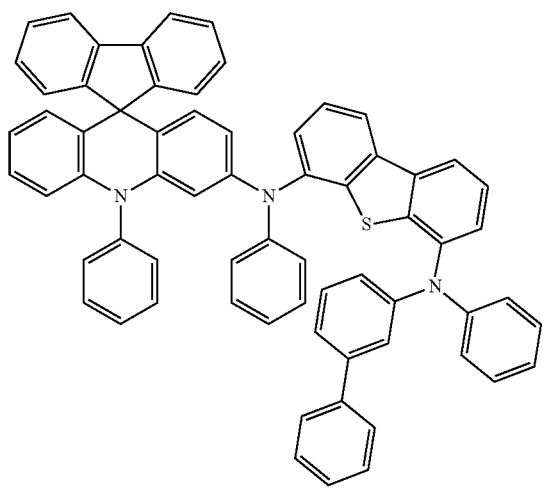
P-9
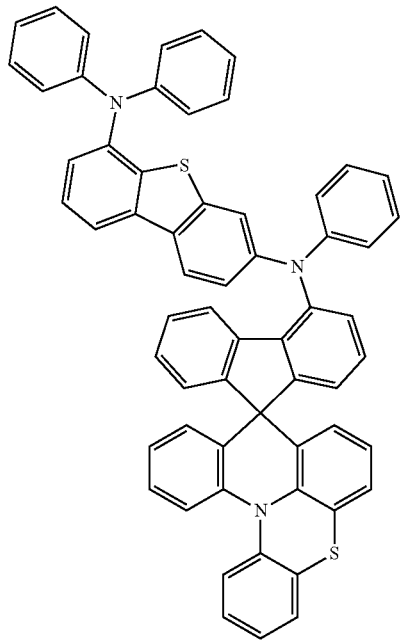
P-7
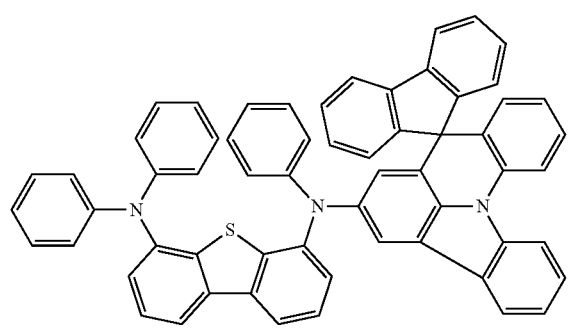
P-10
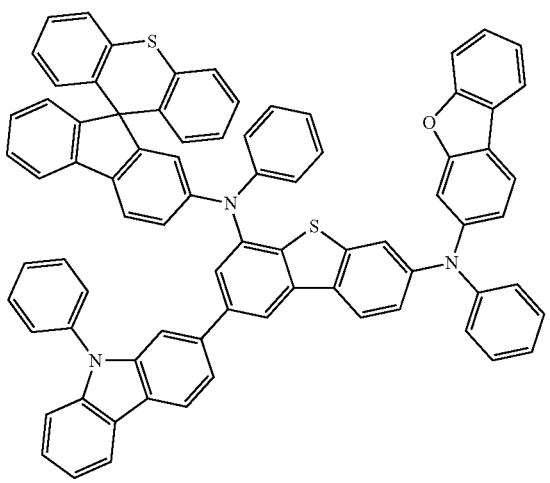
P-8
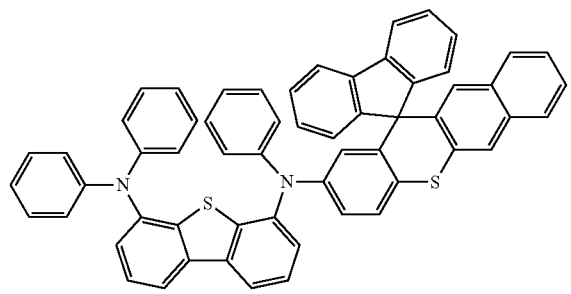
P-11
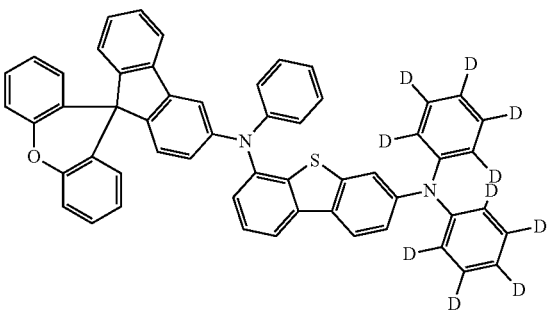

P-12
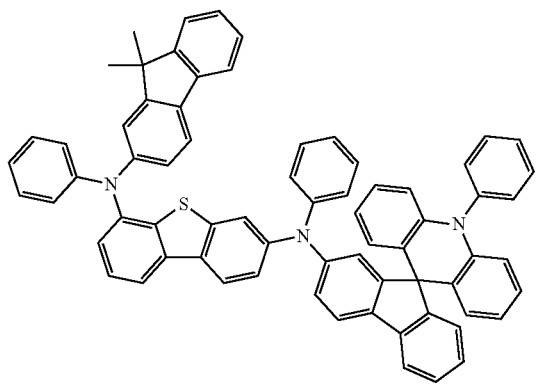
P-13
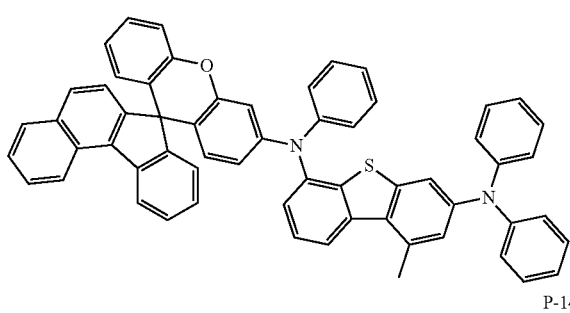
P-14
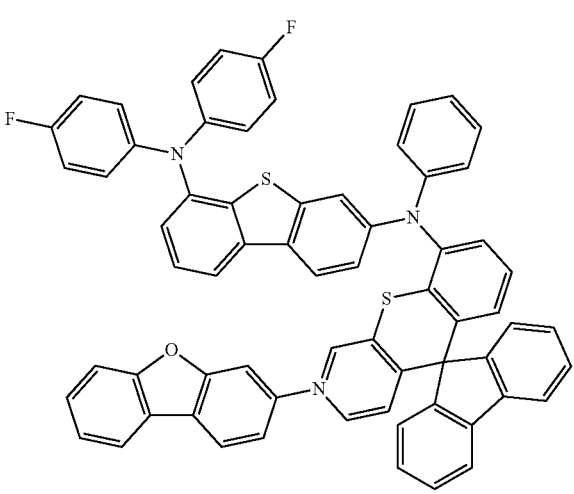
P-15
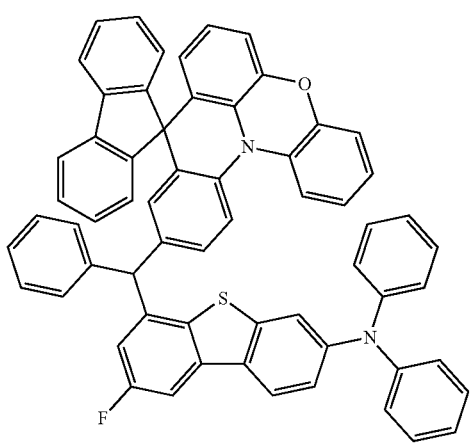
P-16
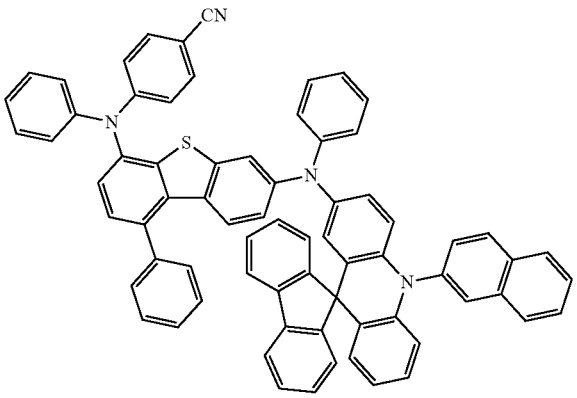
P-17
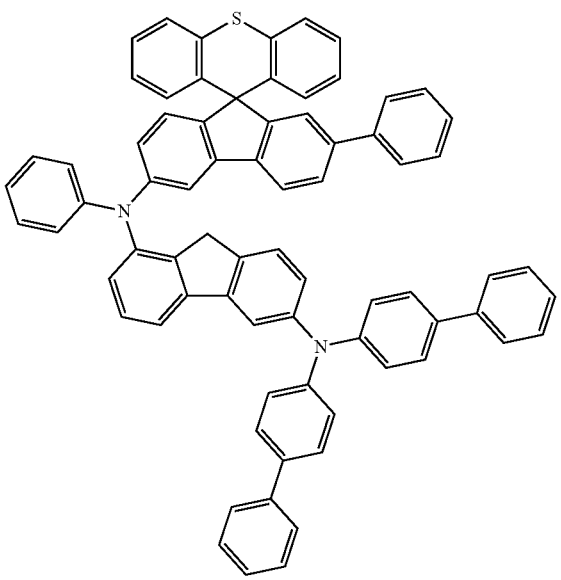
P-18
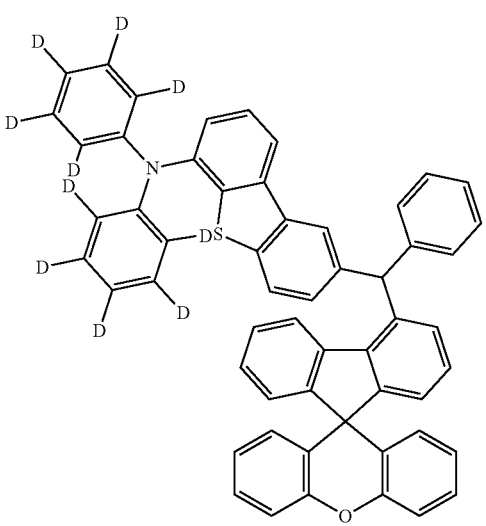

P-19
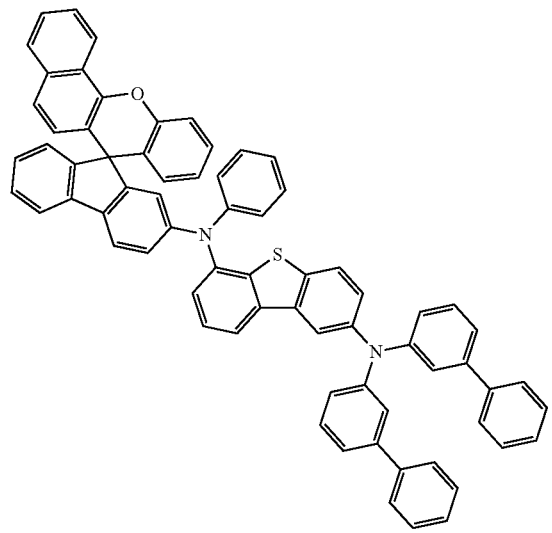
P-20
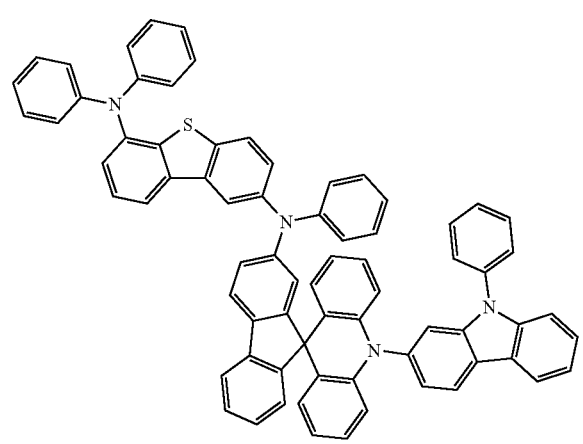
P-21
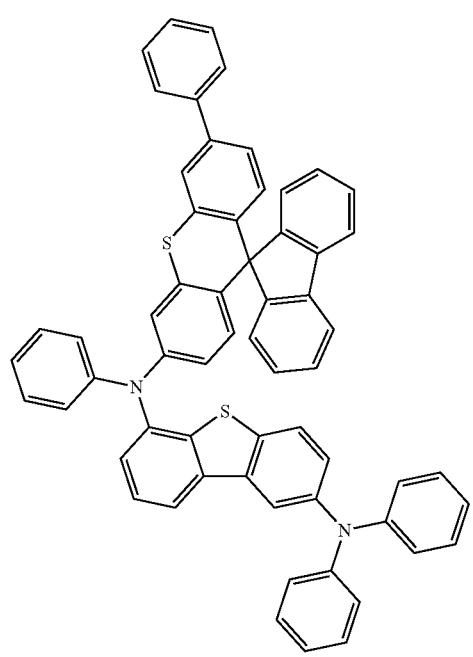
P-22
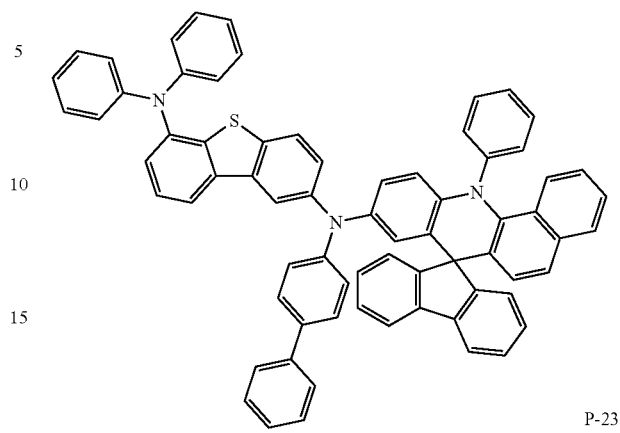
P-23
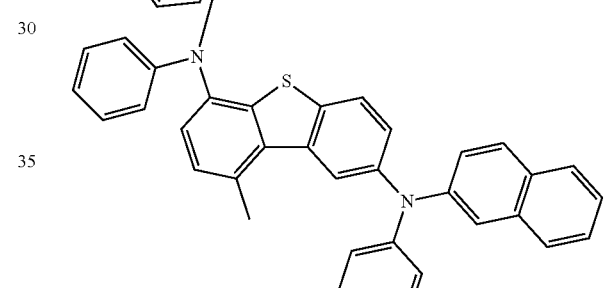
P-24
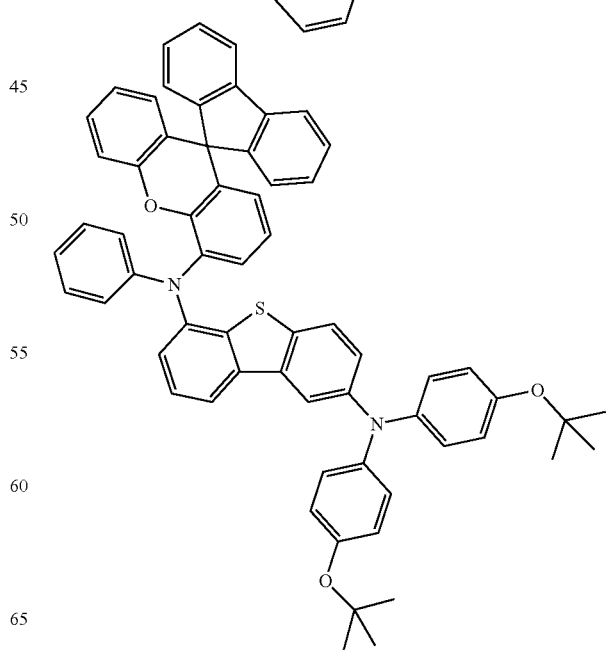

-continued
P-25
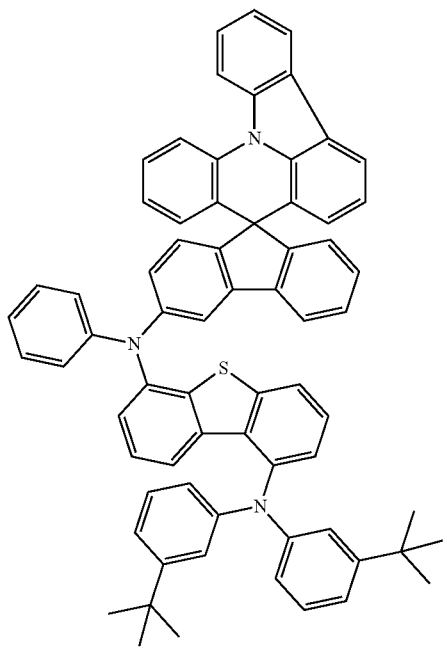
P-26
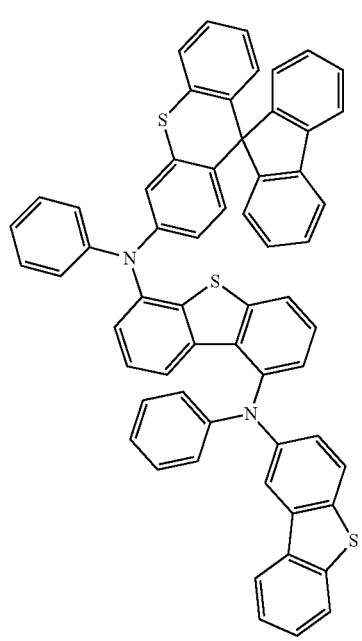
P-27
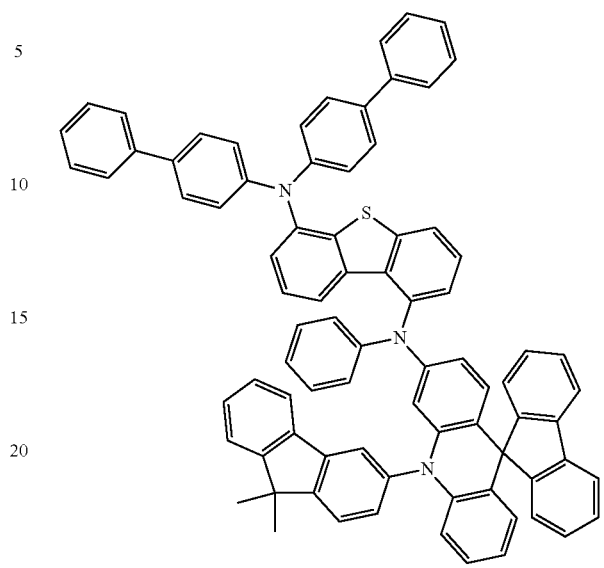
P-28
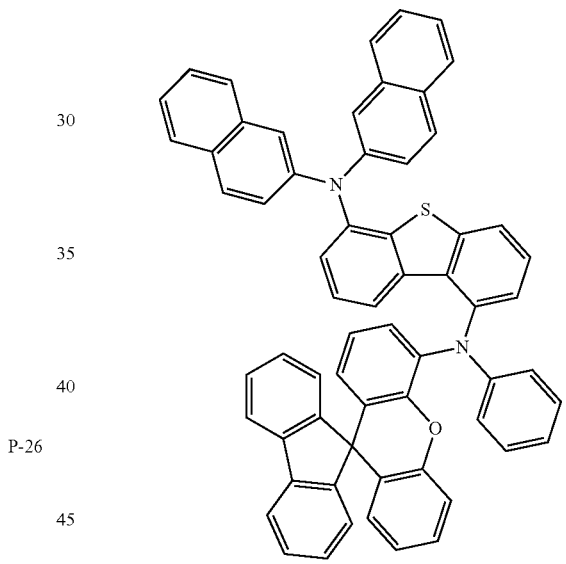
P-29
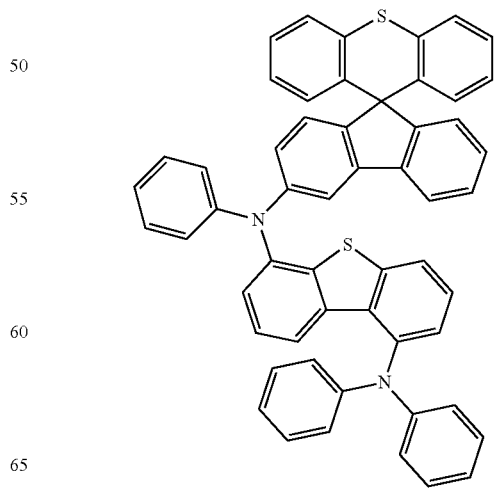

P-30
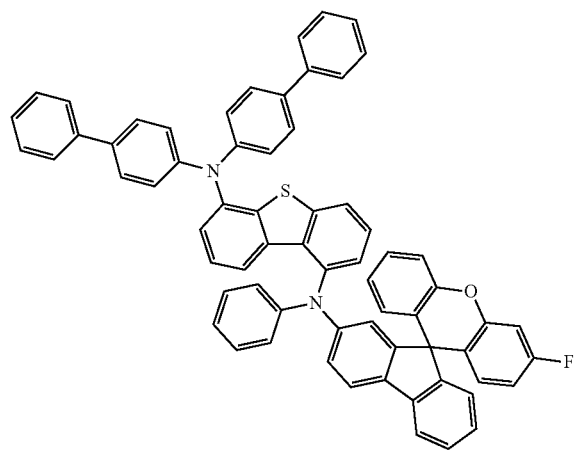
P-33
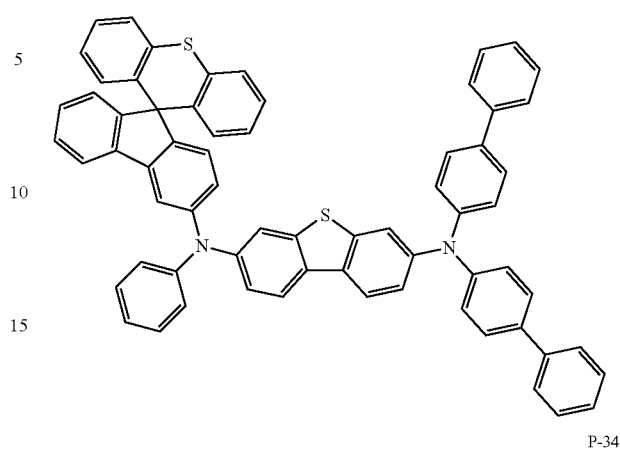
P-31
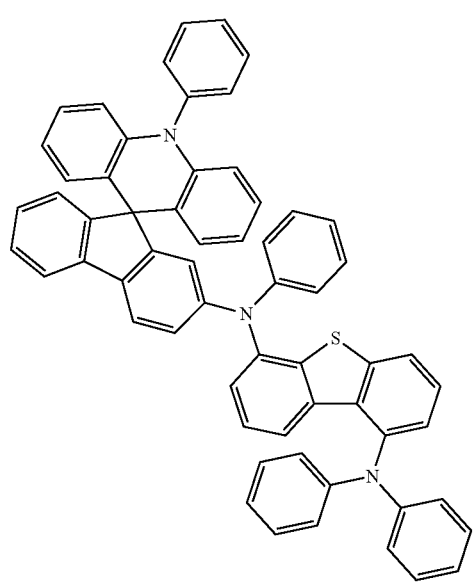
P-34
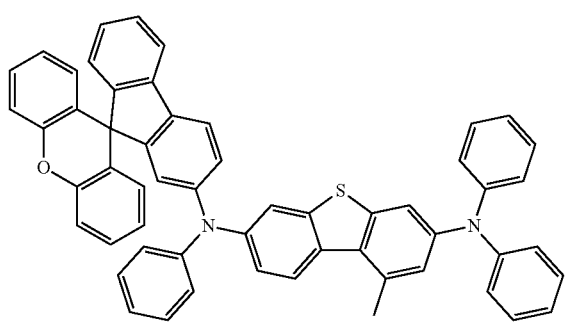
P-35
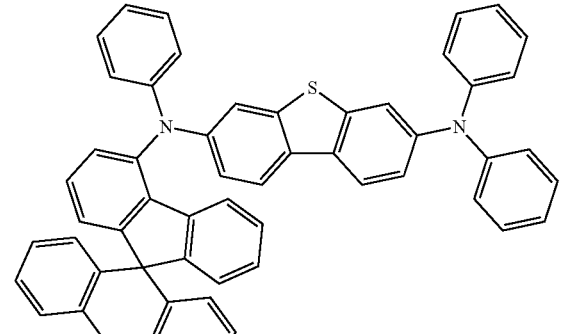
P-32
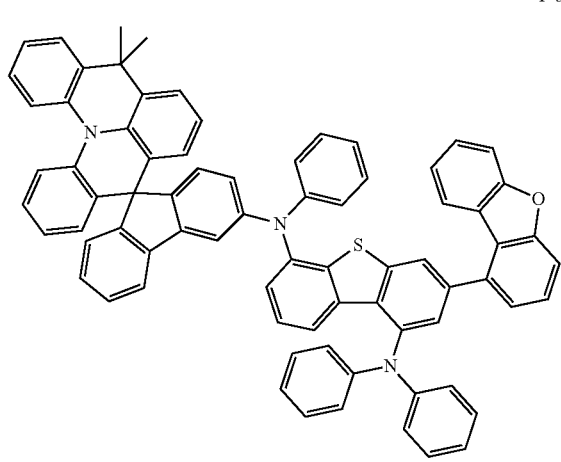
P-36
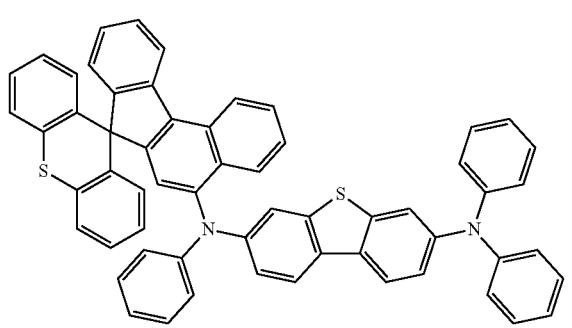

-continued
P-37
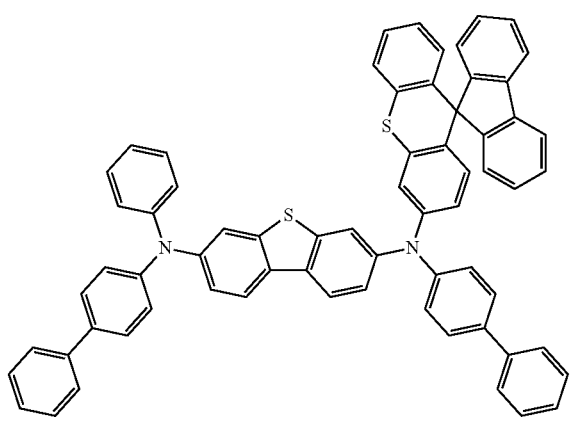
P-38
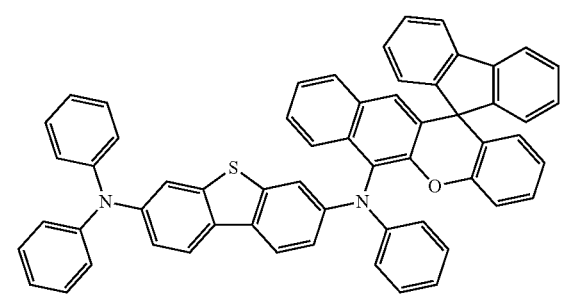
P-39
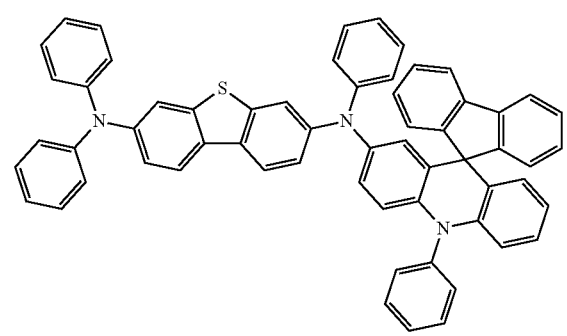
P-40
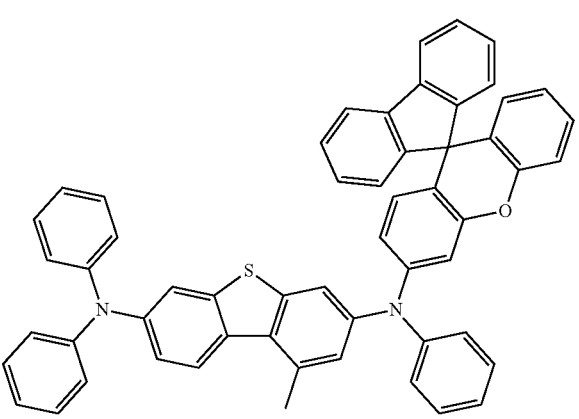
-continued
P-41
P-42
P-43
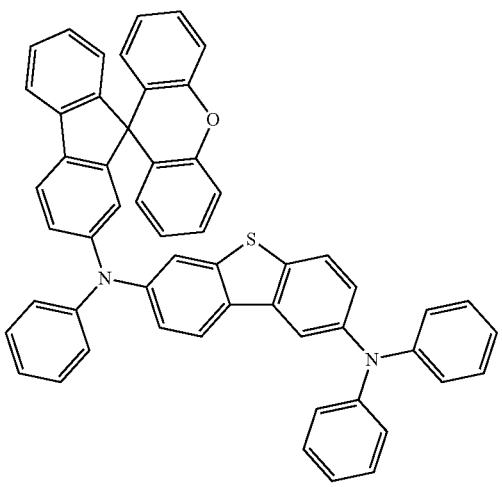

-continued
P-44
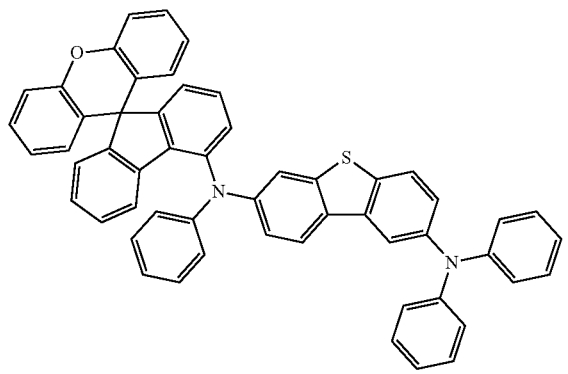
P-45
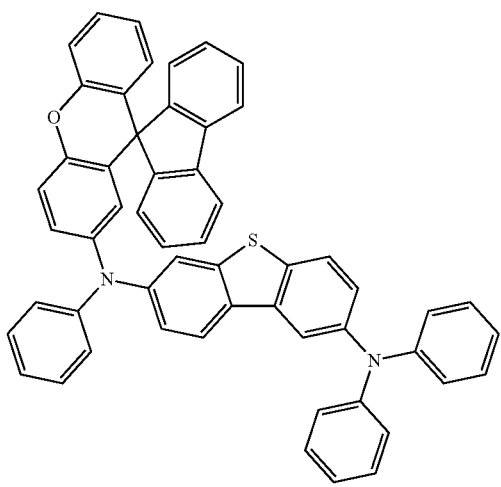
P-46
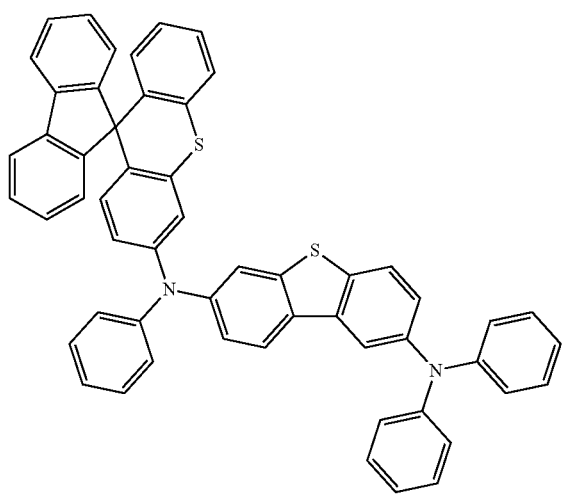
-continued
P-47
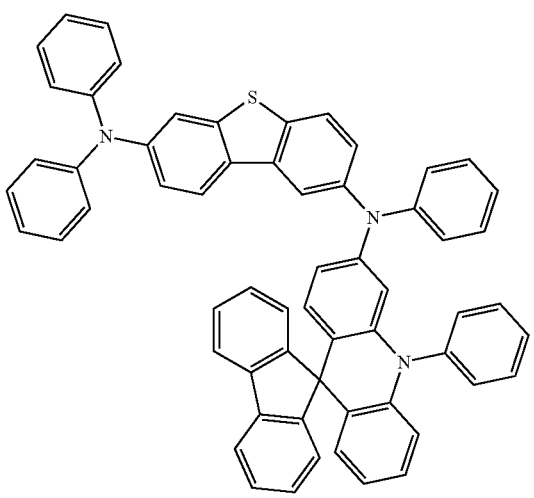
P-48
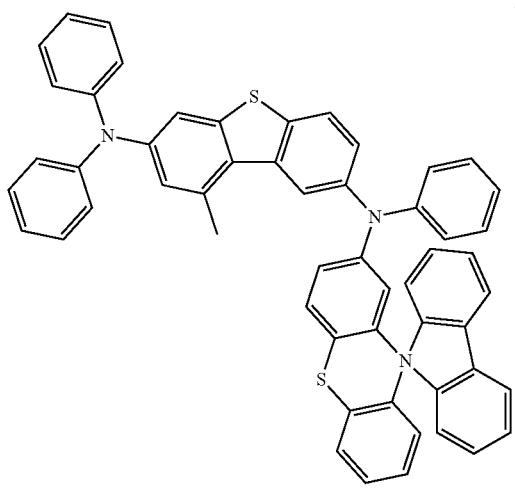
P-49
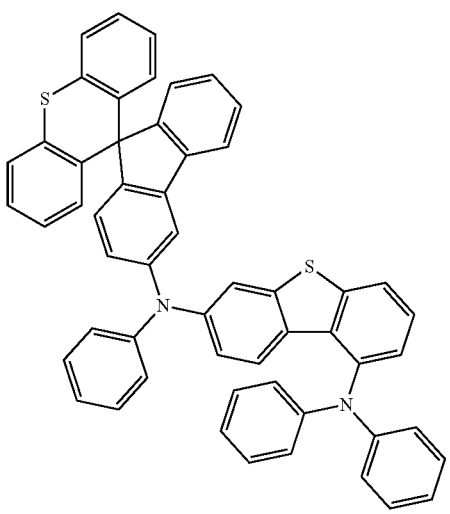

P-50
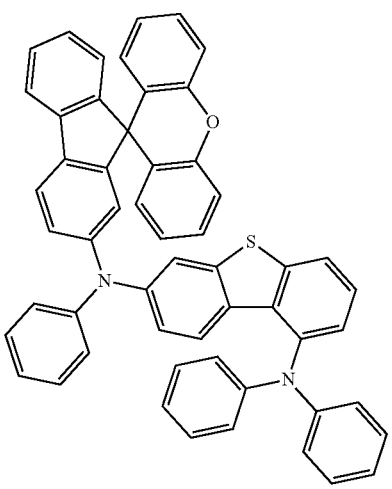
P-51
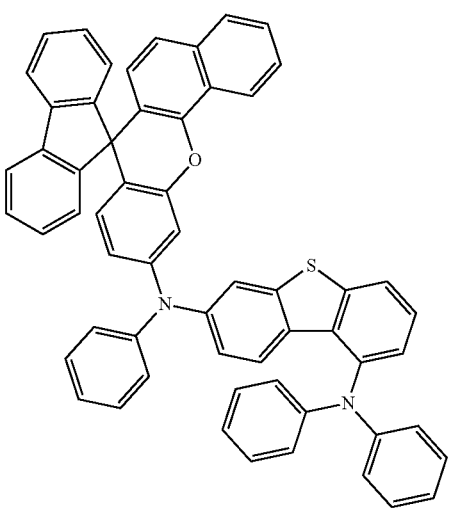
P-52
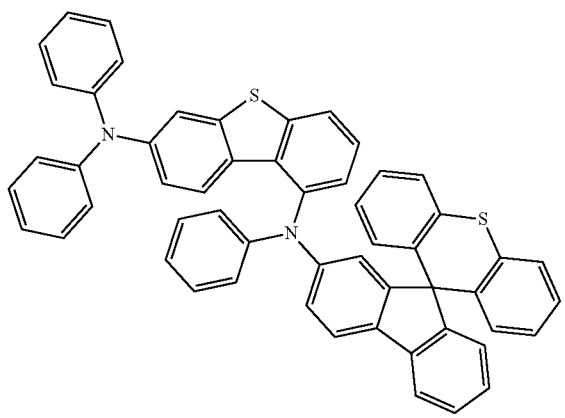
P-53
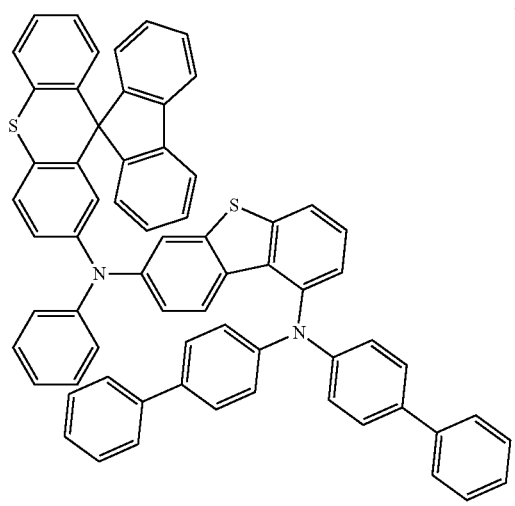
P-54
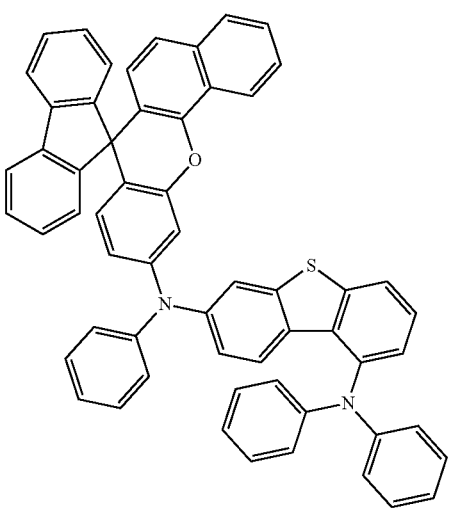
P-55
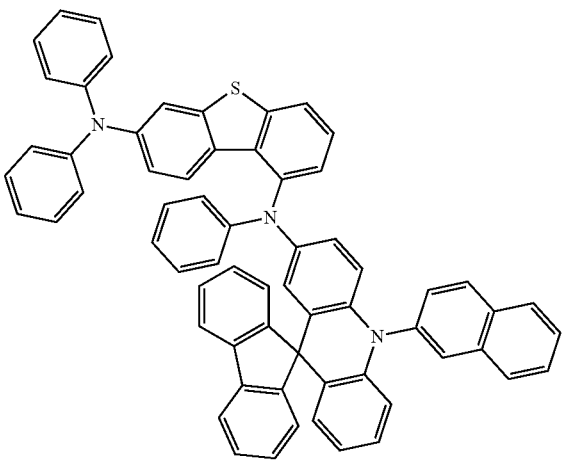

P-56
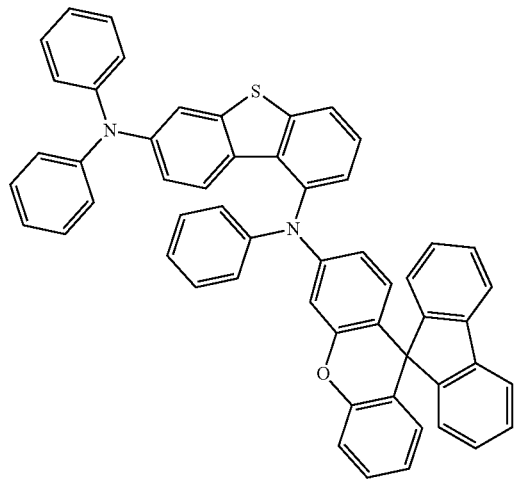
P-57
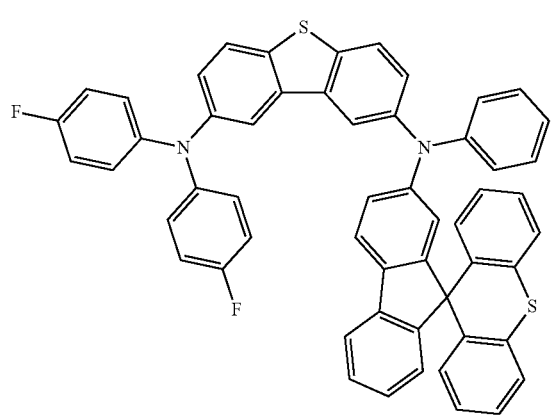
P-58
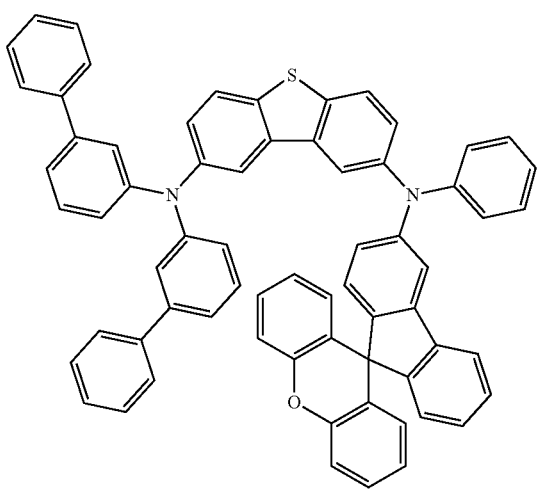
P-59
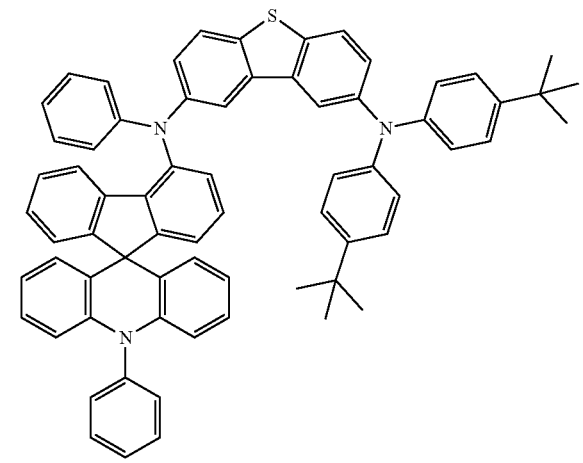
P-60, P-61, P-62
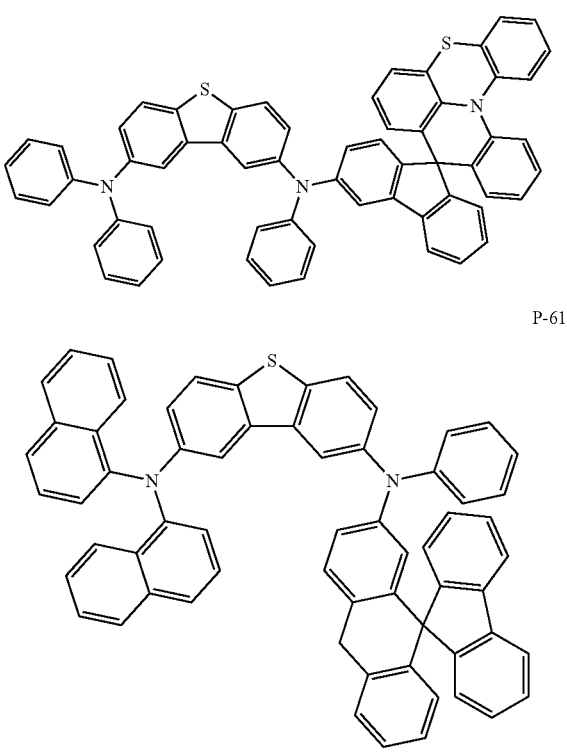

P-63
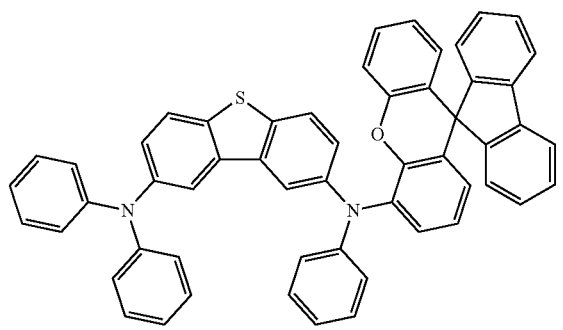
P-64
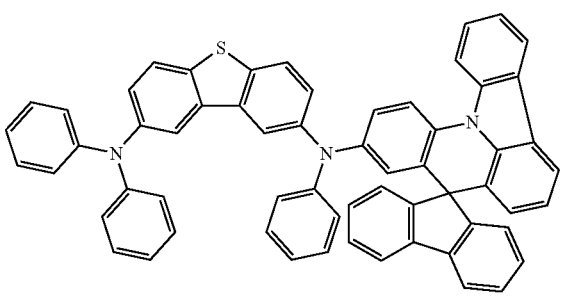
P-65
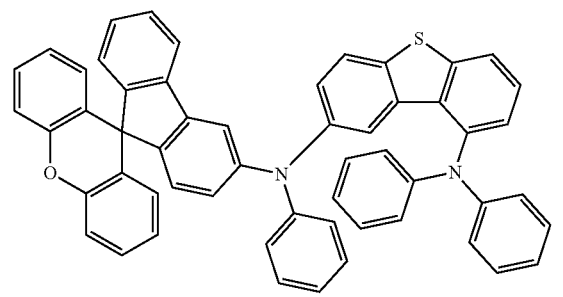
P-66
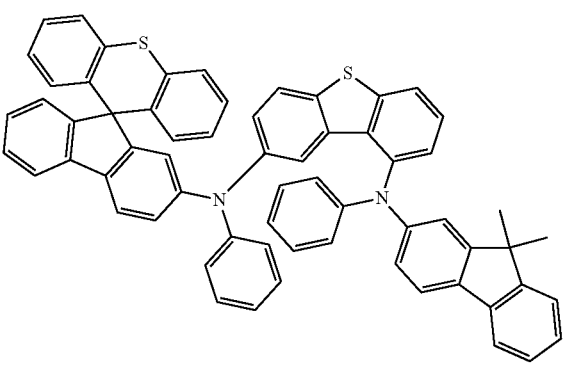
P-67
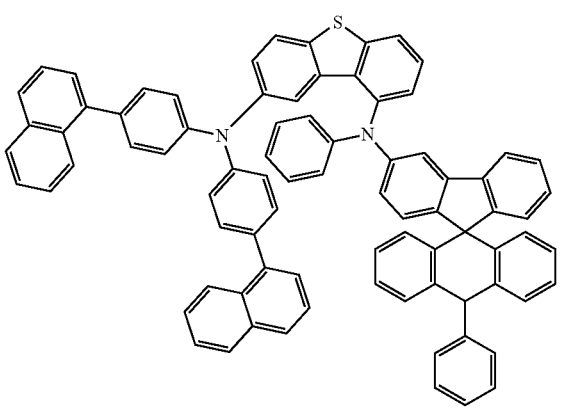
P-68
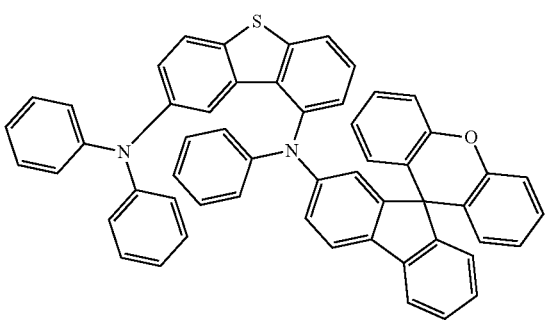
P-69
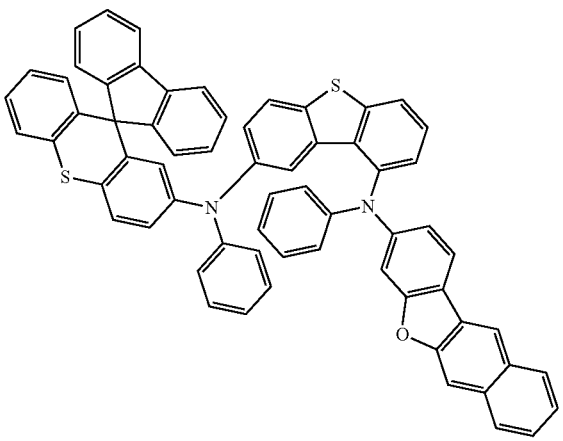
P-70
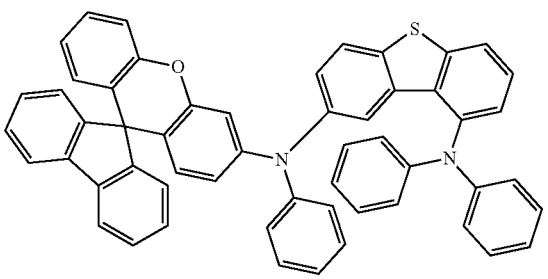

-continued
P-71
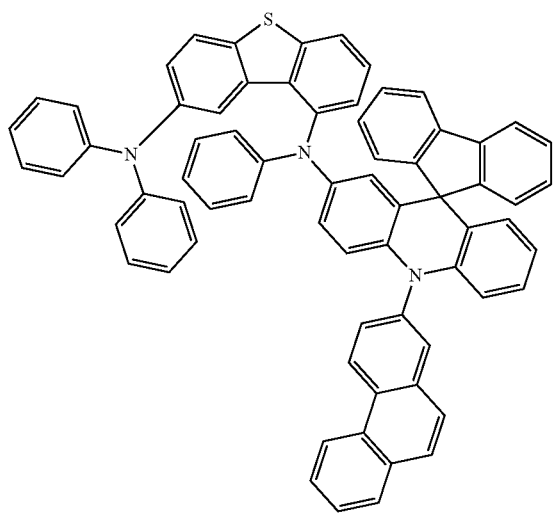
P-72
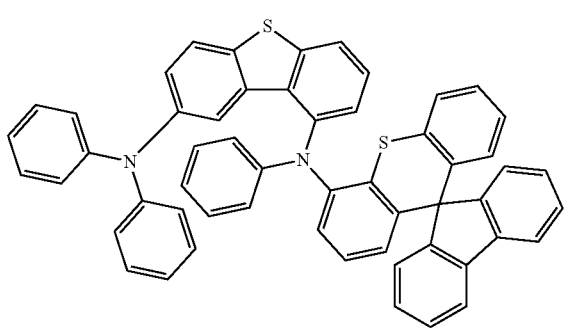
P-73
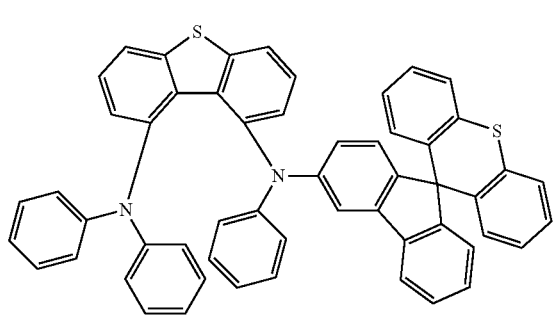
P-74
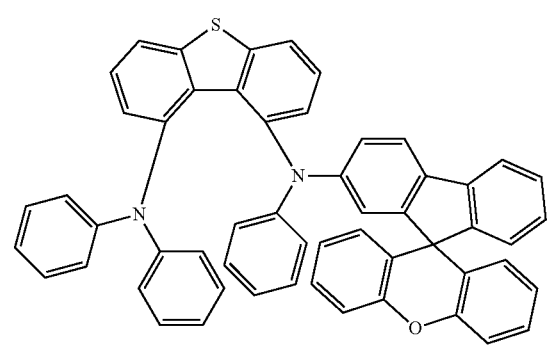
-continued
P-75
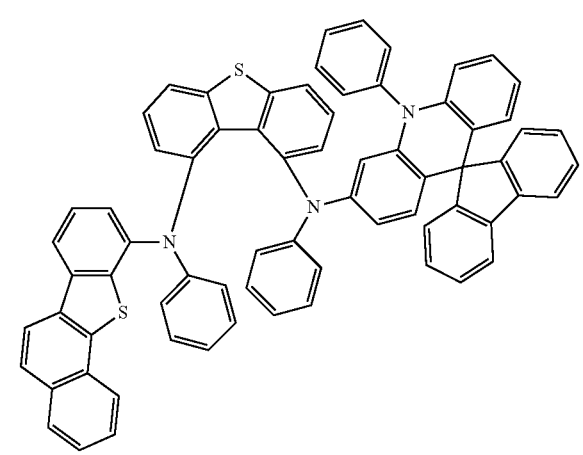
P-76
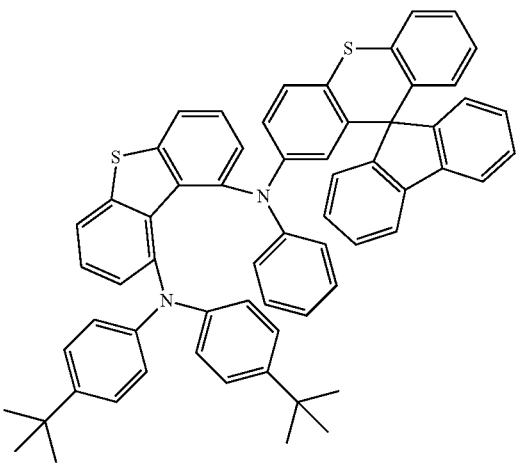
P-77
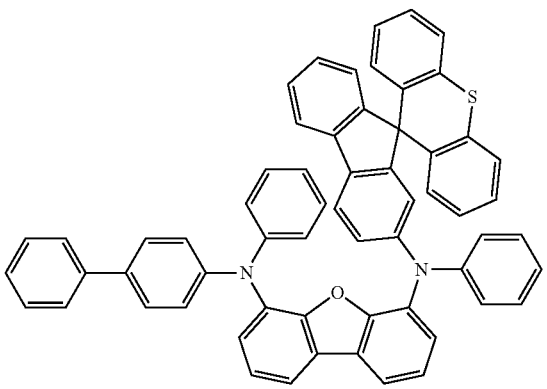

P-78
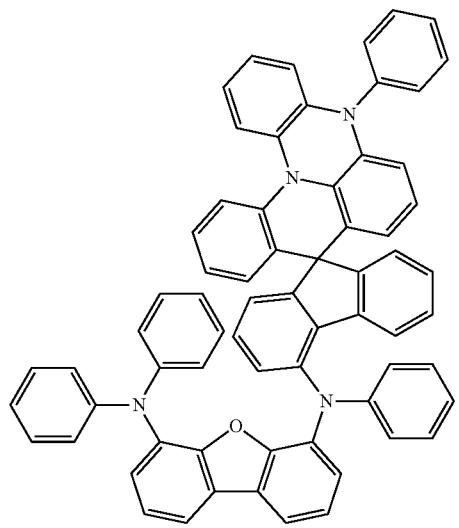
P-79
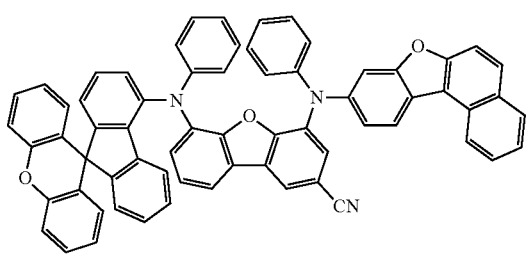
P-80
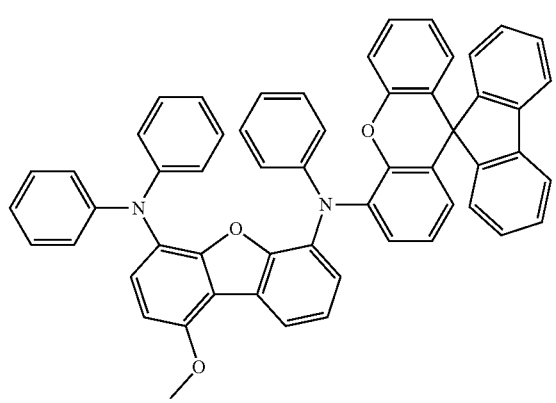
P-81
P-82
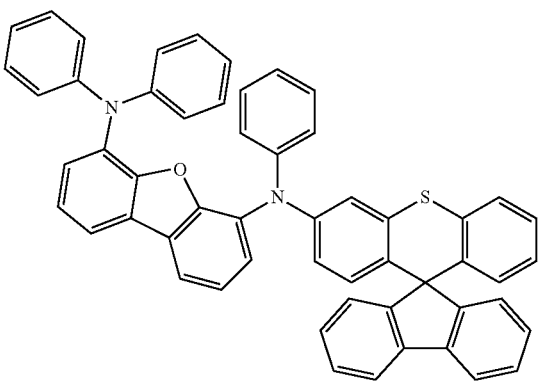
P-83
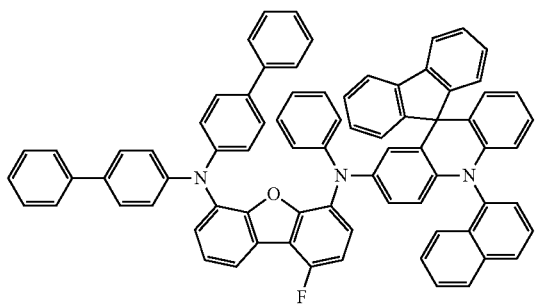
P-84
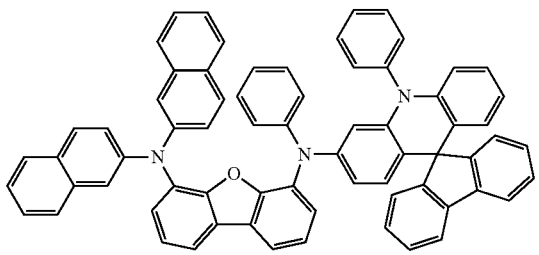
P-85
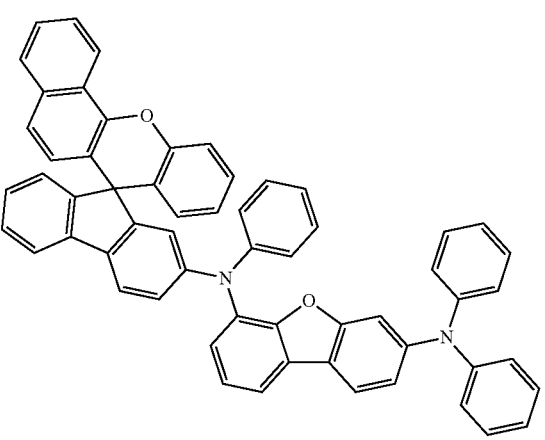

P-86
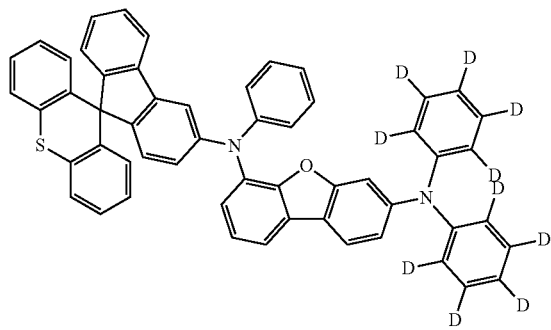
P-87
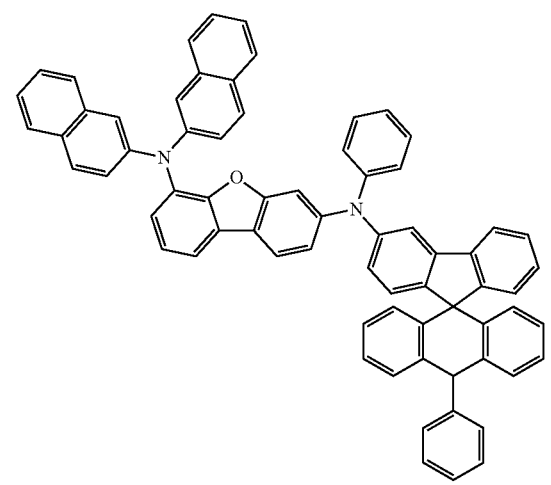
P-88
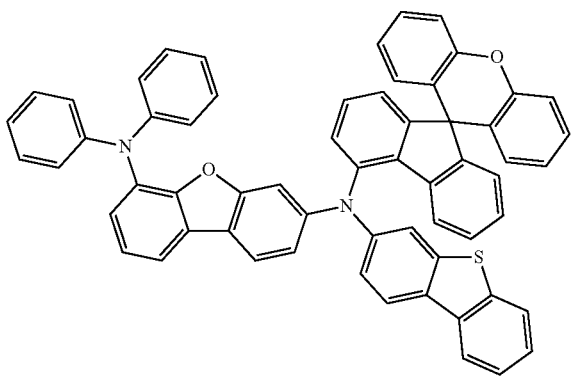
P-89
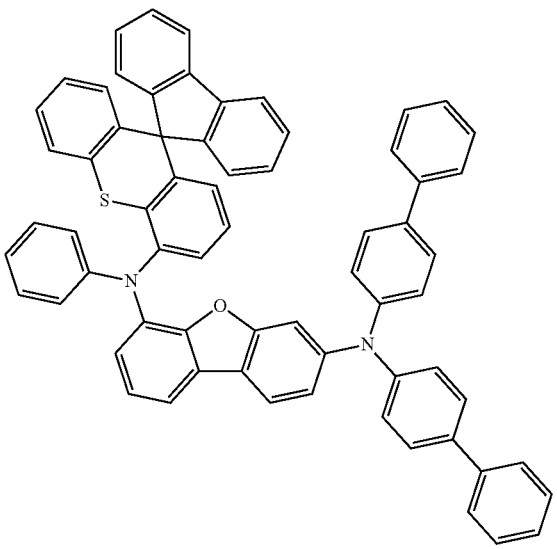
P-90
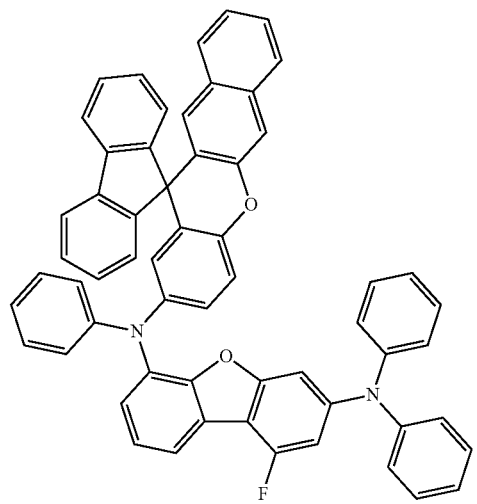
P-91
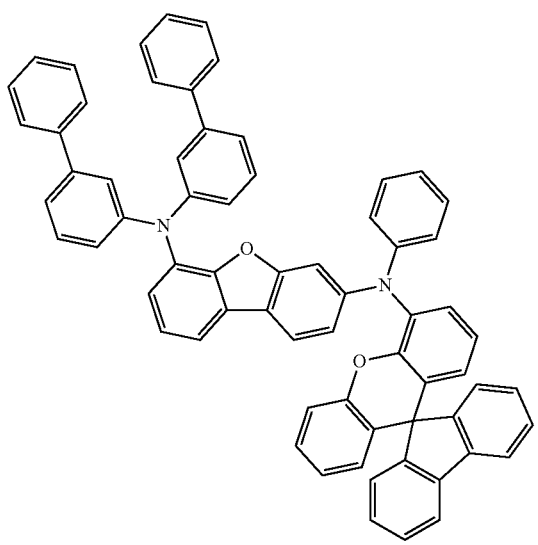

P-92
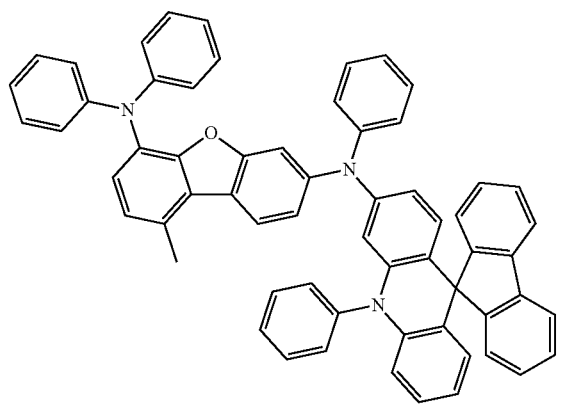
P-93
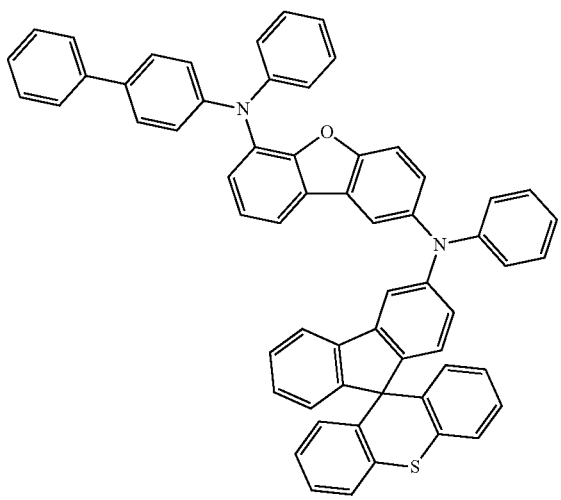
P-94
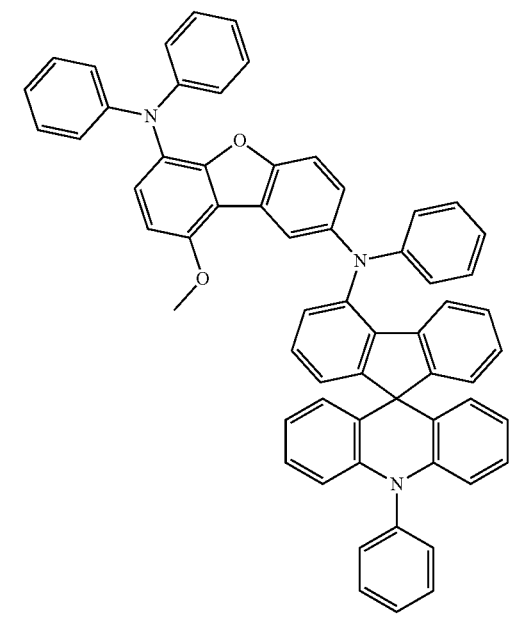
P-95
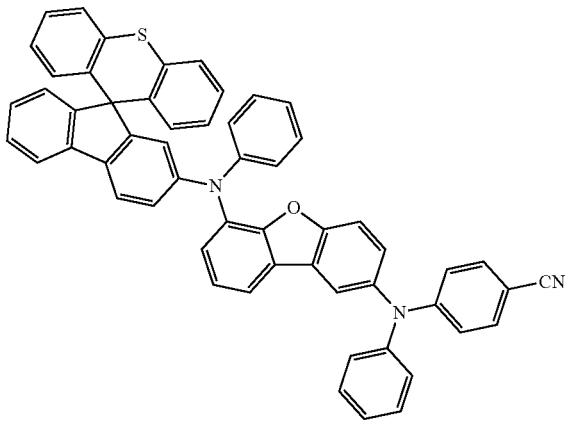
P-96
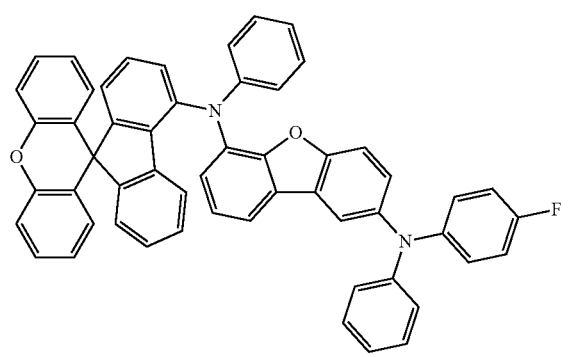
P-97
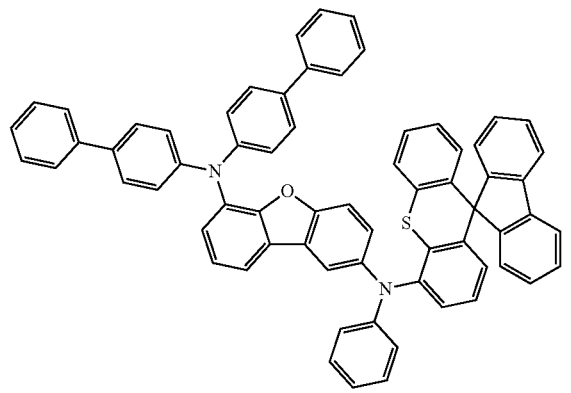
P-98
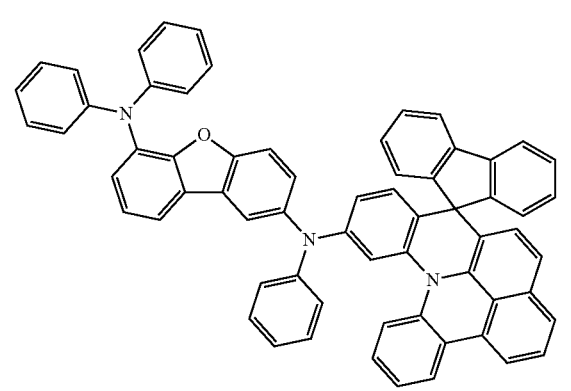

P-99
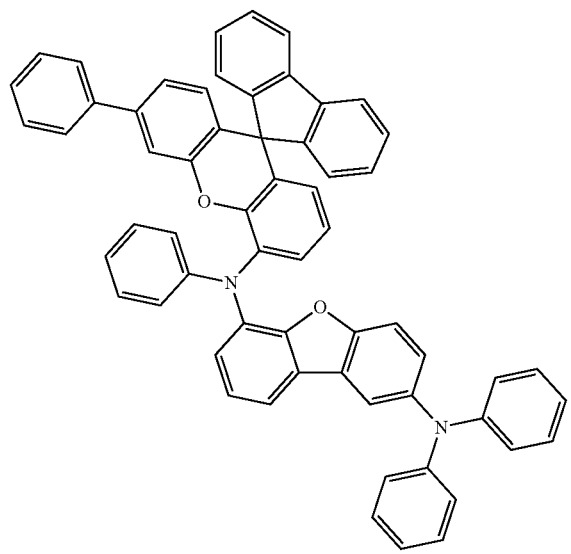
P-100
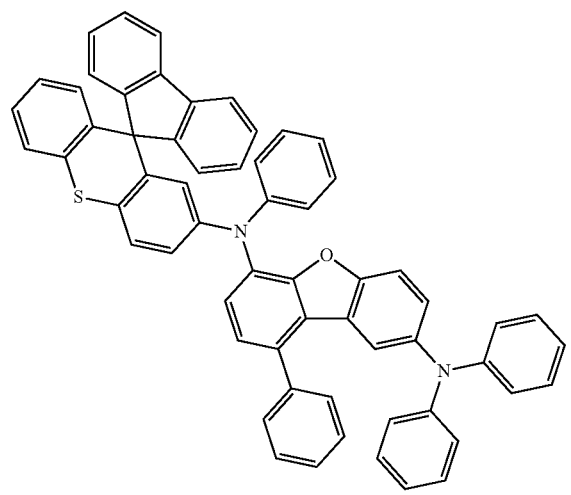
P-101
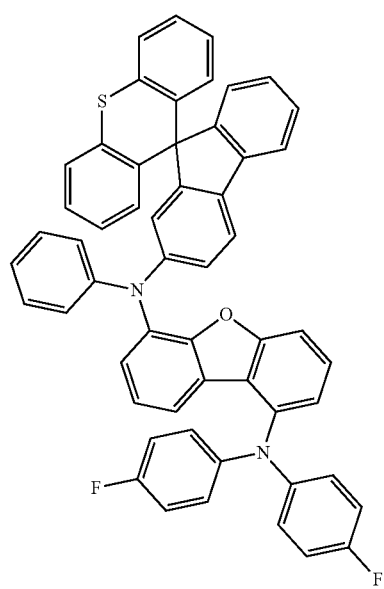
P-102
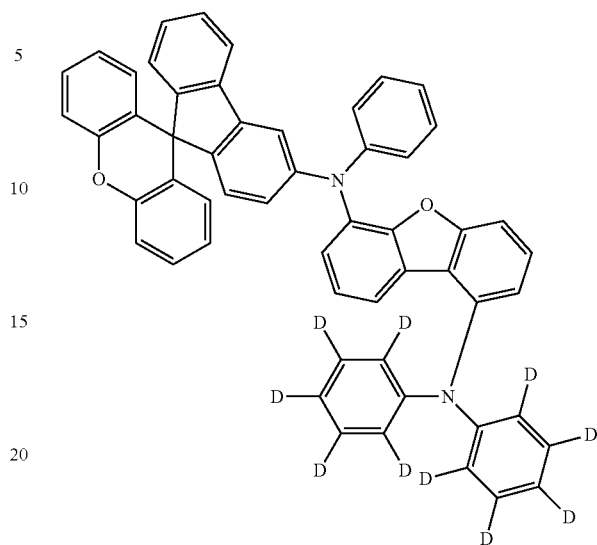
P-103
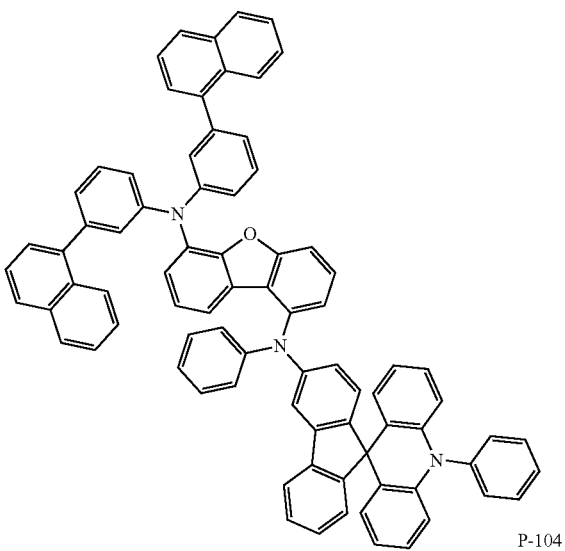
P-104
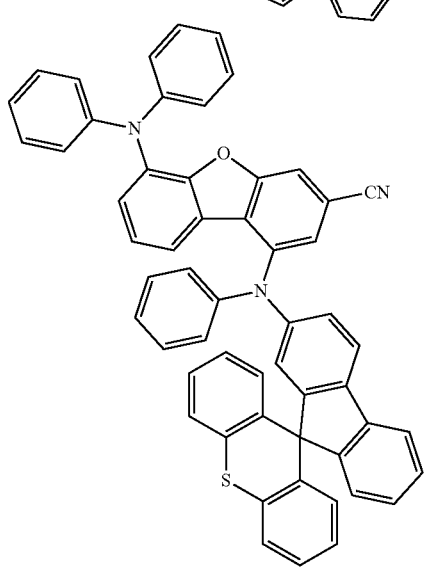

P-105
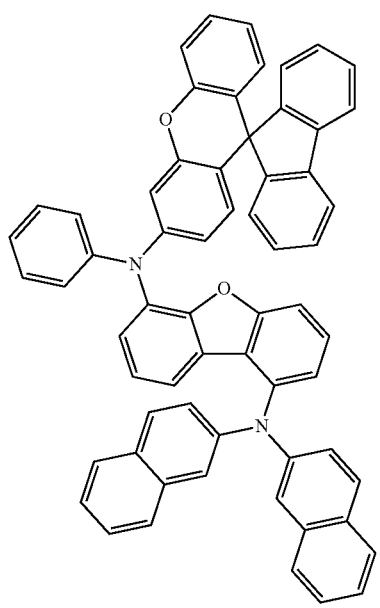
P-106
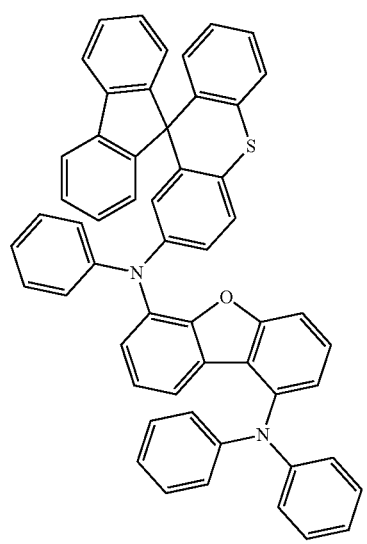
P-107
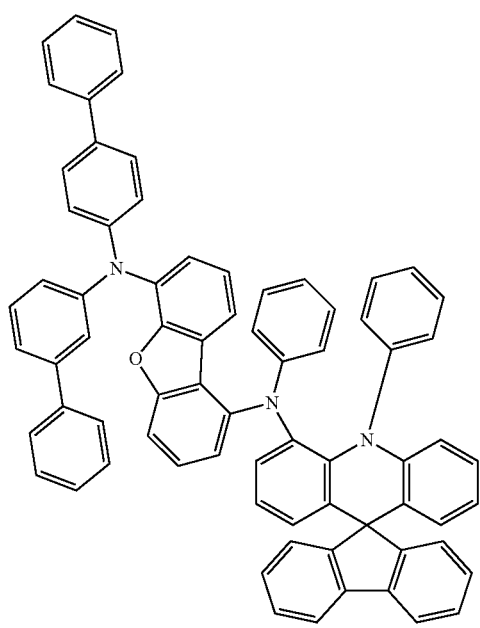
P-108
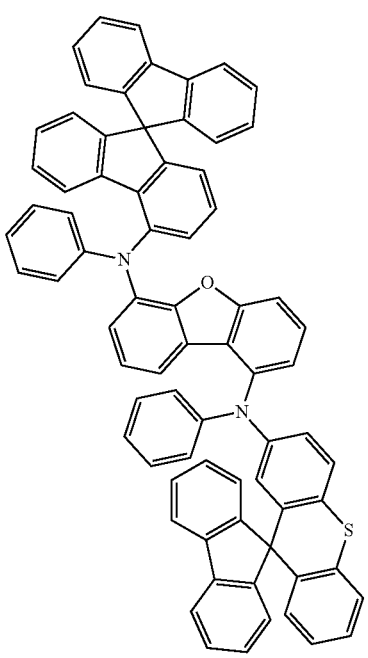

P-109
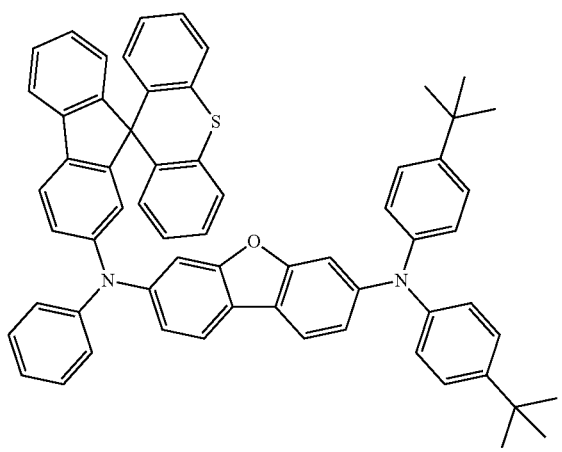
P-113
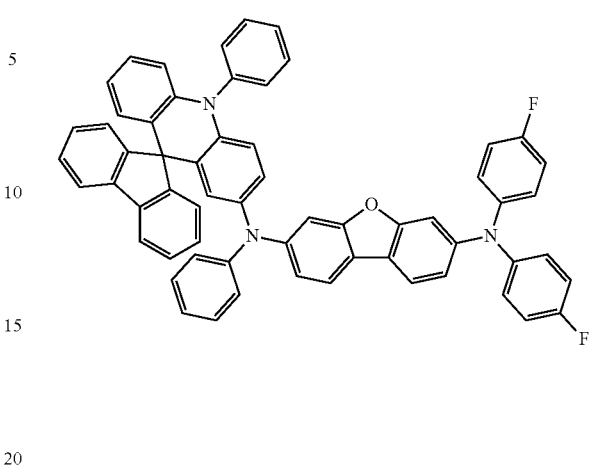
P-110
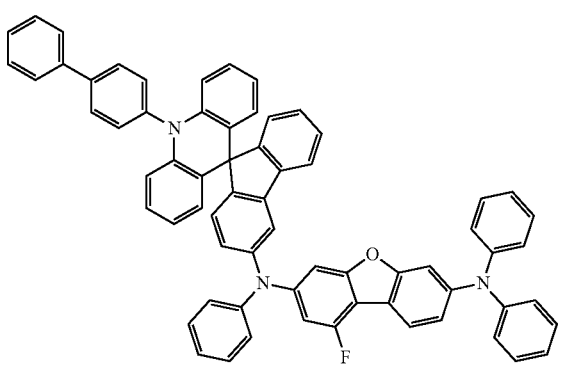
P-114
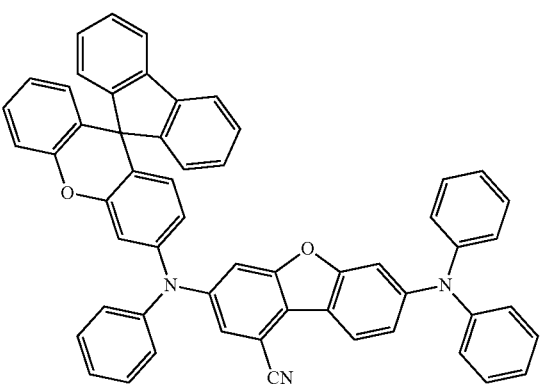
P-111
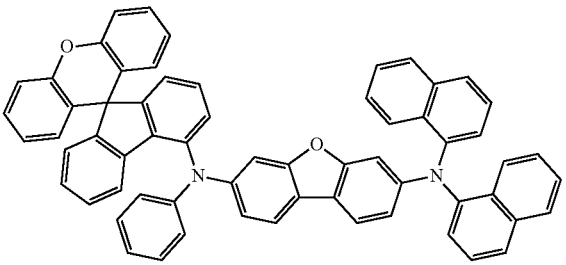
P-112
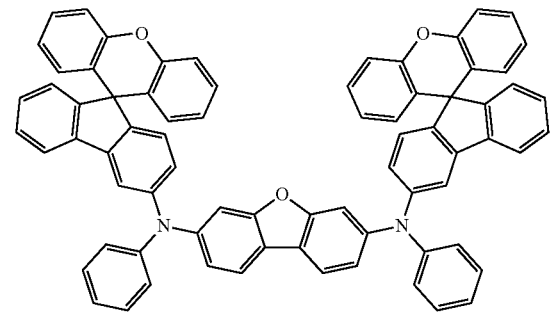
P-115
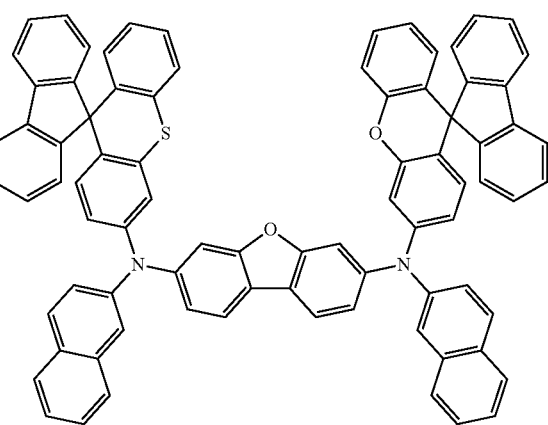

P-116
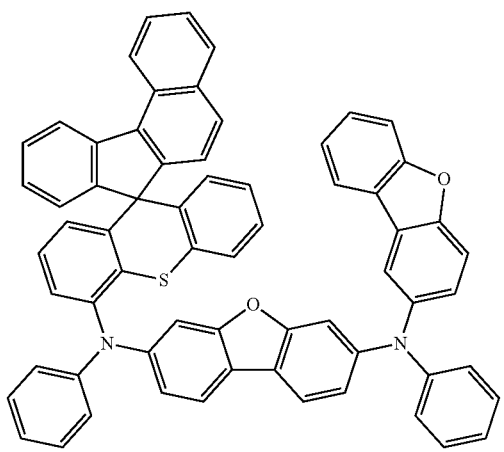
P-119
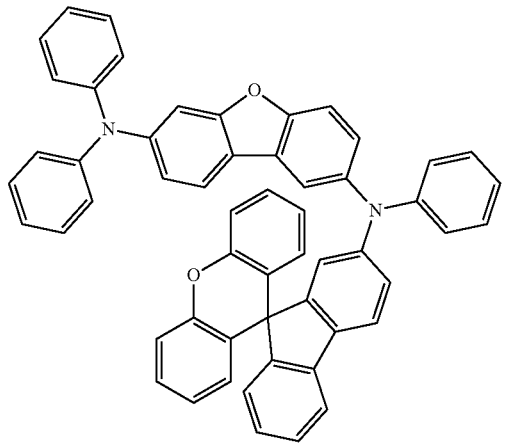
P-117
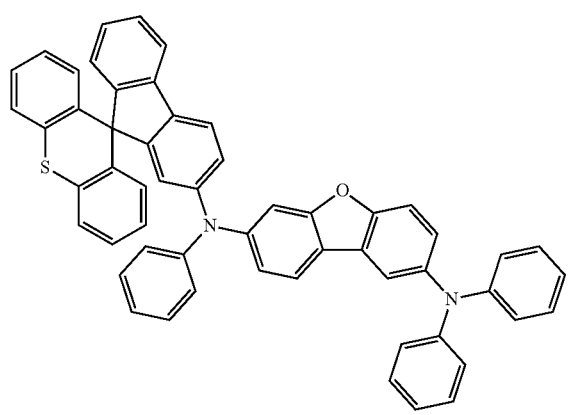
P-120
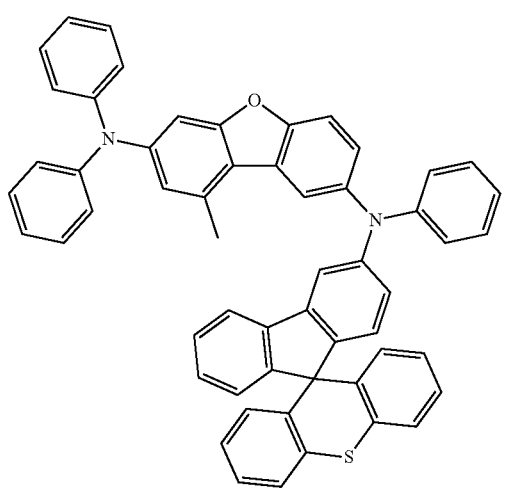
P-118
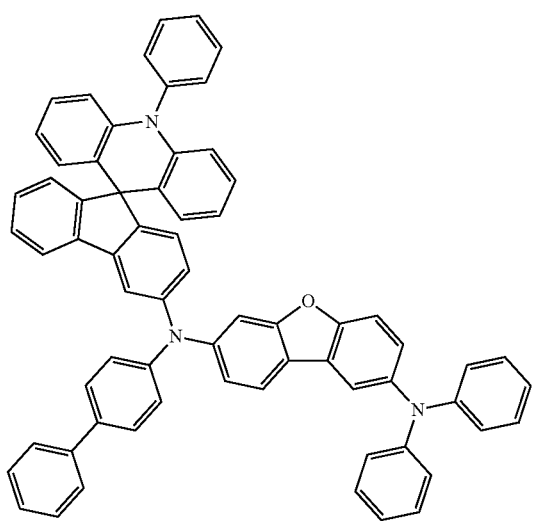
P-121
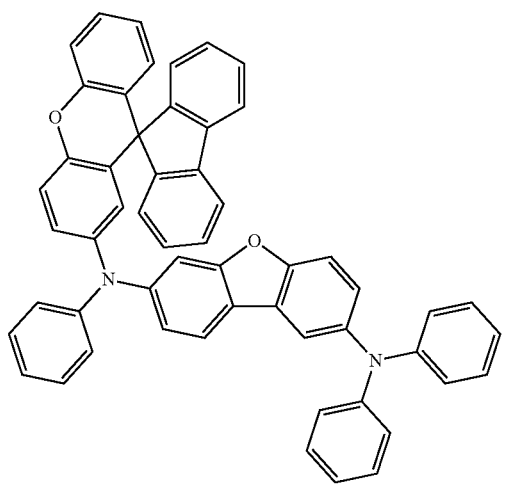

-continued
P-122
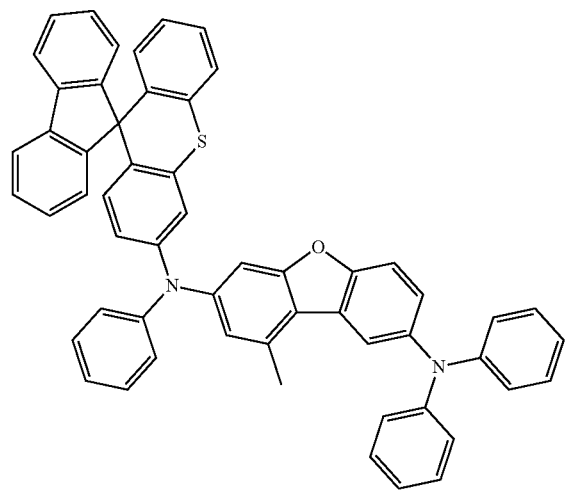
P-123
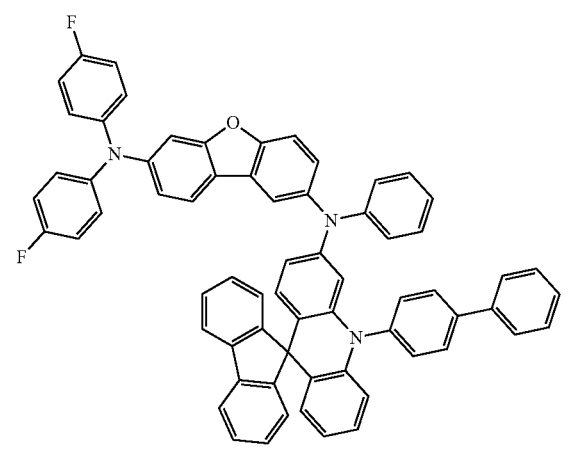
P-124
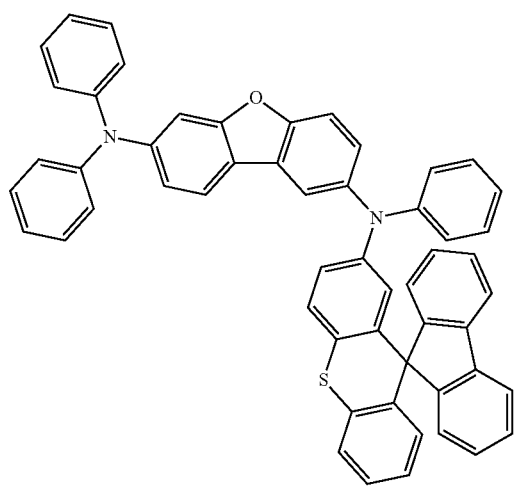
-continued
P-125
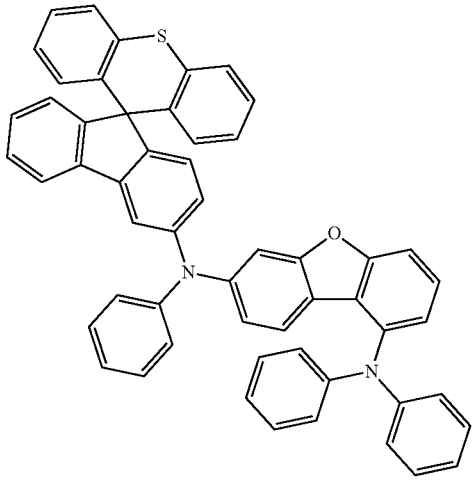
P-126
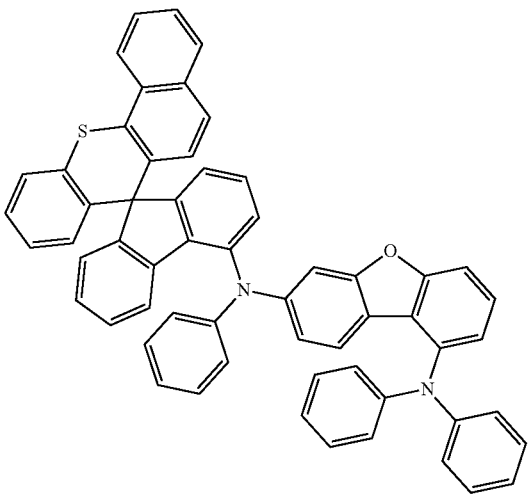
P-127
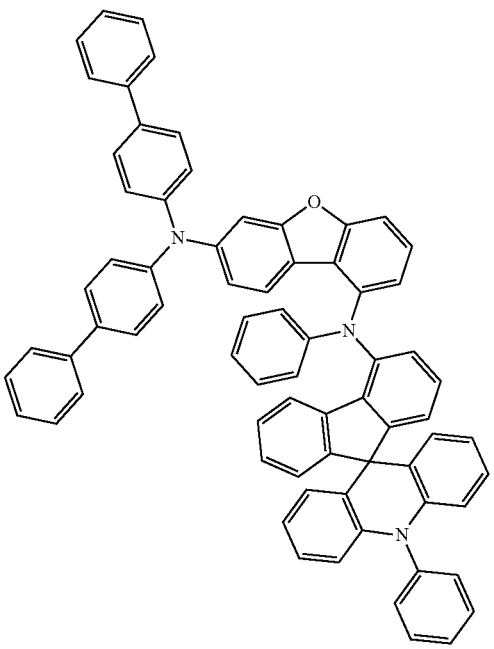

P-128
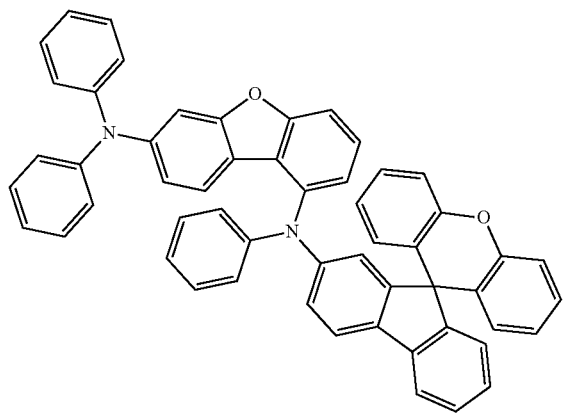
P-129
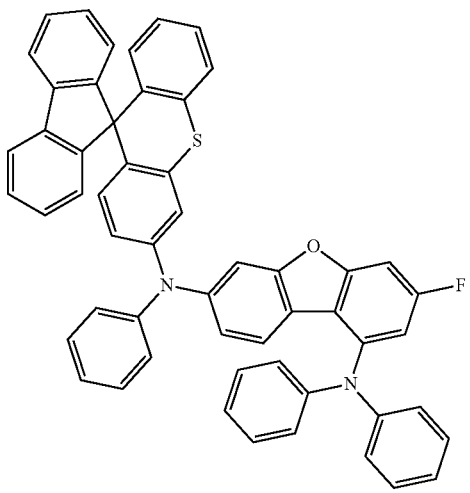
P-130
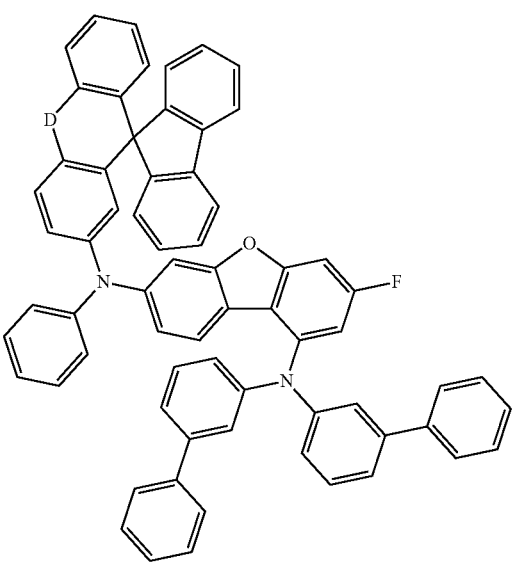
P-131
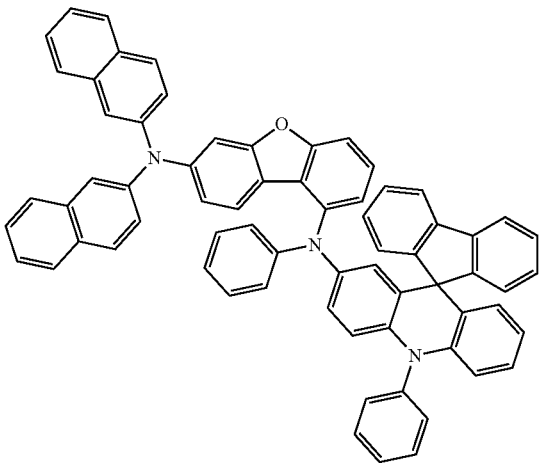
P-132
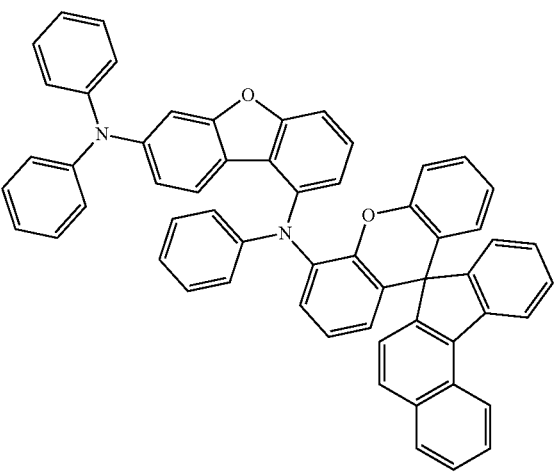
P-133
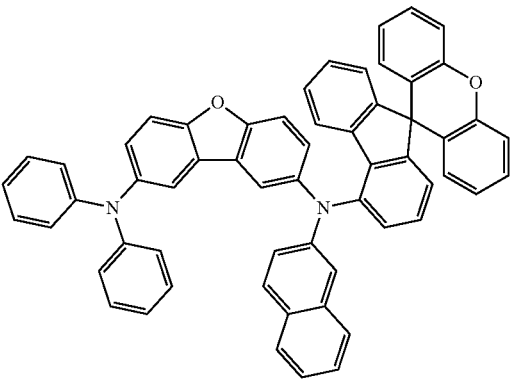

P-134
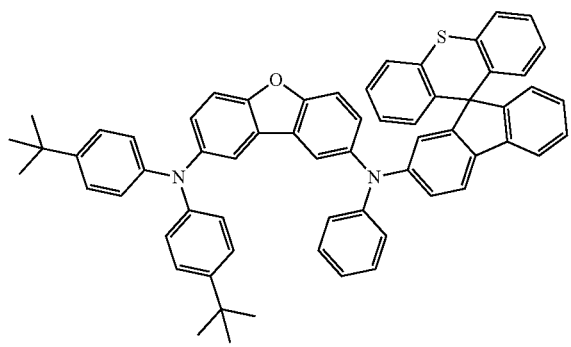
P-138
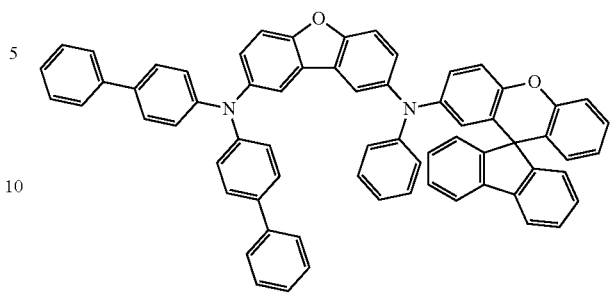
P-135
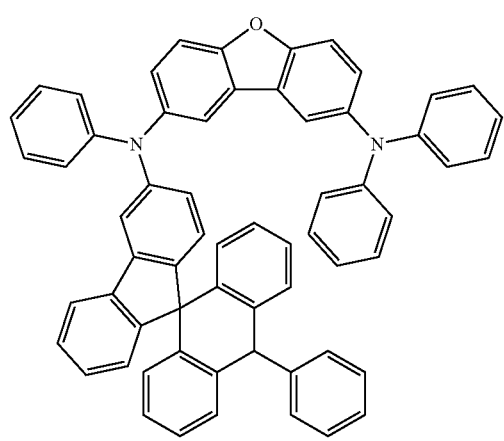
P-139
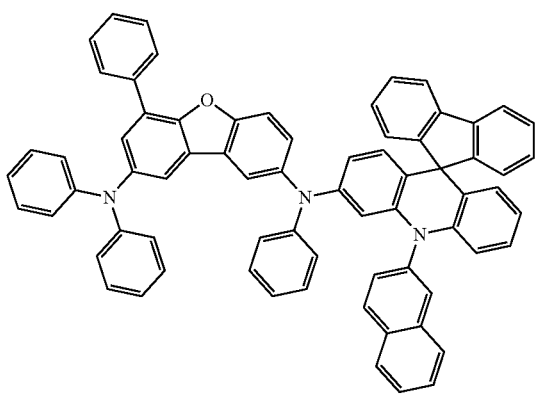
P-136
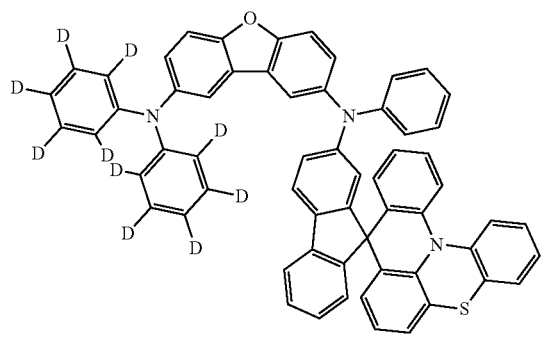
P-140
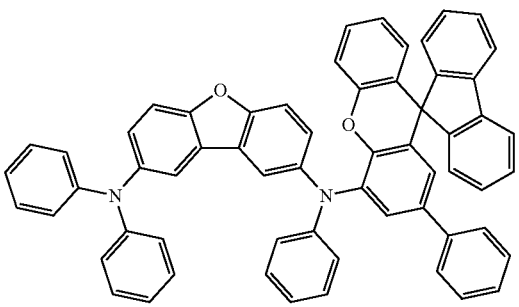
P-137
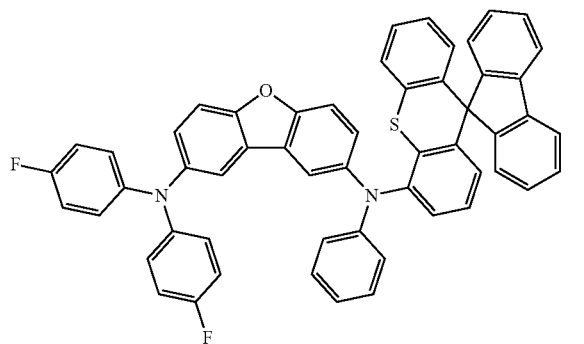
P-141
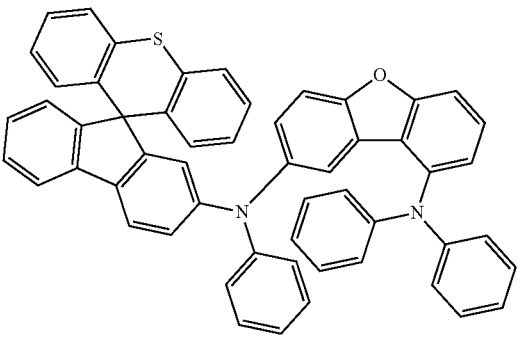

P-142
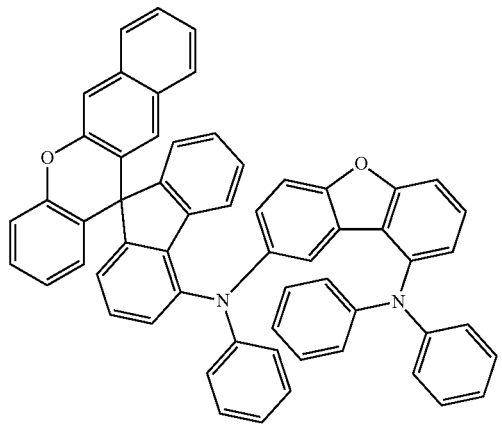
P-143
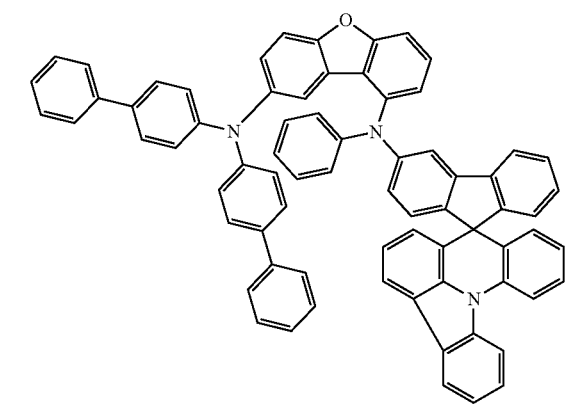
P-144
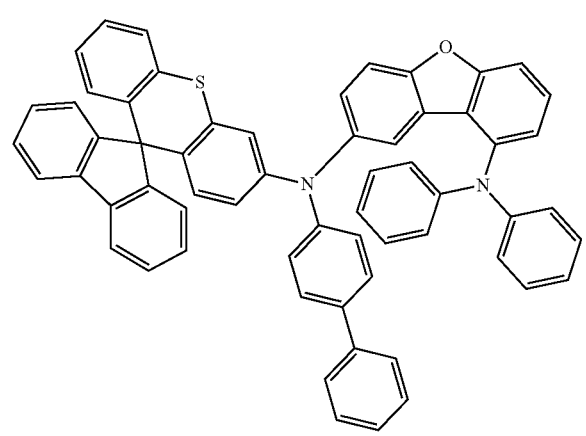
P-145
P-146
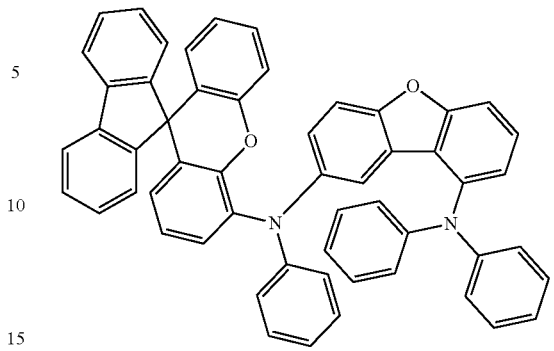
P-147
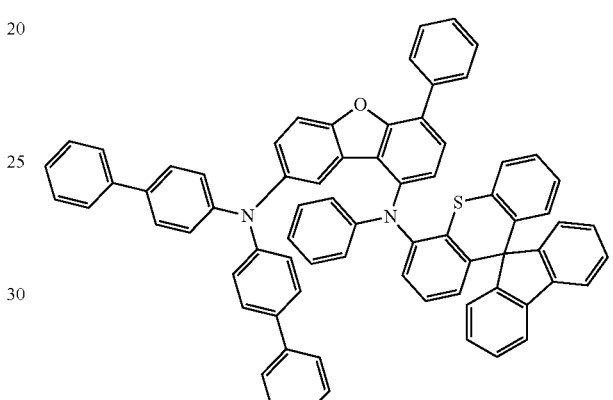
P-148
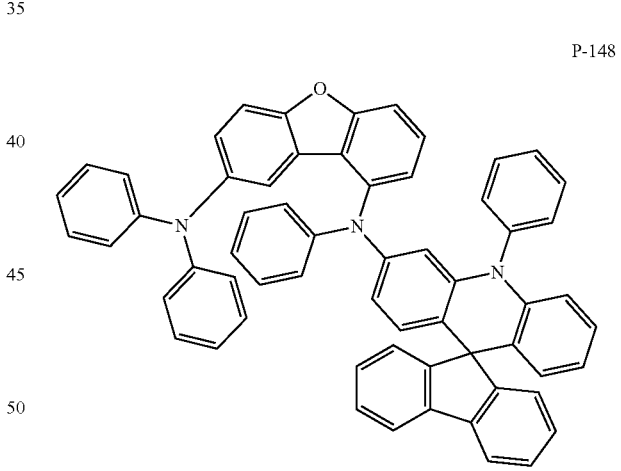
P-149

P-150
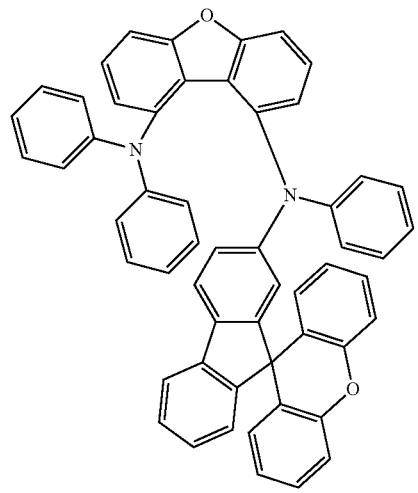
P-154
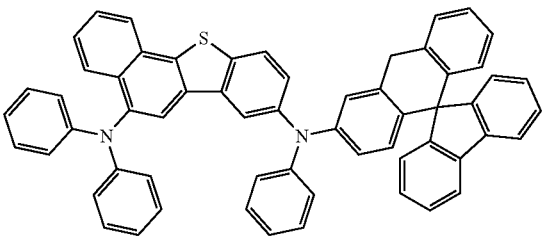
P-151
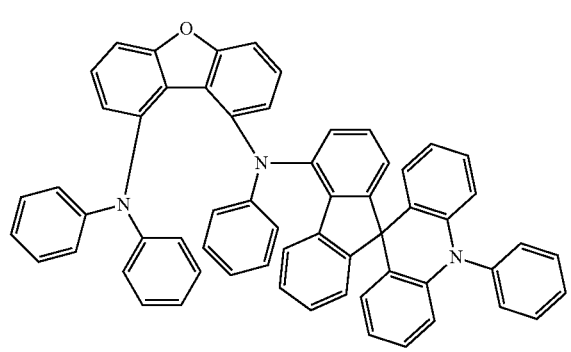
P-155
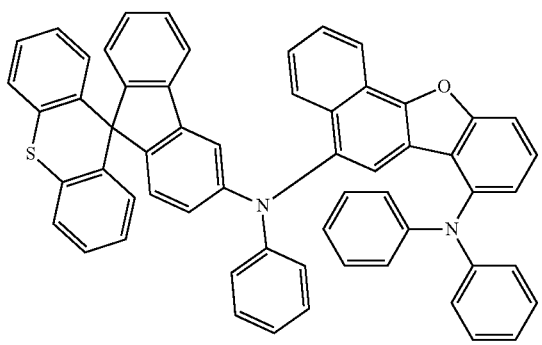
P-152
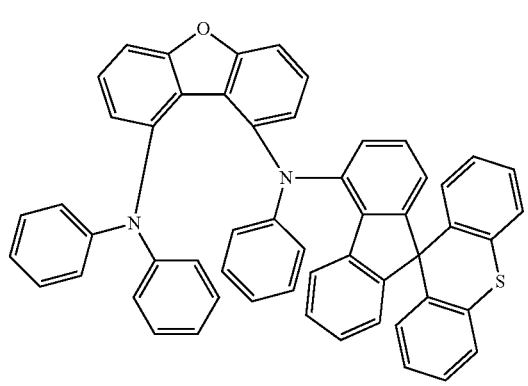
P-156
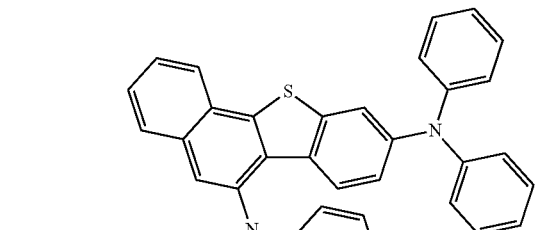
P-153
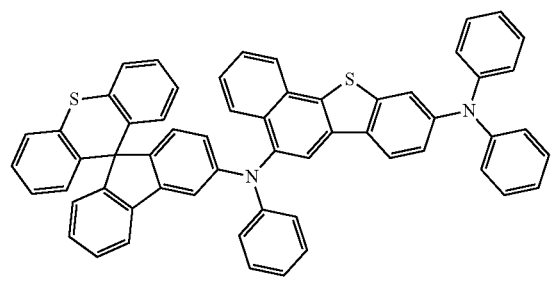
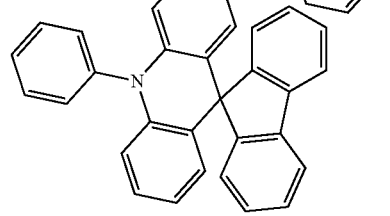

-continued
P-157
P-158
P-159
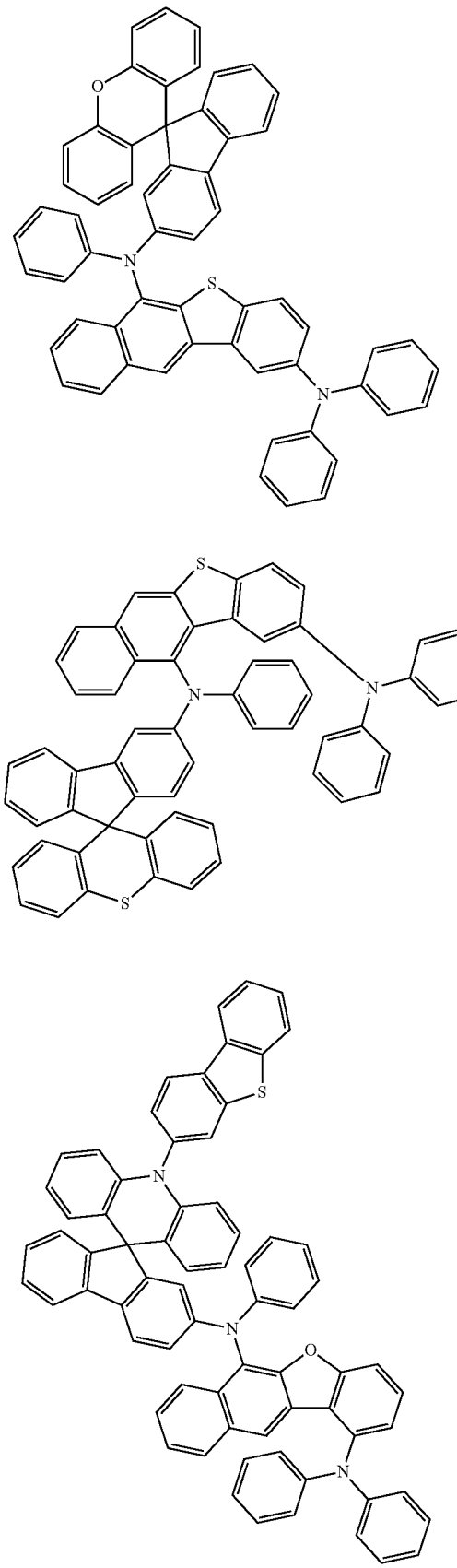
P-160
P-161
P-162
P-163
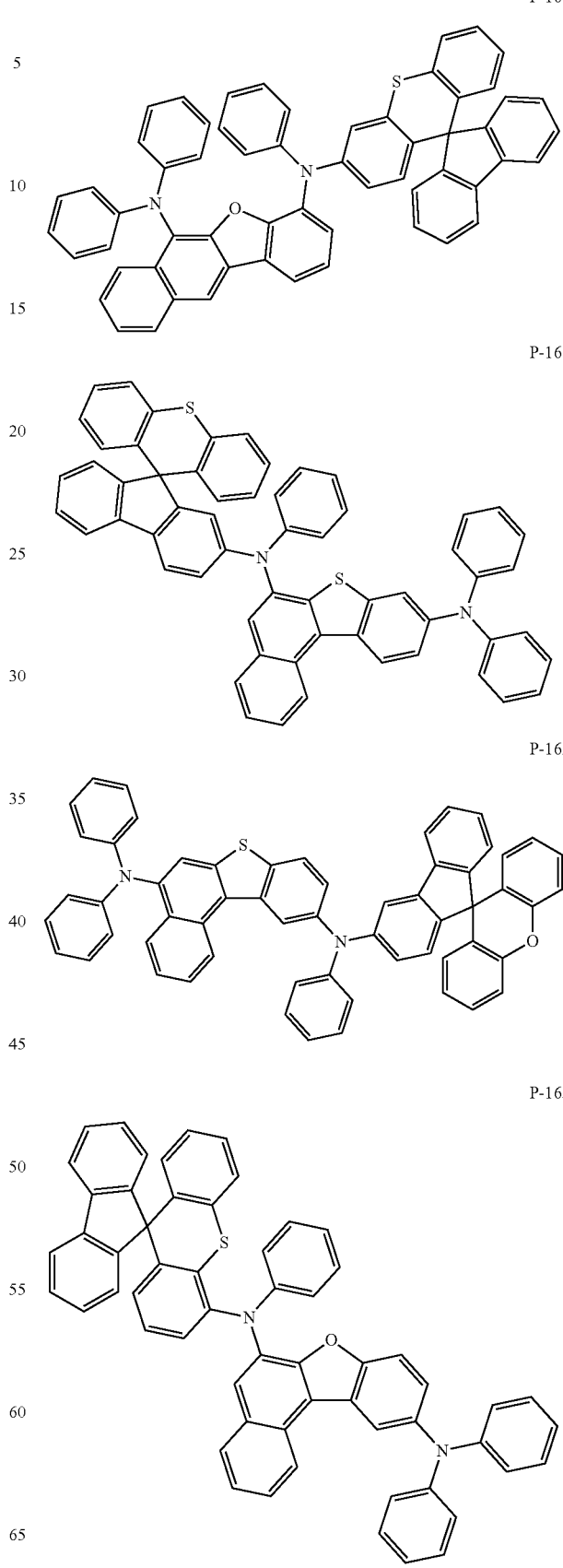

-continued
P-164
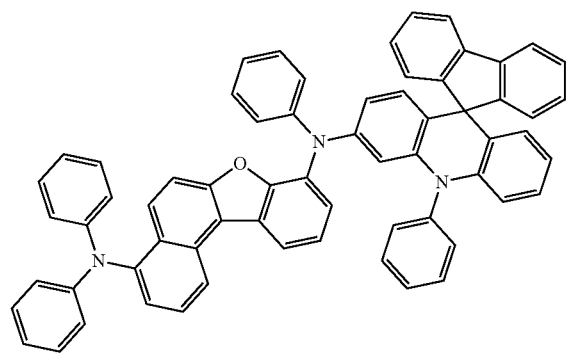
P-165
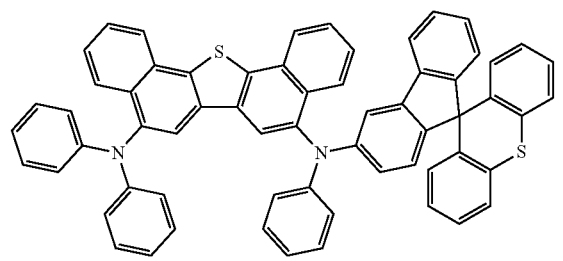
P-166
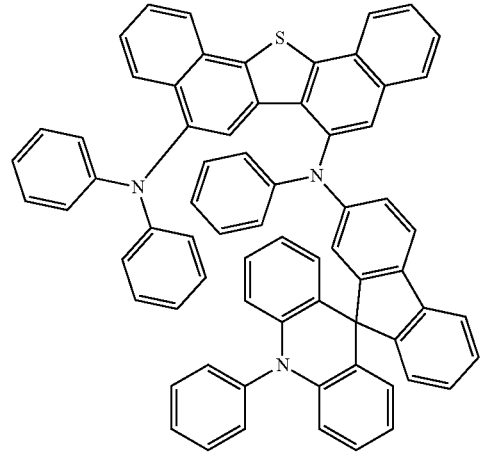
P-167
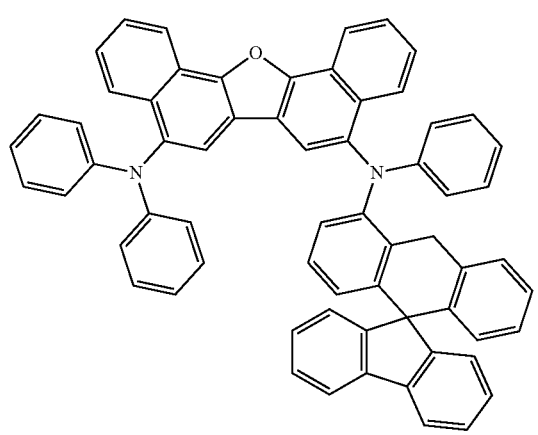
P-168
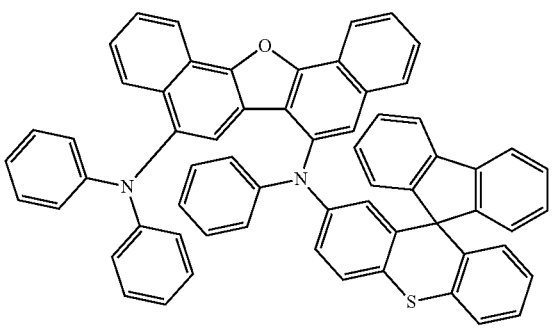
P-169
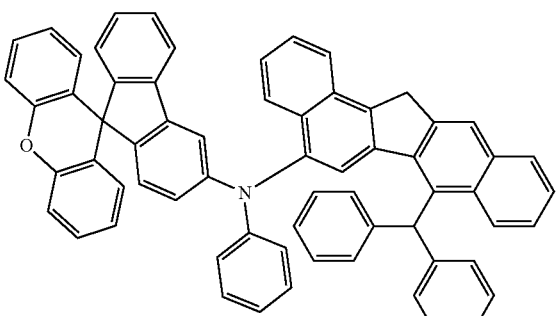
P-170
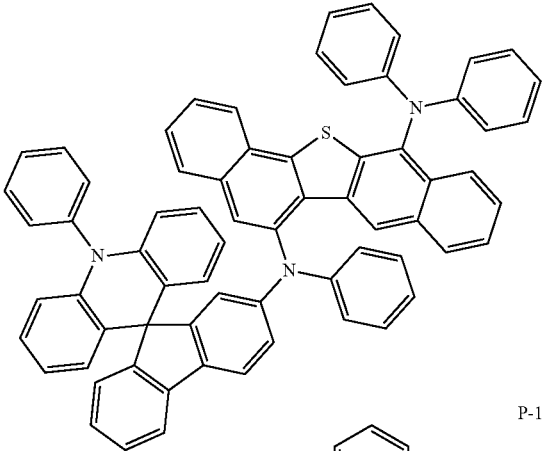
P-171
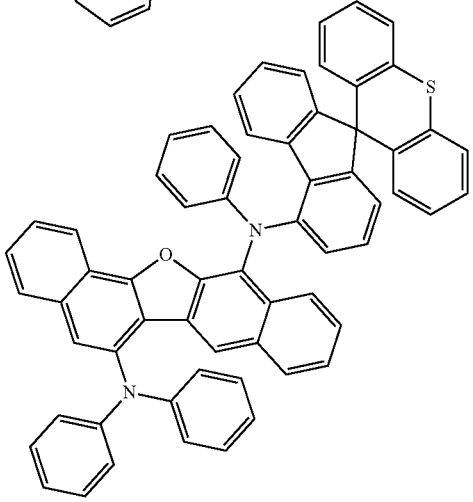

P-172
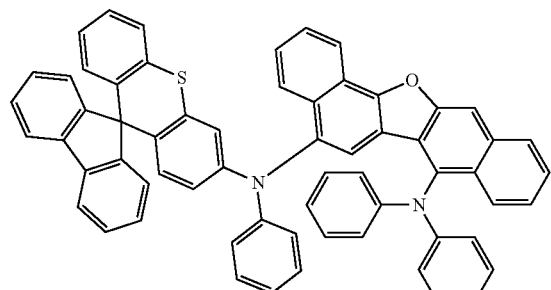
P-173
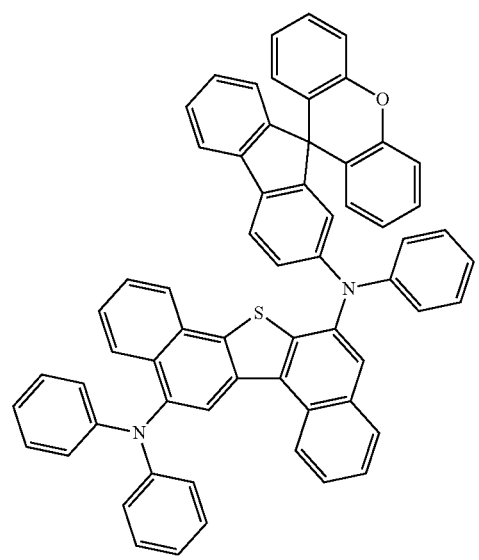
P-174
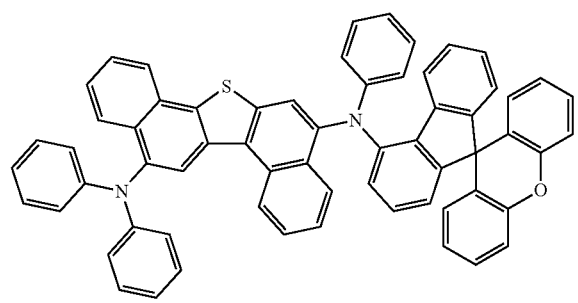
P-175
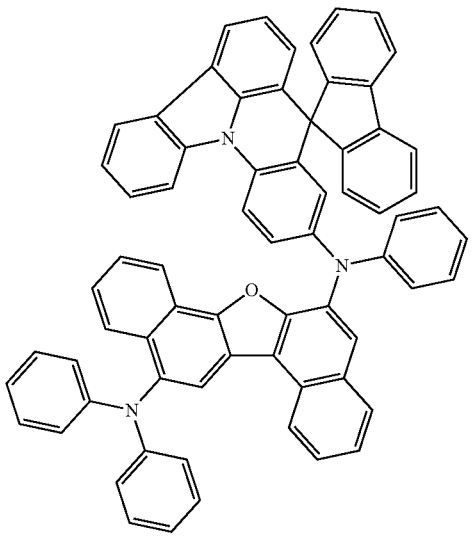
P-176
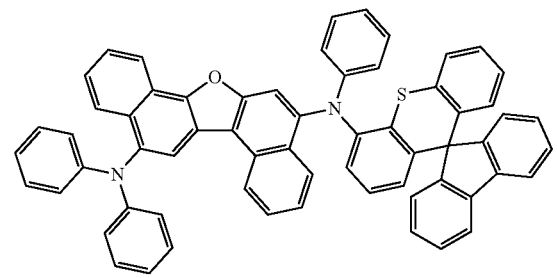
P-177
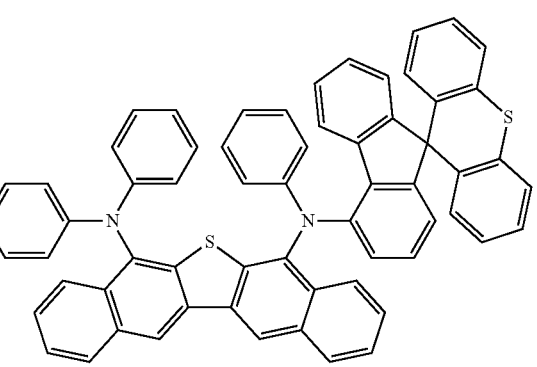

-continued
P-178
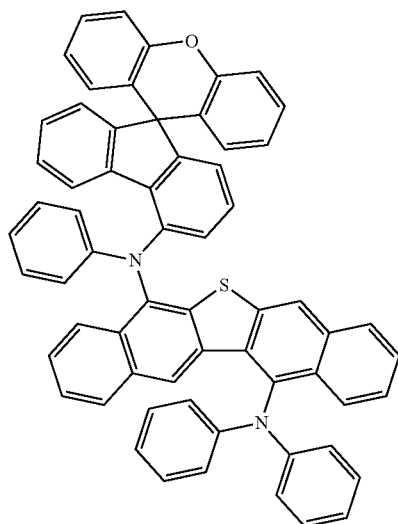
P-179
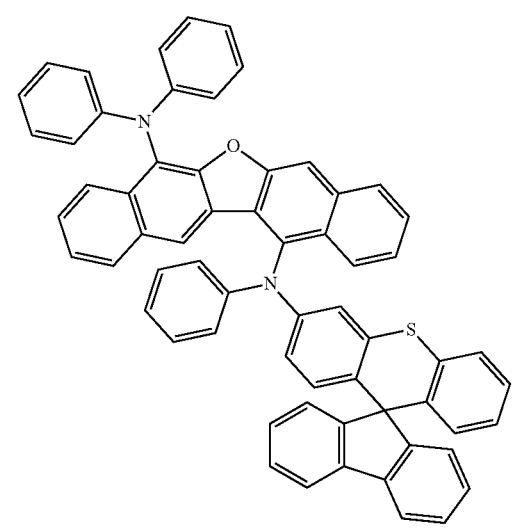
P-180
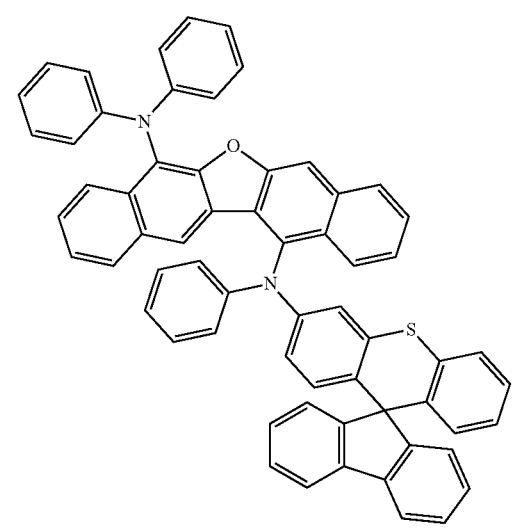
-continued
P-181
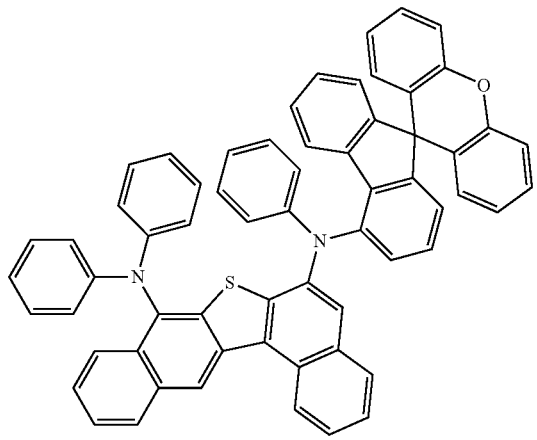
P-182
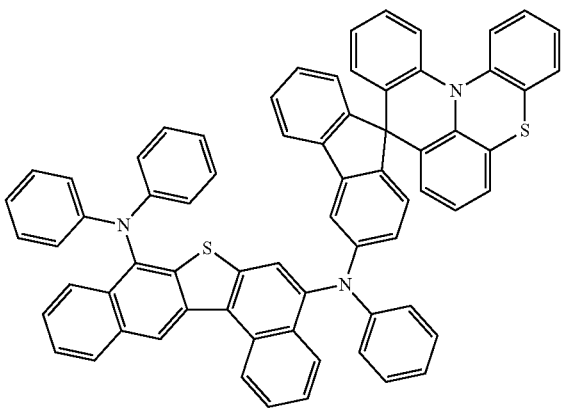
P-183
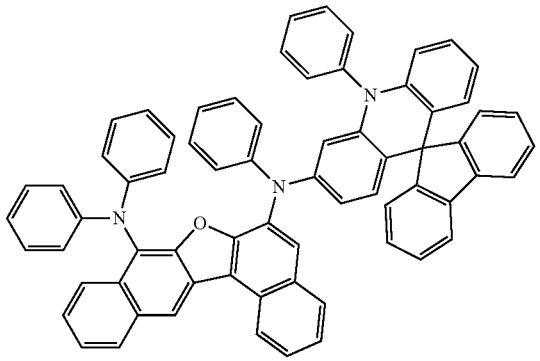

P-184
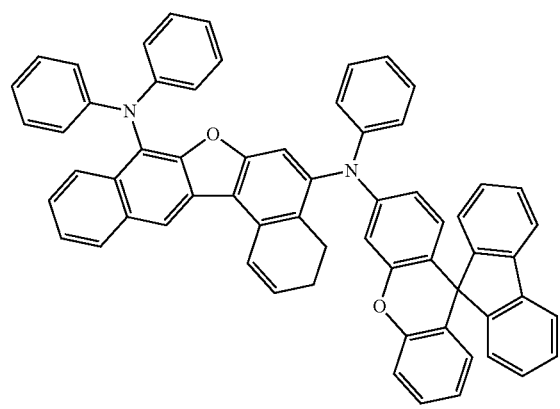
P-185
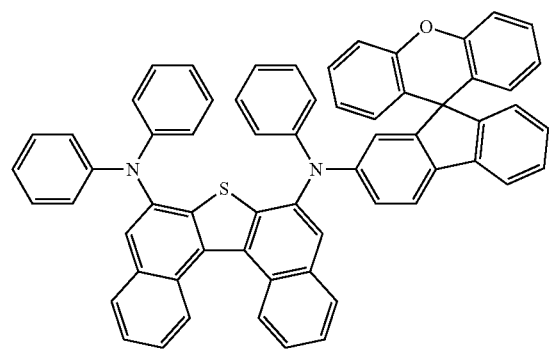
P-186
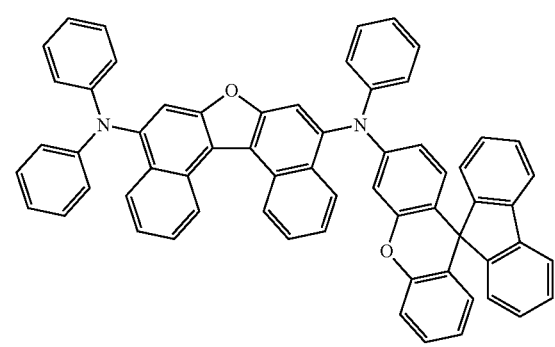
P-187
P-188
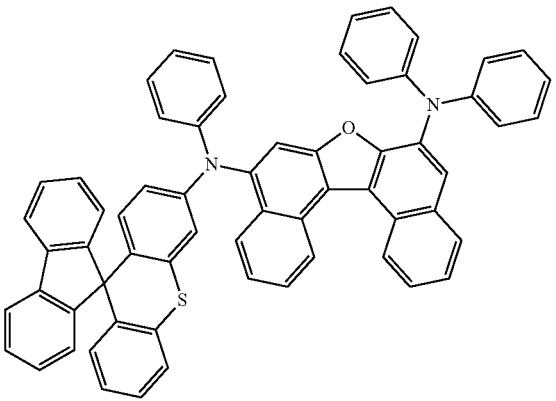
P-189
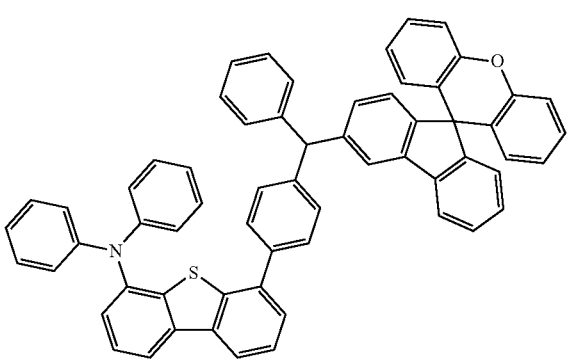
P-190
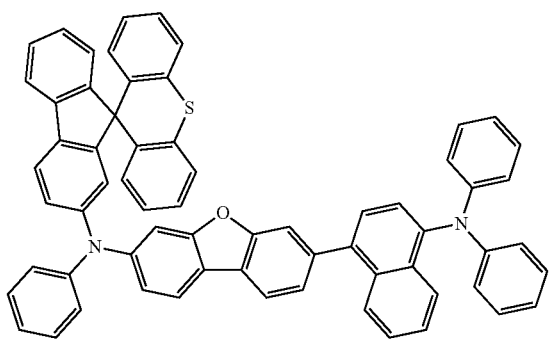

P-191
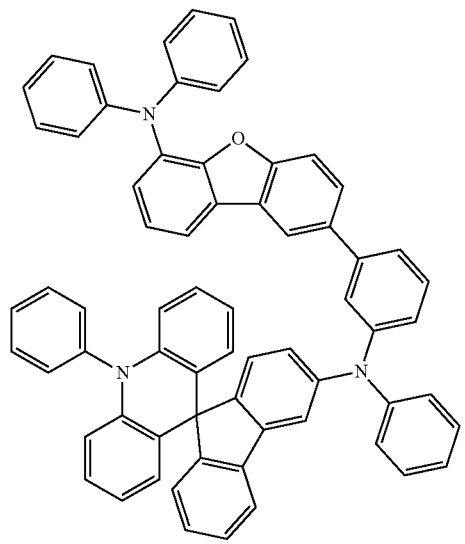
P-194
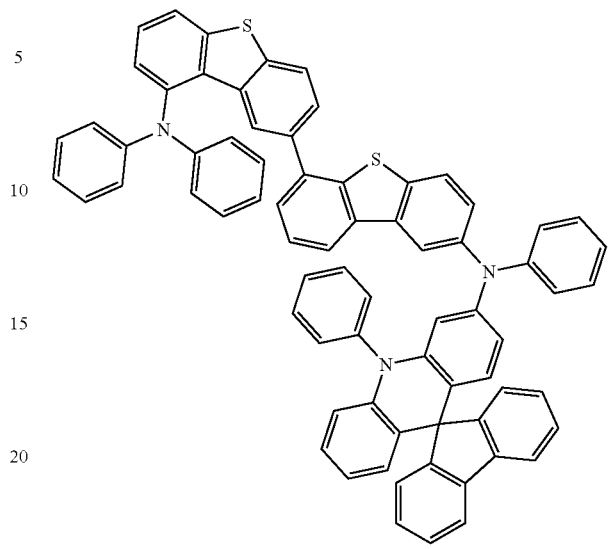
P-192
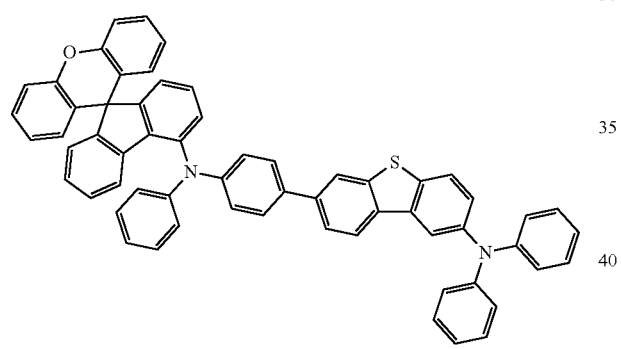
P-195
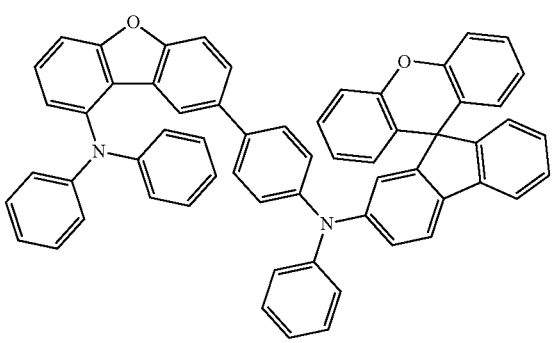
P-193
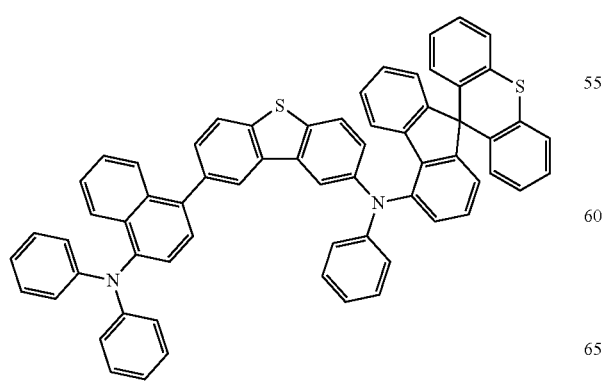
P-196
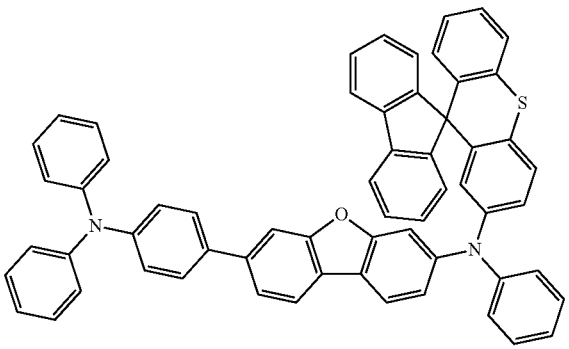

P-197
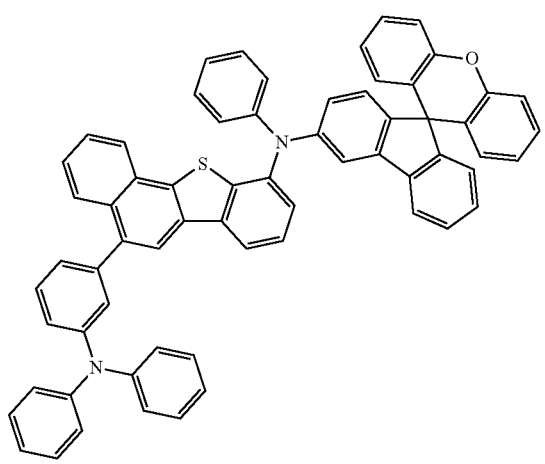
P-198
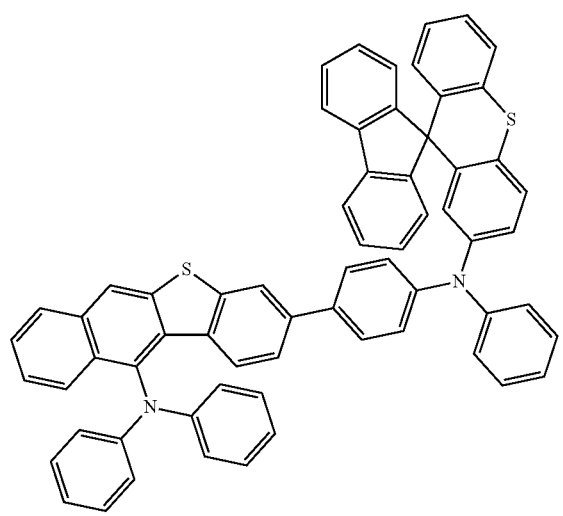
P-199
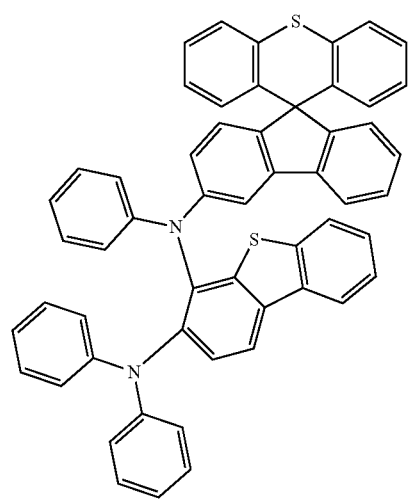
P-200
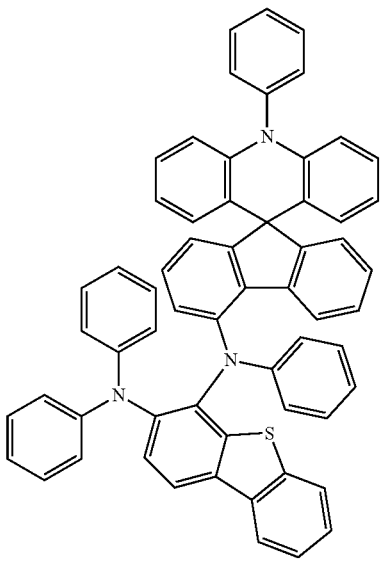
P-201
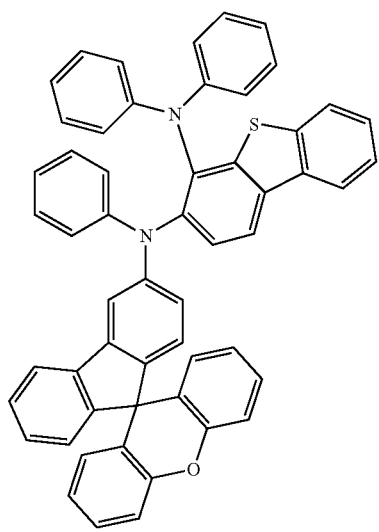
P-202
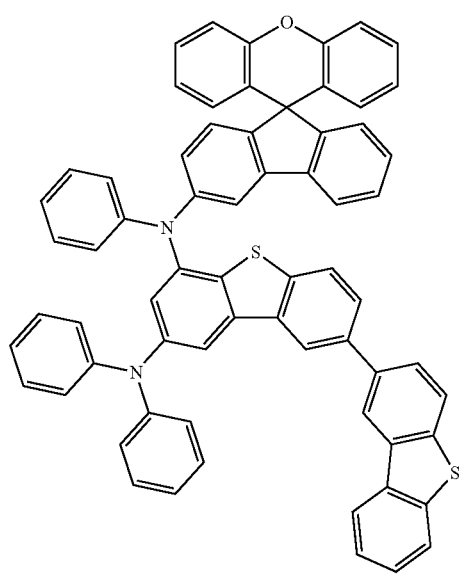

P-203
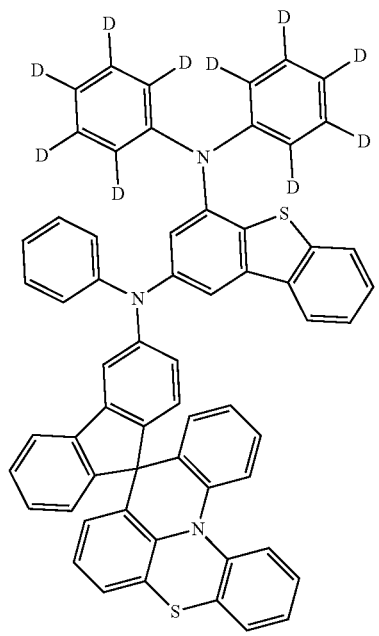
P-204
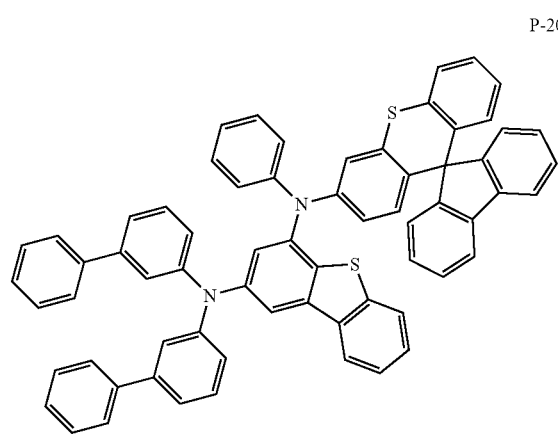
P-205
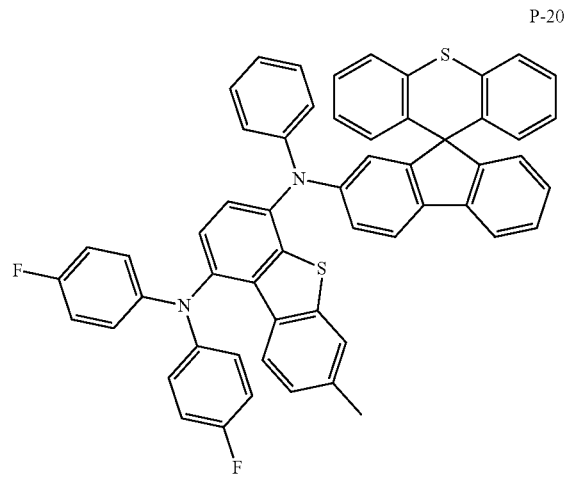
P-206
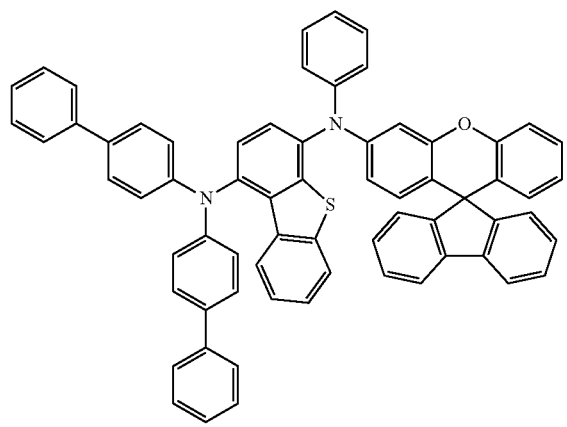
P-207
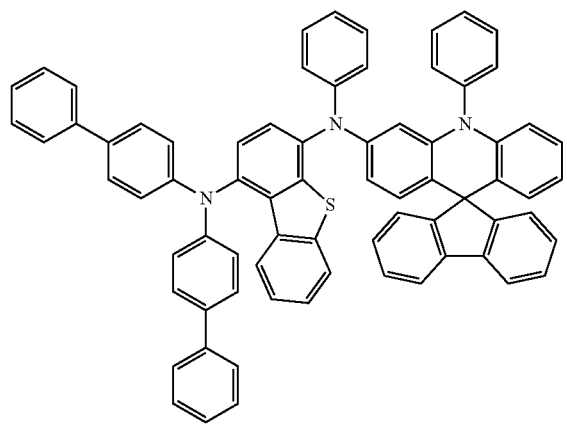
P-208
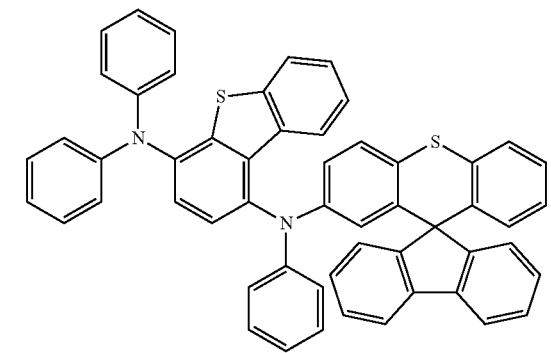

P-209
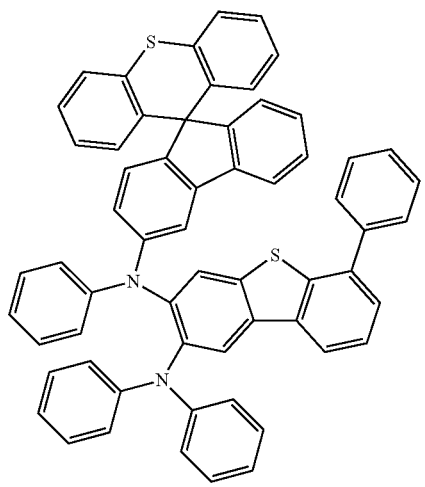
P-210
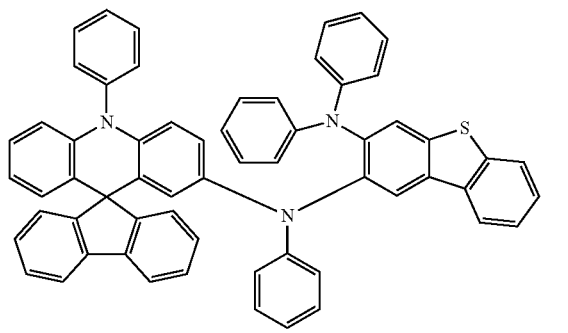
P-211
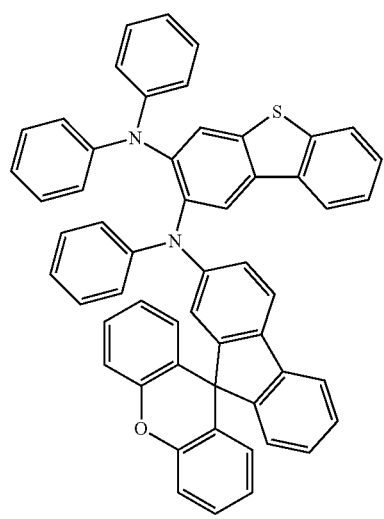
P-212
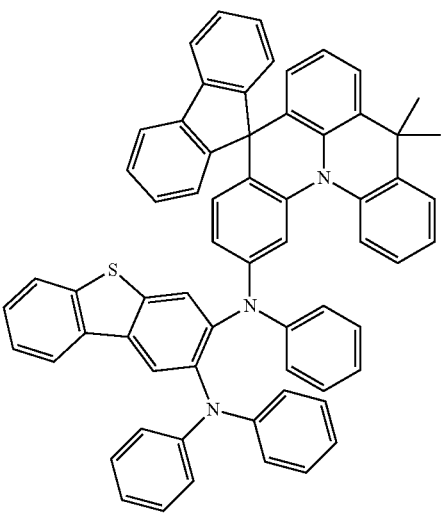
P-213
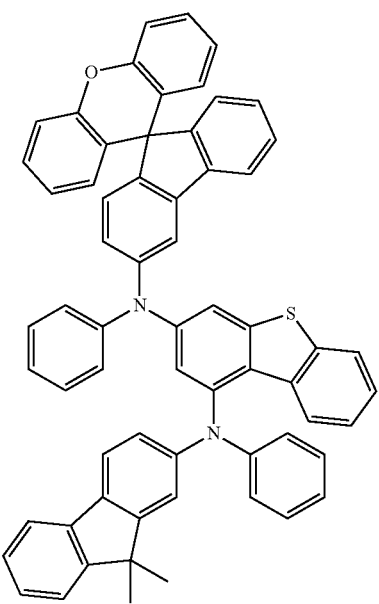

P-214
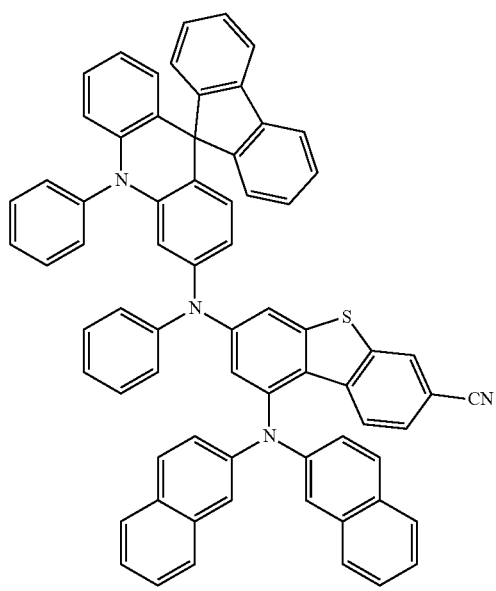
P-215
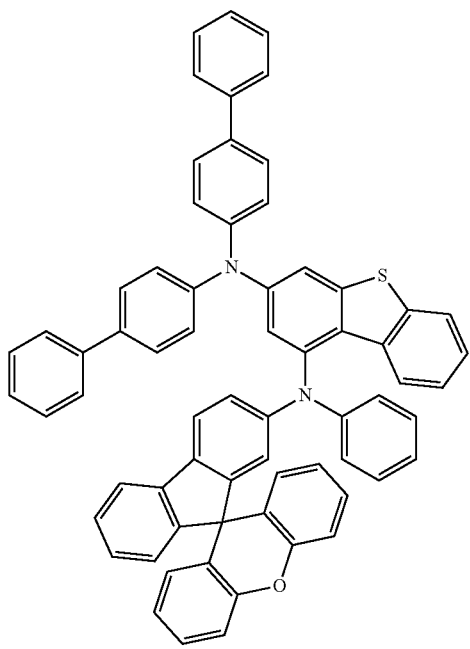
P-216
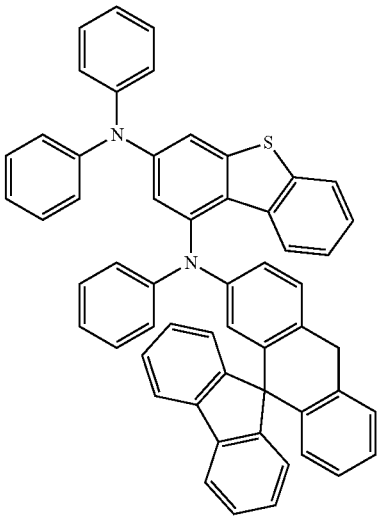
P-217
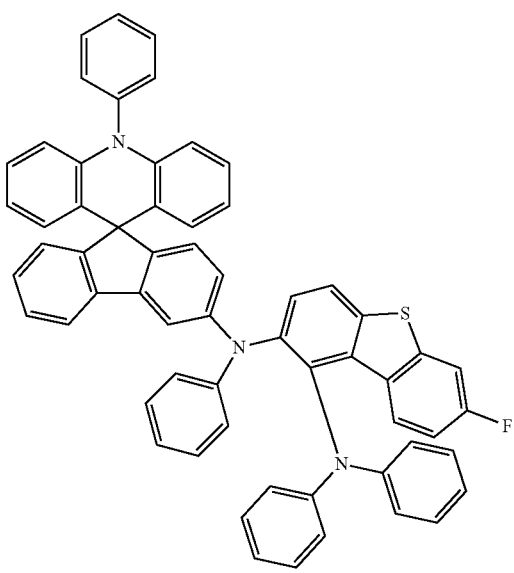
P-218
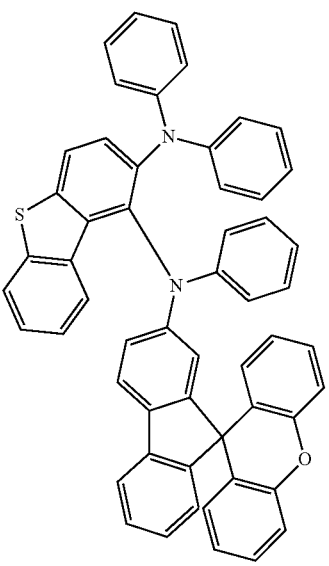

-continued
P-219
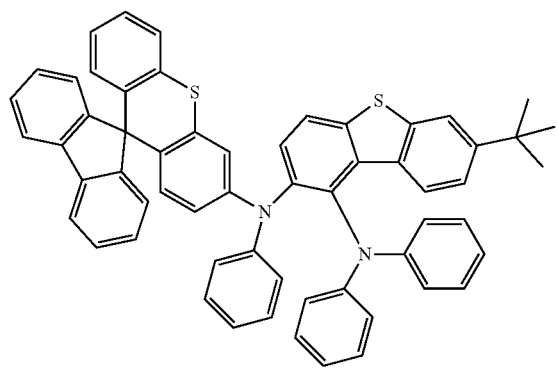
P-220
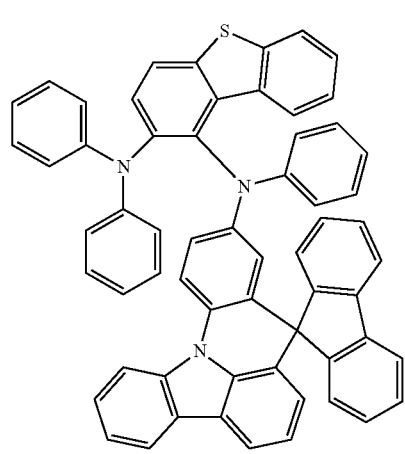
P-221
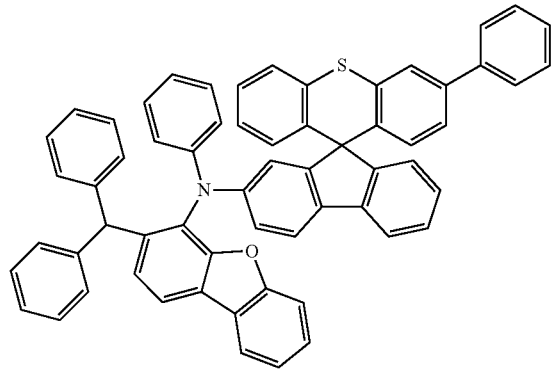
P-222
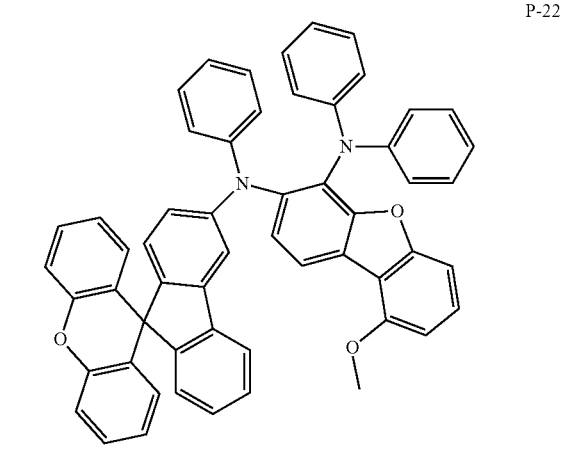
P-223
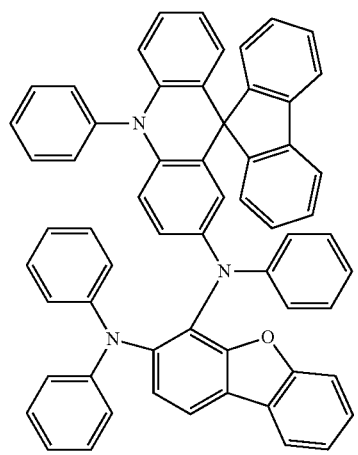
P-224
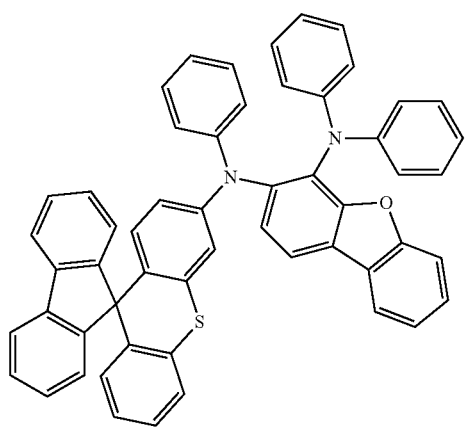
P-225
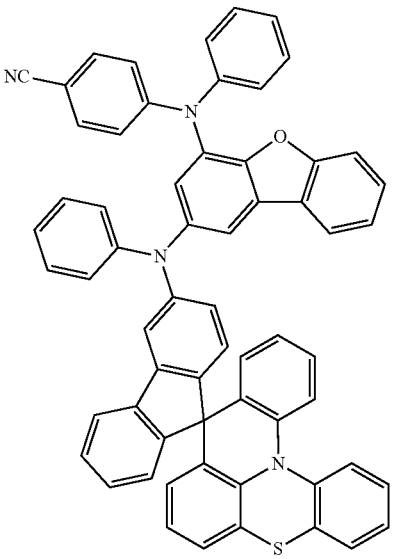

P-226
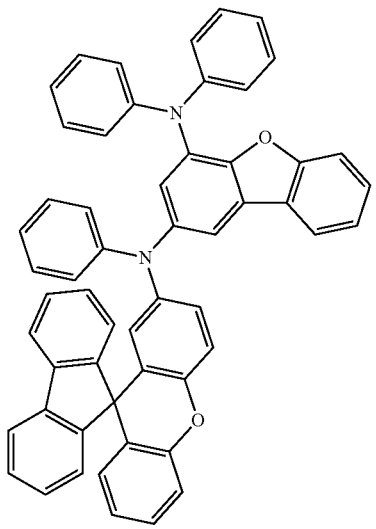
P-227
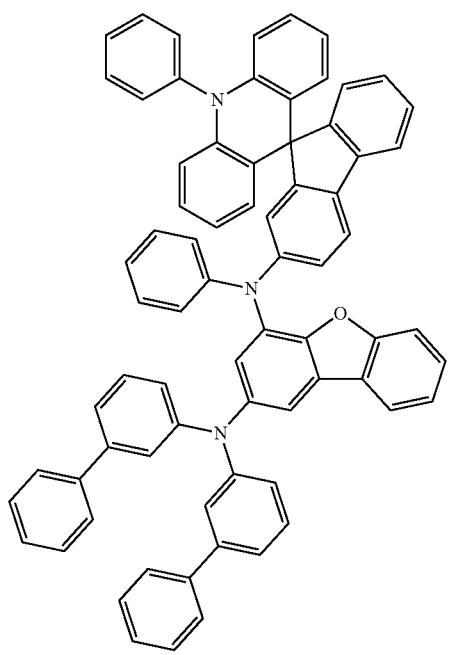
P-228
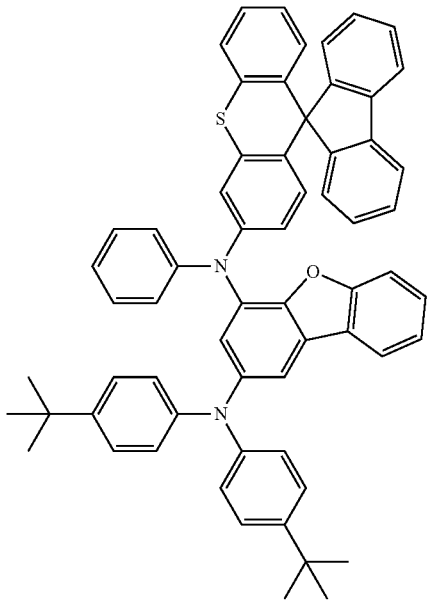
P-229
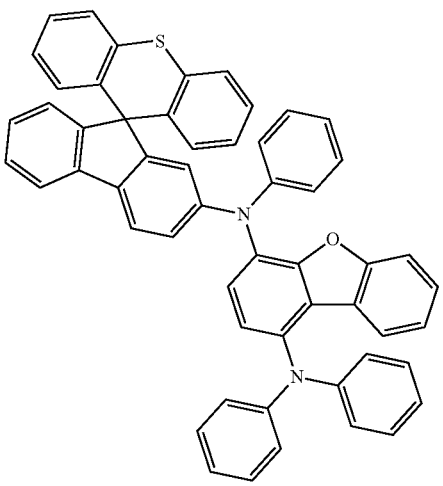

P-230
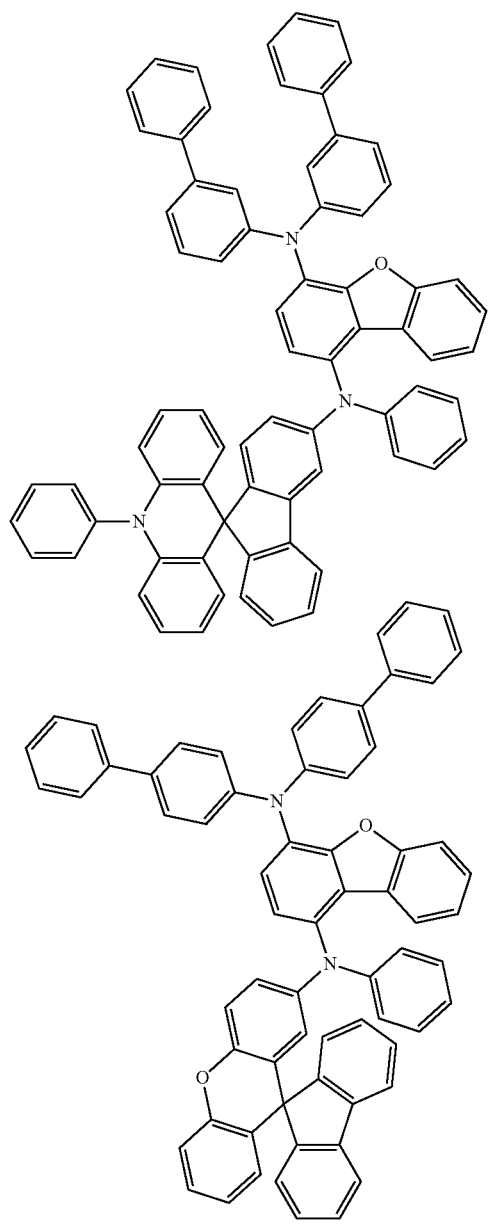
P-231
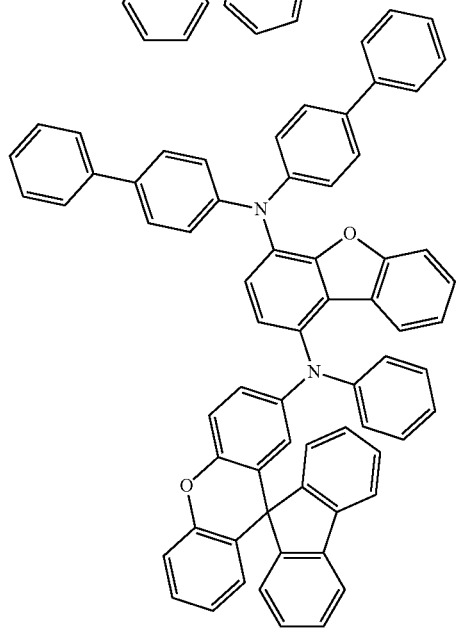
P-232
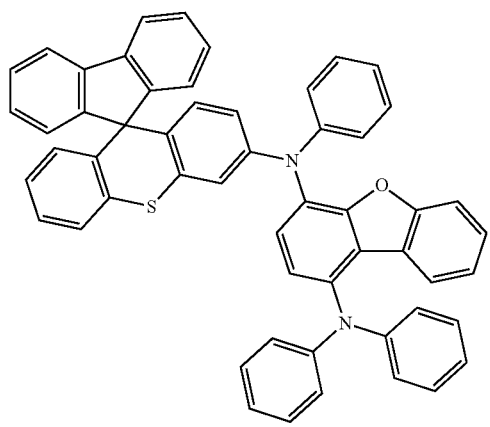
P-233
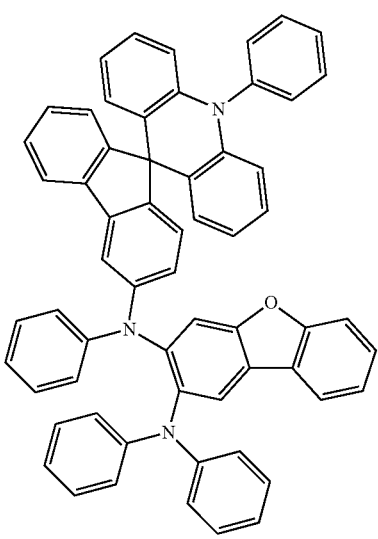
P-234
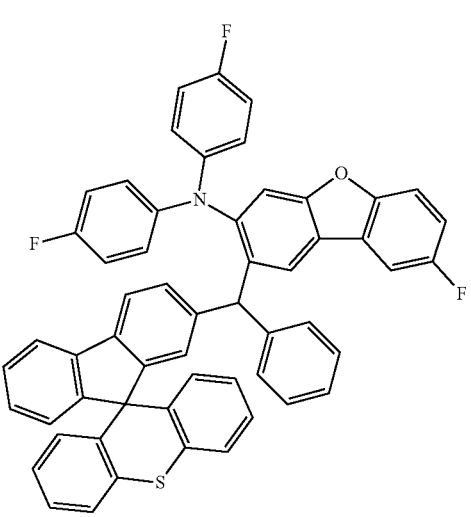
P-235
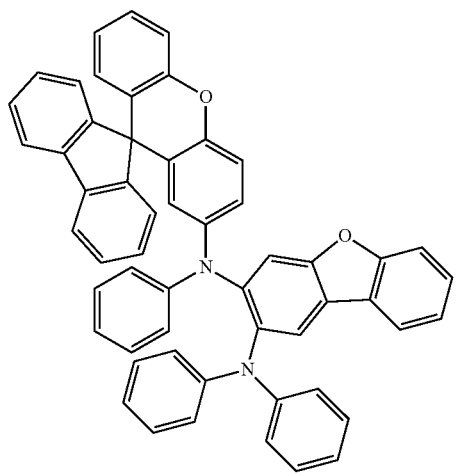

P-236
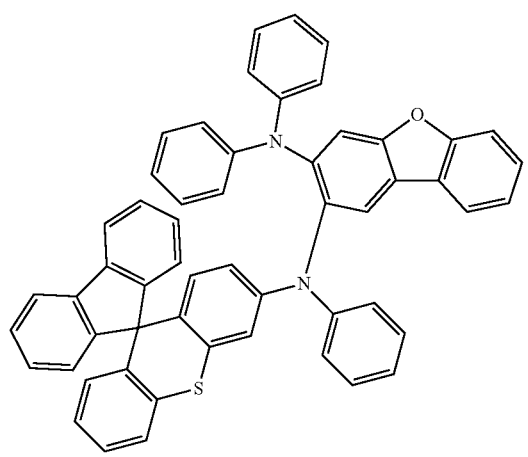
P-237
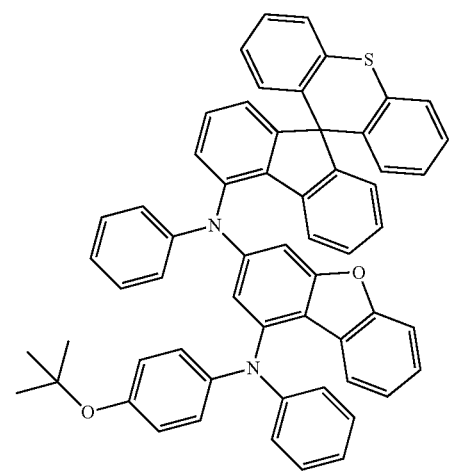
P-238
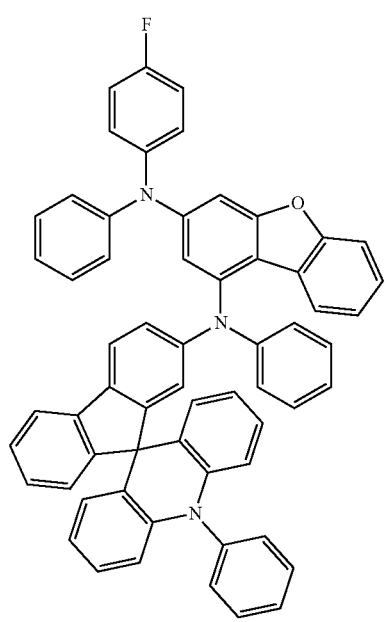
P-239
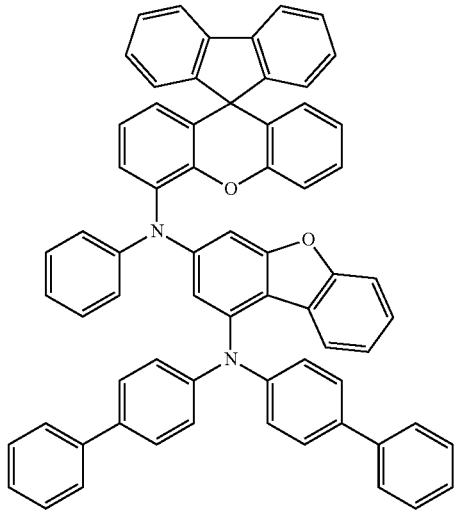
P-240
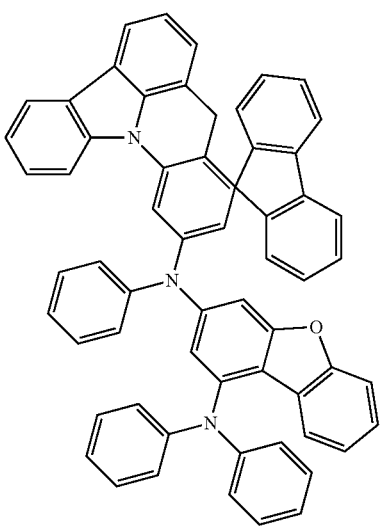
P-241
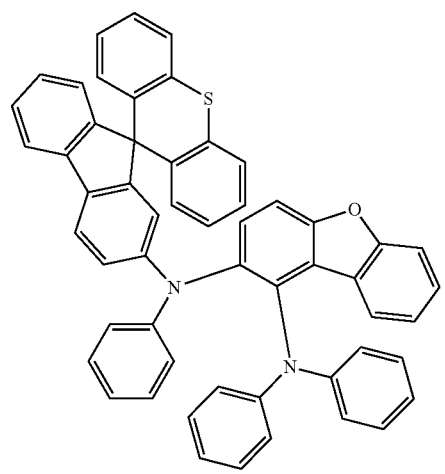

-continued
P-242
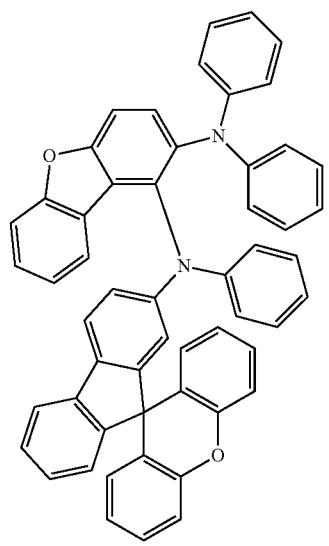
P-243
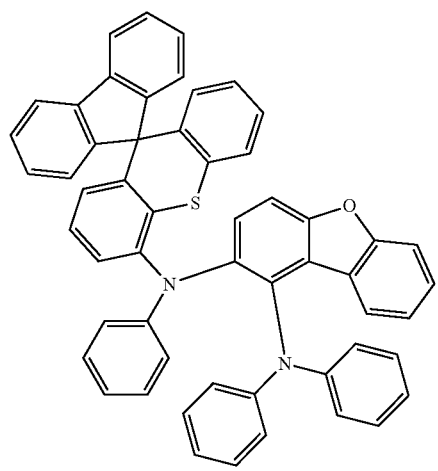
P-244
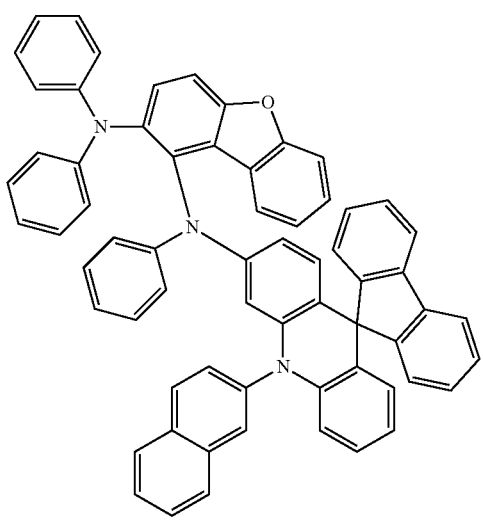
-continued
P-245
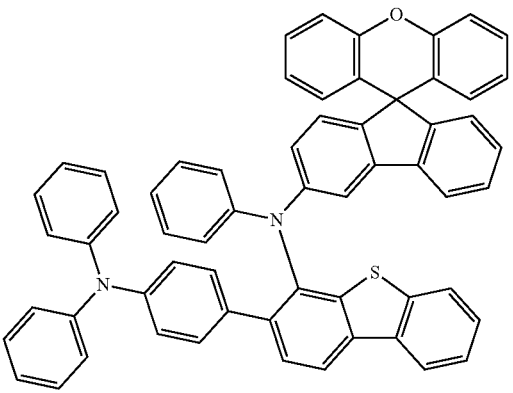
P-246
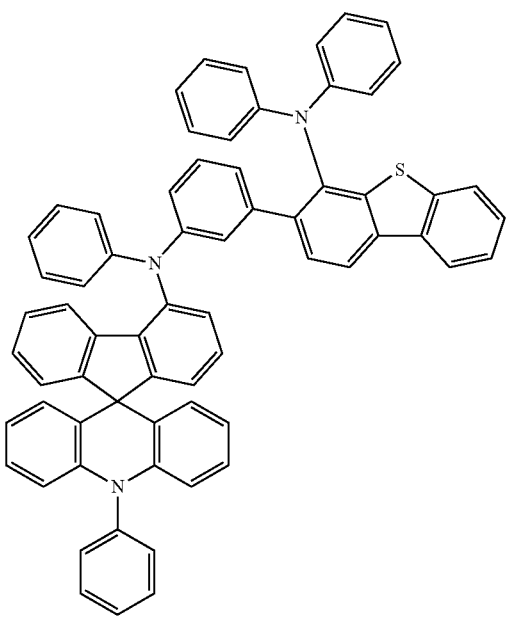
P-247
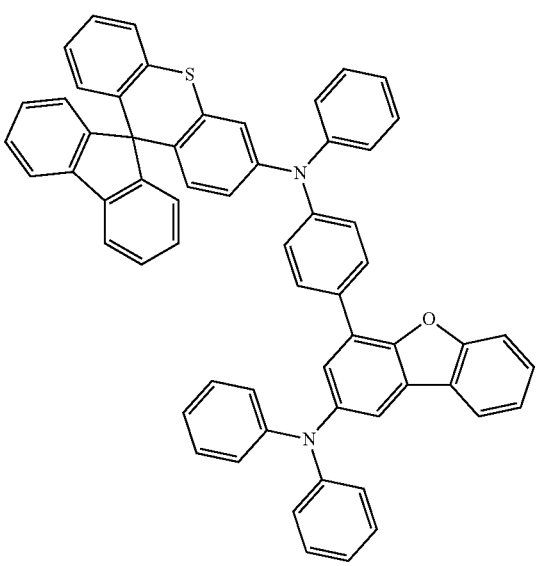

P-248
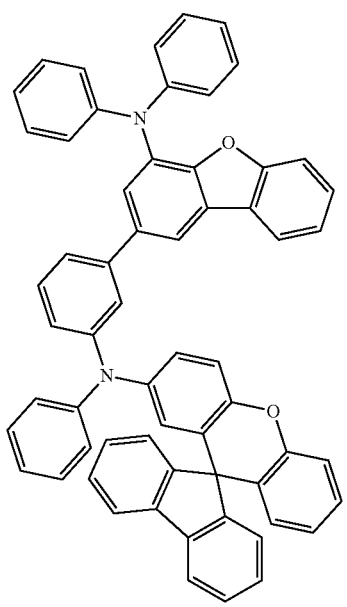
P-249
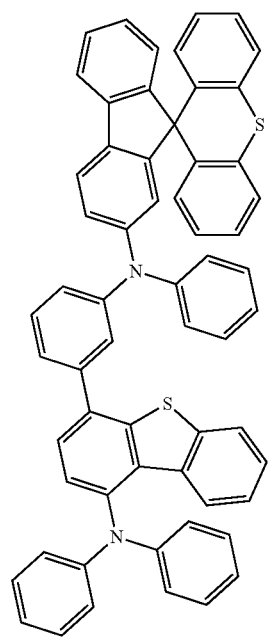
P-250
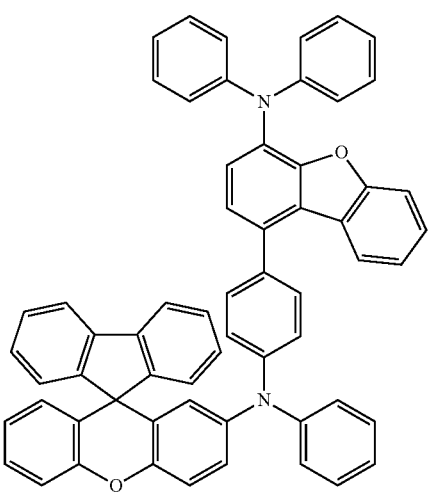
P-251
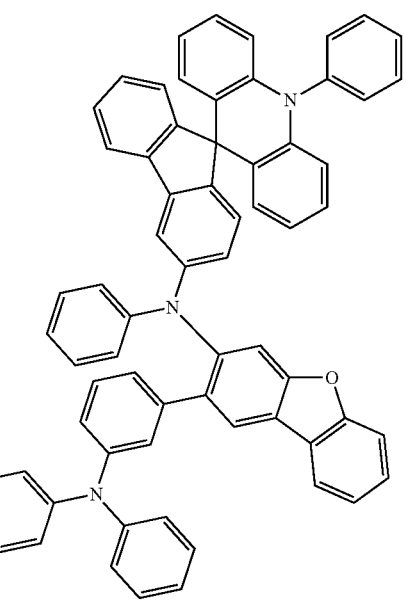
P-252
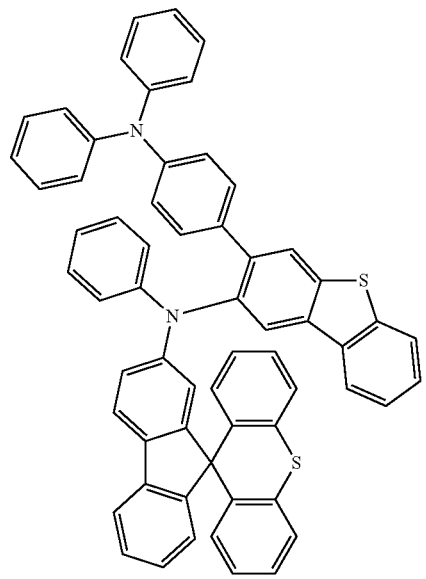

P-253
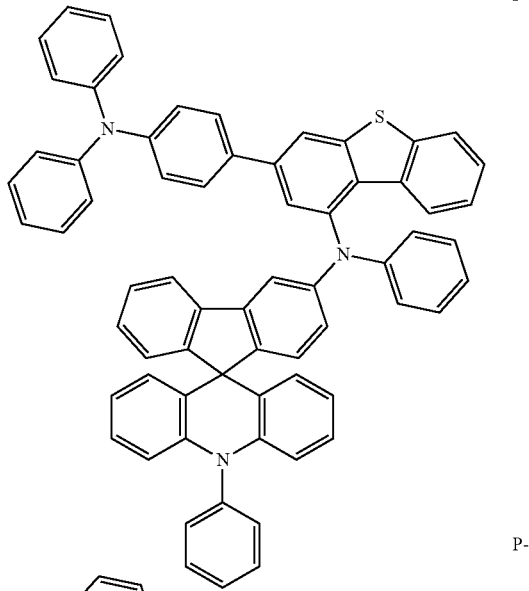
P-254
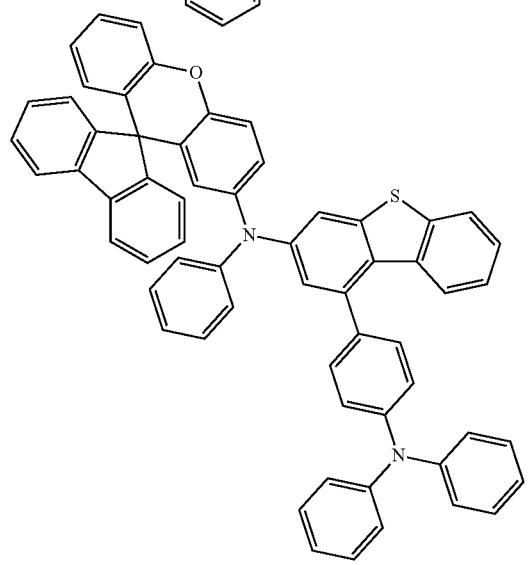
P-255
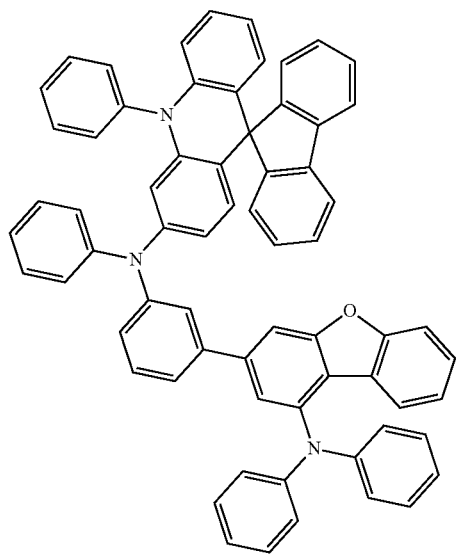
P-256
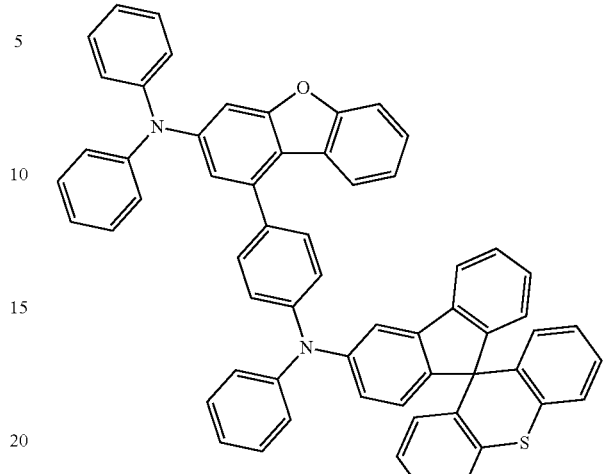
P-257
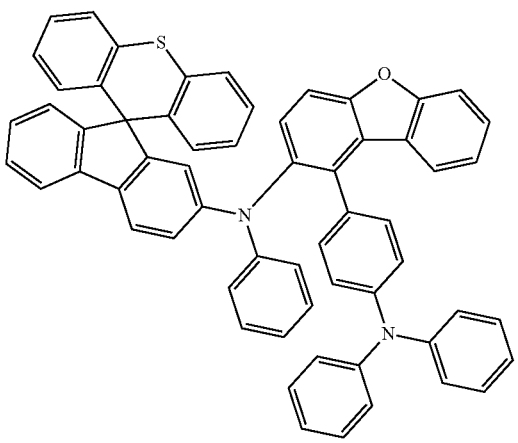
P-258
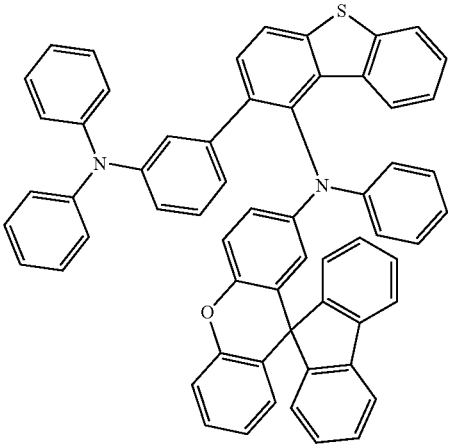

P-259
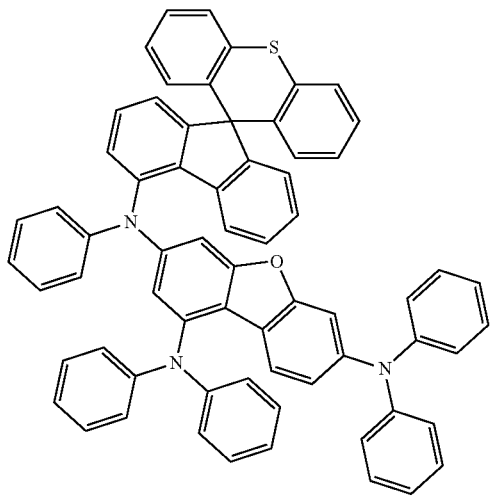
P-260
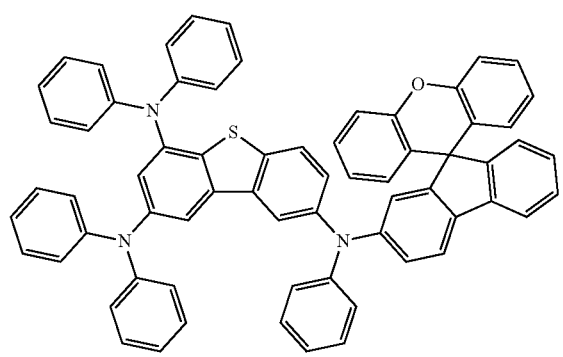
P-261
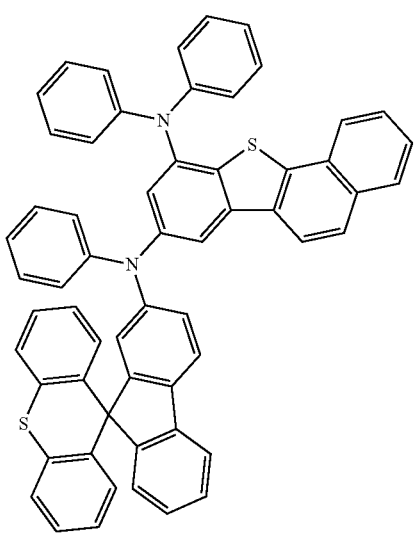
P-262
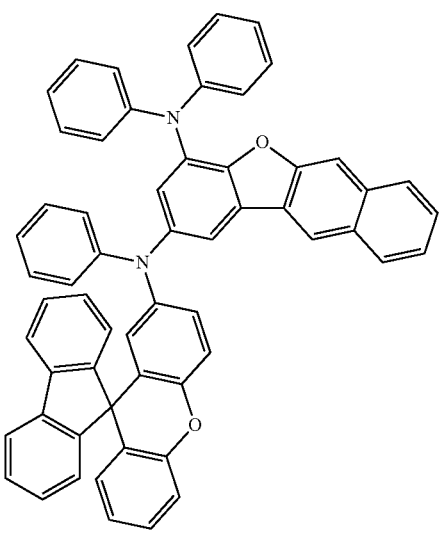
P-263
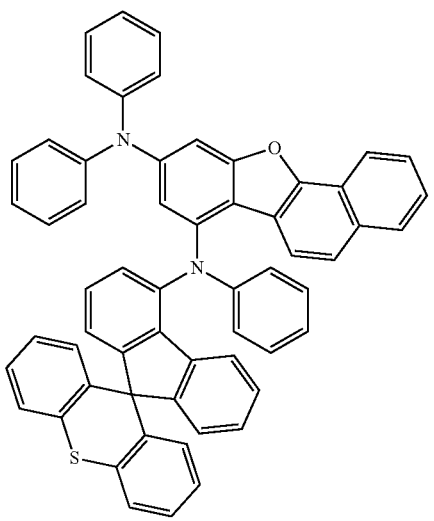
P-264
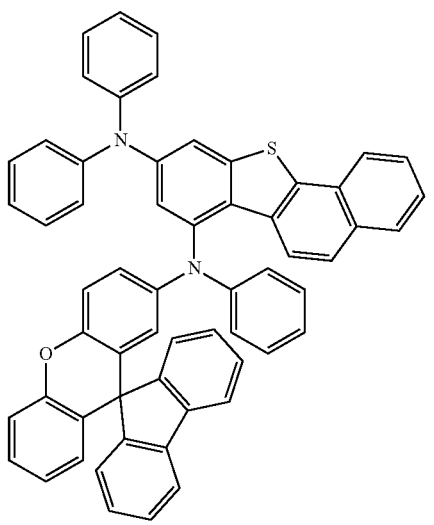

P-265

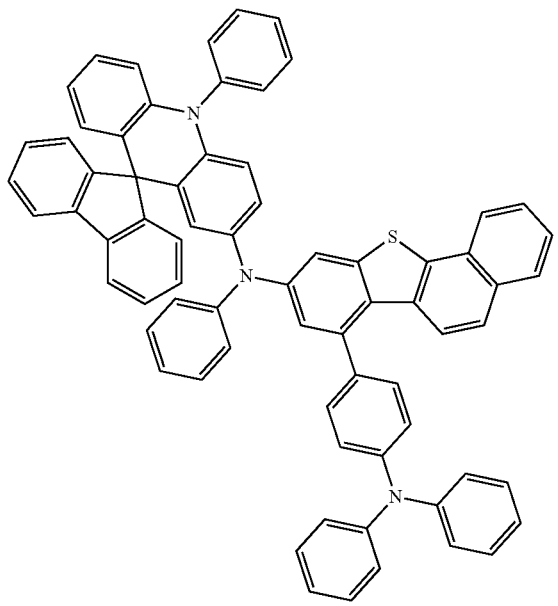

P-266

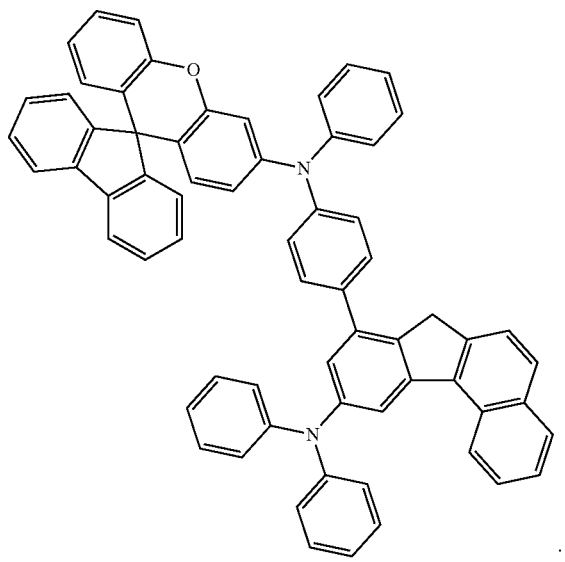

layer, an electron transport layer and an electron injection layer, preferably, the compound may be comprised in the emission-auxiliary layer.

The organic material layer may comprise two or more stacks, wherein the stacks may comprise a hole transport layer, a light emitting layer, and an electron transport layer formed in sequence on the anode, and a charge generation layer may be formed between the two or more stacks.

In another aspect of the present invention, the present invention provides an electronic device comprising a display device and a control unit for controlling the display device, wherein the display device comprises the organic electric element comprising compound represented by Formula 1.

Hereinafter, synthesis example of the compound represented by Formula 1 and preparation method of an organic electroluminescent element according to the present invention will be described in detail by way of examples. However, the present invention is not limited to the following examples.

SYNTHESIS EXAMPLE

The compound (final product) represented by Formula 1 according to the present invention can be synthesized according to the reaction route of the following Reaction Scheme 1, but there is no limitation thereto.

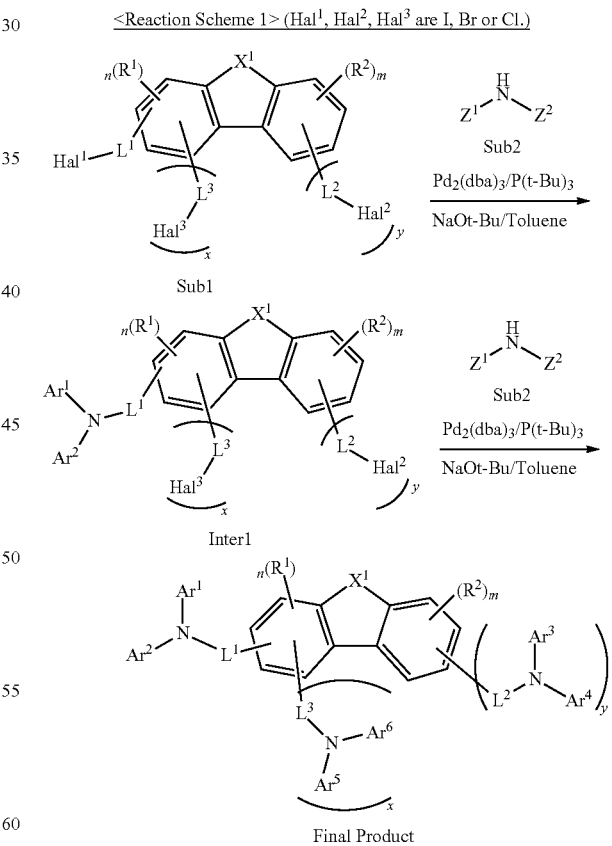

<Reaction Scheme 1> ($Hal^1$, $Hal^2$, $Hal^3$ are I, Br or Cl.)

Final Product

In another aspect of the present invention, the present invention provides an organic electric element comprising an anode, a cathode, and an organic material layer formed between the anode and the cathode, wherein the organic material layer comprises a single compound or two or more compounds represented by Formula 1.

In another aspect of the present invention, the present invention provides an organic electric element comprising an anode, a cathode, an organic material layer formed between the anode and the cathode, and a layer for improving luminous efficiency. Here, the layer for improving luminous efficiency is formed on one side of the anode or the cathode, the one side is not facing the organic material layer and the layer for improving luminous efficiency comprises compound represented by Formula 1.

The organic material layer comprises at least one of a hole injection layer, a hole transport layer, an emission-auxiliary layer, a light emitting layer, an electron transport-auxiliary I. Synthesis of Sub1

Sub 1 of the Reaction Scheme 1 can be synthesized according to the reaction route of the following Reaction Scheme 2-1 or 2-2, but there is no limitation thereto. Sub 1 can be synthesized according to the reaction route of the following Reaction Scheme 2-1 where $X^1$ is S and according to the reaction route of the following Reaction Scheme 2-2 where $X^1$ is O.

<Reaction Scheme 2-1> ($Hal^1$, $Hal^2$, $Hal^3$ are I, Br, or Cl.)

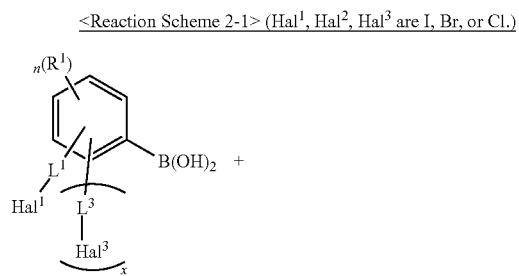

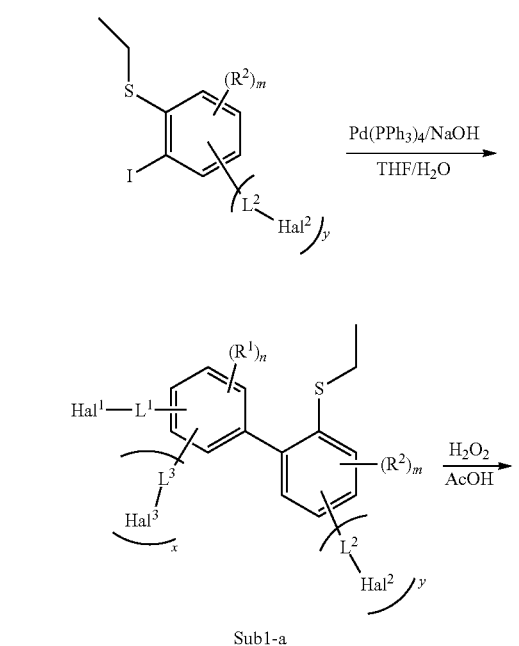

Sub1-a

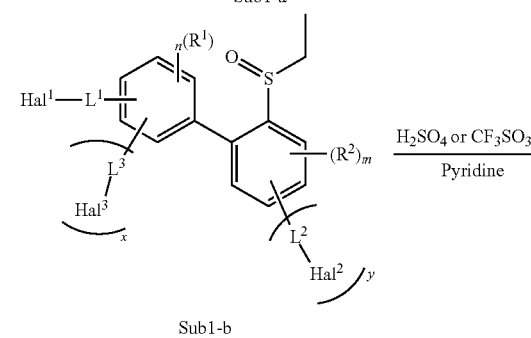

Sub1-b

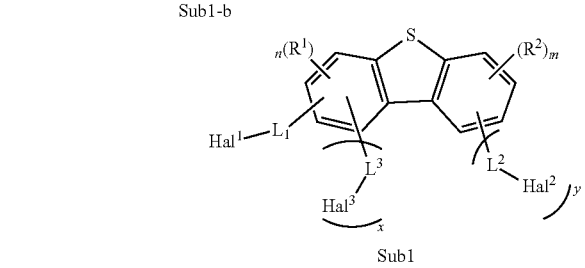

Sub1

<Reaction Scheme 2-2> ($Hal^1$, $Hal^2$, $Hal^3$ are I, Br or Cl.)

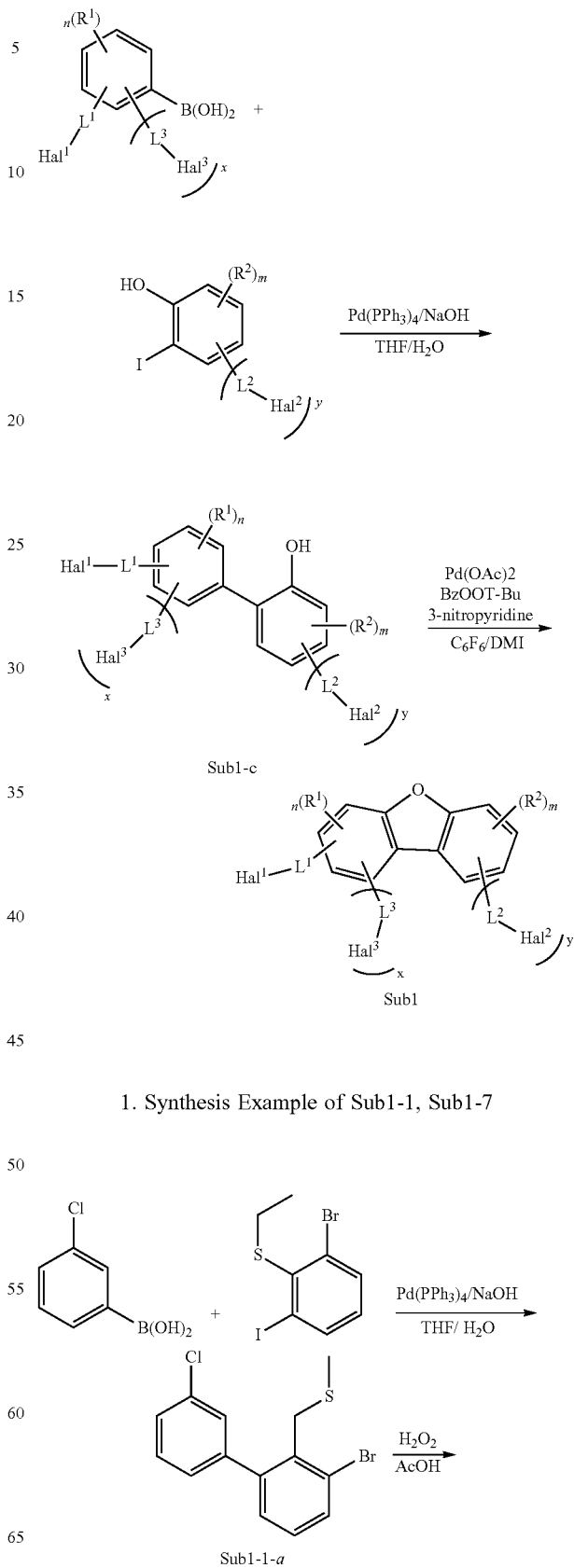

Sub1-c

Sub1

1. Synthesis Example of Sub1-1, Sub1-7

Sub1-1-*a*

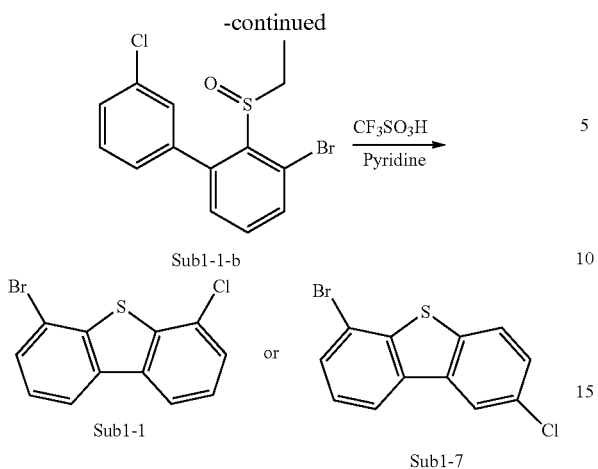

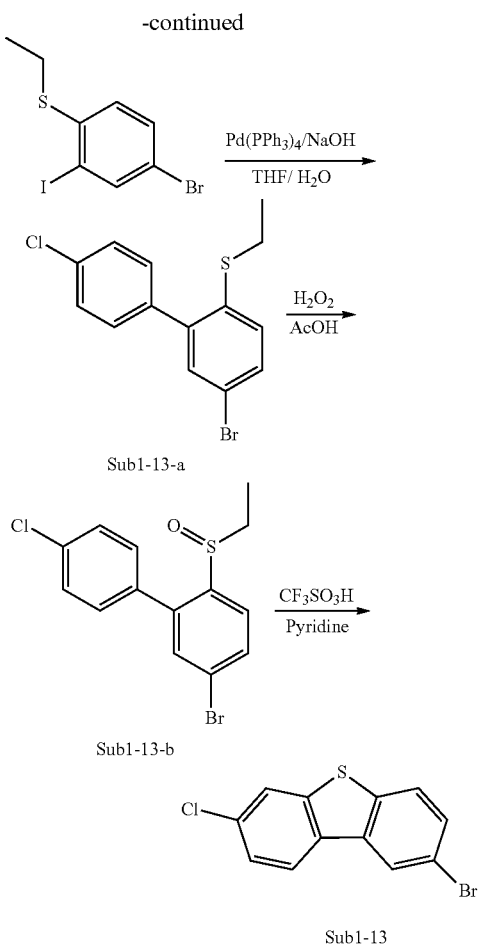

(1) Synthesis Example of Sub1-1-a (3-chlorophenyl) boronic acid (50.0 g, 320 mmol) was dissolved in THF (1.6 L), (2-bromo-6-iodophenyl) (ethyl) sulfane (110 g, 320 mmol), NaOH (38.4 g, 959 mmol), Pd(PPh$_3$)$_4$ (22.2 g, 19.2 mmol) and water (800 mL) were added thereto and the mixture was stirred at 80° C. When the reaction was completed, the reaction product was extracted with CH$_2$Cl$_2$ and water, and then the organic layer was dried with MgSO$_4$ and concentrated. Then, the concentrate was separated through a silica gel column and recrystallized to obtain 88.0 g (yield: 84%) of the product.

(2) Synthesis Example of Sub1-1-b

Acetic acid (1.1 L) and 35% Hydrogen peroxide (H$_2$O$_2$) (76.7 mL) were added to Sub1-1-a (88.0 g, 269 mmol) and the mixture was stirred at room temperature. When the reaction was completed, the reaction product was neutralized with an aqueous NaOH solution and extracted with EA (ethylacetate) and water. Thereafter, the organic layer was dried with MgSO$_4$ and concentrated. Then, the concentrate was separated through a silica gel column and recrystallized to obtain 82.2 g (yield: 89%) of the product.

(3) Synthesis Example of Sub1-1, Sub1-7

After adding Sub1-1-b (82.2 g, 239 mmol) to an excess of trifluoromethane-sulfonic acid, the mixture was stirred at room temperature for 24 hours Thereafter, water and pyridine (8:1) were slowly added thereto and the mixture was refluxed for 30 minutes. The reaction product was cooled down and extracted with CH$_2$Cl$_2$ and water. Thereafter, the organic layer was dried with MgSO$_4$ and concentrated. Then, the concentrate was separated through a silica gel column and recrystallized to obtain Sub1-1 28.5 g (yield: 40%) and Sub1-7 29.9 g (yield: 42%) of the products.

2. Synthesis Example of Sub1-13

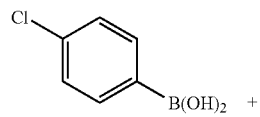

(1) Synthesis Example of Sub1-13-a

The reaction was carried out in the same manner as in the synthesis method of Sub1-1-a using (4-chlorophenyl) boronic acid (20.0 g, 128 mmol), THF, (4-bromo-2-iodophenyl) (ethyl) sulfane (43.9 g, 128 mmol), NaOH (15.4 g, 384 mmol), Pd(PPh$_3$)$_4$ (8.87 g, 7.67 mmol) and water to obtain 33.9 g (yield: 81%) of product.

(2) Synthesis Example of Sub1-13-b

The reaction was carried out in the same manner as in the synthesis method of Sub1-1-b using Sub1-13-a (33.9 g, 104 mmol), acetic acid (414 mL) and 35% Hydrogen peroxide (H$_2$O$_2$) (29.6 mL) to obtain 32.8 g (yield: 92%) of product.

(3) Synthesis Example of Sub1-13

The reaction was carried out in the same manner as in the synthesis method of Sub1-1 using Sub1-13-b (32.8 g, 95.3 mmol) instead of Sub1-1-b to obtain 23.8 g (yield: 84%) of the product.

3. Synthesis Example of Sub1-35

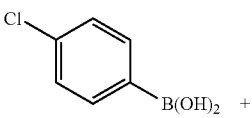

-continued

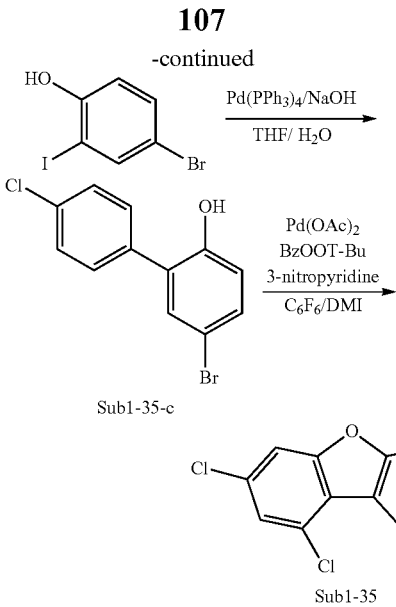

Sub1-35-c

Sub1-35

(1) Synthesis Example of Sub1-35-c

The reaction was carried out in the same manner as in the synthesis method of Sub1-1-a using (4-chlorophenyl) boronic acid (20.0 g, 128 mmol), 4-bromo-2-iodophenol (38.2 g, 128 mmol), NaOH (15.3 g, 384 mmol), Pd(PPh$_3$)$_4$ (8.87 g, 7.67 mmol) to obtain 29.7 g (yield: 82%) of product.

(2) Synthesis Example of Sub1-35

Pd(OAc)$_2$ (1.18 g, 5.24 mmol), 3-nitropyridine (0.65 g, 5.24 mmol), BzOOt-Bu (tert-butyl peroxybenzoate) (40.7 g, 210 mmol), C$_6$F$_6$ (hexafluorobenzene) (160 mL), DMI (N,N'-dimethylimidazolidinone) (105 mL) were added to Sub1-35-c (29.7 g, 105 mmol) and the mixture was refluxed at 90° C. for 3 hours. When the reaction was completed, the reaction product was cooled to room temperature, and extracted with EA and water.

The organic layer was dried with MgSO$_4$ and concentrated. Thereafter, the concentrate was separated by a silica gel column and recrystallized to obtain 19.2 g (yield: 65%) of the product.

4. Synthesis Example of Sub1-40

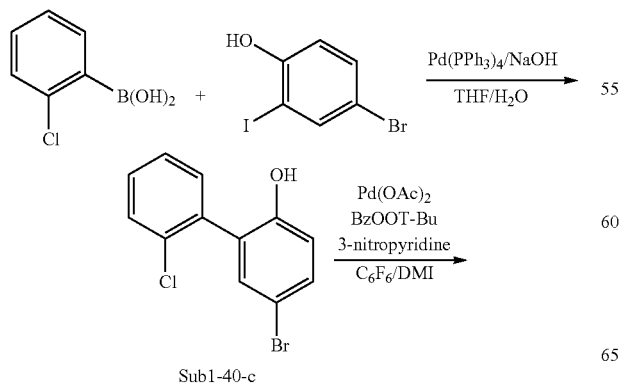

Sub1-40-c

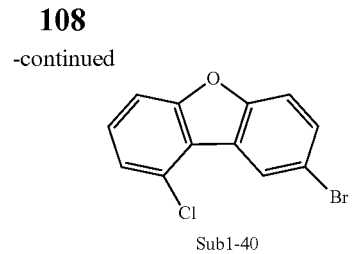

Sub1-40

(1) Synthesis Example of Sub1-40-c

The reaction was carried out in the same manner as in the synthesis method of Sub1-1-a using (2-chlorophenyl) boronic acid (20.0 g, 128 mmol), 4-bromo-2-iodophenol (38.2 g, 128 mmol), NaOH (15.3 g, 384 mmol), Pd(PPh$_3$)$_4$ (8.87 g, 7.67 mmol) to obtain 29.0 g (yield: 80%) of product.

(2) Synthesis Example of Sub1-40

The reaction was carried out in the same manner as in the synthesis method of Sub1-1-a using Sub1-40-c (29.0 g, 102 mmol), Pd(OAc)$_2$ (1.15 g, 5.12 mmol), 3-nitropyridine (0.64 g, 5.12 mmol), BzOOt-Bu (tert-butyl peroxybenzoate) (39.7 g, 205 mmol), C$_6$F$_6$ (hexafluorobenzene) (150 mL), DMI (N,N'-dimethylimidazolidinone) (100 mL) were added to Sub1-40-c (29.0 g, 102 mmol) to obtain 17.9 g (yield 62%) of product.

5. Synthesis Example of Sub1-46

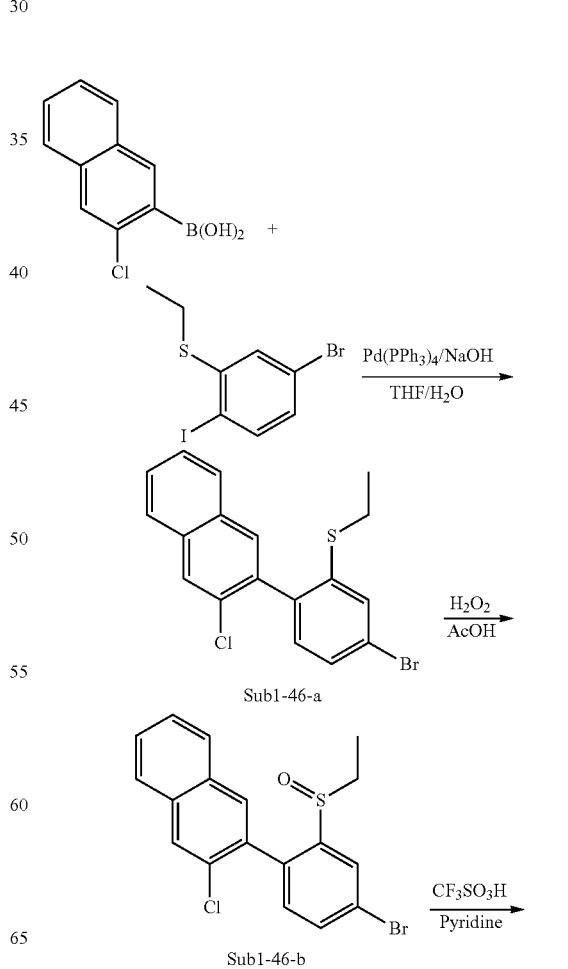

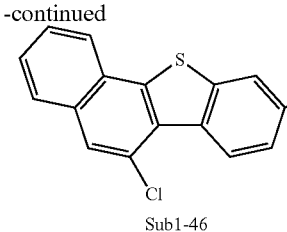

Sub1-46

(1) Synthesis Example of Sub1-46-a

The reaction was carried out in the same manner as in the synthesis method of Sub1-1-a using (3-chloronaphthalen-2-yl) boronic acid (20.0 g, 96.9 mmol), (5-bromo-2-iodophenyl) (ethyl) sulfane (33.2 g, 96.9 mmol), NaOH (11.6 g, 291 mmol), Pd(PPh$_3$)$_4$ (6.72 g, 5.81 mmol) to obtain 31.5 g (yield: 86%) of product.

(2) Synthesis Example of Sub1-46-b

The reaction was carried out in the same manner as in the synthesis method of Sub1-1-b using Sub1-46-a (31.5 g, 83.3 mmol), acetic acid (333 mL), 35% Hydrogen peroxide (H$_2$O$_2$) (23.8 mL) to obtain 28.5 g (yield: 87%) of product.

(3) Synthesis Example of Sub1-46

The reaction was carried out in the same manner as in the synthesis method of Sub1-1 using Sub1-1-46-b (28.5 g, 72.5 mmol) to obtain 20.9 g (yield: 83%) of product.

6. Synthesis Example of Sub1-88

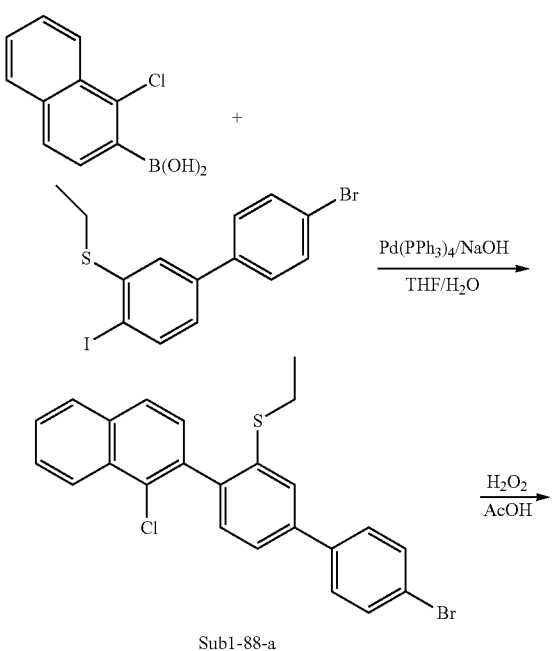

Sub1-88-a

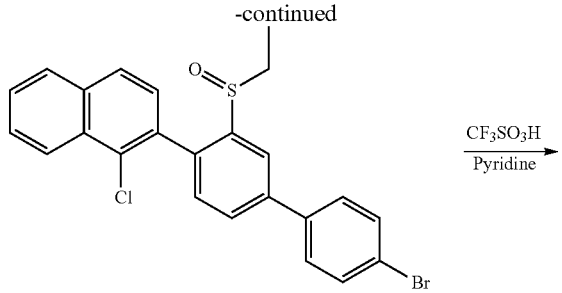

Sub1-88-b

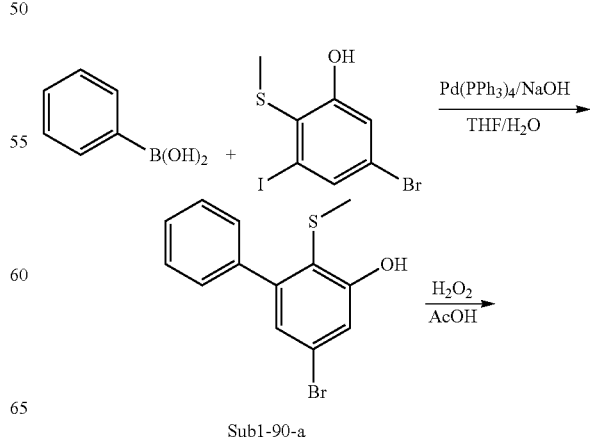

Sub1-88

(1) Synthesis Example of Sub1-88-a

The reaction was carried out in the same manner as in the synthesis method of Sub1-1-a using (1-chloronaphthalen-2-yl) boronic acid (20.0 g, 96.9 mmol), (4'-bromo-4-iodo-[1,1'-biphenyl]-3-yl) (ethyl) sulfane (40.6 g, 96.9 mmol), NaOH (11.6 g, 291 mmol), Pd(PPh$_3$)$_4$ (6.72 g, 5.81 mmol) to obtain 35.6 g (yield: 81%) of product.

(2) Synthesis Example of Sub1-88-b

The reaction was carried out in the same manner as in the synthesis method of Sub1-1-b using Sub1-88-a (35.6 g, 78.5 mmol), acetic acid (314 mL), 35% Hydrogen peroxide (H$_2$O$_2$) (22.4 mL) to obtain 34.3 g (yield: 93%) of product.

(3) Synthesis Example of Sub1-88

The reaction was carried out in the same manner as in the synthesis method of Sub1-1 using Sub1-1-88-b (34.3 g, 73.0 mmol) instead of Sub1-1-b to obtain 23.8 g (yield: 77%) of the product.

7. Synthesis Example of Sub1-90

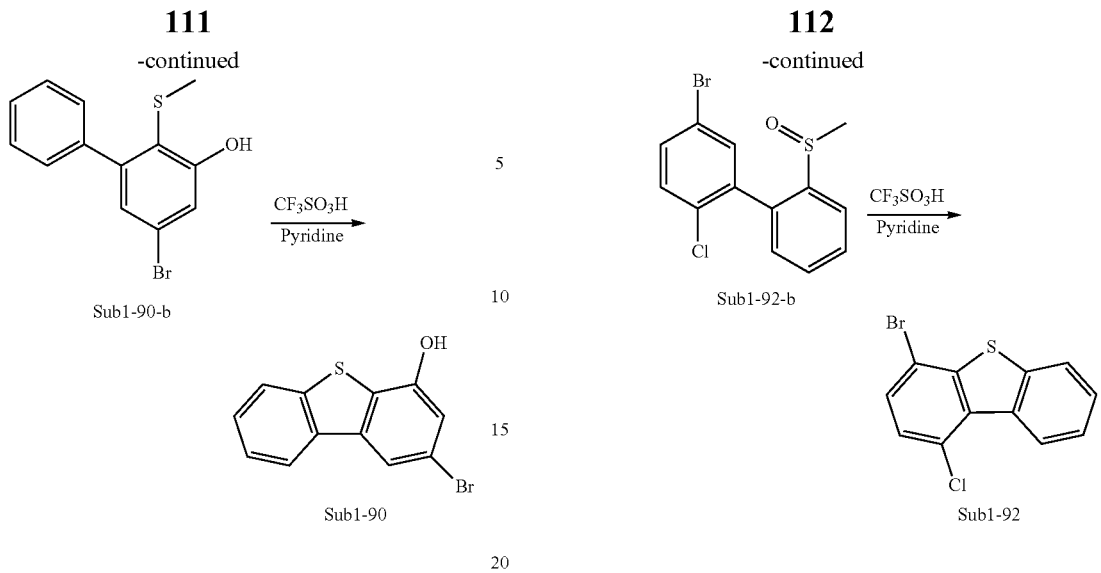

(1) Synthesis Example of Sub1-90-a

The reaction was carried out in the same manner as in the synthesis method of Sub1-1-a using Phenylboronic acid (20.0 g, 164 mmol), 5-bromo-3-iodo-2-(methylthio) phenol (56.6 g, 164 mmol), NaOH (19.7 g, 492 mmol), Pd(PPh$_3$)$_4$ (11.4 g, 9.84 mmol) to obtain 41.2 g (yield: 85%) of product.

(2) Synthesis Example of Sub1-90-b

The reaction was carried out in the same manner as in the synthesis method of Sub1-1-b using Sub1-90-a (41.2 g, 139 mmol), acetic acid (40 mL), 35% Hydrogen peroxide (H$_2$O$_2$) (560 mL) to obtain 40.8 g (yield: 94%) of product.

(3) Synthesis Example of Sub1-90

The reaction was carried out in the same manner as in the synthesis method of Sub1-1 using Sub1-1-90-b (40.8 g, 131 mmol) to obtain 28.9 g (yield: 79%) of product.

8. Synthesis Example of Sub1-92

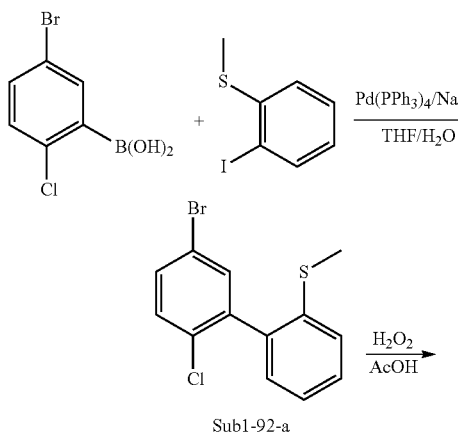

(1) Synthesis Example of Sub1-92-a

The reaction was carried out in the same manner as in the synthesis method of Sub1-1-a using (5-bromo-2-chlorophenyl) boronic acid (30.0 g, 128 mmol), (2-iodophenyl)(methyl)sulfane (31.9 g, 128 mmol), NaOH (15.3 g, 383 mmol), Pd(PPh$_3$)$_4$ (8.84 g, 7.65 mmol) to obtain 32.8 g (yield: 82%) of product.

(2) Synthesis Example of Sub1-92-b

The reaction was carried out in the same manner as in the synthesis method of Sub1-1-b using Sub1-92-a (32.8 g, 105 mmol), acetic acid (30 mL), 35% Hydrogen peroxide (H$_2$O$_2$) (420 mL) to obtain 33.1 g (yield: 96%) of product.

(3) Synthesis Example of Sub1-92

The reaction was carried out in the same manner as in the synthesis method of Sub1-1 using Sub1-1-92-b (33.1 g, 100 mmol) to obtain 21.5 g (yield: 72%) of product.

9. Synthesis Example of Sub1-96

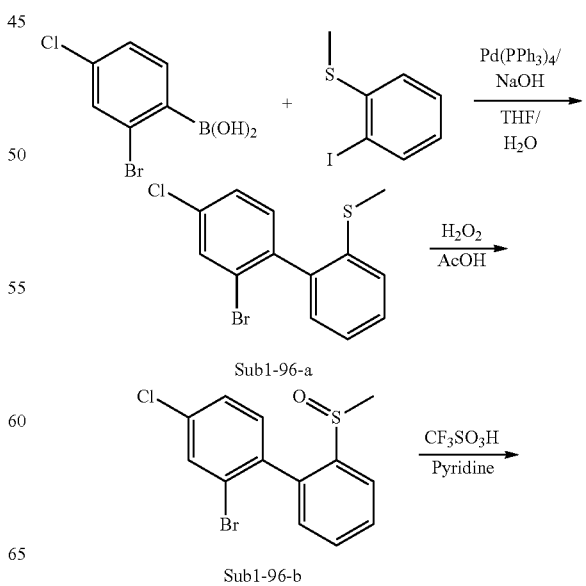

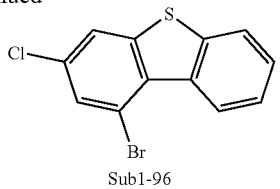
Sub1-96

(1) Synthesis Example of Sub1-96-a

The reaction was carried out in the same manner as in the synthesis method of Sub1-1-a using (2-bromo-4-chlorophenyl) boronic acid (30.0 g, 128 mmol), (2-iodophenyl)(methyl)sulfane (31.9 g, 128 mmol), NaOH (15.3 g, 383 mmol), Pd(PPh$_3$)$_4$ (8.84 g, 7.65 mmol) to obtain 32.4 g (yield: 81%) of product.

(2) Synthesis Example of Sub1-96-b

The reaction was carried out in the same manner as in the synthesis method of Sub1-1-b using Sub1-96-a (32.4 g, 103 mmol), acetic acid (30 mL), 35% Hydrogen peroxide (H$_2$O$_2$) (420 mL) to obtain 32.0 g (yield: 94%) of product.

(3) Synthesis Example of Sub1-96

The reaction was carried out in the same manner as in the synthesis method of Sub1-1 using Sub1-1-96-b (32.0 g, 97.1 mmol) to obtain 22.0 g (yield: 76%) of product.

10. Synthesis Example of Sub1-102

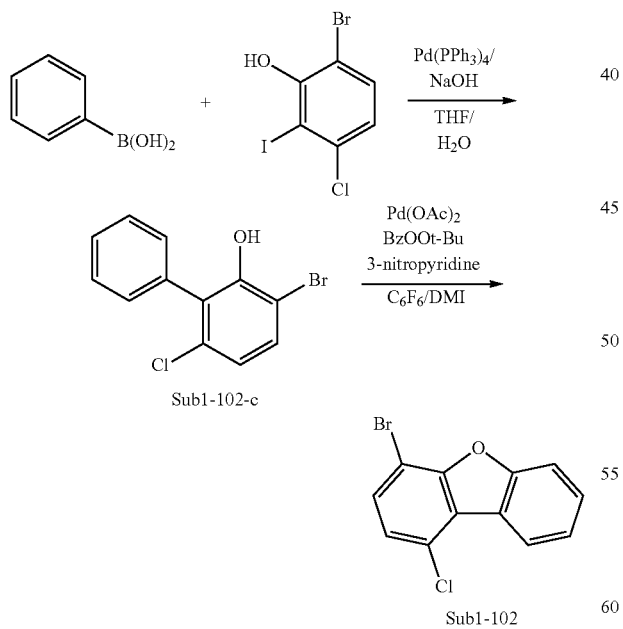
Sub1-102-c

Sub1-102

(1) Synthesis Example of Sub1-102-c

The reaction was carried out in the same manner as in the synthesis method of Sub1-1-a using (2-chlorophenyl) boronic acid (20.0 g, 164 mmol), 4-bromo-2-iodophenol (54.7 g, 164 mmol), NaOH (19.7 g, 492 mmol), Pd(PPh$_3$)$_4$ (11.4 g, 9.84 mmol) to obtain 40.0 g (yield: 86%) of product.

(2) Synthesis Example of Sub1-102

The reaction was carried out in the same manner as in the synthesis method of Sub1-35 using Sub1-102-c (40.0 g, 141 mmol), Pd(OAc)$_2$ (1.58 g, 7.05 mmol), 3-nitropyridine (0.88 g, 7.05 mmol), BzOOt-Bu (tert-butyl peroxybenzoate) (54.8 g, 282 mmol), C$_6$F$_6$ (hexafluorobenzene) (210 mL), DMI (N,N'-dimethylimidazolidinone) (140 mL) to obtain 25.0 g (yield 63%) of product.

11. Synthesis Example of Sub1-106

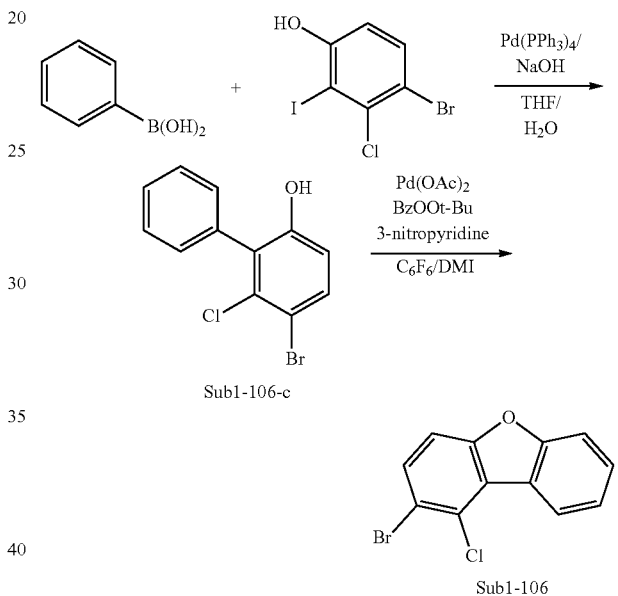
Sub1-106-c

Sub1-106

(1) Synthesis Example of Sub1-106-c

The reaction was carried out in the same manner as in the synthesis method of Sub1-1-a using Phenylboronic acid (20.0 g, 164 mmol), 3-bromo-4-chloro-2-iodophenol (54.7 g, 164 mmol), NaOH (19.7 g, 492 mmol), Pd(PPh$_3$)$_4$ (11.4 g, 9.84 mmol) to obtain 38.6 g (yield: 83%) of product.

(2) Synthesis Example of Sub1-106

The reaction was carried out in the same manner as in the synthesis method of Sub1-35 using Sub1-106-c (38.6 g, 136 mmol), Pd(OAc)$_2$ (1.53 g, 6.81 mmol), 3-nitropyridine (0.85 g, 6.81 mmol), BzOOt-Bu (tert-butyl peroxybenzoate) (52.9 g, 272 mmol), C$_6$F$_6$ (hexafluorobenzene) (200 mL), DMI (N,N'-dimethylimidazolidinone) (140 mL) to obtain 24.9 g (yield 65%) of product.

The compounds belonging to Sub 1 may be, but not limited to, the following compounds, and Table 1 shows FD-MS (Field Desorption-Mass Spectrometry) values of the following compounds.

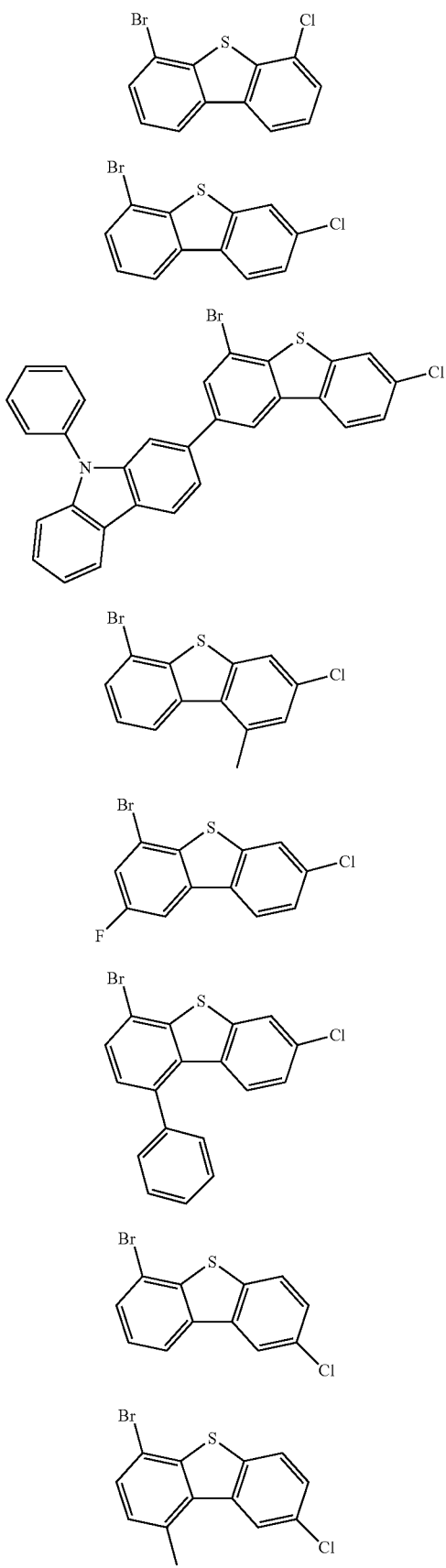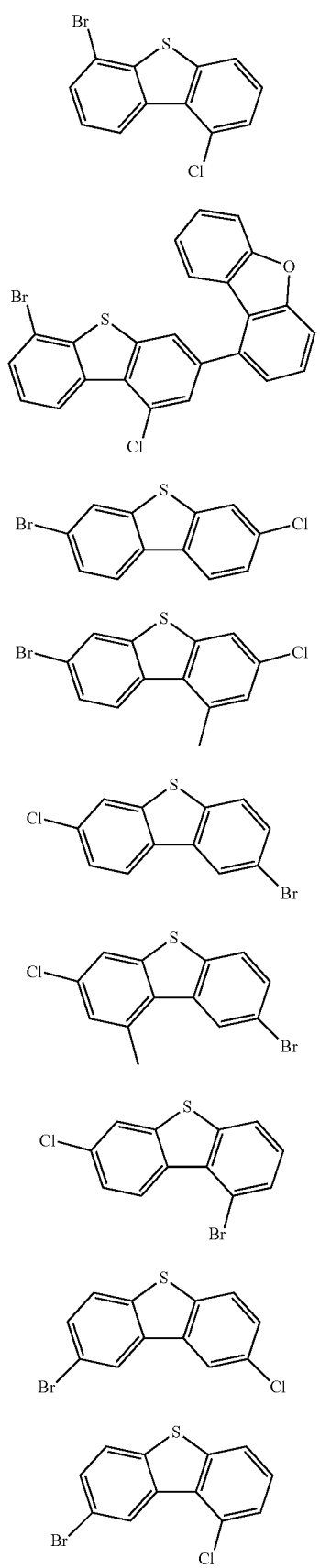

-continued
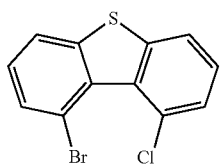
Sub1-18
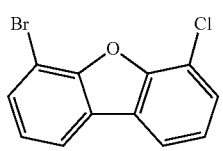
Sub1-19
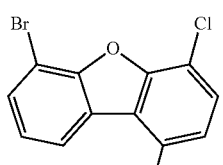
Sub1-20
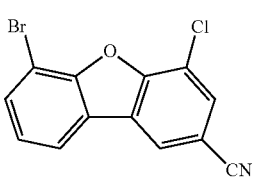
Sub1-21
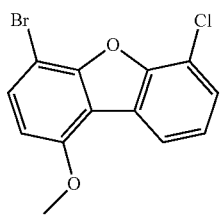
Sub1-22
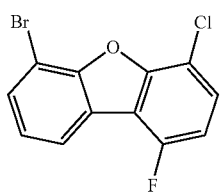
Sub1-23
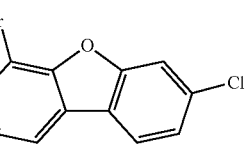
Sub1-24
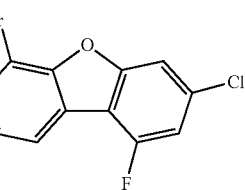
Sub1-25
-continued
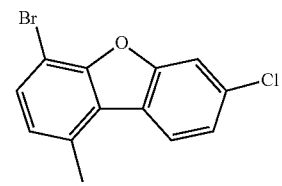
Sub1-26
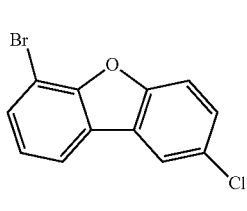
Sub1-27
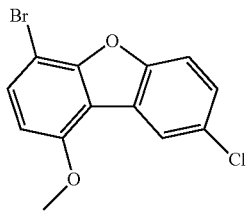
Sub1-28
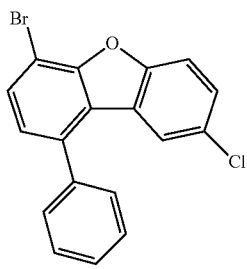
Sub1-29
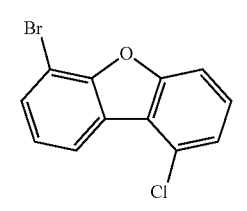
Sub1-30
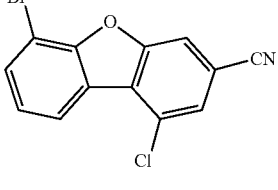
Sub1-31
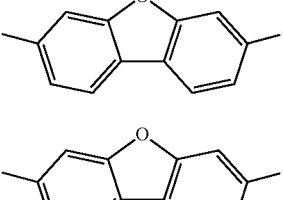
Sub1-32
Sub1-33

Sub1-34 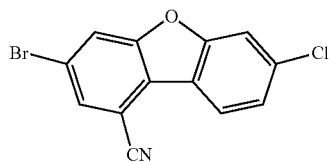
Sub1-35 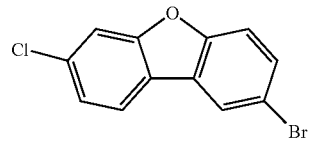
Sub1-36 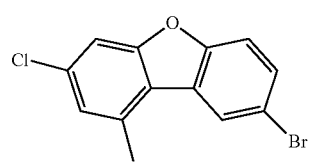
Sub1-37 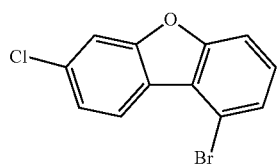
Sub1-38 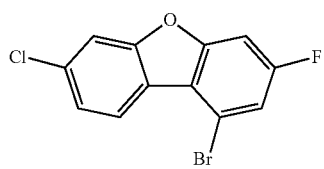
Sub1-39 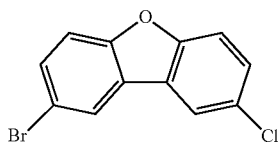
Sub1-40 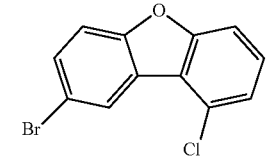
Sub1-41 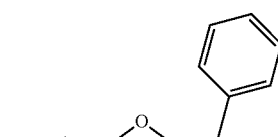
Sub1-42 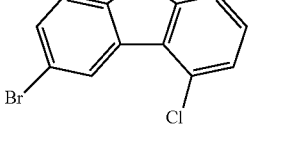
Sub1-43 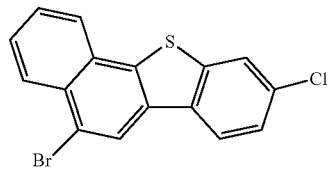
Sub1-44
Sub1-45
Sub1-46
Sub1-47
Sub1-48
Sub1-49
Sub1-50

Sub1-51
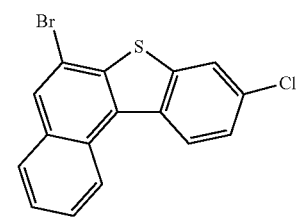
Sub1-52
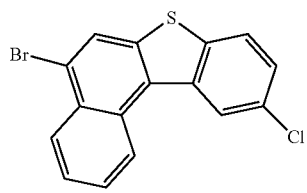
Sub1-53
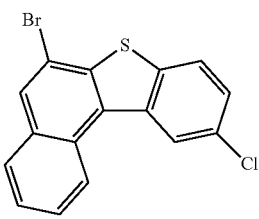
Sub1-54
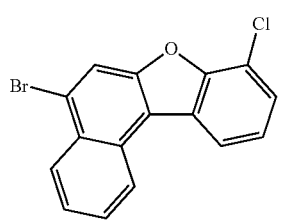
Sub1-55
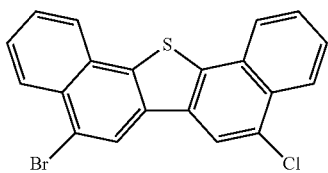
Sub1-56
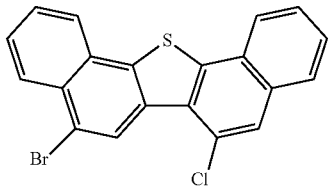
Sub1-57
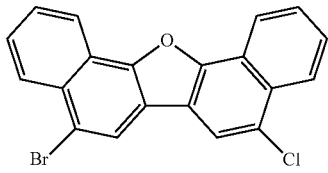
Sub1-58
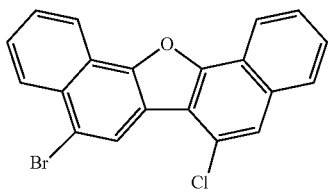
Sub1-59
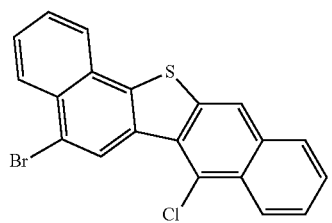
Sub1-60
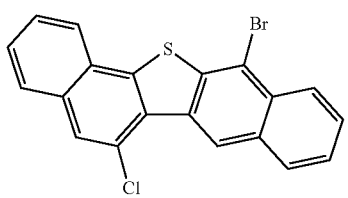
Sub1-61
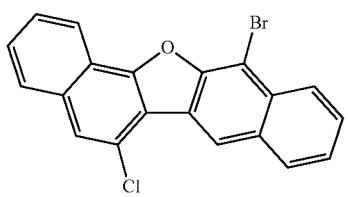
Sub1-62
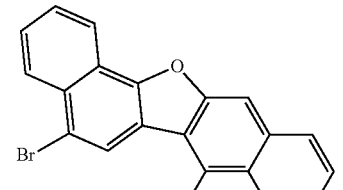
Sub1-63
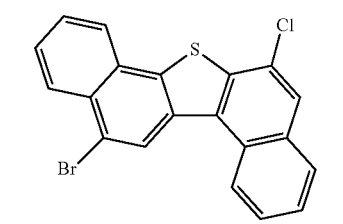
Sub1-64
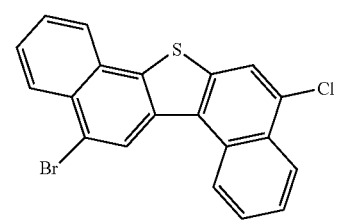
Sub1-65

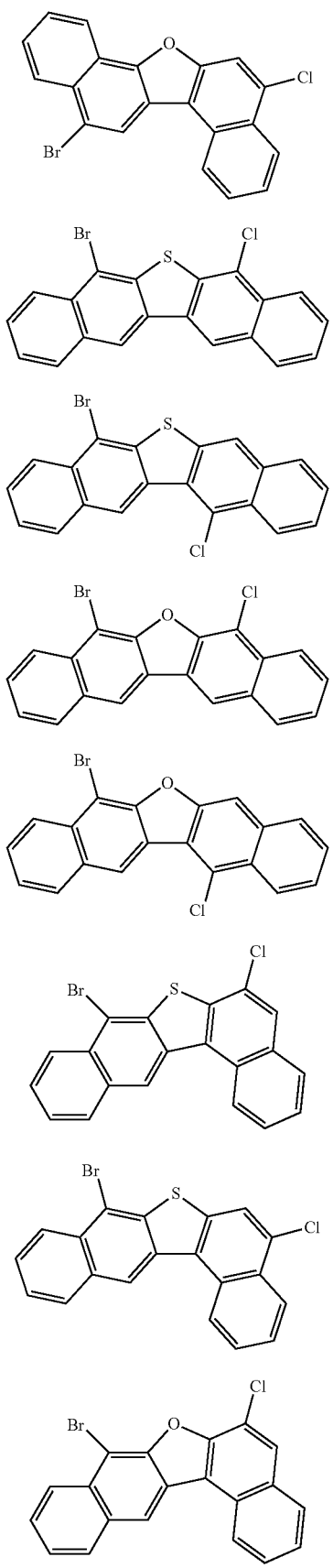
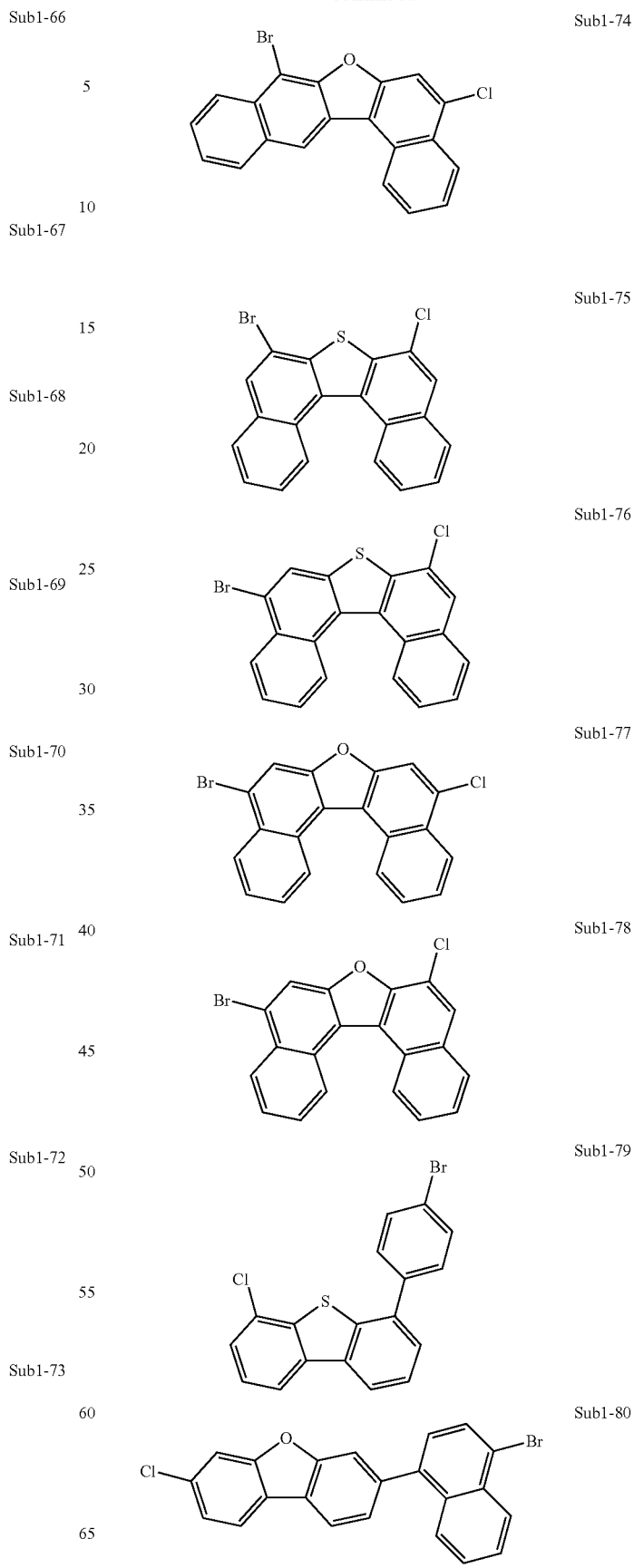

Sub1-81
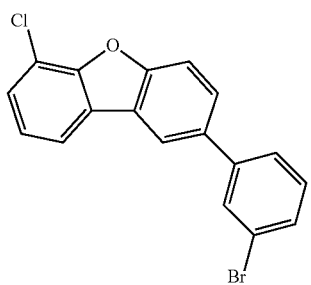
Sub1-82
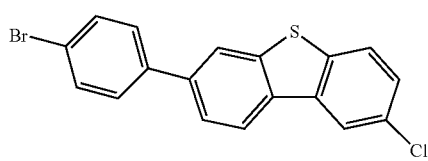
Sub1-83
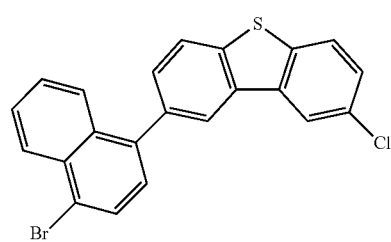
Sub1-84
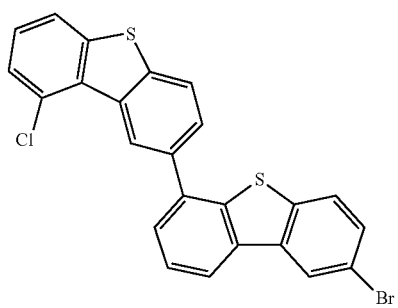
Sub1-85
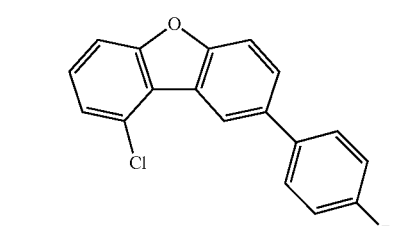
Sub1-86
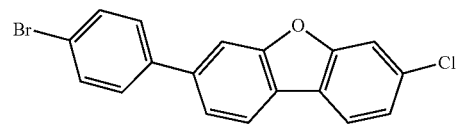
Sub1-87
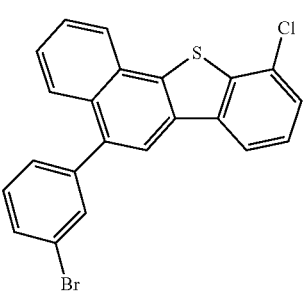
Sub1-88
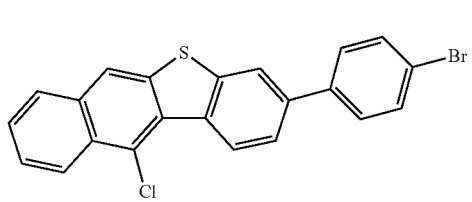
Sub1-89
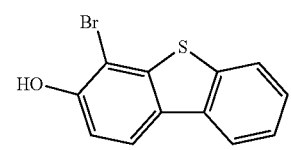
Sub1-90
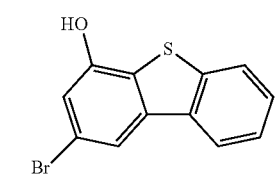
Sub1-91
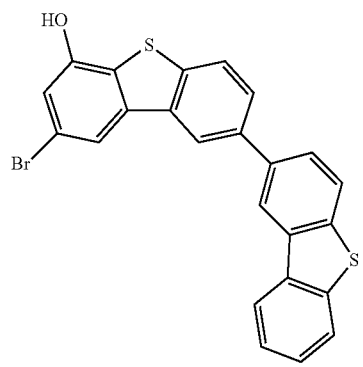
Sub1-92
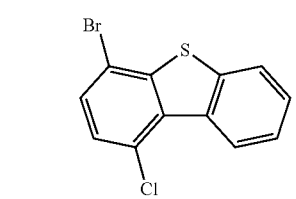
Sub1-93
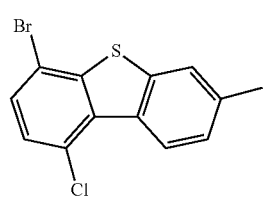

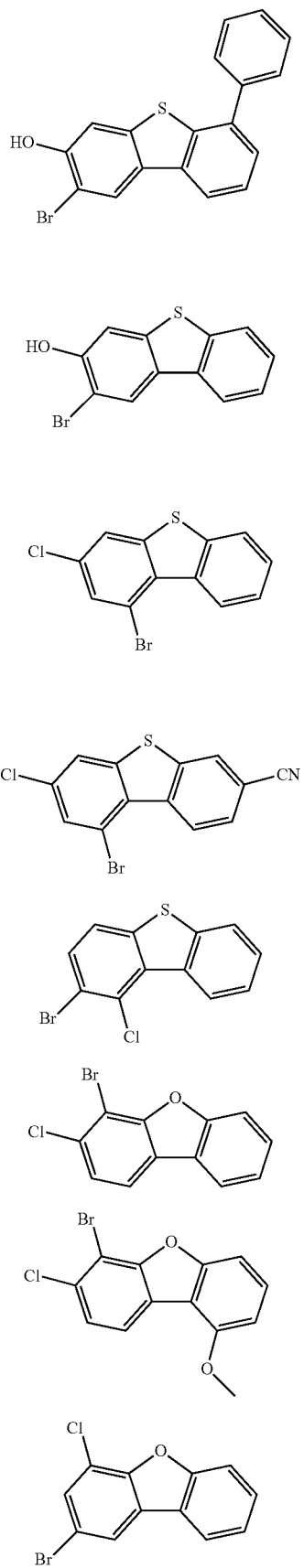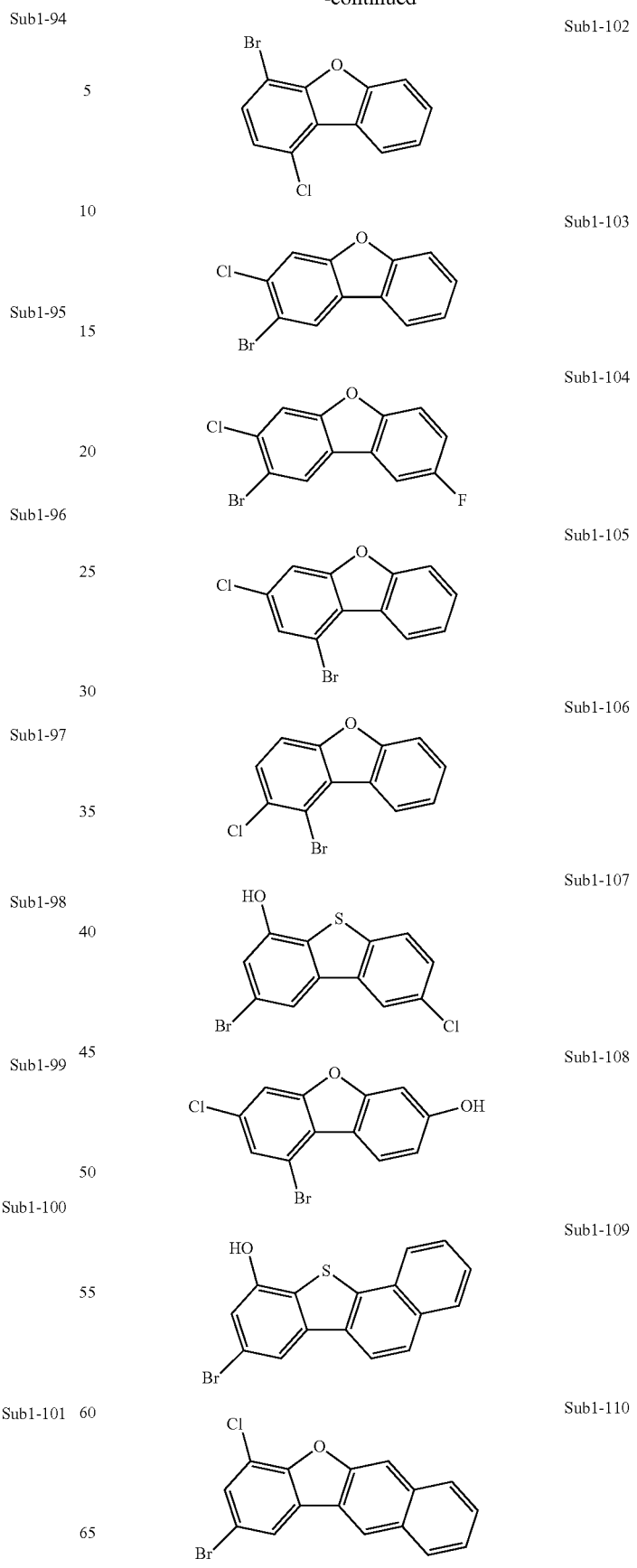

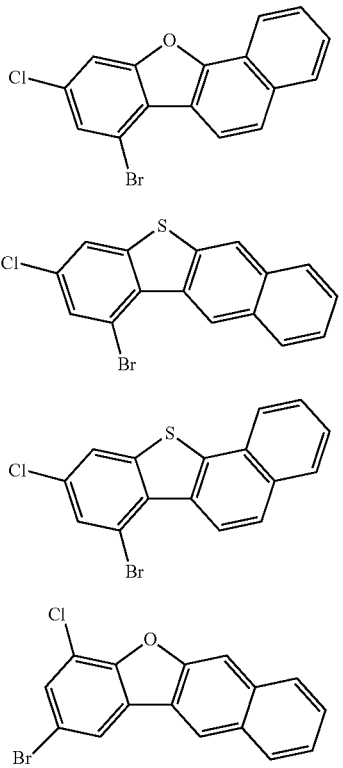

Sub1-111

Sub1-112

Sub1-113

Sub1-114

TABLE 1

| Compound | FD-MS |
|---|---|
| Sub 1-1 | m/z = 295.91($C_{12}H_6BrClS$ = 297.59) |
| Sub 1-2 | m/z = 295.91($C_{12}H_6BrClS$ = 297.59) |
| Sub 1-3 | m/z = 537.00($C_{30}H_{17}BrClNS$ = 538.89) |
| Sub 1-4 | m/z = 309.92($C_{13}H_8BrClS$ = 311.62) |
| Sub 1-5 | m/z = 313.90($C_{12}H_5BrClFS$ = 315.58) |
| Sub 1-6 | m/z = 371.94($C_{18}H_{10}BrClS$ = 373.69) |
| Sub 1-7 | m/z = 295.91($C_{12}H_6BrClS$ = 297.59) |
| Sub 1-8 | m/z = 309.92($C_{13}H_8BrClS$ = 311.62) |
| Sub 1-9 | m/z = 295.91($C_{12}H_6BrClS$ = 297.59) |
| Sub 1-10 | m/z = 461.95($C_{24}H_{12}BrClOS$ = 463.77) |
| Sub 1-11 | m/z = 295.91($C_{12}H_6BrClS$ = 297.59) |
| Sub 1-12 | m/z = 309.92($C_{13}H_8BrClS$ = 311.62) |
| Sub 1-13 | m/z = 295.91($C_{12}H_6BrClS$ = 297.59) |
| Sub 1-14 | m/z = 309.92($C_{13}H_8BrClS$ = 311.62) |
| Sub 1-15 | m/z = 295.91($C_{12}H_6BrClS$ = 297.59) |
| Sub 1-16 | m/z = 295.91($C_{12}H_6BrClS$ = 297.59) |
| Sub 1-17 | m/z = 295.91($C_{12}H_6BrClS$ = 297.59) |
| Sub 1-18 | m/z = 295.91($C_{12}H_6BrClS$ = 297.59) |
| Sub 1-19 | m/z = 279.93($C_{12}H_6BrClO$ = 281.53) |
| Sub 1-20 | m/z = 355.96($C_{18}H_{10}BrClO$ = 357.63) |
| Sub 1-21 | m/z = 304.92($C_{13}H_5BrClNO$ = 306.54) |
| Sub 1-22 | m/z = 309.94($C_{13}H_8BrClO_2$ = 311.56) |
| Sub 1-23 | m/z = 297.92($C_{12}H_5BrClFO$ = 299.52) |
| Sub 1-24 | m/z = 279.93($C_{12}H_6BrClO$ = 281.53) |
| Sub 1-25 | m/z = 297.92($C_{12}H_5BrClFO$ = 299.52) |
| Sub 1-26 | m/z = 293.94($C_{13}H_8BrClO$ = 295.56) |
| Sub 1-27 | m/z = 279.93($C_{12}H_6BrClO$ = 281.53) |
| Sub 1-28 | m/z = 309.94($C_{13}H_8BrClO_2$ = 311.56) |
| Sub 1-29 | m/z = 355.96($C_{18}H_{10}BrClO$ = 357.63) |
| Sub 1-30 | m/z = 279.93($C_{12}H_6BrClO$ = 281.53) |
| Sub 1-31 | m/z = 304.92($C_{13}H_5BrClNO$ = 306.54) |
| Sub 1-32 | m/z = 279.93($C_{12}H_6BrClO$ = 281.53) |
| Sub 1-33 | m/z = 297.92($C_{12}H_5BrClFO$ = 299.52) |
| Sub 1-34 | m/z = 304.92($C_{13}H_5BrClNO$ = 306.54) |
| Sub 1-35 | m/z = 279.93($C_{12}H_6BrClO$ = 281.53) |
| Sub 1-36 | m/z = 293.94($C_{13}H_8BrClO$ = 295.56) |
| Sub 1-37 | m/z = 279.93($C_{12}H_6BrClO$ = 281.53) |
| Sub 1-38 | m/z = 297.92($C_{12}H_5BrClFO$ = 299.52) |
| Sub 1-39 | m/z = 279.93($C_{12}H_6BrClO$ = 281.53) |
| Sub 1-40 | m/z = 279.93($C_{12}H_6BrClO$ = 281.53) |
| Sub 1-41 | m/z = 355.96($C_{18}H_{10}BrClO$ = 357.63) |
| Sub 1-42 | m/z = 279.93($C_{12}H_6BrClO$ = 281.53) |
| Sub 1-43 | m/z = 345.92($C_{16}H_8BrClS$ = 347.65) |
| Sub 1-44 | m/z = 329.94($C_{16}H_8BrClO$ = 331.59) |
| Sub 1-45 | m/z = 329.94($C_{16}H_8BrClO$ = 331.59) |
| Sub 1-46 | m/z = 329.94($C_{16}H_8BrClO$ = 331.59) |
| Sub 1-47 | m/z = 345.92($C_{16}H_8BrClS$ = 347.65) |
| Sub 1-48 | m/z = 345.92($C_{16}H_8BrClS$ = 347.65) |
| Sub 1-49 | m/z = 329.94($C_{16}H_8BrClO$ = 331.59) |
| Sub 1-50 | m/z = 329.94($C_{16}H_8BrClO$ = 331.59) |
| Sub 1-51 | m/z = 345.92($C_{16}H_8BrClS$ = 347.65) |
| Sub 1-52 | m/z = 345.92($C_{16}H_8BrClS$ = 347.65) |
| Sub 1-53 | m/z = 329.94($C_{16}H_8BrClO$ = 331.59) |
| Sub 1-54 | m/z = 329.94($C_{16}H_8BrClO$ = 331.59) |
| Sub 1-55 | m/z = 395.94($C_{20}H_{10}BrClS$ = 397.71) |
| Sub 1-56 | m/z = 395.94($C_{20}H_{10}BrClS$ = 397.71) |
| Sub 1-57 | m/z = 379.96($C_{20}H_{10}BrClO$ = 381.65) |
| Sub 1-58 | m/z = 379.96($C_{20}H_{10}BrClO$ = 381.65) |
| Sub 1-59 | m/z = 395.94($C_{20}H_{10}BrClS$ = 397.71) |
| Sub 1-60 | m/z = 395.94($C_{20}H_{10}BrClS$ = 397.71) |
| Sub 1-61 | m/z = 379.96($C_{20}H_{10}BrClO$ = 381.65) |
| Sub 1-62 | m/z = 379.96($C_{20}H_{10}BrClO$ = 381.65) |
| Sub 1-63 | m/z = 395.94($C_{20}H_{10}BrClS$ = 397.71) |
| Sub 1-64 | m/z = 395.94($C_{20}H_{10}BrClS$ = 397.71) |
| Sub 1-65 | m/z = 379.96($C_{20}H_{10}BrClO$ = 381.65) |
| Sub 1-66 | m/z = 379.96($C_{20}H_{10}BrClO$ = 381.65) |
| Sub 1-67 | m/z = 395.94($C_{20}H_{10}BrClS$ = 397.71) |
| Sub 1-68 | m/z = 395.94($C_{20}H_{10}BrClS$ = 397.71) |
| Sub 1-69 | m/z = 379.96($C_{20}H_{10}BrClO$ = 381.65) |
| Sub 1-70 | m/z = 379.96($C_{20}H_{10}BrClO$ = 381.65) |
| Sub 1-71 | m/z = 395.94($C_{20}H_{10}BrClS$ = 397.71) |
| Sub 1-72 | m/z = 395.94($C_{20}H_{10}BrClS$ = 397.71) |
| Sub 1-73 | m/z = 379.96($C_{20}H_{10}BrClO$ = 381.65) |
| Sub 1-74 | m/z = 379.96($C_{20}H_{10}BrClO$ = 381.65) |
| Sub 1-75 | m/z = 395.94($C_{20}H_{10}BrClS$ = 397.71) |
| Sub 1-76 | m/z = 395.94($C_{20}H_{10}BrClS$ = 397.71) |
| Sub 1-77 | m/z = 379.96($C_{20}H_{10}BrClO$ = 381.65) |
| Sub 1-78 | m/z = 379.96($C_{20}H_{10}BrClO$ = 381.65) |
| Sub 1-79 | m/z = 371.94($C_{18}H_{10}BrClS$ = 373.69) |
| Sub 1-80 | m/z = 405.98($C_{22}H_{12}BrClO$ = 407.69) |
| Sub 1-81 | m/z = 355.96($C_{18}H_{10}BrClO$ = 357.63) |
| Sub 1-82 | m/z = 371.94($C_{18}H_{10}BrClS$ = 373.69) |
| Sub 1-83 | m/z = 421.95($C_{22}H_{12}BrClS$ = 423.75) |
| Sub 1-84 | m/z = 477.93($C_{24}H_{12}BrClS_2$ = 479.83) |
| Sub 1-85 | m/z = 355.96($C_{18}H_{10}BrClO$ = 357.63) |
| Sub 1-86 | m/z = 371.99($C_{19}H_{14}BrClO$ = 373.67) |
| Sub 1-87 | m/z = 421.95($C_{22}H_{12}BrClS$ = 423.75) |
| Sub 1-88 | m/z = 421.95($C_{22}H_{12}BrClS$ = 423.75) |
| Sub 1-89 | m/z = 310.00($C_{14}H_{15}BrOS$ = 311.24) |
| Sub 1-90 | m/z = 310.00($C_{14}H_{15}BrOS$ = 311.24) |
| Sub 1-91 | m/z = 492.02($C_{26}H_{21}BrOS_2$ = 493.48) |
| Sub 1-92 | m/z = 327.97($C_{14}H_{14}BrClS$ = 329.68) |
| Sub 1-93 | m/z = 341.98($C_{15}H_{16}BrClS$ = 343.71) |
| Sub 1-94 | m/z = 386.03($C_{20}H_{19}BrOS$ = 387.34) |
| Sub 1-95 | m/z = 293.97($C_{13}H_{11}BrOS$ = 295.19) |
| Sub 1-96 | m/z = 311.94($C_{13}H_{10}BrClS$ = 313.64) |
| Sub 1-97 | m/z = 336.93($C_{14}H_9BrClNS$ = 338.65) |
| Sub 1-98 | m/z = 327.97($C_{14}H_{14}BrClS$ = 329.68) |
| Sub 1-99 | m/z = 311.99($C_{14}H_{14}BrClO$ = 313.62) |
| Sub 1-100 | m/z = 342.00($C_{15}H_{16}BrClO_2$ = 343.65) |
| Sub 1-101 | m/z = 311.99($C_{14}H_{14}BrClO$ = 313.62) |
| Sub 1-102 | m/z = 311.99($C_{14}H_{14}BrClO$ = 313.62) |
| Sub 1-103 | m/z = 295.96($C_{13}H_{10}BrClO$ = 297.58) |
| Sub 1-104 | m/z = 313.95($C_{13}H_9BrClFO$ = 315.57) |
| Sub 1-105 | m/z = 295.96($C_{13}H_{10}BrClO$ = 297.58) |
| Sub 1-106 | m/z = 311.99($C_{14}H_{14}BrClO$ = 313.62) |
| Sub 1-107 | m/z = 343.96($C_{14}H_{14}BrClOS$ = 345.68) |
| Sub 1-108 | m/z = 311.96($C_{13}H_{10}BrClO_2$ = 313.58) |
| Sub 1-109 | m/z = 360.02($C_{18}H_{17}BrOS$ = 361.30) |
| Sub 1-110 | m/z = 362.01($C_{18}H_{16}BrClO$ = 363.68) |
| Sub 1-111 | m/z = 345.98($C_{17}H_{12}BrClO$ = 347.64) |
| Sub 1-112 | m/z = 361.95($C_{17}H_{12}BrClS$ = 363.70) |
| Sub 1-113 | m/z = 361.95($C_{17}H_{12}BrClS$ = 363.70) |
| Sub 1-114 | m/z = 362.01($C_{18}H_{16}BrClO$ = 363.68) |

I. Synthesis of Sub 2

Sub 2 of Reaction Scheme 1 can be synthesized by the reaction route of the following Reaction Scheme 3, as disclosed in Korean Patent Registration No. 10-1251451, published on Apr. 5, 2013 and filed by the present applicant, but it is not limited thereto. In the following Reaction Scheme 3, $Z^1$ is $Ar^1$, $Ar^3$ or $Ar^5$, $Z^2$ is $Ar^2$, $Ar^4$ or $Ar^6$, and $Hal^4$ is Br or Cl.

<Reaction Scheme 3>

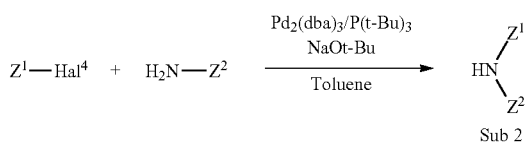

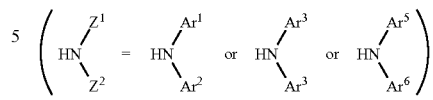

Where $Z^1$ is represented by Formula A-1 or Formula A-2, $Z^1$-$Hal^4$ of Reaction Scheme 3 may be synthesized by the reaction route of the following Reaction Scheme 4, but there is no limitation thereto. $X^2$, $R^3$ to $R^6$, o to r are the same as defined for Formula A-1 or Formula A-2, X' is —OH, —SH, —NH$_2$, one of $R^4$ and $R^6$ is $Hal^4$, and $Hal^5$ is Br or Cl.

<Reaction Scheme 4>

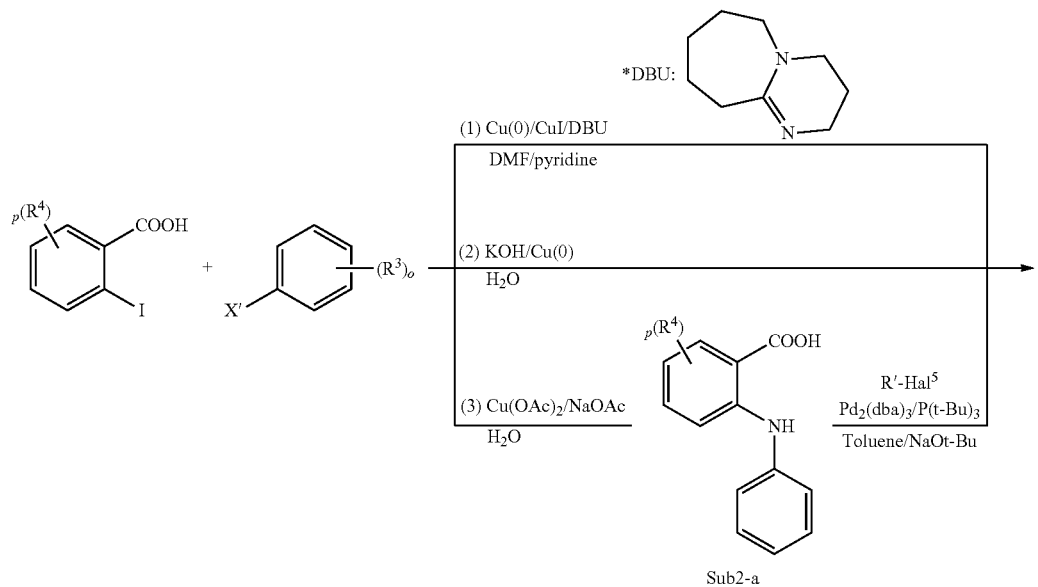

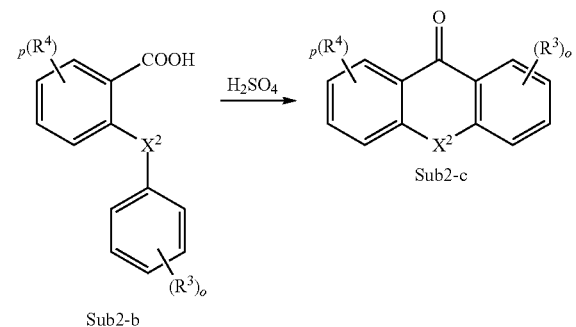

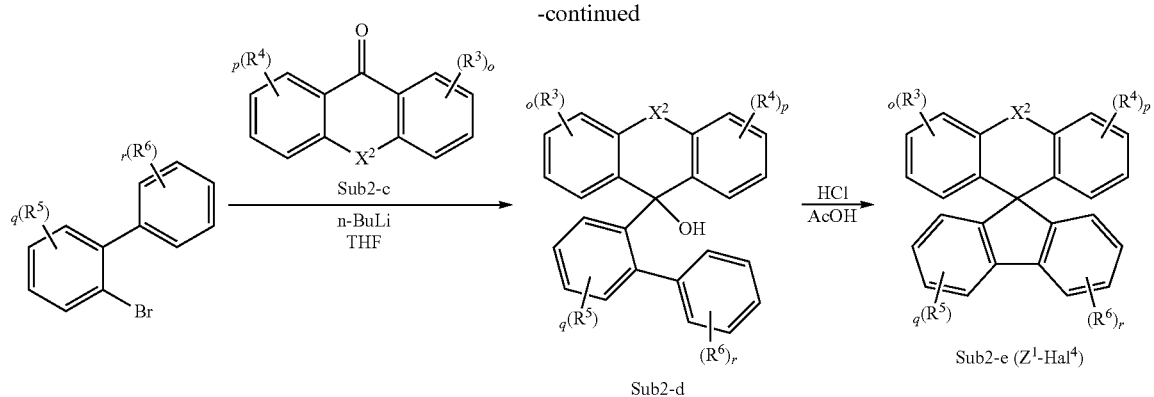

The reaction proceeds according to the synthetic route of (1) where X' is —OH, the synthetic route of (2) where X' is —SH, and the synthetic route of (3) where X' is —NH₂.

1. Synthesis Example of Sub 2-29

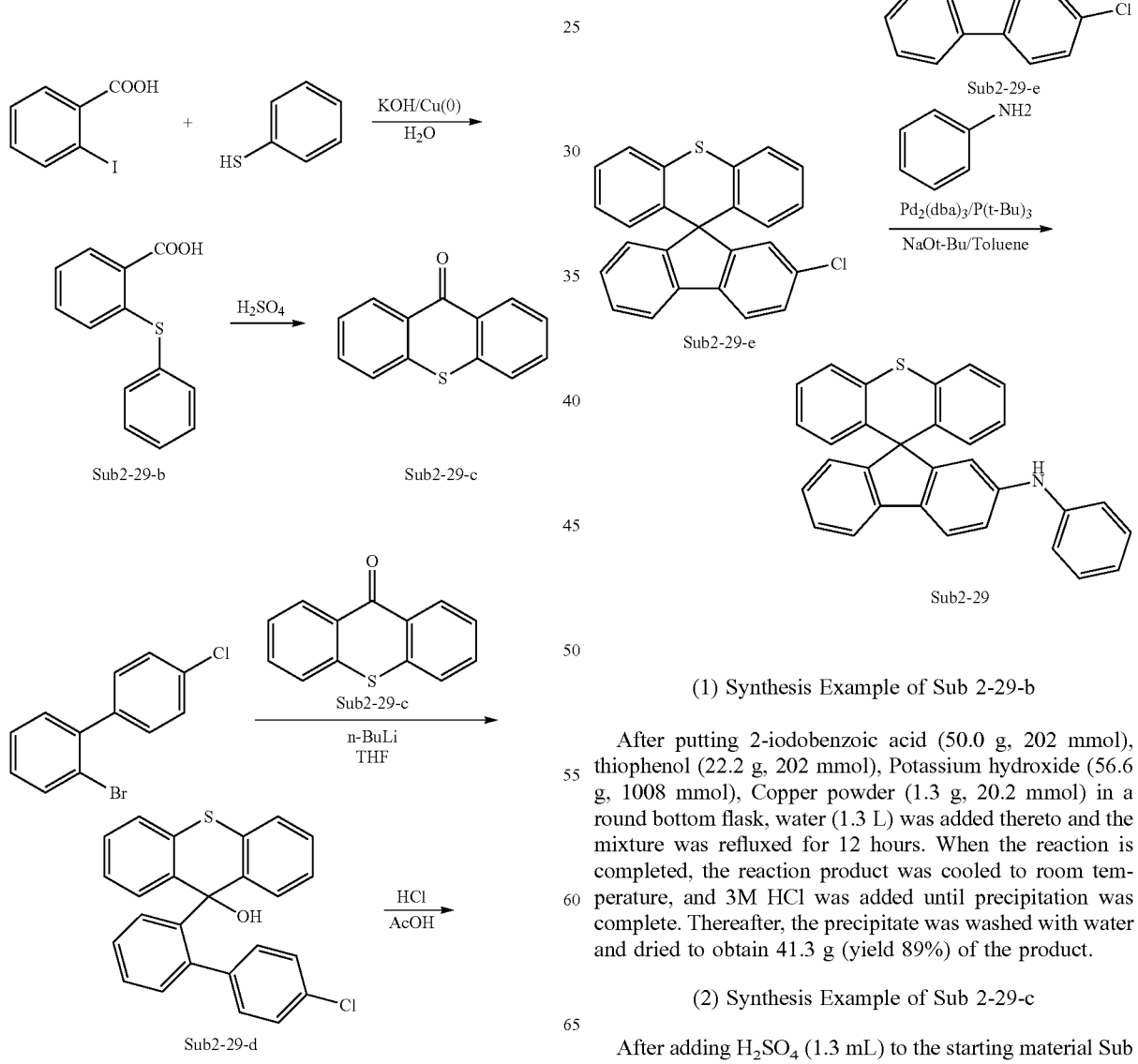

(1) Synthesis Example of Sub 2-29-b

After putting 2-iodobenzoic acid (50.0 g, 202 mmol), thiophenol (22.2 g, 202 mmol), Potassium hydroxide (56.6 g, 1008 mmol), Copper powder (1.3 g, 20.2 mmol) in a round bottom flask, water (1.3 L) was added thereto and the mixture was refluxed for 12 hours. When the reaction is completed, the reaction product was cooled to room temperature, and 3M HCl was added until precipitation was complete. Thereafter, the precipitate was washed with water and dried to obtain 41.3 g (yield 89%) of the product.

(2) Synthesis Example of Sub 2-29-c

After adding H₂SO₄ (1.3 mL) to the starting material Sub 2-29-b (41.3 g, 179 mmol), the mixture was refluxed until the starting material was dissolved. When the starting material was dissolved, the solution was cooled to room temperature and then ice water was added to precipitate. After that, the precipitate was washed with water, dried and dissolved in $CH_2Cl_2$. Then, the resultant was separated through a silica gel column and recrystallized to obtain 25.9 g (yield 68%) of the product.

(3) Synthesis Example of Sub 2-29-d 2-bromo-4'-chloro-1,1'-biphenyl (32.6 g, 122 mmol) was dissolved in THF (270 mL) under a nitrogen atmosphere, and then cooled to −78° C. Then n-BuLi (49 mL) was slowly added thereto and the mixture was stirred for 30 minutes. Subsequently, after Sub 2-29-c (25.9 g, 122 mmol) was dissolved in THF (140 mL), the solution was slowly added dropwise to the mixture. After stirring at −78° C. for one hour, the temperature was gradually raised to room temperature. When the reaction is completed, the resultant was extracted with ethyl acetate and water, and the organic layer is dried with $MgSO_4$ and concentrated. Thereafter, the concentrate was separated by a silica gel column and recrystallized to obtain 40.1 g (yield 82%) of the product.

(4) Synthesis Example of Sub 2-29-e

Sub 2-29-d (40.1 g, 100 mmol), acetic acid (250 mL) and concentrated hydrochloric acid (40 mL) were placed in a round bottom flask and stirred under nitrogen atmosphere at 60-80° C. for 3 hours. When the reaction was completed, the reaction product was extracted with $CH_2Cl_2$ and water, and the organic layer is dried with $MgSO_4$ and concentrated. Thereafter, the concentrate was separated by a silica gel column and recrystallized to obtain 31.8 g (yield 83%) of the product.

(5) Synthesis Example of Sub 2-29

After dissolving Sub 2-29-e (31.8 g, 83.0 mmol) in toluene (420 mL), aniline (7.7 g, 83.0 mmol), $Pd_2(dba)_3$ (2.28 g, 2.49 mmol), $P(t-Bu)_3$ (1.01 g, 4.98 mmol) and NaOt-Bu (16.0 g, 166 mmol)) were added and stirred at 90° C. When the reaction was completed, the reaction product was extracted with $CH_2Cl_2$ and water, and the organic layer is dried with $MgSO_4$ and concentrated. Thereafter, the concentrate was separated by a silica gel column and recrystallized to obtain 28.5 g (yield 78%) of the product.

2. Synthesis Example of Sub 2-39

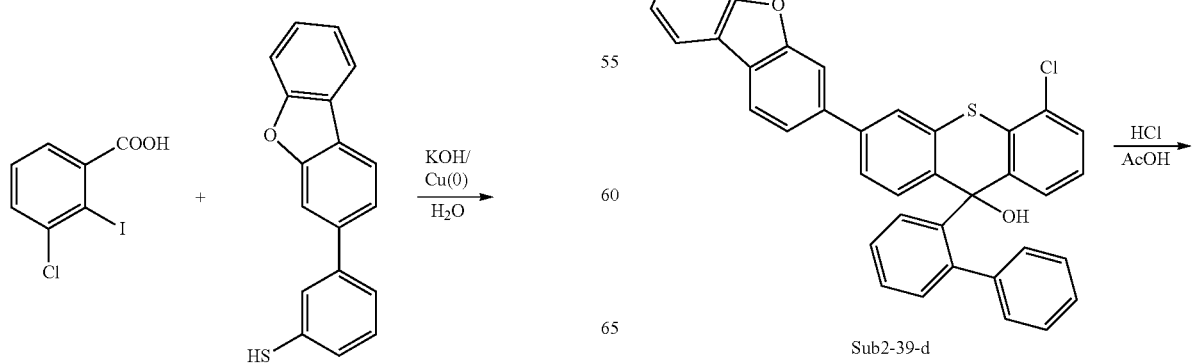

-continued

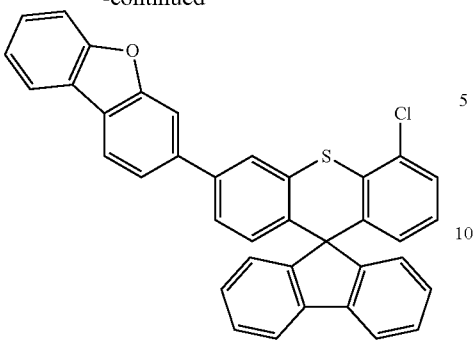

Sub2-39-e

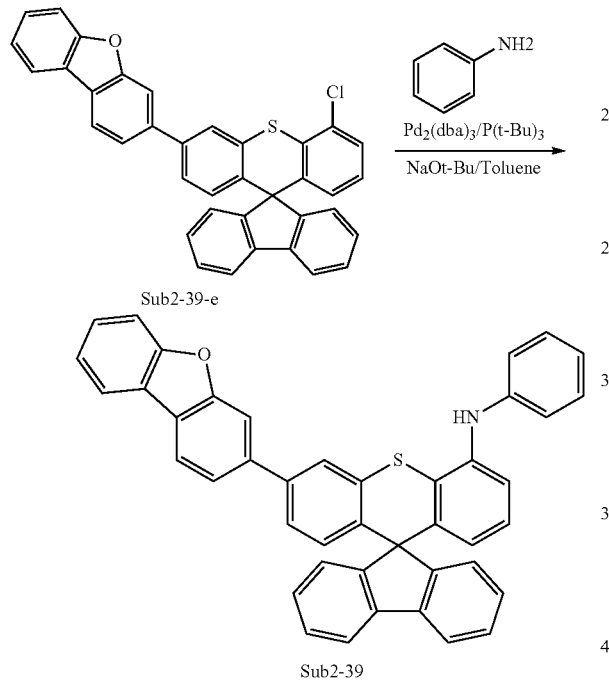

Sub2-39

(1) Synthesis Example of Sub 2-39-b

The reaction was carried out in the same manner as in the synthesis method of Sub 2-29-b using 3-chloro-2-iodobenzoic acid (20.0 g, 70.8 mmol), 3-(dibenzo[b,d]furan-3-yl)benzenethiol (19.6 g, 70.8 mmol), KOH (19.9 g, 354 mmol), Copper powder (0.45 g, 7.08 mmol) to obtain 25.6 g (yield 84%).

(2) Synthesis Example of Sub 2-39-c

The reaction was carried out in the same manner as in the synthesis method of Sub 2-29-c using Sub 2-39-b (25.6 g, 59.4 mmol), $H_2SO_4$ (420 mL) to obtain 14.7 g (yield 60%).

(3) Synthesis Example of Sub 2-39-d

The reaction was carried out in the same manner as in the synthesis method of Sub 2-29-d using 2-bromo-1,1'-biphenyl (8.3 g, 35.6 mmol), n-BuLi (14 mL), Sub 2-39-c (14.7 g, 35.6 mmol) to obtain 16.4 g (yield 81%).

(4) Synthesis Example of Sub 2-39-e

The reaction was carried out in the same manner as in the synthesis method of Sub 2-29-e using Sub 2-39-d (16.4 g, 28.8 mmol), acetic acid (72 mL) and concentrated hydrochloric acid (12 mL) to obtain 12.0 g (yield 76%).

(5) Synthesis Example of Sub 2-39

The reaction was carried out in the same manner as in the synthesis method of Sub 2-29 using Sub 2-39-e (12.0 g, 21.9 mmol), aniline (2.0 g, 21.9 mmol), $Pd_2(dba)_3$ (0.60 g, 0.66 mmol), $P(t-Bu)_3$ (0.27 g, 1.31 mmol), NaOt-Bu (4.2 g, 43.7 mmol) to obtain 9.4 g (yield 71%).

3. Synthesis Example of Sub 2-46

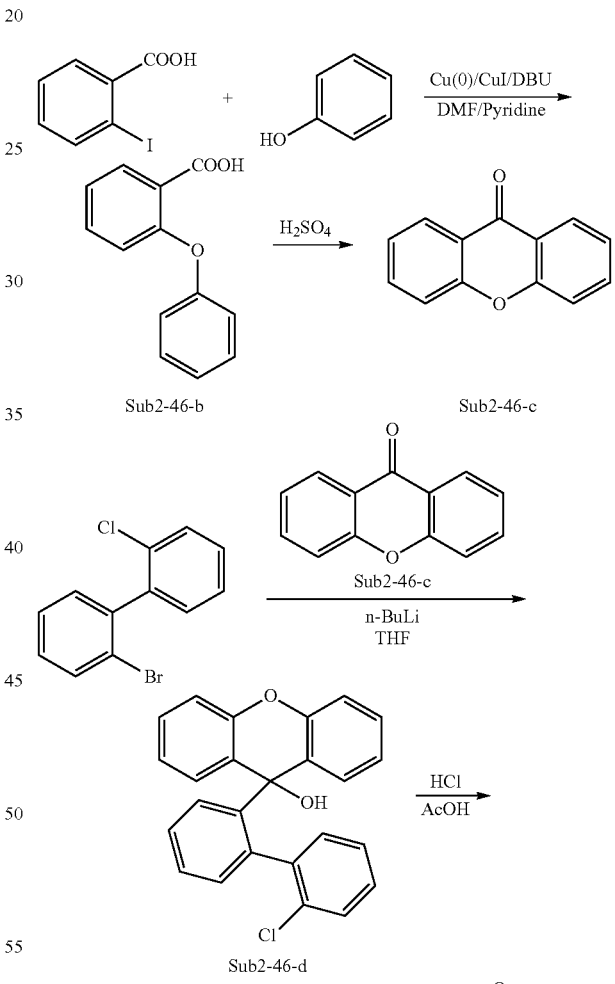

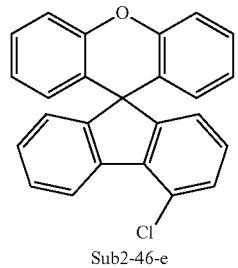

Sub2-46-e

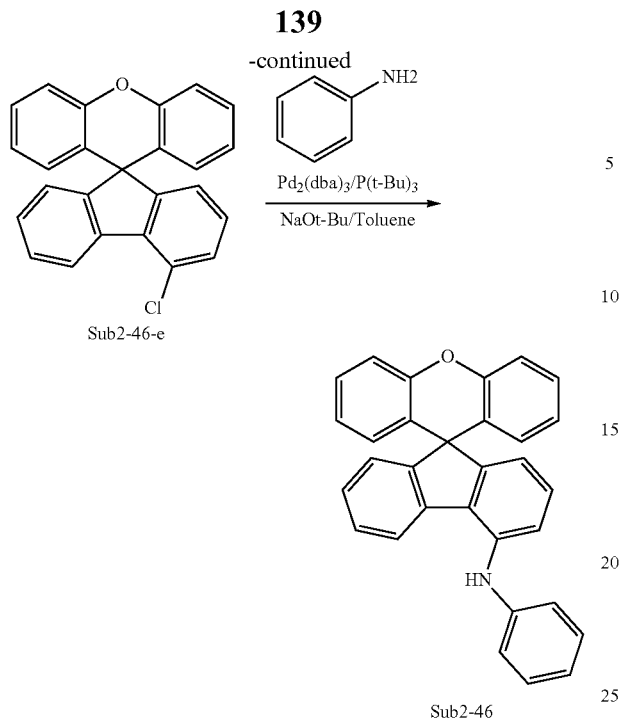

(1) Synthesis Example of Sub 2-46-b

After putting 2-iodobenzoic acid (50.0 g, 202 mmol), Phenol (37.9 g, 403 mmol), 1,8-diazabicyclo[5.4.0]undec-7-ene (DBU) (90.4 g, 605 mmol), pyridine (3.2 mL), copper powder (1.7 g, 26.2 mmol) and CuI (1.7 g, 9.07 mmol) in a round flask, DMF (1.6 L) was added thereto and the mixture was refluxed for 3 hours. When the reaction was completed, the reaction product was cooled to room temperature, and 3M HCl was added until precipitation was complete. Thereafter, the precipitate was washed with water and dried to obtain 41.8 g (yield 86%) of the product.

(2) Synthesis Example of Sub 2-46-c

The reaction was carried out in the same manner as in the synthesis method of Sub 2-29-c using Sub 2-46-b (41.8 g, 195 mmol), H₂SO₄ (14 L) to obtain 26.4 g (yield 69%) of product.

(3) Synthesis Example of Sub 2-46-d

The reaction was carried out in the same manner as in the synthesis method of Sub 2-29-d using 2-bromo-2'-chloro-1,1'-biphenyl (36.0 g, 135 mmol), n-BuLi (54 mL), Sub 2-46-c (26.4 g, 135 mmol) to obtain 45.1 g (yield 87%) of product.

(4) Synthesis Example of Sub 2-46-e

The reaction was carried out in the same manner as in the synthesis method of Sub 2-29-e using Sub 2-46-d (45.1 g, 117 mmol), acetic acid (290 mL) and concentrated hydrochloric acid (50 mL) to obtain 40.4 g (yield 94%) of product.

(5) Synthesis Example of Sub 2-46

The reaction was carried out in the same manner as in the synthesis method of Sub 2-29 using Sub 2-46-e (40.4 g, 110 mmol), aniline (10.3 g, 110 mmol), Pd₂(dba)₃ (3.03 g, 3.30 mmol), P(t-Bu)₃ (1.34 g, 6.61 mmol), NaOt-Bu (21.2 g, 220 mmol) to obtain 35.0 g (yield 75%) of product.

4. Synthesis Example of Sub 2-47

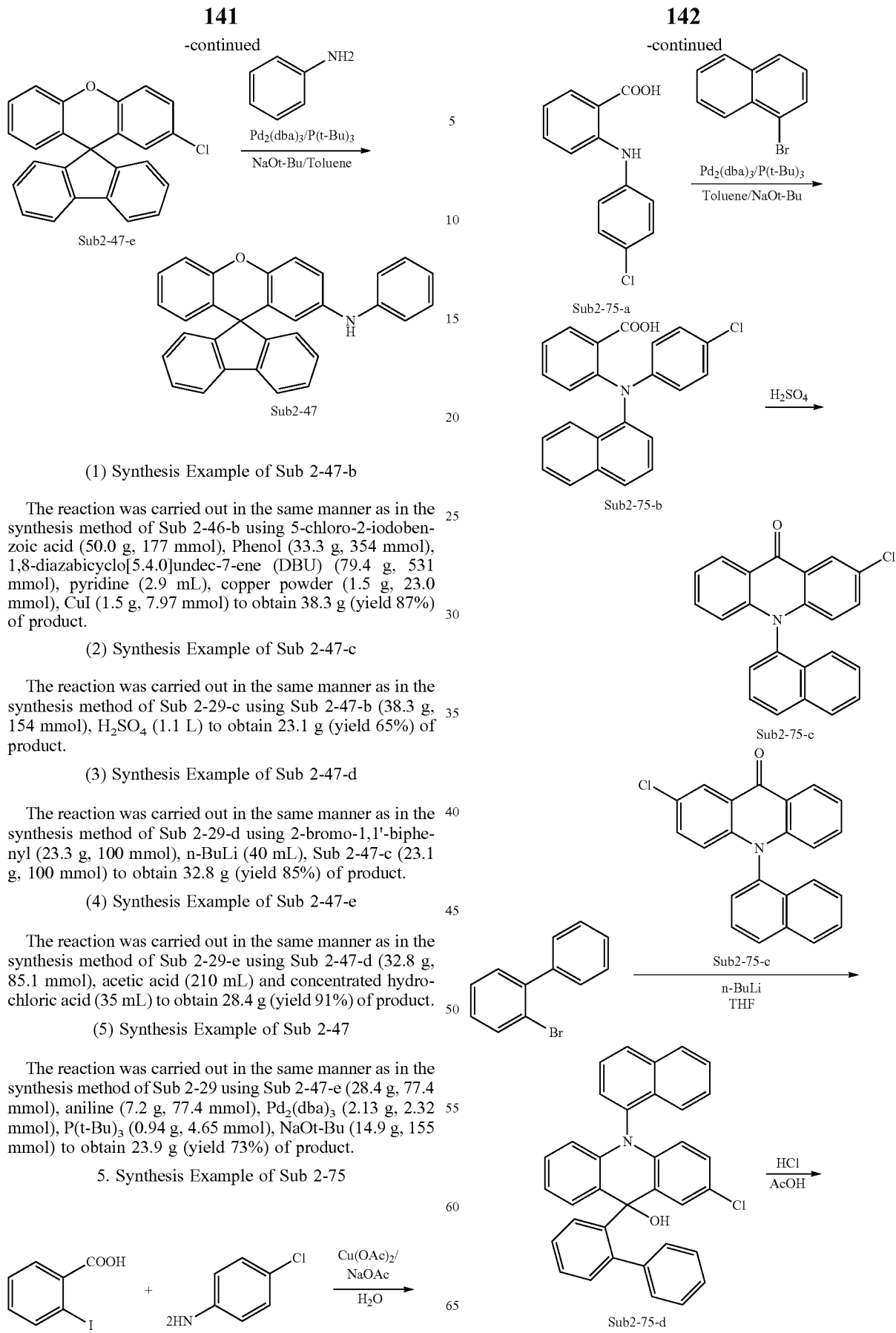

(1) Synthesis Example of Sub 2-47-b

The reaction was carried out in the same manner as in the synthesis method of Sub 2-46-b using 5-chloro-2-iodobenzoic acid (50.0 g, 177 mmol), Phenol (33.3 g, 354 mmol), 1,8-diazabicyclo[5.4.0]undec-7-ene (DBU) (79.4 g, 531 mmol), pyridine (2.9 mL), copper powder (1.5 g, 23.0 mmol), CuI (1.5 g, 7.97 mmol) to obtain 38.3 g (yield 87%) of product.

(2) Synthesis Example of Sub 2-47-c

The reaction was carried out in the same manner as in the synthesis method of Sub 2-29-c using Sub 2-47-b (38.3 g, 154 mmol), $H_2SO_4$ (1.1 L) to obtain 23.1 g (yield 65%) of product.

(3) Synthesis Example of Sub 2-47-d

The reaction was carried out in the same manner as in the synthesis method of Sub 2-29-d using 2-bromo-1,1'-biphenyl (23.3 g, 100 mmol), n-BuLi (40 mL), Sub 2-47-c (23.1 g, 100 mmol) to obtain 32.8 g (yield 85%) of product.

(4) Synthesis Example of Sub 2-47-e

The reaction was carried out in the same manner as in the synthesis method of Sub 2-29-e using Sub 2-47-d (32.8 g, 85.1 mmol), acetic acid (210 mL) and concentrated hydrochloric acid (35 mL) to obtain 28.4 g (yield 91%) of product.

(5) Synthesis Example of Sub 2-47

The reaction was carried out in the same manner as in the synthesis method of Sub 2-29 using Sub 2-47-e (28.4 g, 77.4 mmol), aniline (7.2 g, 77.4 mmol), $Pd_2(dba)_3$ (2.13 g, 2.32 mmol), $P(t-Bu)_3$ (0.94 g, 4.65 mmol), NaOt-Bu (14.9 g, 155 mmol) to obtain 23.9 g (yield 73%) of product.

5. Synthesis Example of Sub 2-75

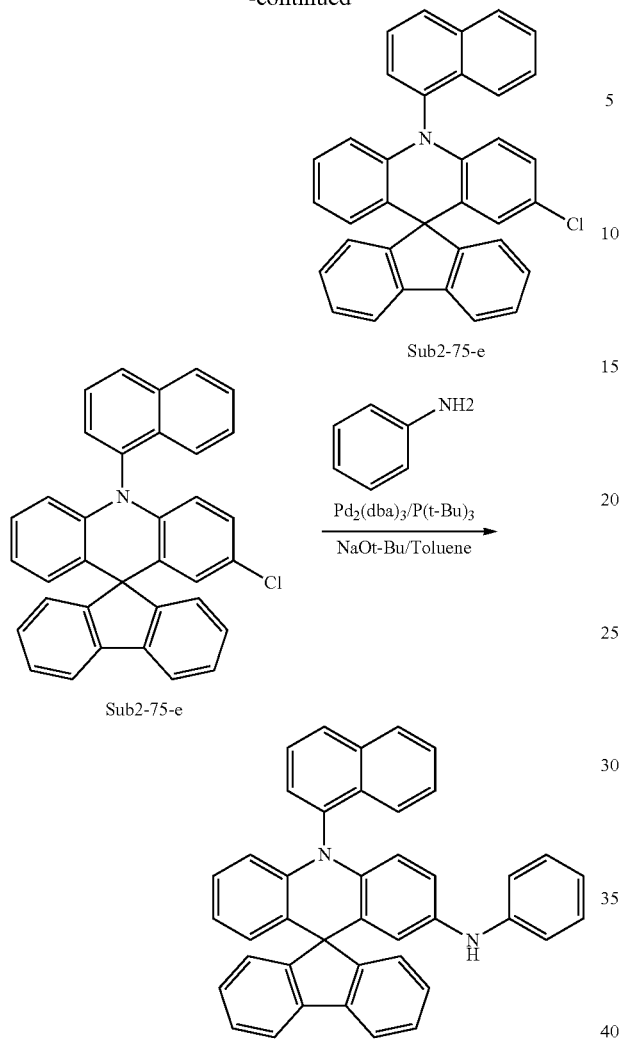

(1) Synthesis Example of Sub 2-75-a

After putting 2-iodobenzoic acid (20.0 g, 80.6 mmol), 4-chloroaniline (20.6 g, 161 mmol), Cu(OAc)$_2$ (1.0 g), Sodium acetate (7.9 g, 96.8 mmol) in a round flask, water (540 mL) was added thereto and the mixture was refluxed for 5 hours. When the reaction was completed, the reaction product was cooled to room temperature, and 3M HCl was added until precipitation was complete. Thereafter, the precipitate was washed with water and dried to obtain 16.4 g (yield 82%) of the product.

(2) Synthesis Example of Sub 2-75-b

After dissolving Sub 2-75-a (16.4 g, 66.2 mmol) in toluene (330 ml), 1-bromonaphthalene (13.7 g, 66.2 mmol), Pd$_2$(dba)$_3$ (1.82 g, 1.99 mmol), P(t-Bu)$_3$ (0.80 g, 3.97 mmol) and NaOt-Bu (12.7 g, 132 mmol) were added the solution and the mixture was stirred at 60° C. When the reaction was completed, the reaction product was extracted with CH$_2$Cl$_2$ and water, and the organic layer was dried with MgSO$_4$ and concentrated. Thereafter, the concentrate was separated by a silica gel column and recrystallized to obtain 18.3 g (yield 74%) of the product.

(3) Synthesis Example of Sub 2-75-c

The reaction was carried out in the same manner as in the synthesis method of Sub 2-29-c using Sub 2-75-b (18.3 g, 49.0 mmol), H$_2$SO$_4$ (350 mL) to obtain 11.8 g (yield 68%) of product.

(4) Synthesis Example of Sub 2-75-d

The reaction was carried out in the same manner as in the synthesis method of Sub 2-29-d using 2-bromo-2'-chloro-1,1'-biphenyl (7.7 g, 33.2 mmol), n-BuLi (13 mL), Sub 2-75-c (11.8 g, 33.2 mmol) to obtain 13.9 g (yield 82%) of product.

(5) Synthesis Example of Sub 2-75-e

The reaction was carried out in the same manner as in the synthesis method of Sub 2-29-e using Sub 2-75-d (13.9 g, 27.2 mmol), acetic acid (68 mL) and concentrated hydrochloric acid (11 mL) to obtain 12.3 g (yield 92%) of product.

(6) Synthesis Example of Sub 2-75

The reaction was carried out in the same manner as in the synthesis method of Sub 2-29 using Sub 2-75-e (12.3 g, 25.0 mmol), aniline (2.3 g, 25.0 mmol), Pd$_2$(dba)$_3$ (0.69 g, 0.75 mmol), P(t-Bu)$_3$ (0.30 g, 1.50 mmol), NaOt-Bu (4.8 g, 50.0 mmol) to obtain 10.7 g (yield 78%) of product.

6. Synthesis Example of Sub 2-81

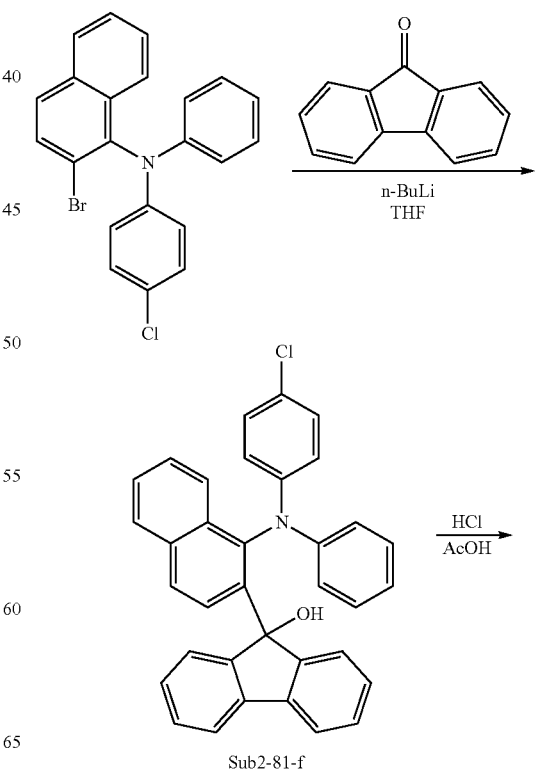

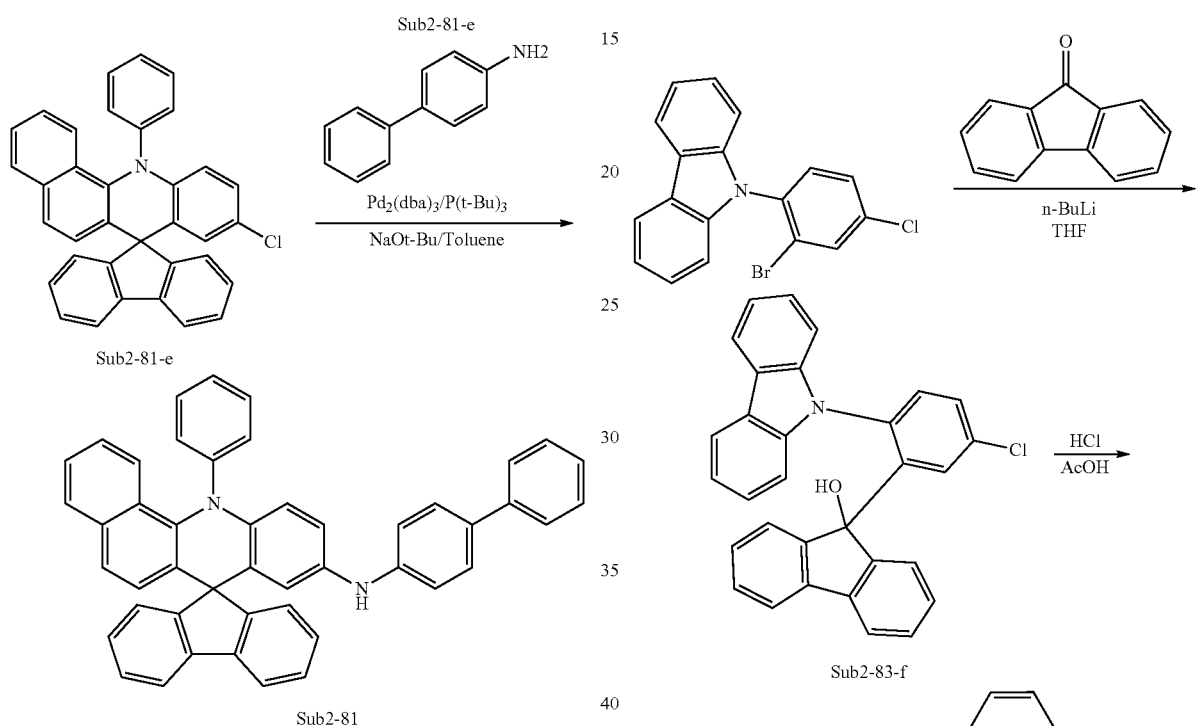

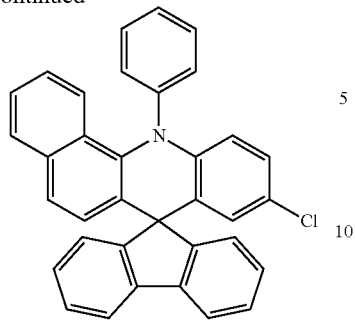

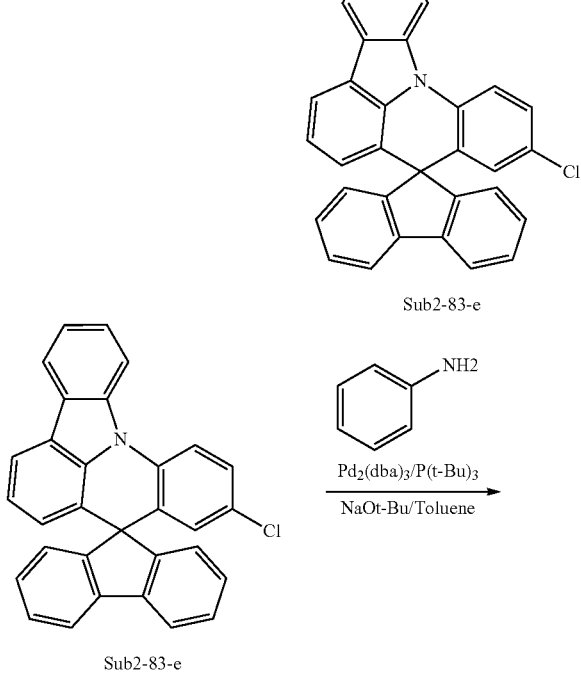

(3) Synthesis Example of Sub 2-81

The reaction was carried out in the same manner as in the synthesis method of Sub 2-29 using Sub 2-81-e (9.8 g, 19.9 mmol), [1,1'-biphenyl]-4-amine (3.4 g, 19.9 mmol), Pd$_2$(dba)$_3$ (0.55 g, 0.60 mmol), P(t-Bu)$_3$ (0.24 g, 1.20 mmol), NaOt-Bu (3.8 g, 39.8 mmol) to obtain 9.5 g (yield 76%) of product.

7. Synthesis Example of Sub 2-83

(1) Synthesis Example of Sub 2-81-f 2-bromo-N-(4-chlorophenyl)-N-phenylnaphthalen-1-amine (20.0 g, 48.9 mmol) was dissolved in THF (100 mL) under a nitrogen atmosphere, and then cooled to −78° C. Then n-BuLi (20 mL) was slowly added thereto and the mixture was stirred for 30 minutes. Subsequently, after 9H-fluoren-9-one (8.8 g, 48.9 mmol) was dissolved in THF (60 mL), the solution was slowly added dropwise to the mixture. After stirring at −78° C. for one hour, the temperature was gradually raised to room temperature. When the reaction is completed, the resultant was extracted with ethyl acetate and water, and the organic layer is dried with MgSO$_4$ and concentrated. Thereafter, the concentrate was separated by a silica gel column and recrystallized to obtain 21.2 g (yield 85%) of the product.

(2) Synthesis Example of Sub 2-81-e

The reaction was carried out in the same manner as in the synthesis method of Sub 2-29-e using Sub 2-81-f (21.2 g, 41.6 mmol), acetic acid (100 mL) and concentrated hydrochloric acid (20 mL) to obtain 9.8 g (yield 48%) of product.

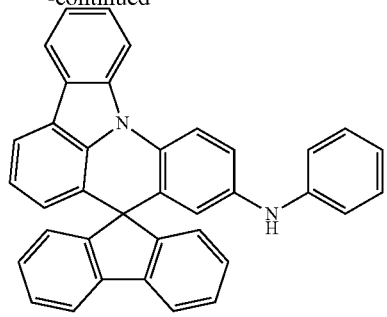
Sub2-83

(1) Synthesis Example of Sub 2-83-f

The reaction was carried out in the same manner as in the synthesis method of Sub 2-81-f using 9-(2-bromo-4-chlorophenyl)-9H-carbazole (20.0 g, 56.1 mmol), n-BuLi (22 mL), 9H-fluoren-9-one (10.1 g, 56.1 mmol) to obtain 22.3 g (yield 81%) of product.

(2) Synthesis Example of Sub 2-83-e

The reaction was carried out in the same manner as in the synthesis method of Sub 2-29-e using Sub 2-83-f (22.3 g, 45.4 mmol), acetic acid (110 mL) and concentrated hydrochloric acid (20 mL) to obtain 17.8 g (yield 89%) of product.

(3) Synthesis Example of Sub 2-83

The reaction was carried out in the same manner as in the synthesis method of Sub 2-29 using Sub 2-83-e (17.8 g, 40.5 mmol), aniline (3.8 g, 40.5 mmol), Pd$_2$(dba)$_3$ (1.11 g, 1.21 mmol), P(t-Bu)$_3$ (0.49 g, 2.43 mmol), NaOt-Bu (7.8 g, 80.9 mmol) to obtain 14.3 g (yield 71%) of product.

The compounds belonging to Sub 2 may be, but not limited to, the following compounds, and Table 2 shows FD-MS (Field Desorption-Mass Spectrometry) values of the following compounds.

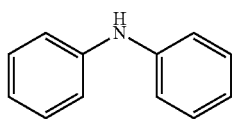
Sub2-1

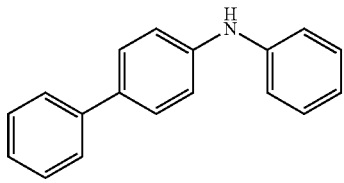
Sub2-2

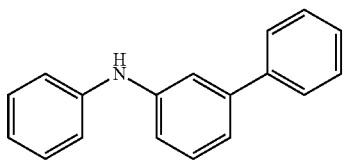
Sub2-3

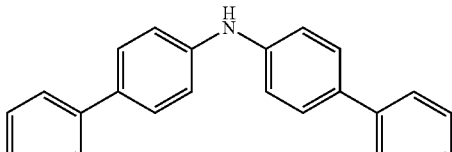
Sub2-4

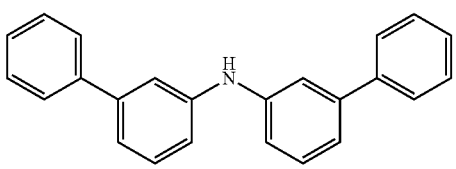
Sub2-5

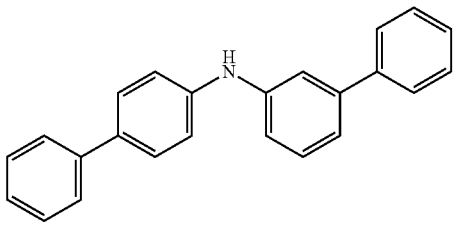
Sub2-6

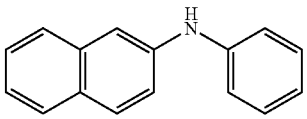
Sub2-7

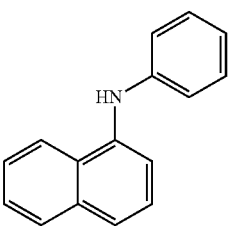
Sub2-8

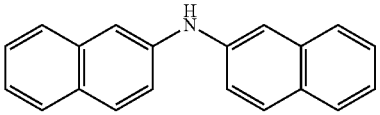
Sub2-9

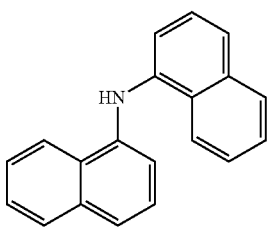
Sub2-10

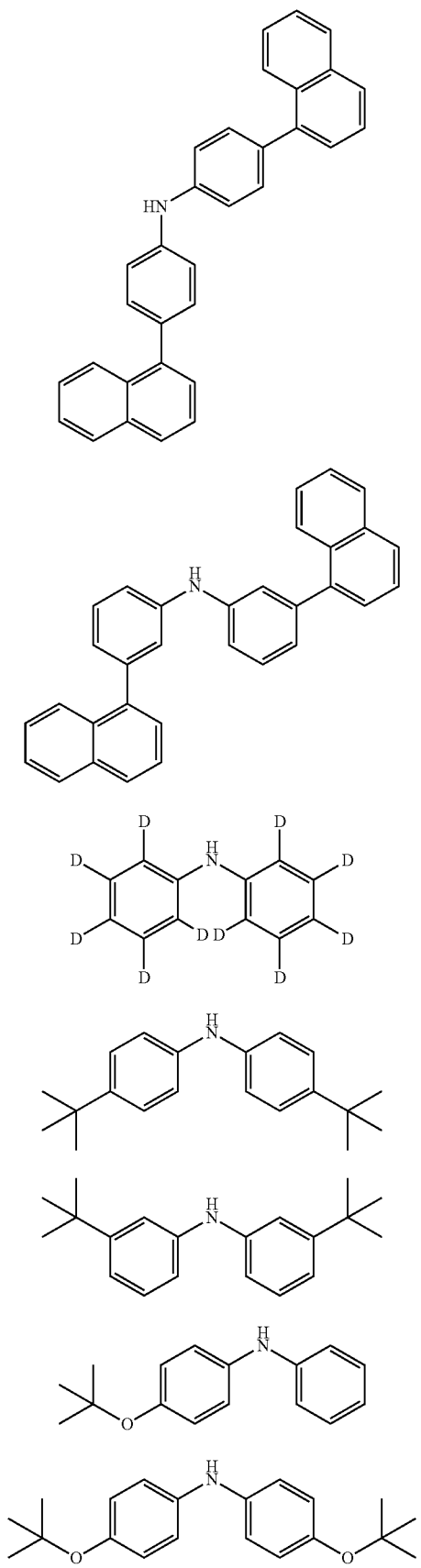
Sub2-11
Sub2-12
Sub2-13
Sub2-14
Sub2-15
Sub2-16
Sub2-17
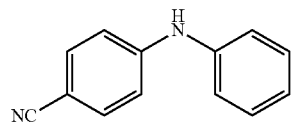
Sub2-18
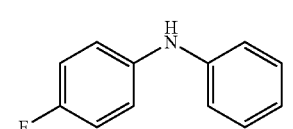
Sub2-19
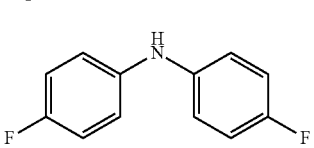
Sub2-20
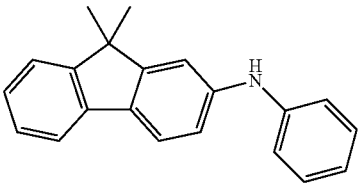
Sub2-21
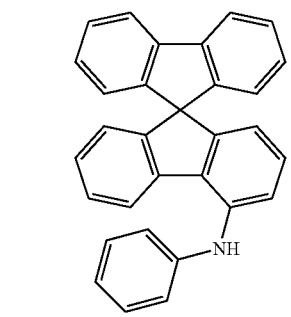
Sub2-22
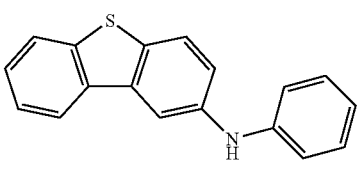
Sub2-23
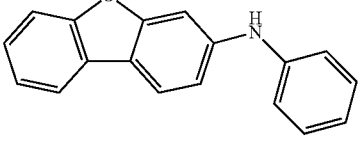
Sub2-24
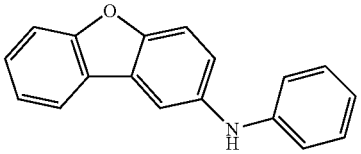
Sub2-25
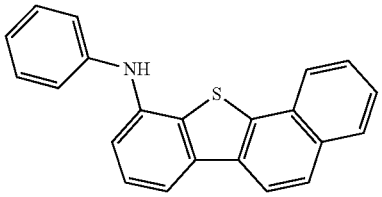
Sub2-26

-continued
Sub2-27
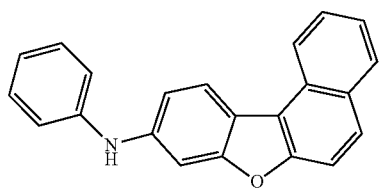
Sub2-28
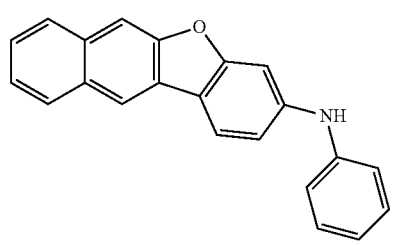
Sub2-29
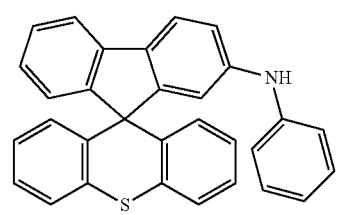
Sub2-30
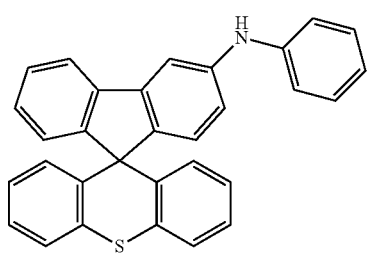
Sub2-31
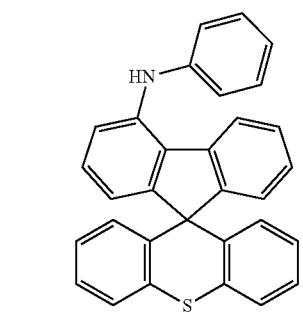
Sub2-32
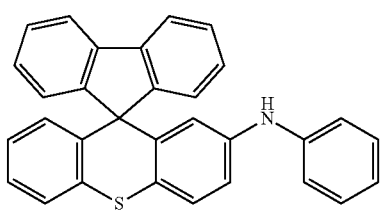
-continued
Sub2-33
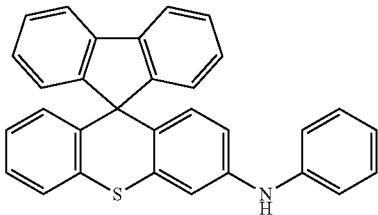
Sub2-34
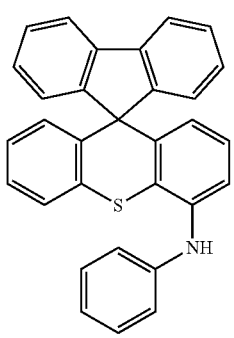
Sub2-35
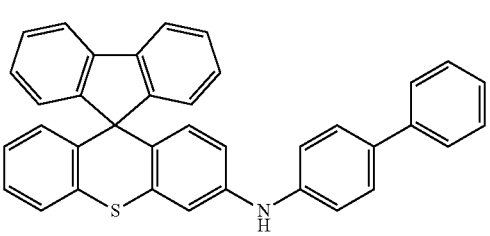
Sub2-36
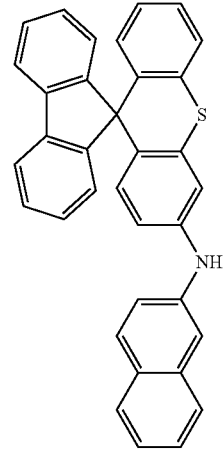
Sub2-37
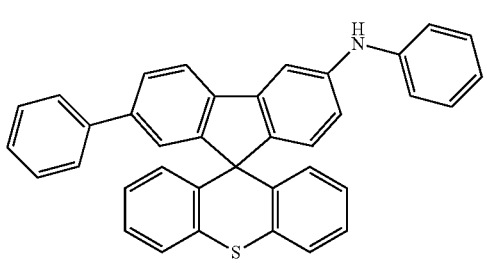

-continued
Sub2-38
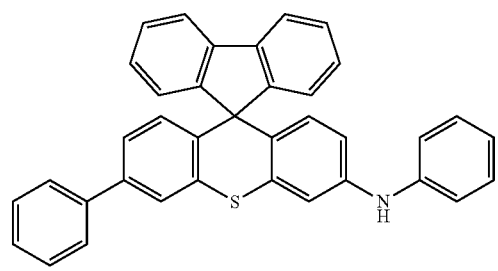
Sub2-39
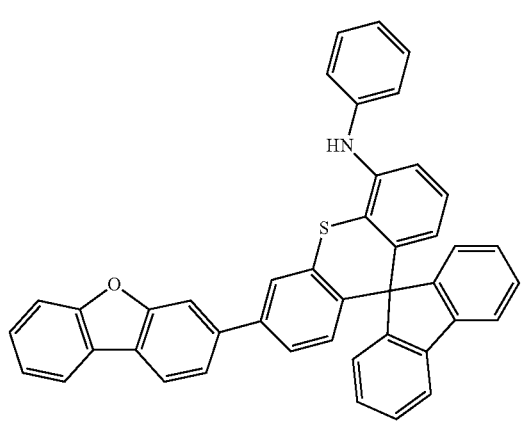
Sub2-40
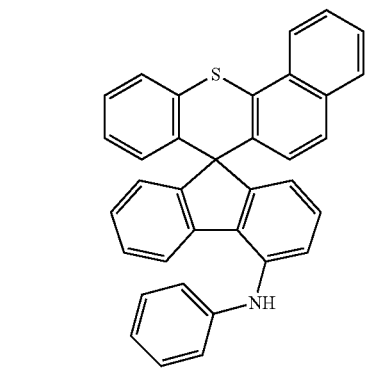
Sub2-41
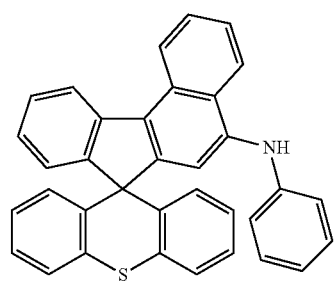
Sub2-42
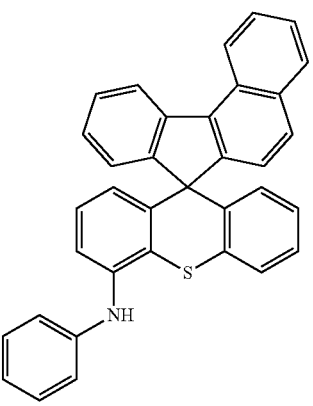
Sub2-43
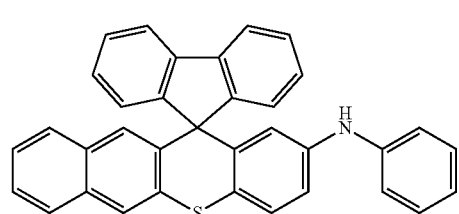
Sub2-44
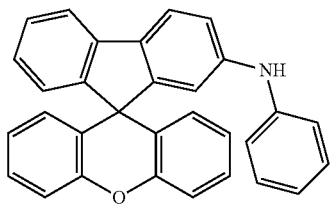
Sub2-45
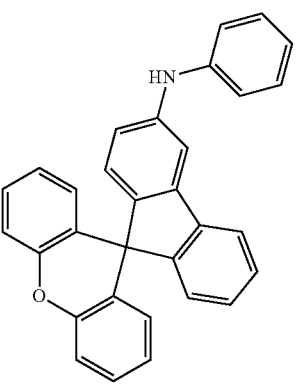
Sub2-46
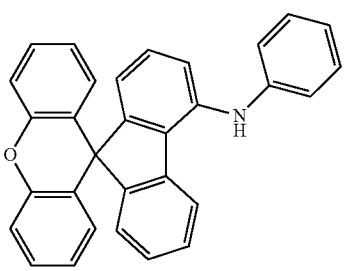

Sub2-47
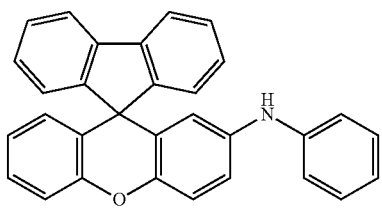
Sub2-48
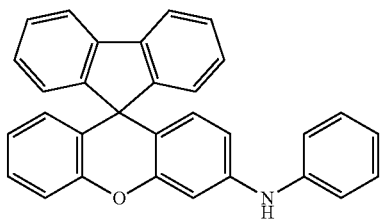
Sub2-49
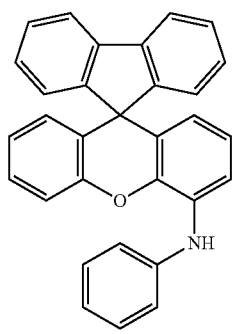
Sub2-50
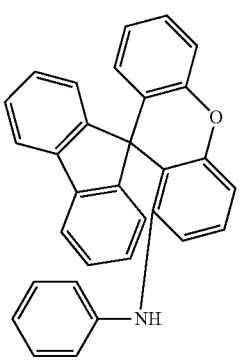
Sub2-51
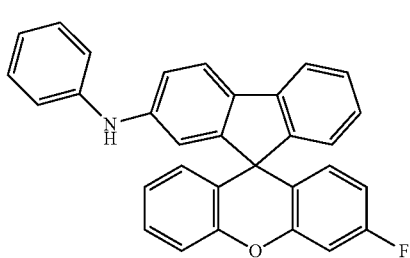
Sub2-52
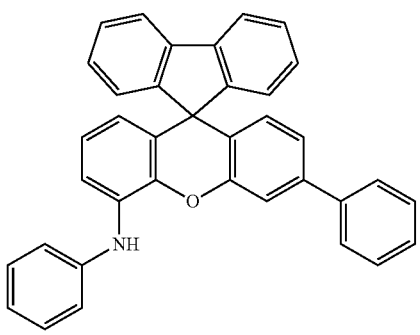
Sub2-53
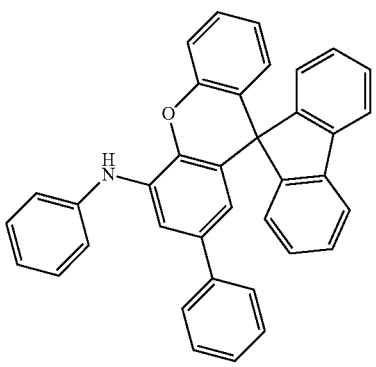
Sub2-54
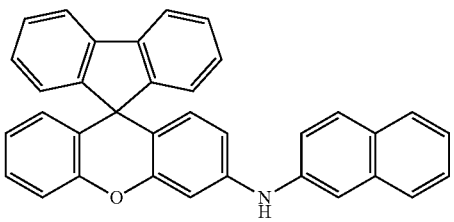
Sub2-55
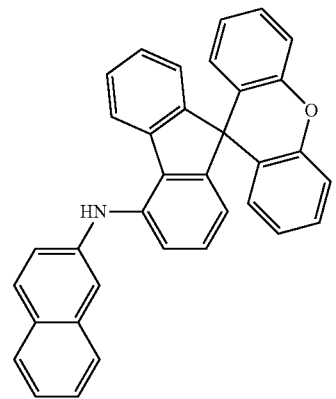

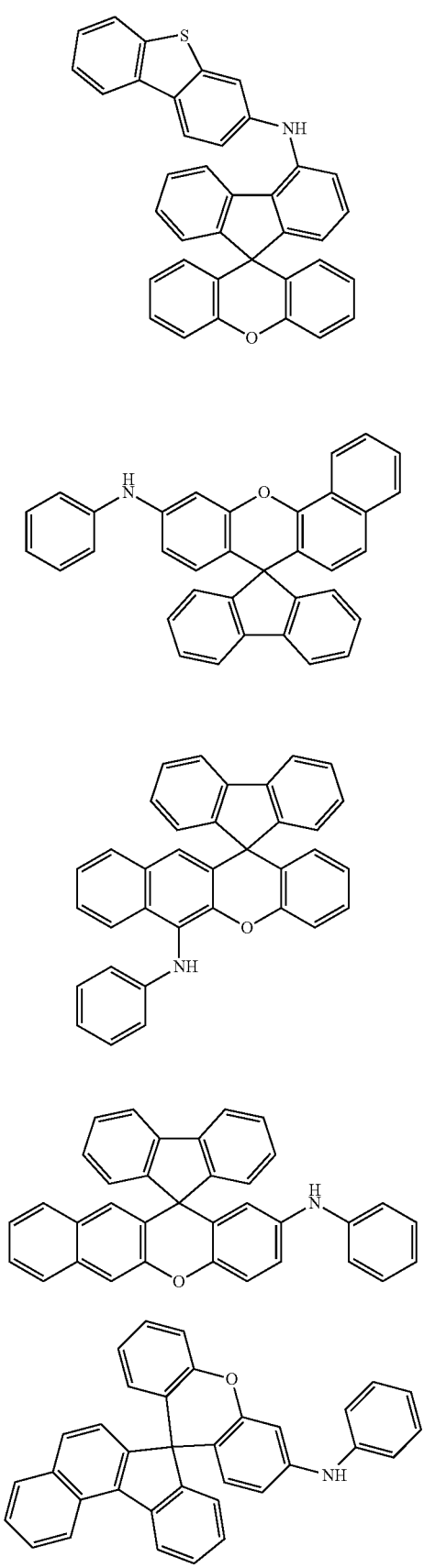
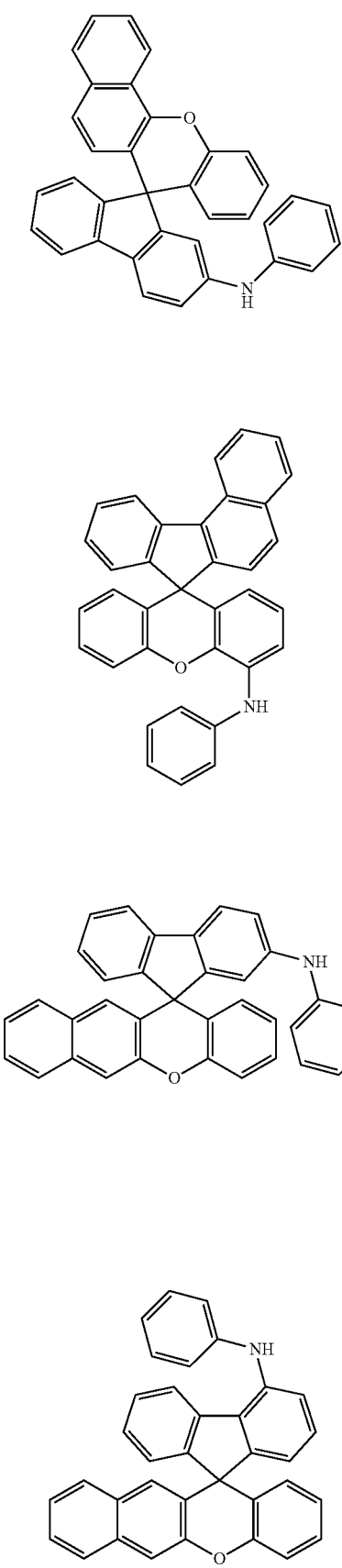

Sub2-65
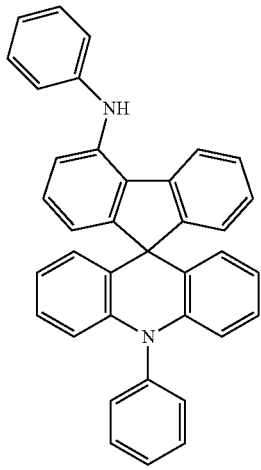
Sub2-66
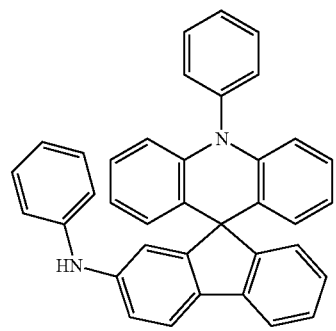
Sub2-67
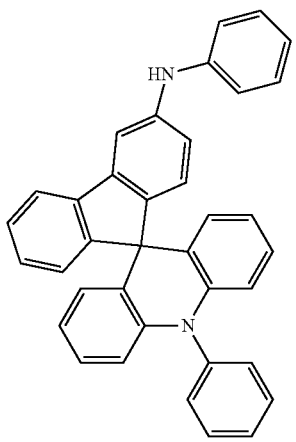
Sub2-68
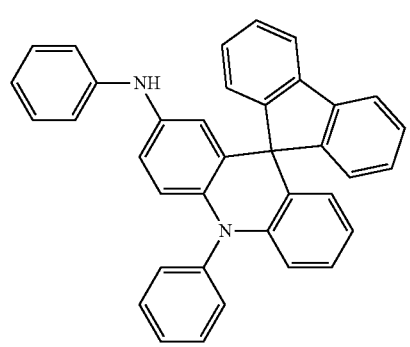
Sub2-69
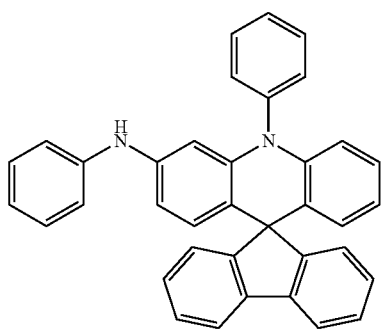
Sub2-70
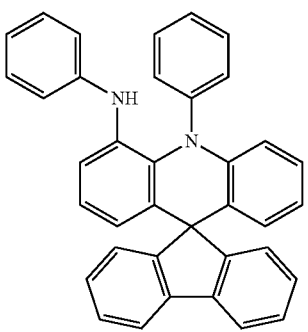
Sub2-71
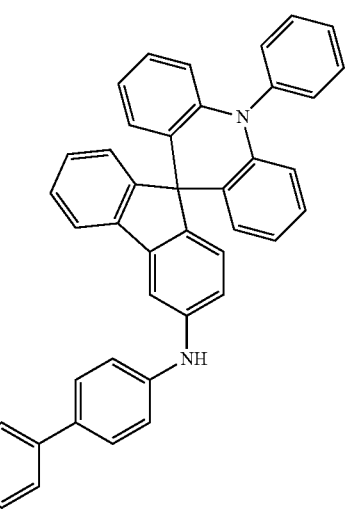

Sub2-72
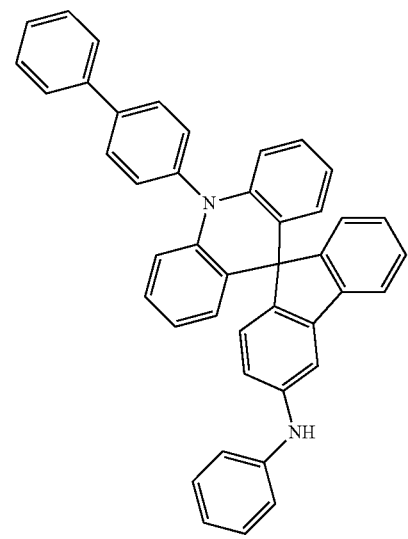
Sub2-76
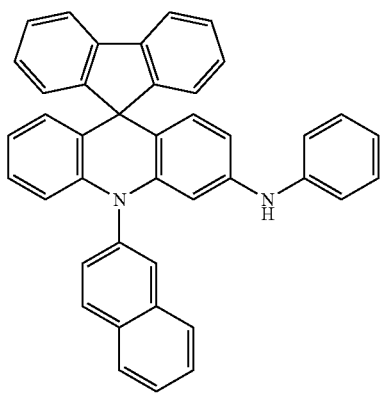
Sub2-73
Sub2-77
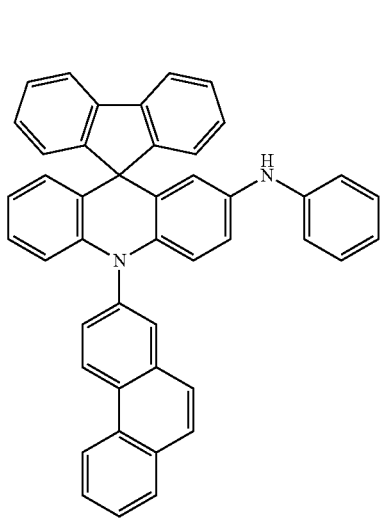
Sub2-74
Sub2-75
Sub2-78
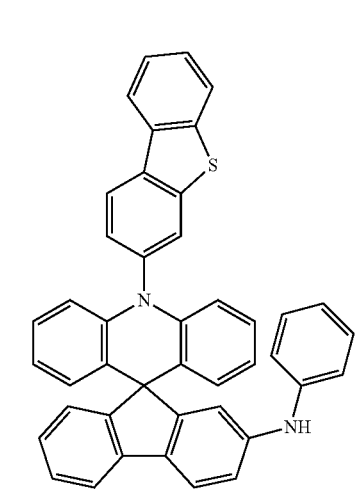

Sub2-79
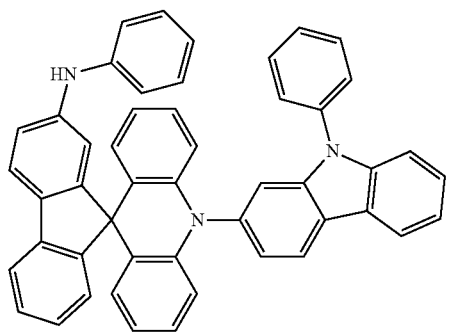
Sub2-80
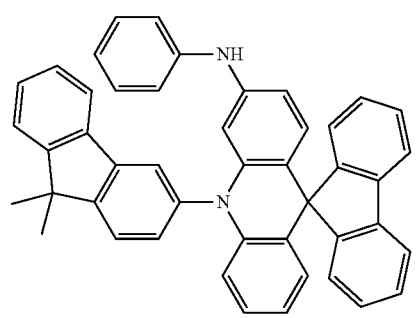
Sub2-81
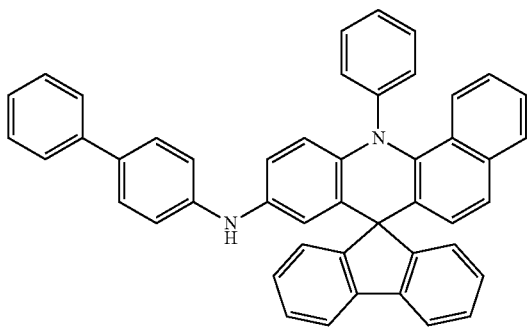
Sub2-82
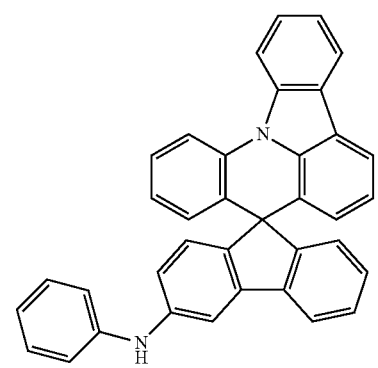
Sub2-83
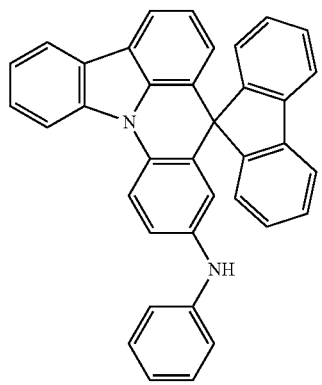
Sub2-84
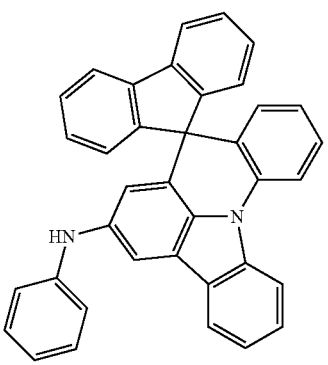
Sub2-85
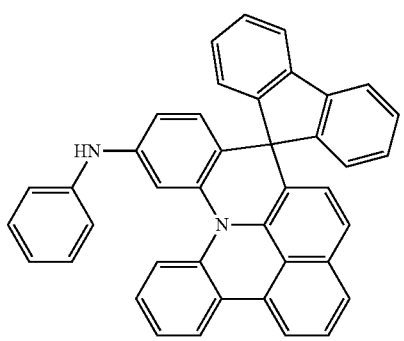
Sub2-86
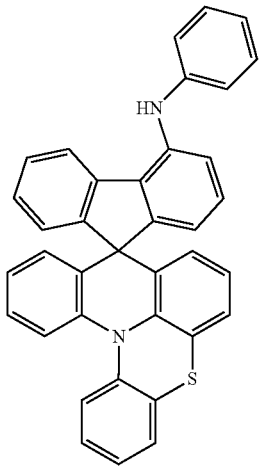

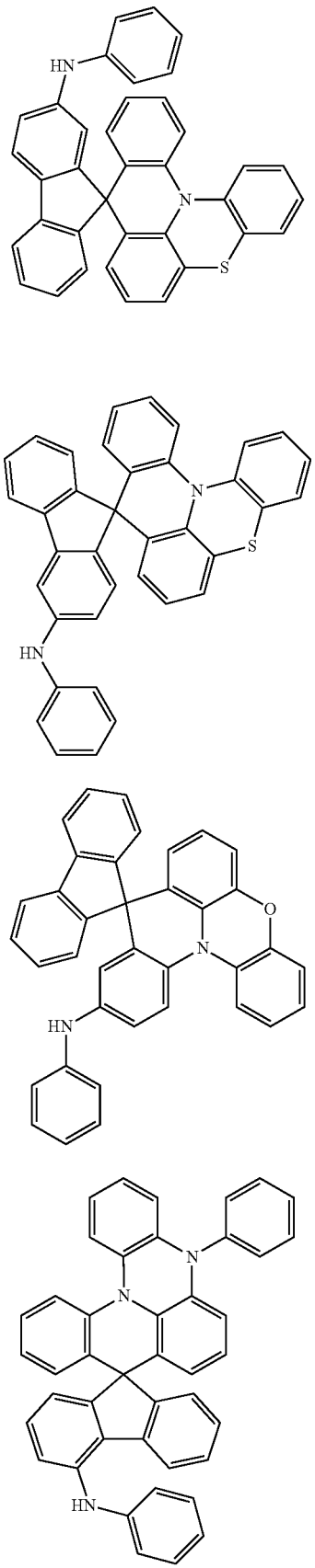

Sub2-87

Sub2-88

Sub2-89

Sub2-90

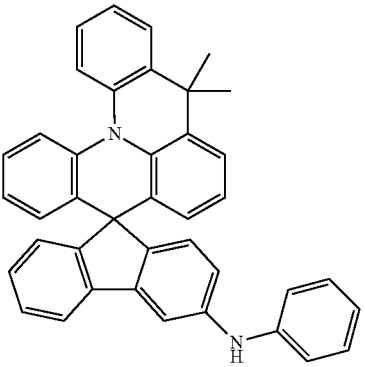

Sub2-91

TABLE 2

| OwOHHd | FD-MS |
|---|---|
| Sub 2-1 | m/z = 169.09($C_{12}H_{11}N$ = 169.23) |
| Sub 2-2 | m/z = 245.12($C_{18}H_{15}N$ = 245.33) |
| Sub 2-3 | m/z = 245.12($C_{18}H_{15}N$ = 245.33) |
| Sub 2-4 | m/z = 321.15($C_{24}H_{19}N$ = 321.42) |
| Sub 2-5 | m/2 = 321.15($C_{24}H_{19}N$ = 321.42) |
| Sub 2-6 | m/z = 321.15($C_{24}H_{19}N$ = 321.42) |
| Sub 2-7 | m/z = 219.10($C_{16}H_{13}N$ = = 219.29) |
| Sub 2-8 | m/z = 219.10($C_{16}H_{13}N$ = 219.29) |
| Sub 2-9 | m/z = 269.12($C_{20}H_{15}N$ = 269.35) |
| Sub 2-10 | m/z = 269.12($C_{20}H_{15}N$ = 269.35) |
| Sub 2-11 | m/z = 421.18($C_{32}H_{23}N$ = 421.54) |
| Sub 2-12 | m/z = 421.18($C_{32}H_{23}N$ = 421.54) |
| Sub 2-13 | m/z = 179.15($C_{12}HD_{10}N$ = 179.29) |
| Sub 2-14 | m/z = 281.21($C_{20}H_{27}N$ = 281.44) |
| Sub 2-15 | m/z = 281.21($C_{20}H_{27}N$ = 281.44) |
| Sub 2-16 | m/z = 241.15($C_{16}H_{19}NO$ = 241.33) |
| Sub 2-17 | m/z = 313.20($C_{20}H_{27}NO_2$ = 313.44) |
| Sub 2-18 | m/z = 194.08($C_{13}H_{10}N_2$ = 194.24) |
| Sub 2-19 | m/z = 187.08($C_{12}H_{10}FN$ = 187.22) |
| Sub 2-20 | m/z = 205.07($C_{12}H_9F_2N$ = 205.21) |
| Sub 2-21 | m/z = 285.15($C_{21}H_{19}N$ = 285.39) |
| Sub 2-22 | m/z = 407.17($C_{31}H_{21}N$ = 407.52) |
| Sub 2-23 | m/z = 275.08($C_{18}H_{13}NS$ = 275.37) |
| Sub 2-24 | m/z = 259.10($C_{18}H_{13}NO$ = 259.31) |
| Sub 2-25 | m/z = 259.10($C_{18}H_{13}NO$ = 259.31) |
| Sub 2-26 | m/z = 325.09($C_{22}H_{15}NS$ = 325.43) |
| Sub 2-27 | m/z = 309.12($C_{22}H_{15}NO$ = 309.37) |
| Sub 2-28 | m/z = 309.12($C_{22}H_{15}NO$ = 309.37) |
| Sub 2-29 | m/z = 439.14($C_{31}H_{21}NS$ = 439.58) |
| Sub 2-30 | m/z = 439.14($C_{31}H_{21}NS$ = 439.58) |
| Sub 2-31 | m/z = 439.14($C_{31}H_{21}NS$ = 439.58) |
| Sub 2-32 | m/z = 439.14($C_{31}H_{21}NS$ = 439.58) |
| Sub 2-33 | m/z = 439.14($C_{31}H_{21}NS$ = 439.58) |
| Sub 2-34 | m/z = 439.14($C_{31}H_{21}NS$ = 439.58) |
| Sub 2-35 | m/z = 515.17($C_{37}H_{25}NS$ = 515.67) |
| Sub 2-36 | m/z = 489.16($C_{35}H_{23}NS$ = 489.64) |
| Sub 2-37 | m/z = 515.17($C_{37}H_{25}NS$ = 515.67) |
| Sub 2-38 | m/z = 515.17($C_{37}H_{25}NS$ = 515.67) |
| Sub 2-39 | m/z = 605.18($C_{43}H_{27}NOS$ = 605.76) |
| Sub 2-40 | m/z = 489.16($C_{35}H_{23}NS$ = 489.64) |
| Sub 2-41 | m/z = 489.16($C_{35}H_{23}NS$ = 489.64) |
| Sub 2-42 | m/z = 489.16($C_{35}H_{23}NS$ = 489.64) |
| Sub 2-43 | m/z = 489.16($C_{35}H_{23}NS$ = 489.64) |
| Sub 2-44 | m/z = 423.16($C_{31}H_{21}NO$ = 423.52) |
| Sub 2-45 | m/z = 423.16($C_{31}H_{21}NO$ = 423.52) |
| Sub 2-46 | m/z = 423.16($C_{31}H_{21}NO$ = 423.52) |
| Sub 2-47 | m/z = 423.16($C_{31}H_{21}NO$ = 423.52) |
| Sub 2-48 | m/z = 423.16($C_{31}H_{21}NO$ = 423.52) |
| Sub 2-49 | m/z = 423.16($C_{31}H_{21}NO$ = 423.52) |
| Sub 2-50 | m/z = 423.16($C_{31}H_{21}NO$ = 423.52) |
| Sub 2-51 | m/z = 441.15($C_{31}H_{20}FNO$ = 441.51) |
| Sub 2-52 | m/z = 499.19($C_{37}H_{25}NO$ = 499.61) |
| Sub 2-53 | m/z = 499.19($C_{37}H_{25}NO$ = 499.61) |
| Sub 2-54 | m/z = 473.18($C_{35}H_{23}NO$ = 473.58) |
| Sub 2-55 | m/z = 473.18($C_{35}H_{23}NO$ = 473.58) |

TABLE 2-continued

| OwOHHd | FD-MS |
|---|---|
| Sub 2-56 | m/z = 529.15($C_{37}H_{23}NOS$ = 529.66) |
| Sub 2-57 | m/z = 473.18($C_{35}H_{23}NO$ = 473.58) |
| Sub 2-58 | m/z = 473.18($C_{35}H_{23}NO$ = 473.58) |
| Sub 2-59 | m/z = 473.18($C_{35}H_{23}NO$ = 473.58) |
| Sub 2-60 | m/z = 473.18($C_{35}H_{23}NO$ = 473.58) |
| Sub 2-61 | m/z = 473.18($C_{35}H_{23}NO$ = 473.58) |
| Sub 2-62 | m/z = 473.18($C_{35}H_{23}NO$ = 473.58) |
| Sub 2-63 | m/z = 473.18($C_{35}H_{23}NO$ = 473.58) |
| Sub 2-64 | m/z = 473.18($C_{35}H_{23}NO$ = 473.58) |
| Sub 2-65 | m/z = 498.21($C_{37}H_{26}N_2$ = 498.63) |
| Sub 2-66 | m/z = 498.21($C_{37}H_{26}N_2$ = 498.63) |
| Sub 2-67 | m/z = 498.21($C_{37}H_{26}N_2$ = 498.63) |
| Sub 2-68 | m/z = 498.21($C_{37}H_{26}N_2$ = 498.63) |
| Sub 2-69 | m/z = 498.21($C_{37}H_{26}N_2$ = 498.63) |
| Sub 2-70 | m/z = 498.21($C_{37}H_{26}N_2$ = 498.63) |
| Sub 2-71 | m/z = 574.24($C_{43}H_{30}N_2$ = 574.73) |
| Sub 2-72 | m/z = 574.24($C_{43}H_{30}N_2$ = 574.73) |
| Sub 2-73 | m/z = 574.24($C_{43}H_{30}N_2$ = 574.73) |
| Sub 2-74 | m/z = 548.23($C_{41}H_{28}N_2$ = 548.69) |
| Sub 2-75 | m/z = 548.23($C_{41}H_{28}N_2$ = 548.69) |
| Sub 2-76 | m/z = 548.23($C_{41}H_{28}N_2$ = 548.69) |
| Sub 2-77 | m/z = 598.24($C_{45}H_{30}N_2$ = 598.75) |
| Sub 2-78 | m/z = 604.20($C_{43}H_{28}N_2S$ = 604.77) |
| Sub 2-79 | m/z = 663.27($C_{49}H_{33}N_3$ = 663.82) |
| Sub 2-80 | m/z = 614.27($C_{46}H_{34}N_2$ = 614.79) |
| Sub 2-81 | m/z = 624.26($C_{47}H_{32}N_2$ = 624.79) |
| Sub 2-82 | m/z = 496.19($C_{37}H_{24}N_2$ = 496.61) |
| Sub 2-83 | m/z = 496.19($C_{37}H_{24}N_2$ = 496.61) |
| Sub 2-84 | m/z = 496.19($C_{37}H_{24}N_2$ = 496.61) |
| Sub 2-85 | m/z = 546.21($C_{41}H_{26}N_2$ = 546.67) |
| Sub 2-86 | m/z = 528.17($C_{37}H_{24}N_2S$ = 528.67) |
| Sub 2-87 | m/z = 528.17($C_{37}H_{24}N_2S$ = 528.67) |
| Sub 2-88 | m/z = 528.17($C_{37}H_{24}N_2S$ = 528.67) |
| Sub 2-89 | m/z = 512.19($C_{37}H_{24}N_2O$ = 512.61) |
| Sub 2-90 | m/z = 587.24($C_{43}H_{29}N_3$ = 587.73) |
| Sub 2-91 | m/z = 538.24($C_{40}H_{30}N_2$ = 538.69) |

III. Synthesis Example of Final Product

1. Synthesis Example of P-1

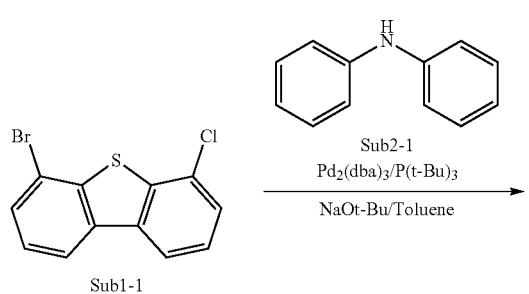

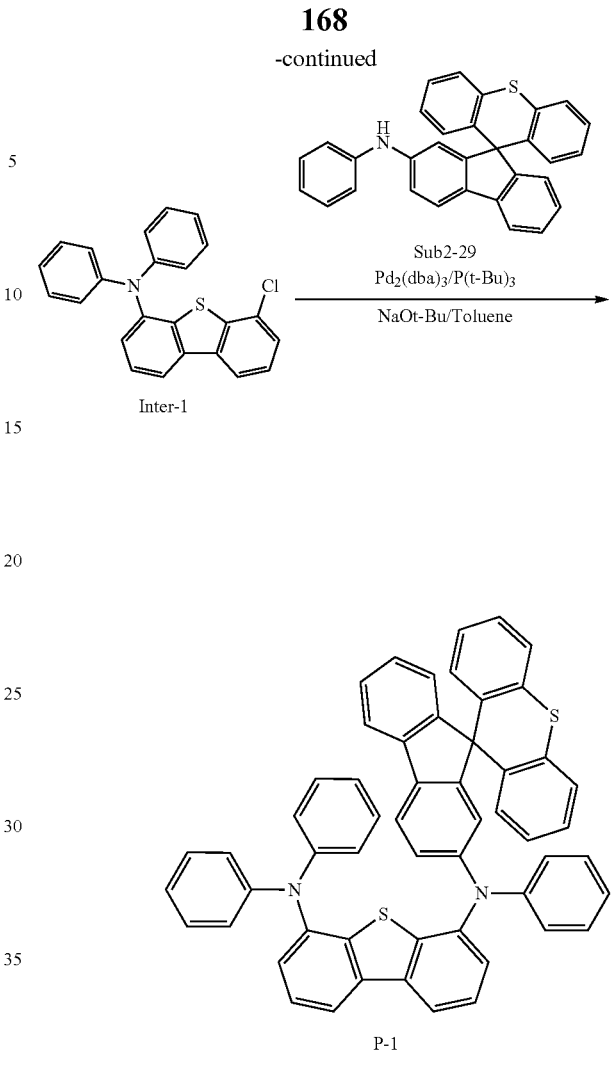

(1) Synthesis Example of Inter-1

After dissolving Sub1-1 (2.00 g, 6.72 mmol) in toluene (35 mL), Sub 2-1 (1.14 g, 6.72 mmol), $Pd_2(dba)_3$ (0.18 g, 0.20 mmol), P(t-Bu)$_3$ (0.08 g, 0.40 mmol) and NaOt-Bu (1.29 g, 13.4 mmol) were added and stirred at 60° C. When the reaction was completed, the reaction product was extracted with $CH_2Cl_2$ and water, and the organic layer is dried with $MgSO_4$ and concentrated. Thereafter, the concentrate was separated by a silica gel column and recrystallized to obtain 1.95 g (yield 75%) of the product.

(2) Synthesis Example of P-1

After Inter-1 (1.95 g, 5.04 mmol) was dissolved in toluene (25 mL), Sub 2-29 (2.22 g, 5.04 mmol), $Pd_2(dba)_3$ (0.14 g, 0.15 mmol), P(t-Bu)$_3$ (0.06 g, 0.30 mmol) and NaOt-Bu (0.97 g, 10.1 mmol) were added thereto and the mixture was refluxed. When the reaction was completed, the reaction product was extracted with $CH_2Cl_2$ and water, and the organic layer is dried with $MgSO_4$ and concentrated. Thereafter, the concentrate was separated by a silica gel column and recrystallized to obtain 2.86 g (yield 72%) of the product.

2. Synthesis Example of P-45

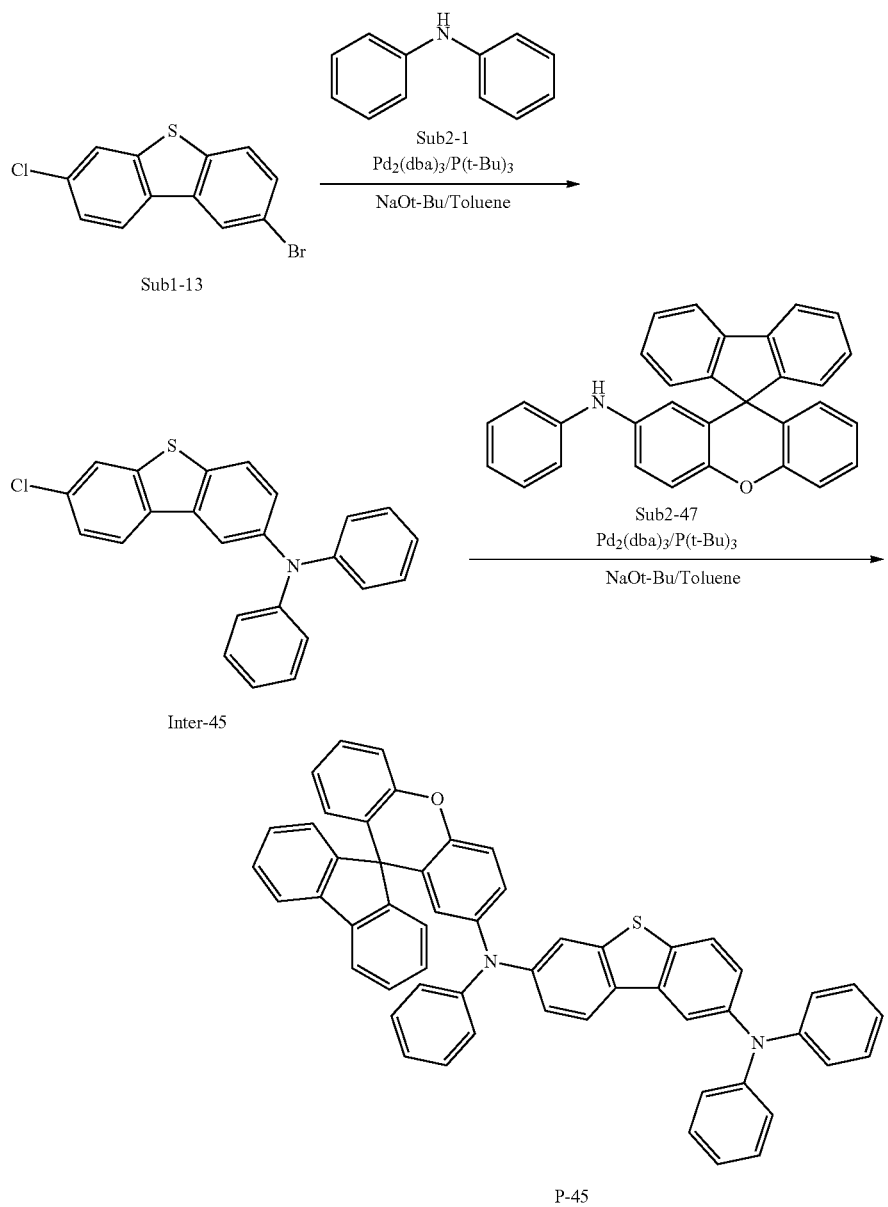

(1) Synthesis Example of Inter-45

The reaction was carried out in the same manner as in the synthesis method of Inter-1 using Sub1-13 (2.00 g, 6.72 mmol), Sub 2-1 (1.14 g, 6.72 mmol), Pd$_2$(dba)$_3$ (0.18 g, 0.20 mmol), P(t-Bu)$_3$ (0.08 g, 0.40 mmol), NaOt-Bu (1.29 g, 13.4 mmol) to obtain 1.87 g (yield 72%) of product.

(2) Synthesis Example of P-45

The reaction was carried out in the same manner as in the synthesis method of P-1 using Inter-45 (1.87 g, 4.84 mmol), Sub 2-29 (2.05 g, 4.84 mmol), Pd$_2$(dba)$_3$ (0.13 g, 0.15 mmol), P(t-Bu)$_3$ (0.06 g, 0.29 mmol), NaOt-Bu (0.93 g, 9.68 mmol) to obtain 2.62 g (yield 70%) of product.

3. Synthesis Example of P-50

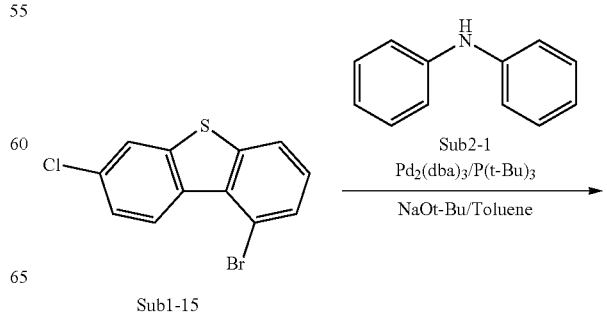

-continued

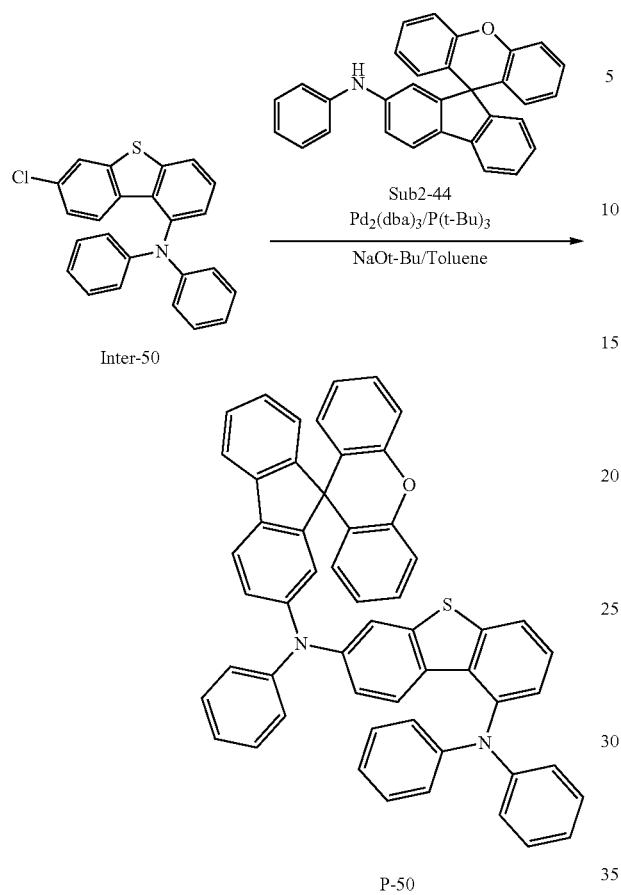

(1) Synthesis Example of Inter-50

The reaction was carried out in the same manner as in the synthesis method of Inter-1 using Sub1-15 (2.00 g, 6.72 mmol), Sub 2-1 (1.14 g, 6.72 mmol), Pd$_2$(dba)$_3$ (0.18 g, 0.20 mmol), P(t-Bu)$_3$ (0.08 g, 0.40 mmol), NaOt-Bu (1.29 g, 13.4 mmol) to obtain 1.82 g (yield 70%) of product.

(2) Synthesis Example of P-50

The reaction was carried out in the same manner as in the synthesis method of P-1 using Inter-50 (1.82 g, 4.70 mmol), Sub 2-44 (1.99 g, 4.70 mmol), Pd$_2$(dba)$_3$ (0.13 g, 0.14 mmol), P(t-Bu)$_3$ (0.06 g, 0.28 mmol), NaOt-Bu (0.90 g, 9.41 mmol) to obtain 2.84 g (yield 78%) of product.

4. Synthesis Example of P-64

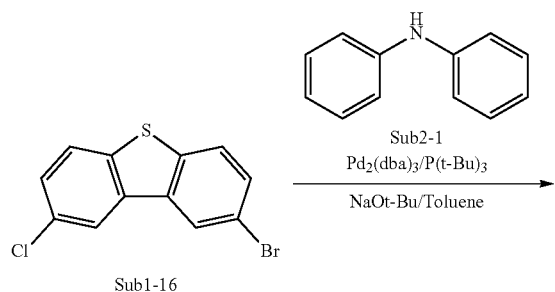

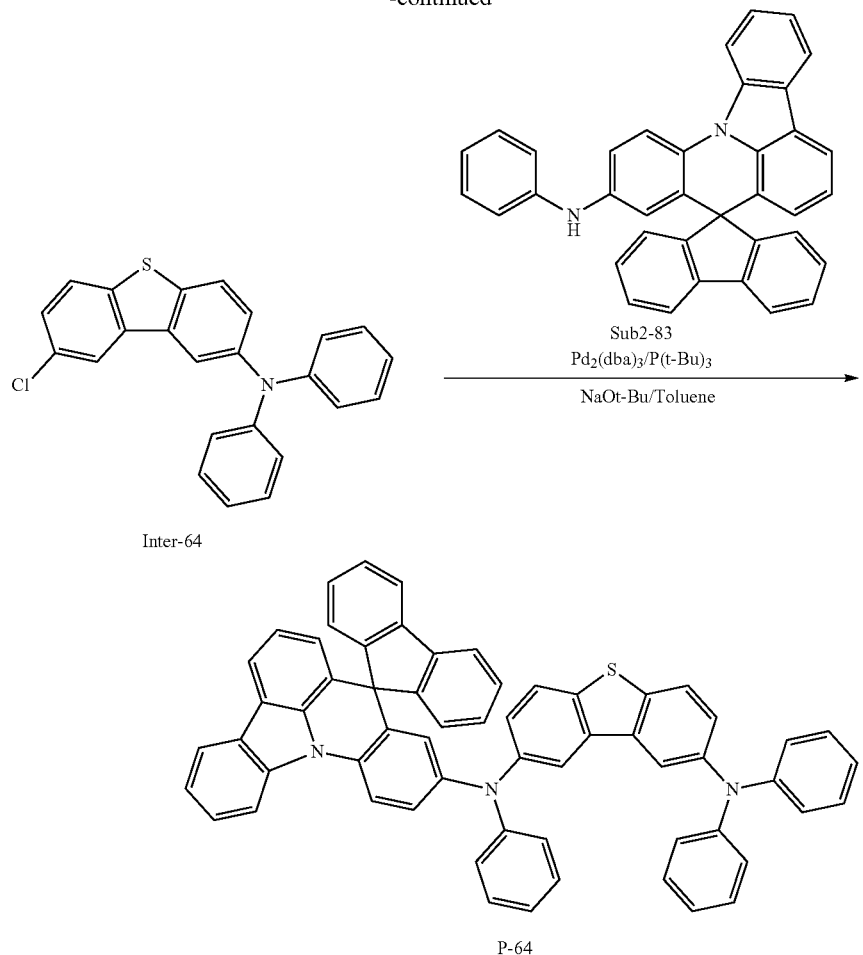

Inter-64

P-64

(1) Synthesis Example of Inter-64

The reaction was carried out in the same manner as in the synthesis method of Inter-1 using Sub1-16 (2.00 g, 6.72 mmol), Sub 2-1 (1.14 g, 6.72 mmol), Pd₂(dba)₃ (0.18 g, 0.20 mmol), P(t-Bu)₃ (0.08 g, 0.40 mmol), NaOt-Bu (1.29 g, 13.4 mmol) to obtain 2.00 g (yield 77%) of product.

(2) Synthesis Example of P-64

The reaction was carried out in the same manner as in the synthesis method of P-1 using Inter-64 (2.00 g, 5.17 mmol), Sub 2-83 (2.57 g, 5.17 mmol), Pd₂(dba)₃ (0.14 g, 0.16 mmol), P(t-Bu)₃ (0.06 g, 0.31 mmol), NaOt-Bu (0.99 g, 10.4 mmol) to obtain 3.15 g (yield 72%) of product.

5. Synthesis Example of P-83

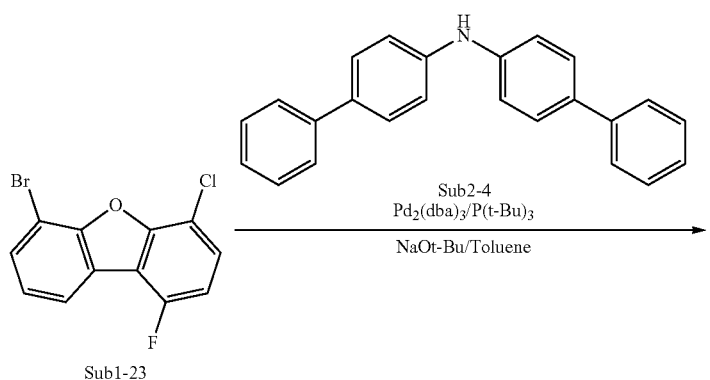

-continued

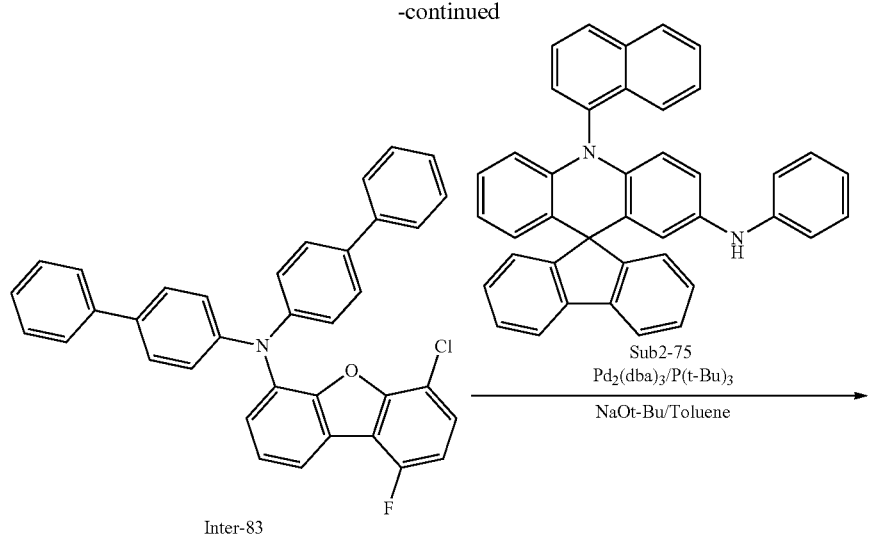

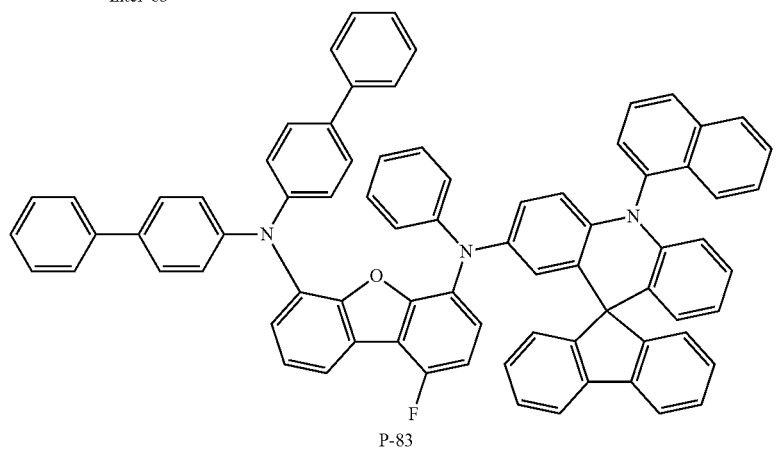

(1) Synthesis Example of Inter-83

The reaction was carried out in the same manner as in the synthesis method of Inter-1 using Sub1-23 (2.00 g, 6.68 mmol), Sub 2-4 (2.15 g, 6.68 mmol), Pd$_2$(dba)$_3$ (0.18 g, 0.20 mmol), P(t-Bu)$_3$ (0.08 g, 0.40 mmol), NaOt-Bu (1.28 g, 13.4 mmol) to obtain 2.63 g (yield 73%) of product.

(2) Synthesis Example of P-83

The reaction was carried out in the same manner as in the synthesis method of P-1 using Inter-83 (2.63 g, 4.87 mmol), Sub 2-75 (2.67 g, 4.87 mmol), Pd$_2$(dba)$_3$ (0.13 g, 0.15 mmol), P(t-Bu)$_3$ (0.06 g, 0.29 mmol), NaOt-Bu (0.94 g, 9.75 mmol) to obtain 3.49 g (yield 68%) of product.

6. Synthesis Example of P-112

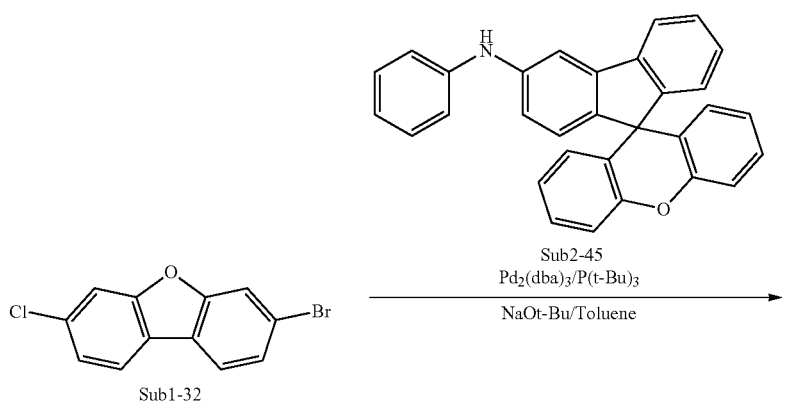

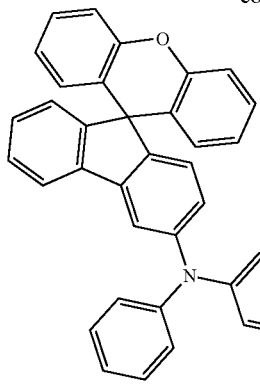
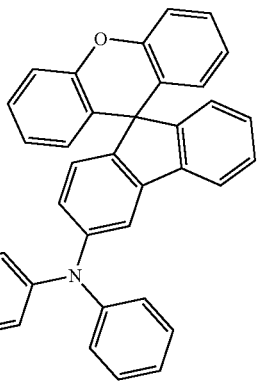

P-112

After Sub1-32 (2.00 g, 7.10 mmol) was dissolved in toluene (40 mL), Sub 2-45 (6.02 g, 14.21 mmol), Pd$_2$(dba)$_3$ (0.20 g, 0.21 mmol), P(t-Bu)$_3$ (0.09 g, 0.43 mmol) and NaOt-Bu (1.37 g, 14.2 mmol) were added thereto and the mixture was refluxed. When the reaction was completed, the reaction product was extracted with CH$_2$Cl$_2$ and water, and the organic layer is dried with MgSO$_4$ and concentrated. Thereafter, the concentrate was separated by a silica gel column and recrystallized to obtain 5.53 g (yield 77%) of the product.

7. Synthesis Example of P-117

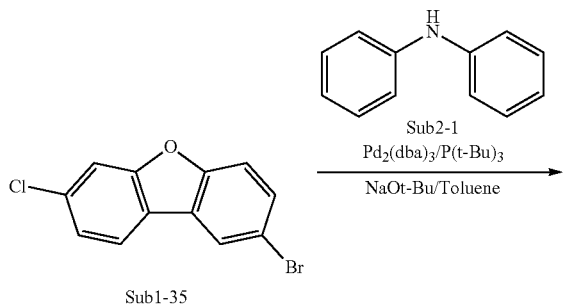

Sub1-35

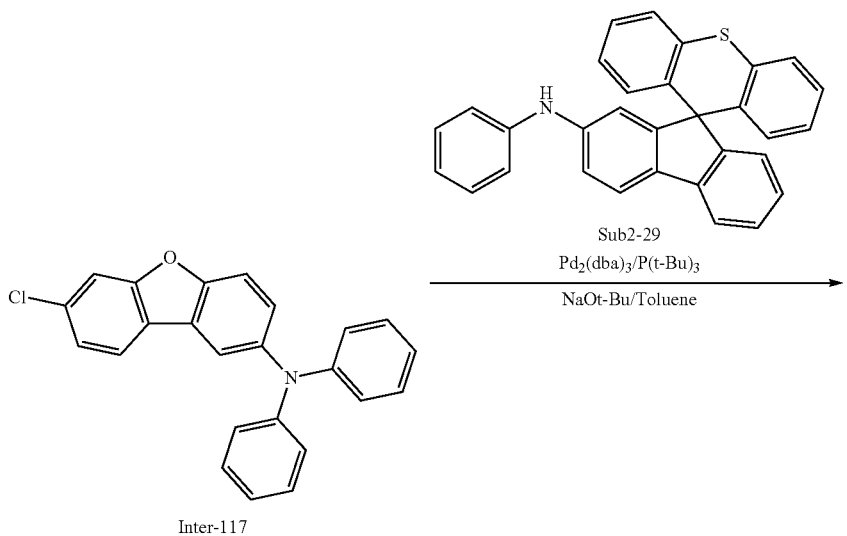

Inter-117

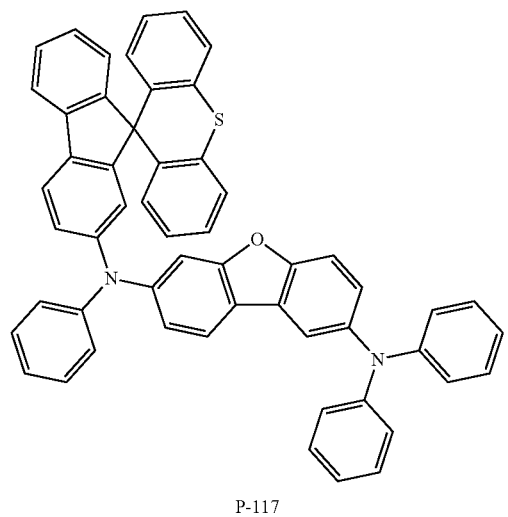

P-117

(1) Synthesis Example of Inter-117

The reaction was carried out in the same manner as in the synthesis method of Inter-1 using Sub1-35 (2.00 g, 7.10 mmol), Sub 2-1 (1.20 g, 7.10 mmol), Pd$_2$(dba)$_3$ (0.20 g, 0.21 mmol), P(t-Bu)$_3$ (0.09 g, 0.43 mmol), NaOt-Bu (1.37 g, 14.2 mmol) to obtain 2.00 g (yield 76%) of product.

(2) Synthesis Example of P-117

The reaction was carried out in the same manner as in the synthesis method of P-1 using Inter-117 (2.00 g, 5.40 mmol), Sub 2-29 (2.37 g, 5.40 mmol), Pd$_2$(dba)$_3$ (0.15 g, 0.16 mmol), P(t-Bu)$_3$ (0.07 g, 0.32 mmol), NaOt-Bu (1.04 g, 10.8 mmol) to obtain 3.09 g (yield 74%) of product.

8. Synthesis Example of P-132

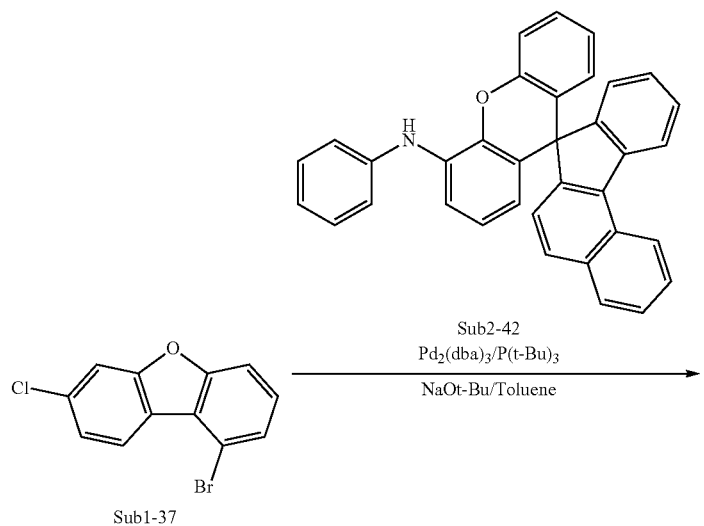

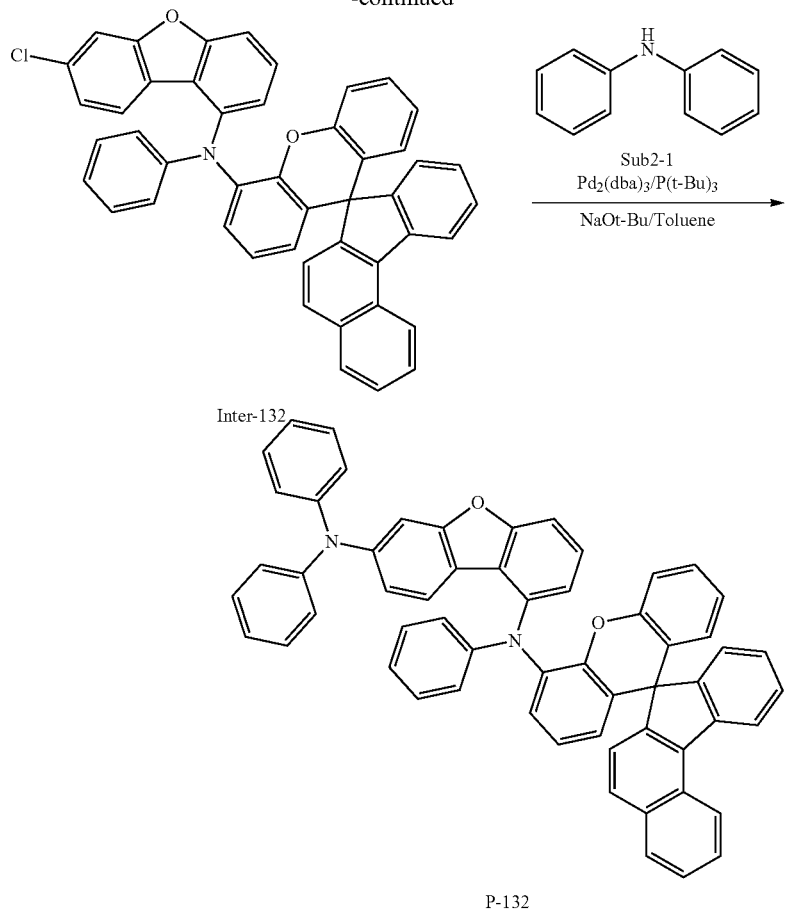

(1) Synthesis Example of Inter-132

The reaction was carried out in the same manner as in the synthesis method of Inter-1 using Sub1-37 (2.00 g, 7.10 mmol), Sub 2-42 (3.36 g, 7.10 mmol), Pd₂(dba)₃ (0.20 g, 0.21 mmol), P(t-Bu)₃ (0.09 g, 0.43 mmol), NaOt-Bu (1.37 g, 14.2 mmol) to obtain 3.40 g (yield 71%) of product.

(2) Synthesis Example of P-132

The reaction was carried out in the same manner as in the synthesis method of P-1 using Inter-132 (3.40 g, 5.04 mmol), Sub 2-1 (0.85 g, 5.04 mmol), Pd₂(dba)₃ (0.14 g, 0.15 mmol), P(t-Bu)₃ (0.06 g, 0.30 mmol), NaOt-Bu (0.97 g, 10.1 mmol) to obtain 3.22 g (yield 79%) of product.

9. Synthesis Example of P-136

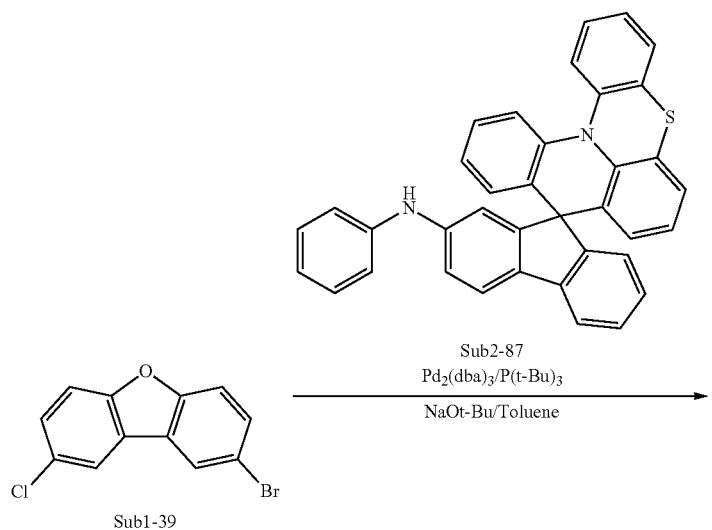

183
-continued

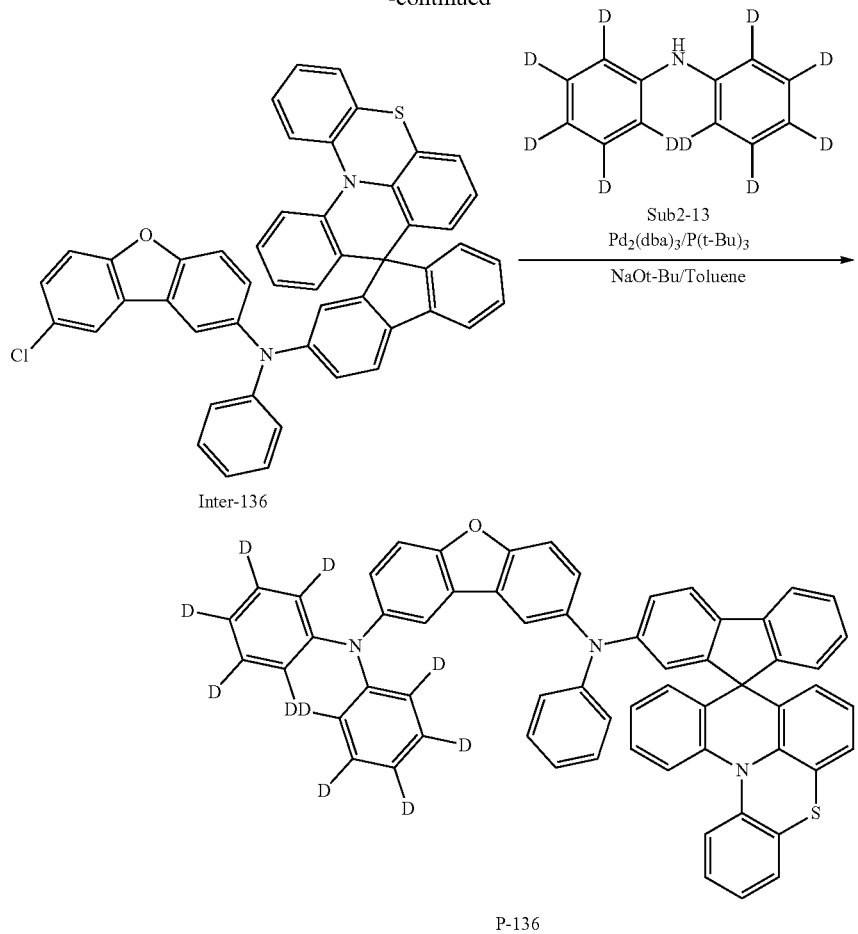

(1) Synthesis Example of Inter-136

The reaction was carried out in the same manner as in the synthesis method of Inter-1 using Sub1-39 (2.00 g, 7.10 mmol), Sub 2-87 (3.76 g, 7.10 mmol), Pd$_2$(dba)$_3$ (0.20 g, 0.21 mmol), P(t-Bu)$_3$ (0.09 g, 0.43 mmol), NaOt-Bu (1.37 g, 14.2 mmol) to obtain 3.89 g (yield 75%) of product.

184

(2) Synthesis Example of P-136

The reaction was carried out in the same manner as in the synthesis method of P-1 using Inter-136 (3.89 g, 5.33 mmol), Sub 2-13 (0.96 g, 5.33 mmol), Pd$_2$(dba)$_3$ (0.15 g, 0.16 mmol), P(t-Bu)$_3$ (0.06 g, 0.32 mmol), NaOt-Bu (1.02 g, 10.7 mmol) to obtain 3.62 g (yield 78%) of product.

10. Synthesis Example of P-145

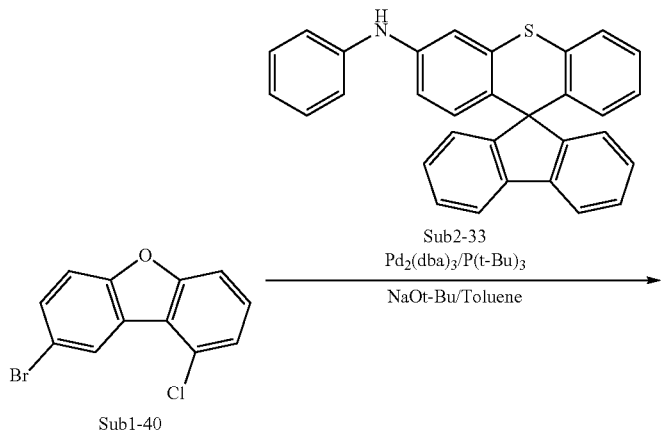

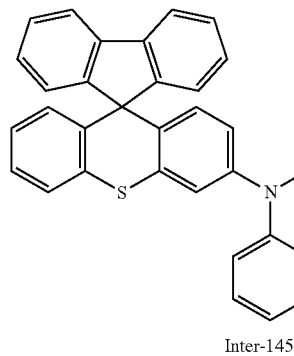

Inter-145

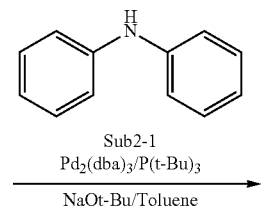

Sub2-1
Pd₂(dba)₃/P(t-Bu)₃
NaOt-Bu/Toluene

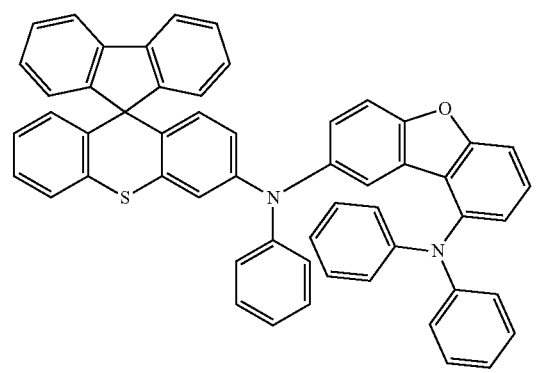

P-145

(1) Synthesis Example of Inter-145

The reaction was carried out in the same manner as in the synthesis method of Inter-1 using Sub1-40 (2.00 g, 7.10 mmol), Sub 2-33 (3.12 g, 7.10 mmol), Pd₂(dba)₃ (0.20 g, 0.21 mmol), P(t-Bu)₃ (0.09 g, 0.43 mmol), NaOt-Bu (1.37 g, 14.2 mmol) to obtain 3.55 g (yield 78%) of product.

(2) Synthesis Example of P-145

The reaction was carried out in the same manner as in the synthesis method of P-1 using Inter-145 (3.55 g, 5.54 mmol), Sub 2-1 (0.94 g, 5.54 mmol), Pd₂(dba)₃ (0.15 g, 0.17 mmol), P(t-Bu)₃ (0.07 g, 0.33 mmol), NaOt-Bu (1.07 g, 11.1 mmol) to obtain 2.87 g (yield 67%) of product.

11. Synthesis Example of P-162

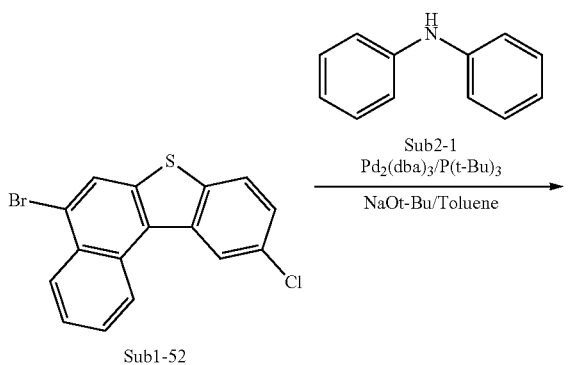

Sub1-52

Sub2-1
Pd₂(dba)₃/P(t-Bu)₃
NaOt-Bu/Toluene

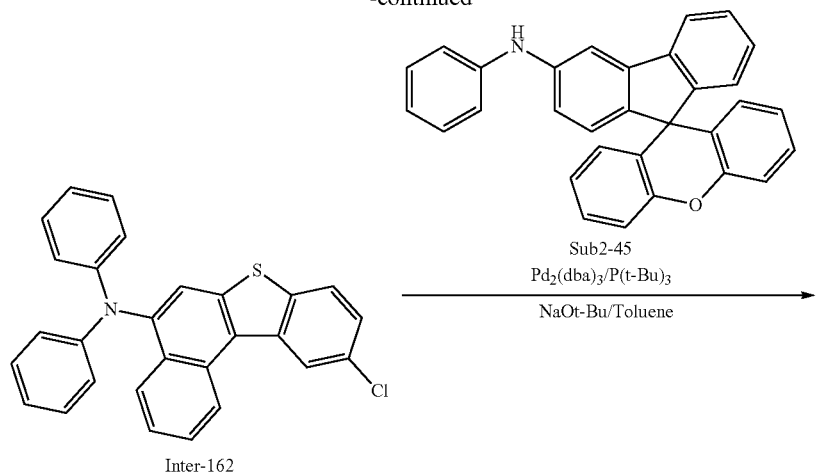

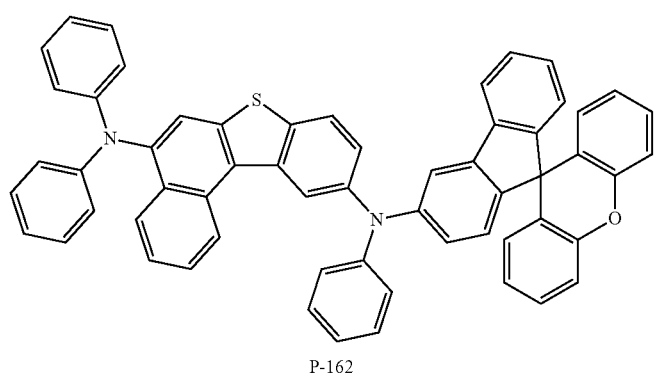

(1) Synthesis Example of Inter-162

The reaction was carried out in the same manner as in the synthesis method of Inter-1 using Sub1-52 (2.00 g, 5.75 mmol), Sub 2-1 (0.97 g, 5.75 mmol), Pd₂(dba)₃ (0.16 g, 0.17 mmol), P(t-Bu)₃ (0.07 g, 0.35 mmol), NaOt-Bu (1.11 g, 11.5 mmol) to obtain 1.83 g (yield 73%) of product.

(2) Synthesis Example of P-162

The reaction was carried out in the same manner as in the synthesis method of P-1 using Inter-162 (1.83 g, 4.20 mmol), Sub 2-45 (1.78 g, 4.20 mmol), Pd₂(dba)₃ (0.12 g, 0.13 mmol), P(t-Bu)₃ (0.05 g, 0.25 mmol), NaOt-Bu (0.81 g, 8.40 mmol) to obtain 2.63 g (yield 76%) of product.

12. Synthesis Example of P-175

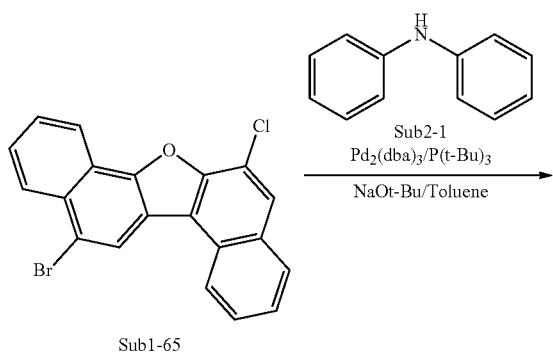

-continued

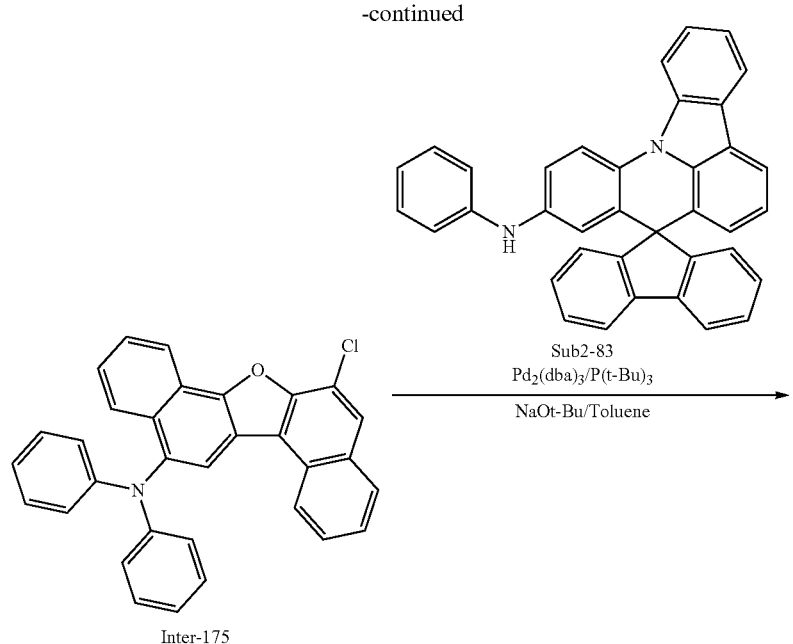

Inter-175

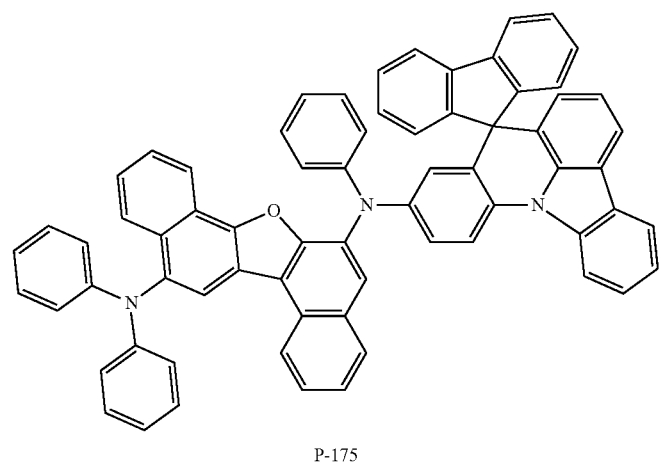

P-175

(1) Synthesis Example of Inter-175

The reaction was carried out in the same manner as in the synthesis method of Inter-1 using Sub1-65 (2.00 g, 5.24 mmol), Sub 2-1 (0.89 g, 5.24 mmol), Pd$_2$(dba)$_3$ (0.14 g, 0.16 mmol), P(t-Bu)$_3$ (0.06 g, 0.31 mmol), NaOt-Bu (1.01 g, 10.5 mmol) to obtain 1.77 g (yield 72%) of product.

(2) Synthesis Example of P-175

The reaction was carried out in the same manner as in the synthesis method of P-1 using Inter-175 (1.77 g, 3.77 mmol), Sub 2-83 (1.87 g, 3.77 mmol), Pd$_2$(dba)$_3$ (0.10 g, 0.11 mmol), P(t-Bu)$_3$ (0.05 g, 0.23 mmol), NaOt-Bu (0.73 g, 7.55 mmol) to obtain 2.49 g (yield 71%) of product.

13. Synthesis Example of P-195

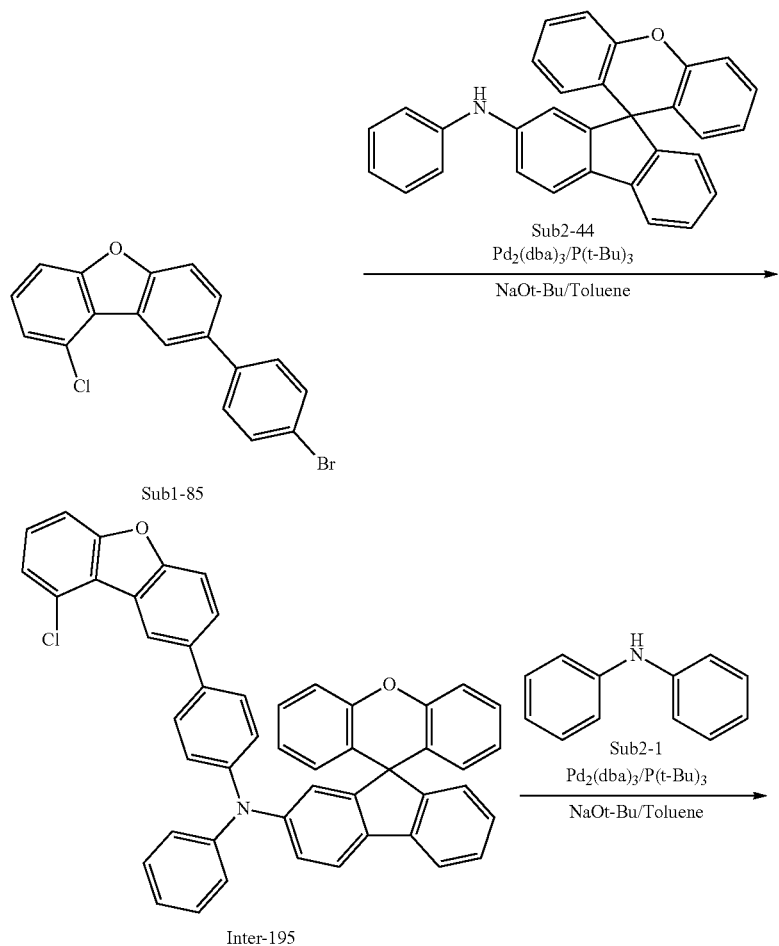

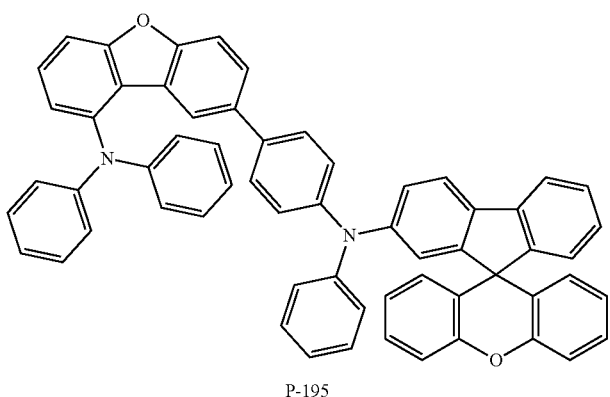

(1) Synthesis Example of Inter-195

The reaction was carried out in the same manner as in the synthesis method of Inter-1 using Sub1-85 (2.00 g, 5.59 mmol), Sub 2-44 (2.37 g, 5.59 mmol), Pd₂(dba)₃ (0.15 g, 0.17 mmol), P(t-Bu)₃ (0.07 g, 0.34 mmol), NaOt-Bu (1.07 g, 11.2 mmol) to obtain 3.17 g (yield 81%) of product.

(2) Synthesis Example of P-195

The reaction was carried out in the same manner as in the synthesis method of P-1 using Inter-195 (3.17 g, 4.53 mmol), Sub 2-1 (0.77 g, 4.53 mmol), Pd₂(dba)₃ (0.12 g, 0.14 mmol), P(t-Bu)₃ (0.05 g, 0.27 mmol), NaOt-Bu (0.87 g, 9.06 mmol) to obtain 2.45 g (yield 65%) of product.

14. Synthesis Example of P-204
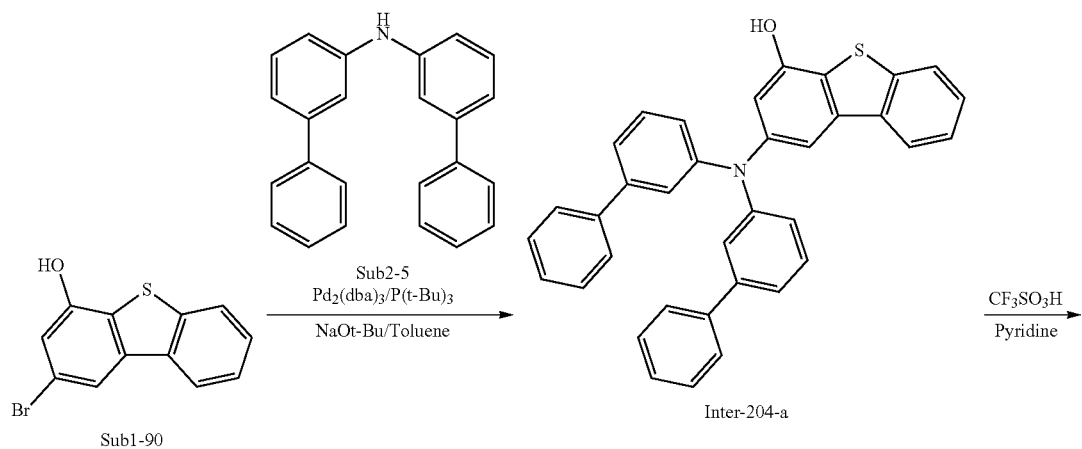
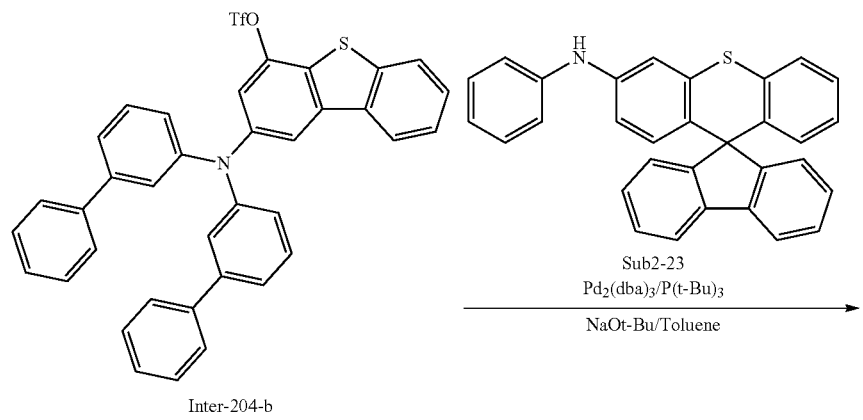
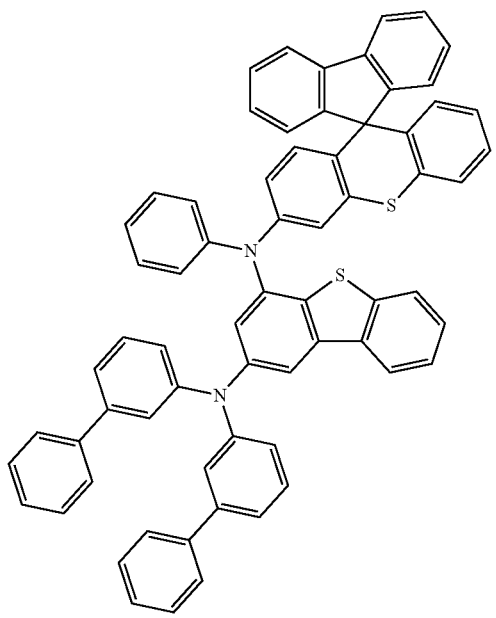
P-204

(1) Synthesis Example of Inter-204-a

The reaction was carried out in the same manner as in the synthesis method of Inter-1 using Sub1-90 (2.00 g, 7.16 mmol), Sub 2-5 (2.30 g, 7.16 mmol), Pd$_2$(dba)$_3$ (0.20 g, 0.21 mmol), P(t-Bu)$_3$ (0.09 g, 0.43 mmol), NaOt-Bu (1.38 g, 14.3 mmol) to obtain 3.05 g (yield 82%) of product.

(2) Synthesis Example of Inter-204-b

After adding an excess of trifluoromethane-sulfonic acid to Inter-204-a (3.05 g, 5.87 mmol), the solution was stirred for 24 hours at room temperature. Water and pyridine (8:1) were slowly added the solution and the mixture was refluxed for 30 minutes. After lowering the temperature, the resultant was extracted with CH$_2$Cl$_2$ and water. The organic layer was dried with MgSO$_4$ and concentrated. Thereafter, the concentrate was separated by a silica gel column and recrystallized to obtain 1.89 g (yield: 73%) of the product.

(3) Synthesis Example of P-204

The reaction was carried out in the same manner as in the synthesis method of P-1 using Inter-204-b (1.89 g, 4.29 mmol), Sub 2-33 (2.80 g, 4.29 mmol), Pd$_2$(dba)$_3$ (0.12 g, 0.13 mmol), P(t-Bu)$_3$ (0.05 g, 0.26 mmol), NaOt-Bu (0.82 g, 8.58 mmol) to obtain 2.91 g (yield 72%) of product.

15. Synthesis Example of P-208

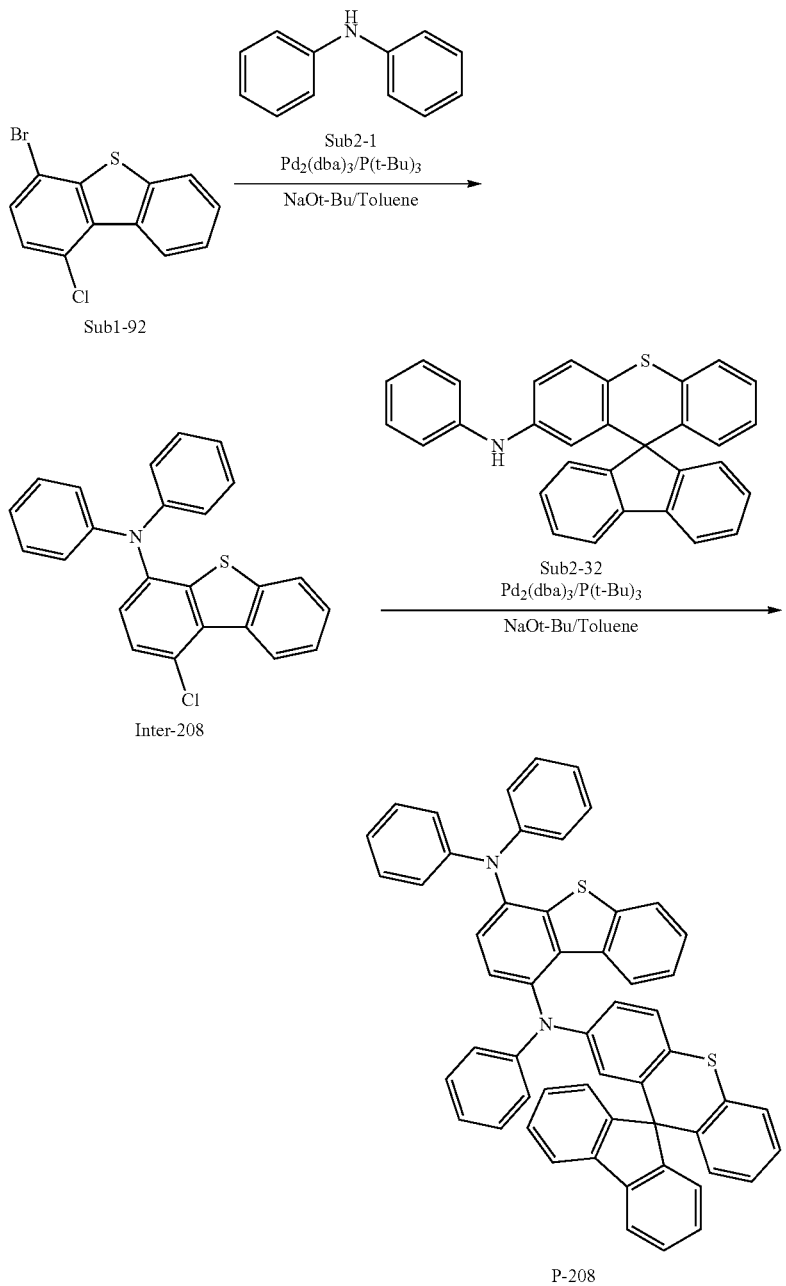

(1) Synthesis Example of Inter-208

The reaction was carried out in the same manner as in the synthesis method of Inter-1 using Sub1-92 (2.00 g, 6.72 mmol), Sub 2-1 (1.14 g, 6.72 mmol), Pd$_2$(dba)$_3$ (0.18 g, 0.20 mmol), P(t-Bu)$_3$ (0.08 g, 0.40 mmol), NaOt-Bu (1.29 g, 13.4 mmol) to obtain 1.84 g (yield 71%) of product.

(2) Synthesis Example of P-208

The reaction was carried out in the same manner as in the synthesis method of P-1 using Inter-208 (1.84 g, 4.77 mmol), Sub 2-32 (2.10 g, 4.77 mmol), Pd$_2$(dba)$_3$ (0.13 g, 0.14 mmol), P(t-Bu)$_3$ (0.06 g, 0.29 mmol), NaOt-Bu (0.92 g, 9.54 mmol) to obtain 3.09 g (yield 82%) of product.

16. Synthesis Example of P-216

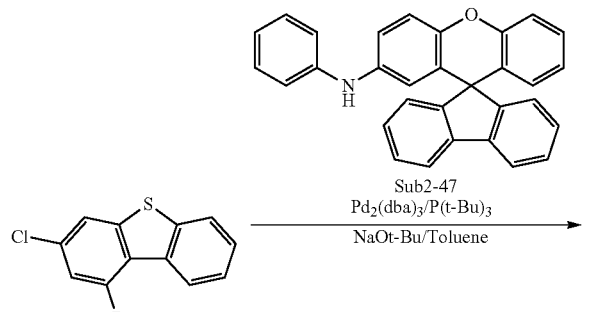

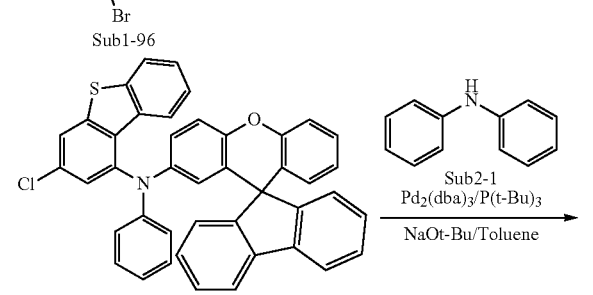

(1) Synthesis Example of Inter-216

The reaction was carried out in the same manner as in the synthesis method of Inter-1 using Sub1-96 (2.00 g, 6.72 mmol), Sub 2-47 (2.85 g, 6.72 mmol), Pd$_2$(dba)$_3$ (0.18 g, 0.20 mmol), P(t-Bu)$_3$ (0.08 g, 0.40 mmol), NaOt-Bu (1.29 g, 13.4 mmol) to obtain 3.36 g (yield 78%) of product.

(2) Synthesis Example of P-216

The reaction was carried out in the same manner as in the synthesis method of P-1 using Inter-216 (3.36 g, 5.24 mmol), Sub 2-1 (0.89 g, 5.24 mmol), Pd$_2$(dba)$_3$ (0.14 g, 0.16 mmol), P(t-Bu)$_3$ (0.06 g, 0.31 mmol), NaOt-Bu (1.01 g, 10.5 mmol) to obtain 3.08 g (yield 76%) of product.

17. Synthesis Example of P-243

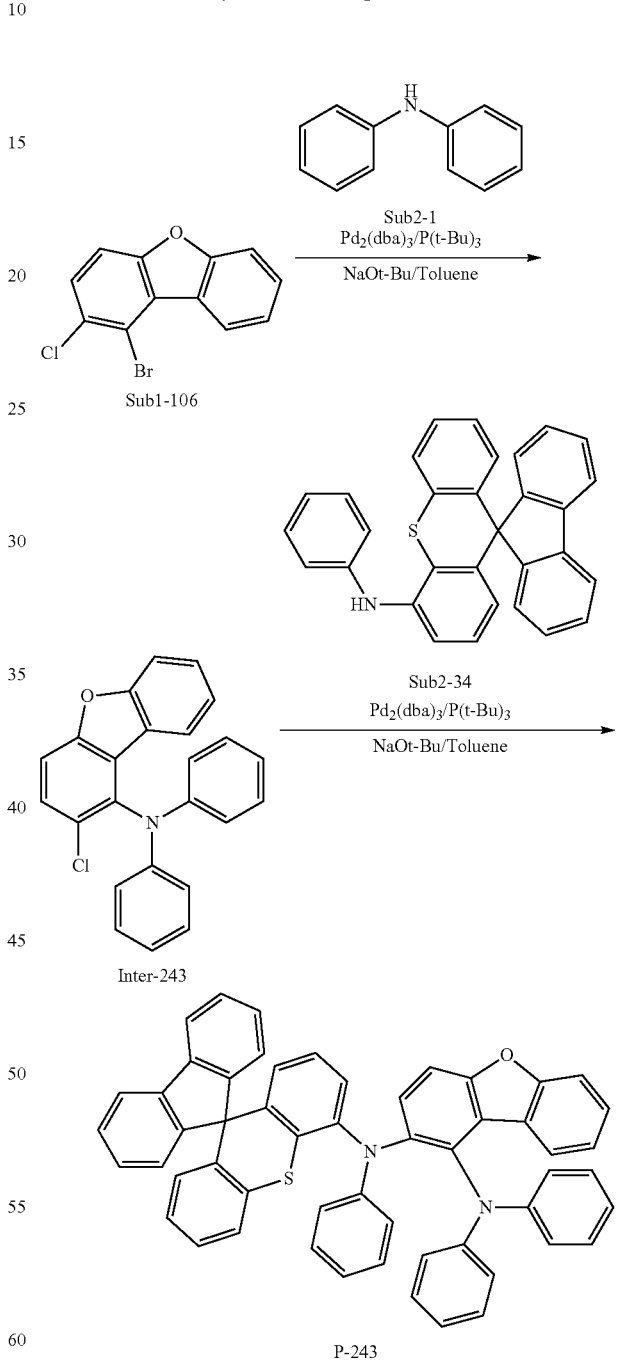

(1) Synthesis Example of Inter-243

The reaction was carried out in the same manner as in the synthesis method of Inter-1 using Sub1-106 (2.00 g, 7.10 mmol), Sub 2-1 (1.20 g, 7.10 mmol), Pd₂(dba)₃ (0.20 g, 0.21 mmol), P(t-Bu)₃ (0.09 g, 0.43 mmol), NaOt-Bu (1.37 g, 14.2 mmol) to obtain 1.92 g (yield 73%) of product.

(2) Synthesis Example of P-243

The reaction was carried out in the same manner as in the synthesis method of P-1 using Inter-243 (1.92 g, 5.19 mmol), Sub 2-34 (2.28 g, 5.19 mmol), Pd₂(dba)₃ (0.14 g, 0.16 mmol), P(t-Bu)₃ (0.06 g, 0.31 mmol), NaOt-Bu (1.00 g, 10.4 mmol) to obtain 1.72 g (yield 43%) of product.

18. Synthesis Example of P-250

(1) Synthesis Example of Inter-250-a

The reaction was carried out in the same manner as in the synthesis method of Inter-1 using Sub1-102 (2.00 g, 7.10 mmol), Sub 2-1 (1.20 g, 7.10 mmol), Pd₂(dba)₃ (0.20 g, 0.21 mmol), P(t-Bu)₃ (0.09 g, 0.43 mmol), NaOt-Bu (1.37 g, 14.2 mmol) to obtain 2.02 g (yield 77%) of product.

(2) Synthesis Example of Inter-250-b

After dissolving Inter-250-a (2.02 g, 5.47 mmol) in THF (27 mL), (4-hydroxyphenyl) boronic acid (0.75 g, 5.47 mmol), NaOH (0.66 g, 16.4 mmol), Pd(PPh₃)₄ (0.38 g, 0.33 mmol) and water (14 mL) were added and the mixture was

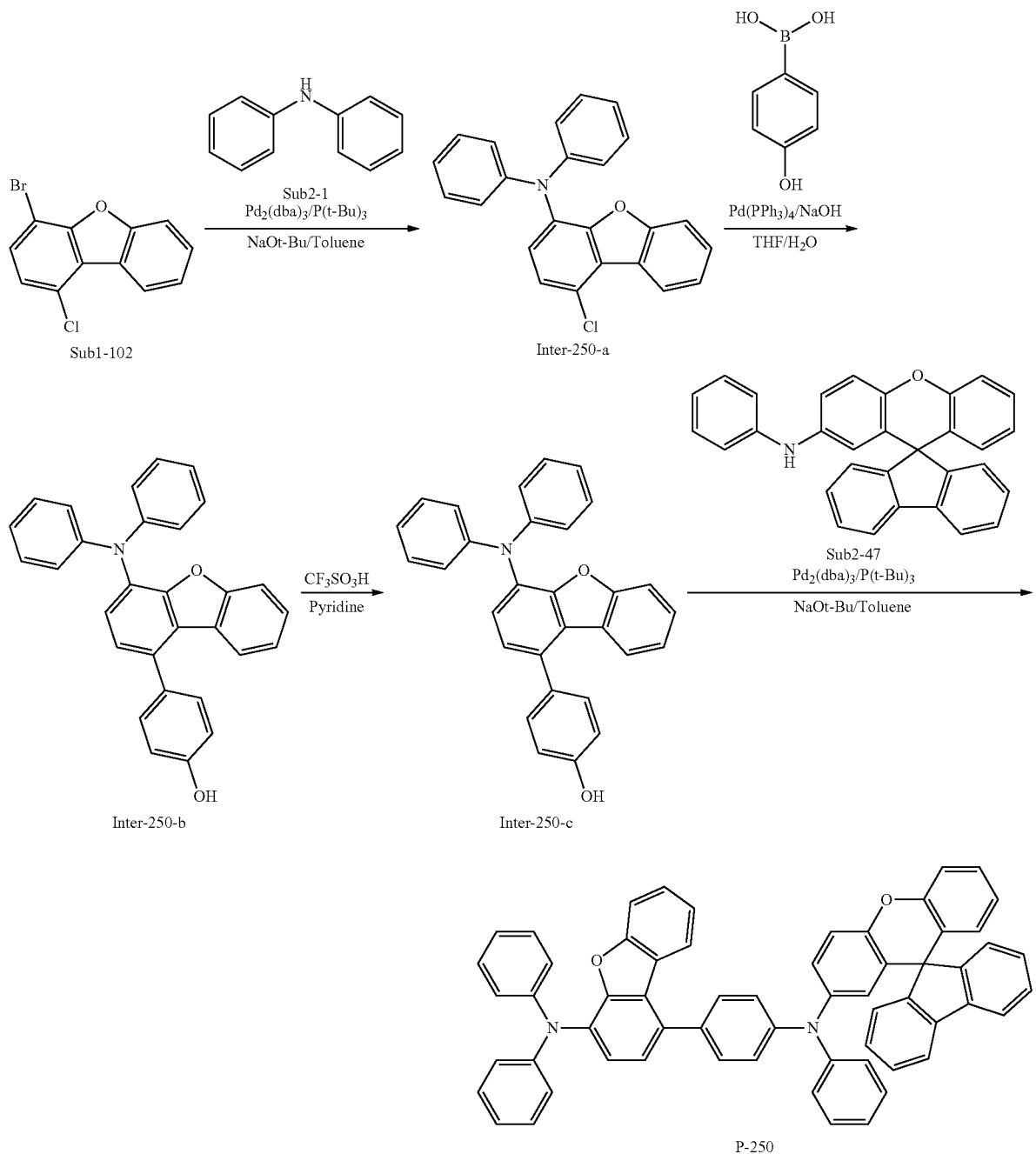

stirred at 80° C. When the reaction was completed, the reaction product was extracted with CH$_2$Cl$_2$ and water, and the organic layer is dried with MgSO$_4$ and concentrated. Thereafter, the concentrate was separated by a silica gel column and recrystallized to obtain 1.92 g (yield: 82%) of the product.

(3) Synthesis Example of Inter-250-c

The reaction was carried out in the same manner as in the synthesis method of Inter-204-b using Inter-250-b (1.92 g, 4.49 mmol) to obtain 1.83 g (yield: 73%) of product.

(4) Synthesis Example of P-250

The reaction was carried out in the same manner as in the synthesis method of P-1 using Inter-250-c (1.83 g, 3.27 mmol), Sub 2-47 (1.39 g, 3.27 mmol), Pd$_2$(dba)$_3$ (0.09 g, 0.10 mmol), P(t-Bu)$_3$ (0.04 g, 0.20 mmol), NaOt-Bu (0.63 g, 6.55 mmol) to obtain 2.05 g (yield 75%) of product.

19. Synthesis Example of P-254

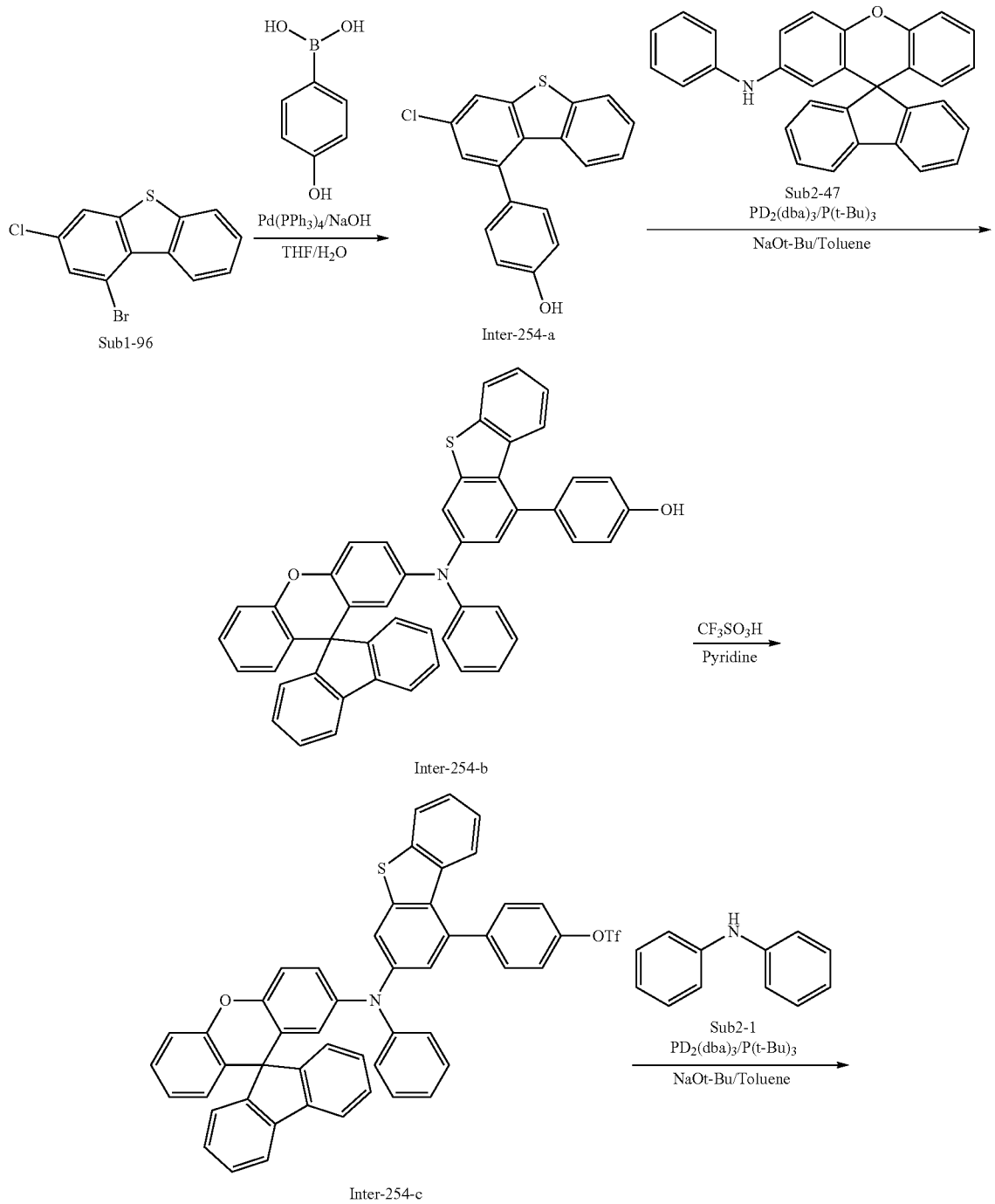

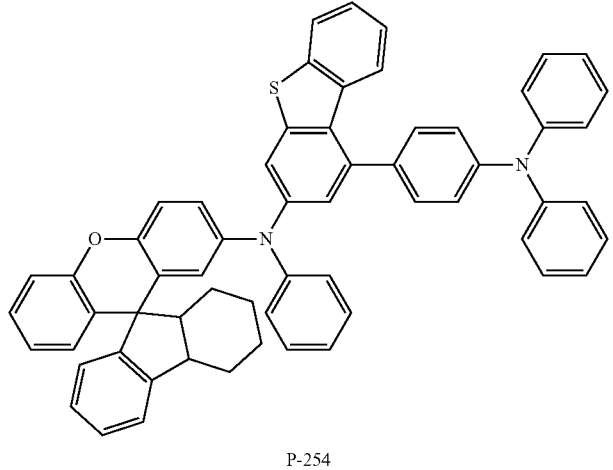

P-254

(1) Synthesis Example of Inter-254-a

The reaction was carried out in the same manner as in the synthesis method of Inter-250-b using Sub1-96 (2.0 g, 6.72 mmol), (4-hydroxyphenyl) boronic acid (0.93 g, 6.72 mmol), NaOH (0.81 g, 20.2 mmol), Pd(PPh$_3$)$_4$ (0.47 g, 0.40 mmol) to obtain 1.75 g (yield: 84%) of product.

(2) Synthesis Example of Inter-254-b

The reaction was carried out in the same manner as in the synthesis method of Inter-1 using Inter-254-a (1.75 g, 5.65 mmol), Sub 2-47 (2.39 g, 5.65 mmol), Pd$_2$(dba)$_3$ (0.16 g, 0.17 mmol), P(t-Bu)$_3$ (0.07 g, 0.34 mmol), NaOt-Bu (1.09 g, 11.3 mmol) to obtain 2.84 g (yield 72%) of product.

(3) Synthesis Example of Inter-254-c

The reaction was carried out in the same manner as in the synthesis method of Inter-204-b using Inter-254-b (2.84 g, 4.06 mmol) to obtain 2.56 g (yield: 76%) of product.

(4) Synthesis Example of P-254

The reaction was carried out in the same manner as in the synthesis method of P-1 using Inter-254-c (2.56 g, 3.09 mmol), Sub 2-1 (0.52 g, 3.09 mmol), Pdz (dba) s (0.08 g, 0.09 mmol), P(t-Bu)$_3$ (0.04 g, 0.19 mmol), NaOt-Bu (0.59 g, 6.18 mmol) to obtain 1.89 g (yield 72%) of product.

The FD-MS values of the compounds P-1 to P-266 of the present invention prepared according to the above synthesis examples are shown in Table 3 below.

TABLE 3

| Compound | FD-MS |
|---|---|
| P-1  | m/z = 788.23($C_{55}H_{36}N_2S_2$ = 789.03) |
| P-2  | m/z = 848.29($C_{61}H_{40}N_2OS$ = 849.06) |
| P-3  | m/z = 860.29($C_{59}H_{44}N_2OS_2$ = 861.13) |
| P-4  | m/z = 897.32($C_{65}H_{43}N_3S$ = 898.14) |
| P-5  | m/z = 822.27($C_{59}H_{38}N_2OS$ = 823.03) |
| P-6  | m/z = 923.33($C_{67}H_{45}N_3S$ = 924.18) |
| P-7  | m/z = 845.29($C_{61}H_{39}N_3S$ = 846.06) |
| P-8  | m/z = 838.25($C_{59}H_{38}N_2S_2$ = 839.09) |
| P-9  | m/z = 877.26($C_{61}H_{39}N_3S_2$ = 878.12) |
| P-10 | m/z = 1119.33($C_{79}H_{49}N_3OS_2$ = 1120.4) |

TABLE 3-continued

| Compound | FD-MS |
|---|---|
| P-11 | m/z = 782.32($C_{55}H_{26}D_{10}N_2OS$ = 783.03) |
| P-12 | m/z = 963.36($C_{70}H_{49}N_3S$ = 964.24) |
| P-13 | m/z = 836.29($C_{60}H_{40}N_2OS$ = 837.05) |
| P-14 | m/z = 990.26($C_{67}H_{40}F_2N_2OS_2$ = 991.19) |
| P-15 | m/z = 879.27($C_{61}H_{38}FN_3OS$ = 880.05) |
| P-16 | m/z = 998.34($C_{72}H_{46}N_4S$ = 999.25) |
| P-17 | m/z = 1016.33($C_{73}H_{48}N_2S_2$ = 1017.32) |
| P-18 | m/z = 782.32($C_{55}H_{26}D_{10}N_2OS$ = 783.03) |
| P-19 | m/z = 974.33($C_{71}H_{46}N_2OS$ = 975.22) |
| P-20 | m/z = 1012.36($C_{73}H_{48}N_4S$ = 1013.28) |
| P-21 | m/z = 864.26($C_{61}H_{40}N_2S_2$ = 865.13) |
| P-22 | m/z = 973.35($C_{71}H_{47}N_3S$ = 974.24) |
| P-23 | m/z = 886.30($C_{64}H_{42}N_2OS$ = 887.11) |
| P-24 | m/z = 916.37($C_{63}H_{52}N_2O_3S$ = 917.18) |
| P-25 | m/z = 957.41($C_{69}H_{55}N_3S$ = 958.28) |
| P-26 | m/z = 894.22($C_{61}H_{38}N_2S_3$ = 895.17) |
| P-27 | m/z = 1115.43($C_{82}H_{57}N_3S$ = 1116.44) |
| P-28 | m/z = 872.29($C_{63}H_{40}N_2OS$ = 873.09) |
| P-29 | m/z = 788.23($C_{55}H_{36}N_2S_2$ = 789.03) |
| P-30 | m/z = 942.31($C_{67}H_{43}FN_2OS$ = 943.15) |
| P-31 | m/z = 847.30($C_{61}H_{41}N_3S$ = 848.08) |
| P-32 | m/z = 1053.38($C_{76}H_{51}N_3OS$ = 1054.32) |
| P-33 | m/z = 940.29($C_{67}H_{44}N_2S_2$ = 941.22) |
| P-34 | m/z = 786.27($C_{56}H_{38}N_2OS$ = 786.99) |
| P-35 | m/z = 847.30($C_{61}H_{41}N_3S$ = 848.08) |
| P-36 | m/z = 838.25($C_{59}H_{38}N_2S_2$ = 839.09) |
| P-37 | m/z = 940.29($C_{67}H_{44}N_2S_2$ = 941.22) |
| P-38 | m/z = 822.27($C_{59}H_{38}N_2OS$ = 823.03) |
| P-39 | m/z = 847.30($C_{61}H_{41}N_3S$ = 848.08) |
| P-40 | m/z = 786.27($C_{56}H_{38}N_2OS$ = 786.99) |
| P-41 | m/z = 772.25($C_{55}H_{36}N_2OS$ = 772.97) |
| P-42 | m/z = 788.23($C_{55}H_{36}N_2S_2$ = 789.03) |
| P-43 | m/z = 861.32($C_{62}H_{43}N_3S$ = 862.11) |
| P-44 | m/z = 772.25($C_{55}H_{36}N_2OS$ = 772.97) |
| P-45 | m/z = 772.25($C_{55}H_{36}N_2OS$ = 772.97) |
| P-46 | m/z = 788.23($C_{55}H_{36}N_2S_2$ = 789.03) |
| P-47 | m/z = 847.30($C_{61}H_{41}N_3S$ = 848.08) |
| P-48 | m/z = 802.25($C_{56}H_{38}N_2S_2$ = 803.05) |
| P-49 | m/z = 788.23($C_{55}H_{36}N_2S_2$ = 789.03) |
| P-50 | m/z = 772.25($C_{55}H_{36}N_2OS$ = 772.97) |
| P-51 | m/z = 847.30($C_{61}H_{41}N_3S$ = 848.08) |
| P-52 | m/z = 788.23($C_{55}H_{36}N_2S_2$ = 789.03) |
| P-53 | m/z = 940.29($C_{67}H_{44}N_2S_2$ = 941.22) |
| P-54 | m/z = 822.27($C_{59}H_{38}N_2OS$ = 823.03) |
| P-55 | m/z = 897.32($C_{65}H_{43}N_3S$ = 898.14) |
| P-56 | m/z = 772.25($C_{55}H_{36}N_2OS$ = 772.97) |
| P-57 | m/z = 824.21($C_{55}H_{34}F_2N_2S_2$ = 825.01) |
| P-58 | m/z = 924.32($C_{67}H_{44}N_2OS$ = 925.16) |
| P-59 | m/z = 959.43($C_{69}H_{57}N_3S$ = 960.30) |
| P-60 | m/z = 877.26($C_{61}H_{39}N_3S_2$ = 878.12) |
| P-61 | m/z = 888.26($C_{63}H_{40}N_2S_2$ = 889.15) |

TABLE 3-continued

| Compound | FD-MS |
|---|---|
| P-62 | m/z = 947.33($C_{69}H_{45}N_3S$ = 948.20) |
| P-63 | m/z = 772.25($C_{55}H_{36}N_2OS$ = 772.97) |
| P-64 | m/z = 845.29($C_{61}H_{39}N_3S$ = 846.06) |
| P-65 | m/z = 772.25($C_{55}H_{36}N_2OS$ = 772.97) |
| P-66 | m/z = 904.29($C_{64}H_{44}N_2S_2$ = 905.19) |
| P-67 | m/z = 1099.40($C_{81}H_{53}N_3S$ = 1100.40) |
| P-68 | m/z = 772.25($C_{55}H_{36}N_2OS$ = 772.97) |
| P-69 | m/z = 928.26($C_{65}H_{40}N_2OS_2$ = 929.17) |
| P-70 | m/z = 772.25($C_{55}H_{36}N_2OS$ = 772.97) |
| P-71 | m/z = 947.33($C_{69}H_{45}N_3S$ = 948.20) |
| P-72 | m/z = 788.23($C_{55}H_{36}N_2S_2$ = 789.03) |
| P-73 | m/z = 788.23($C_{55}H_{36}N_2S_2$ = 789.03) |
| P-74 | m/z = 772.25($C_{55}H_{36}N_2OS$ = 772.97) |
| P-75 | m/z = 1003.31($C_{71}H_{45}N_3S_2$ = 1004.28) |
| P-76 | m/z = 900.36($C_{63}H_{52}N_2S_2$ = 901.24) |
| P-77 | m/z = 848.29($C_{61}H_{40}N_2OS$ = 849.06) |
| P-78 | m/z = 920.35($C_{67}H_{44}N_4O$ = 921.12) |
| P-79 | m/z = 848.29($C_{61}H_{40}N_2OS$ = 849.06) |
| P-80 | m/z = 921.30($C_{66}H_{39}N_3O_3$ = 922.06) |
| P-81 | m/z = 786.29($C_{56}H_{38}N_2O_3$ = 786.93) |
| P-82 | m/z = 772.25($C_{55}H_{36}N_2OS$ = 772.97) |
| P-83 | m/z = 1051.39($C_{77}H_{50}FN_3O$ = 1052.27) |
| P-84 | m/z = 931.36($C_{69}H_{45}N_3O$ = 932.14) |
| P-85 | m/z = 806.29($C_{59}H_{38}N_2O_2$ = 806.97) |
| P-86 | m/z = 782.32($C_{55}H_{26}D_{10}N_2OS$ = 783.03) |
| P-87 | m/z = 931.36($C_{69}H_{45}N_3O$ = 932.14) |
| P-88 | m/z = 862.27($C_{61}H_{40}N_2O_2S$ = 863.05) |
| P-89 | m/z = 924.32($C_{67}H_{44}N_2OS$ = 925.16) |
| P-90 | m/z = 824.28($C_{59}H_{37}FN_2O_2$ = 824.96) |
| P-91 | m/z = 908.34($C_{67}H_{44}N_2O_2$ = 909.10) |
| P-92 | m/z = 845.34($C_{62}H_{43}N_3O$ = 846.05) |
| P-93 | m/z = 848.29($C_{61}H_{40}N_2OS$ = 849.06) |
| P-94 | m/z = 861.34($C_{62}H_{43}N_3O_2$ = 862.05) |
| P-95 | m/z = 797.25($C_{56}H_{35}N_3OS$ = 797.98) |
| P-96 | m/z = 774.27($C_{55}H_{35}FN_2O_2$ = 774.90) |
| P-97 | m/z = 924.32($C_{67}H_{44}N_2OS$ = 925.16) |
| P-98 | m/z = 879.32($C_{65}H_{41}N_3O$ = 880.06) |
| P-99 | m/z = 832.31($C_{61}H_{40}N_2O_2$ = 833.00) |
| P-100 | m/z = 848.29($C_{61}H_{40}N_2OS$ = 849.06) |
| P-101 | m/z = 808.24($C_{55}H_{34}F_2N_2OS$ = 808.95) |
| P-102 | m/z = 766.34($C_{55}H_{26}D_{10}N_2O_2$ = 766.97) |
| P-103 | m/z = 1083.42($C_{81}H_{53}N_3O$ = 1084.34) |
| P-104 | m/z = 797.25($C_{56}H_{35}N_3OS$ = 797.98) |
| P-105 | m/z = 856.31($C_{63}H_{40}N_2O_2$ = 857.03) |
| P-106 | m/z = 772.25($C_{55}H_{36}N_2OS$ = 772.97) |
| P-107 | m/z = 983.39($C_{73}H_{49}N_3O$ = 984.22) |
| P-108 | m/z = 1010.33($C_{74}H_{48}N_2OS$ = 1011.26) |
| P-109 | m/z = 884.38($C_{63}H_{52}N_2OS$ = 885.18) |
| P-110 | m/z = 925.35($C_{67}H_{44}FN_3O$ = 926.11) |
| P-111 | m/z = 856.31($C_{63}H_{40}N_2O_2$ = 857.03) |
| P-112 | m/z = 1010.35($C_{74}H_{46}N_2O_3$ = 1011.19) |
| P-113 | m/z = 867.31($C_{61}H_{39}F_2N_3O$ = 868.00) |
| P-114 | m/z = 781.27($C_{56}H_{35}N_3O_2$ = 781.92) |
| P-115 | m/z = 1126.36($C_{82}H_{50}N_2O_2S$ = 1127.37) |
| P-116 | m/z = 912.28($C_{65}H_{40}N_2O_2S$ = 913.11) |
| P-117 | m/z = 772.25($C_{55}H_{36}N_2OS$ = 772.97) |
| P-118 | m/z = 907.36($C_{67}H_{45}N_3O$ = 908.12) |
| P-119 | m/z = 756.28($C_{55}H_{36}N_2O_2$ = 756.91) |
| P-120 | m/z = 786.27($C_{56}H_{38}N_2O_2$ = 786.99) |
| P-121 | m/z = 756.28($C_{55}H_{36}N_2O_2$ = 756.91) |
| P-122 | m/z = 786.27($C_{56}H_{38}N_2O_2$ = 786.99) |
| P-123 | m/z = 943.34($C_{67}H_{43}F_2N_3O$ = 944.10) |
| P-124 | m/z = 772.25($C_{55}H_{36}N_2OS$ = 772.97) |
| P-125 | m/z = 772.25($C_{55}H_{36}N_2OS$ = 772.97) |
| P-126 | m/z = 822.27($C_{59}H_{38}N_2OS$ = 823.03) |
| P-127 | m/z = 983.39($C_{73}H_{49}N_3O$ = 984.22) |
| P-128 | m/z = 806.29($C_{59}H_{38}N_2O_2$ = 806.97) |
| P-129 | m/z = 790.25($C_{55}H_{35}FN_2OS$ = 790.96) |
| P-130 | m/z = 908.34($C_{67}H_{44}N_2O_2$ = 909.10) |
| P-131 | m/z = 931.36($C_{69}H_{45}N_3O$ = 932.14) |
| P-132 | m/z = 806.29($C_{59}H_{38}N_2O_2$ = 806.97) |
| P-133 | m/z = 806.29($C_{59}H_{38}N_2O_2$ = 806.97) |
| P-134 | m/z = 884.38($C_{63}H_{52}N_2OS$ = 885.18) |
| P-135 | m/z = 831.32($C_{61}H_{41}N_3O$ = 832.02) |
| P-136 | m/z = 871.34($C_{61}H_{29}D_{10}N_3OS$ = 872.12) |
| P-137 | m/z = 808.24($C_{55}H_{34}F_2N_2OS$ = 808.95) |
| P-138 | m/z = 808.24($C_{55}H_{34}F_2N_2OS$ = 808.95) |
| P-139 | m/z = 957.37($C_{71}H_{47}N_3O$ = 958.18) |
| P-140 | m/z = 832.31($C_{61}H_{40}N_2O_2$ = 833.00) |
| P-141 | m/z = 772.25($C_{55}H_{36}N_2OS$ = 772.97) |
| P-142 | m/z = 806.29($C_{59}H_{38}N_2O_2$ = 806.97) |
| P-143 | m/z = 867.31($C_{61}H_{39}F_2N_3O$ = 868.00) |
| P-144 | m/z = 981.37($C_{73}H_{47}N_3$ = 982.20) |
| P-145 | m/z = 848.29($C_{61}H_{40}N_2OS$ = 849.06) |
| P-146 | m/z = 756.28($C_{55}H_{36}N_2O_2$ = 756.91) |
| P-147 | m/z = 1000.35($C_{73}H_{48}N_2OS$ = 1001.26) |
| P-148 | m/z = 831.32($C_{61}H_{41}N_3O$ = 832.02) |
| P-149 | m/z = 756.28($C_{55}H_{36}N_2O_2$ = 756.91) |
| P-150 | m/z = 756.28($C_{55}H_{36}N_2O_2$ = 756.91) |
| P-151 | m/z = 831.32($C_{61}H_{41}N_3O$ = 832.02) |
| P-152 | m/z = 772.25($C_{55}H_{36}N_2OS$ = 772.97) |
| P-153 | m/z = 838.25($C_{59}H_{38}N_2S_2$ = 839.09) |
| P-154 | m/z = 806.29($C_{59}H_{38}N_2O_2$ = 806.97) |
| P-155 | m/z = 822.27($C_{59}H_{38}N_2OS$ = 823.03) |
| P-156 | m/z = 897.32($C_{65}H_{43}N_3S$ = 898.14) |
| P-157 | m/z = 822.27($C_{59}H_{38}N_2OS$ = 823.03) |
| P-158 | m/z = 838.25($C_{59}H_{38}N_2S_2$ = 839.09) |
| P-159 | m/z = 987.33($C_{71}H_{45}N_3OS$ = 988.22) |
| P-160 | m/z = 822.27($C_{59}H_{38}N_2OS$ = 823.03) |
| P-161 | m/z = 838.25($C_{59}H_{38}N_2S_2$ = 839.09) |
| P-162 | m/z = 822.27($C_{59}H_{38}N_2OS$ = 823.03) |
| P-163 | m/z = 822.27($C_{59}H_{38}N_2OS$ = 823.03) |
| P-164 | m/z = 881.34($C_{65}H_{43}N_3O$ = 882.08) |
| P-165 | m/z = 888.26($C_{63}H_{40}N_2S_2$ = 889.15) |
| P-166 | m/z = 947.33($C_{69}H_{45}N_3S$ = 948.20) |
| P-167 | m/z = 856.31($C_{63}H_{40}N_2O_2$ = 857.03) |
| P-168 | m/z = 872.29($C_{63}H_{40}N_2OS$ = 873.09) |
| P-169 | m/z = 872.29($C_{63}H_{40}N_2OS$ = 873.09) |
| P-170 | m/z = 947.33($C_{69}H_{45}N_3S$ = 948.20) |
| P-171 | m/z = 872.29($C_{63}H_{40}N_2OS$ = 873.09) |
| P-172 | m/z = 872.29($C_{63}H_{40}N_2OS$ = 873.09) |
| P-173 | m/z = 872.29($C_{63}H_{40}N_2OS$ = 873.09) |
| P-174 | m/z = 872.29($C_{63}H_{40}N_2OS$ = 873.09) |
| P-175 | m/z = 929.34($C_{69}H_{43}N_3O$ = 930.12) |
| P-176 | m/z = 872.29($C_{63}H_{40}N_2OS$ = 873.09) |
| P-177 | m/z = 888.26($C_{63}H_{40}N_2S_2$ = 889.15) |
| P-178 | m/z = 872.29($C_{63}H_{40}N_2OS$ = 873.09) |
| P-179 | m/z = 931.36($C_{69}H_{45}N_3O$ = 932.14) |
| P-180 | m/z = 872.29($C_{63}H_{40}N_2OS$ = 873.09) |
| P-181 | m/z = 872.29($C_{63}H_{40}N_2OS$ = 873.09) |
| P-182 | m/z = 977.29($C_{69}H_{43}N_3S_2$ = 978.24) |
| P-183 | m/z = 931.36($C_{69}H_{45}N_3O$ = 932.14) |
| P-184 | m/z = 856.31($C_{63}H_{40}N_2O_2$ = 857.03) |
| P-185 | m/z = 872.29($C_{63}H_{40}N_2OS$ = 873.09) |
| P-186 | m/z = 947.33($C_{69}H_{45}N_3S$ = 948.20) |
| P-187 | m/z = 856.31($C_{63}H_{40}N_2O_2$ = 857.03) |
| P-188 | m/z = 872.29($C_{63}H_{40}N_2OS$ = 873.09) |
| P-189 | m/z = 848.29($C_{61}H_{40}N_2OS$ = 849.06) |
| P-190 | m/z = 898.30($C_{65}H_{42}N_2OS$ = 899.12) |
| P-191 | m/z = 907.36($C_{67}H_{45}N_3O$ = 908.12) |
| P-192 | m/z = 848.29($C_{61}H_{40}N_2OS$ = 849.06) |
| P-193 | m/z = 914.28($C_{65}H_{42}N_2S_2$ = 915.19) |
| P-194 | m/z = 1029.32($C_{73}H_{47}N_3S_2$ = 1030.32) |
| P-195 | m/z = 832.31($C_{61}H_{40}N_2O_2$ = 833.00) |
| P-196 | m/z = 864.32($C_{62}H_{44}N_2OS$ = 865.11) |
| P-197 | m/z = 898.3($C_{65}H_{42}N_2OS$ = 899.12) |
| P-198 | m/z = 914.28($C_{65}H_{42}N_2S_2$ = 915.19) |
| P-199 | m/z = 788.23($C_{55}H_{36}N_2S_2$ = 789.03) |
| P-200 | m/z = 847.30($C_{61}H_{41}N_3S$ = 848.08) |
| P-201 | m/z = 772.25($C_{55}H_{36}N_2OS$ = 772.97) |
| P-202 | m/z = 954.27($C_{67}H_{42}N_2OS_2$ = 955.21) |
| P-203 | m/z = 887.32($C_{61}H_{29}D_{10}N_3S_2$ = 888.19) |
| P-204 | m/z = 940.29($C_{67}H_{44}N_2S_2$ = 941.22) |
| P-205 | m/z = 838.23($C_{56}H_{36}F_2N_2S_2$ = 839.03) |
| P-206 | m/z = 924.32($C_{67}H_{44}N_2OS$ = 925.16) |
| P-207 | m/z = 999.36($C_{73}H_{49}N_3S$ = 1000.28) |
| P-208 | m/z = 788.23($C_{55}H_{36}N_2S_2$ = 789.03) |
| P-209 | m/z = 864.26($C_{61}H_{40}N_2S_2$ = 865.13) |
| P-210 | m/z = 847.30($C_{61}H_{41}N_3S$ = 848.08) |
| P-211 | m/z = 772.25($C_{55}H_{36}N_2OS$ = 772.97) |
| P-212 | m/z = 887.33($C_{64}H_{45}N_3S$ = 888.15) |
| P-213 | m/z = 888.32($C_{64}H_{44}N_2OS$ = 889.13) |
| P-214 | m/z = 972.33($C_{70}H_{44}N_4S$ = 973.21) |
| P-215 | m/z = 924.32($C_{67}H_{44}N_2OS$ = 925.16) |
| P-216 | m/z = 772.25($C_{55}H_{36}N_2OS$ = 772.97) |
| P-217 | m/z = 865.29($C_{61}H_{40}FN_3S$ = 866.07) |

TABLE 3-continued

| Compound | FD-MS |
|---|---|
| P-218 | m/z = 772.25($C_{55}H_{36}N_2OS$ = 772.97) |
| P-219 | m/z = 844.29($C_{59}H_{44}N_2S_2$ = 845.14) |
| P-220 | m/z = 845.29($C_{61}H_{39}N_3S$ = 846.06) |
| P-221 | m/z = 848.29($C_{61}H_{40}N_2OS$ = 849.06) |
| P-222 | m/z = 786.29($C_{56}H_{38}N_2O_3$ = 786.93) |
| P-223 | m/z = 831.32($C_{61}H_{41}N_3O$ = 832.02) |
| P-224 | m/z = 772.25($C_{55}H_{36}N_2OS$ = 772.97) |
| P-225 | m/z = 886.28($C_{62}H_{38}N_4OS$ = 887.07) |
| P-226 | m/z = 756.28($C_{55}H_{36}N_2O_2$ = 756.91) |
| P-227 | m/z = 983.39($C_{73}H_{49}N_3O$ = 984.22) |
| P-228 | m/z = 884.38($C_{63}H_{52}N_2OS$ = 885.18) |
| P-229 | m/z = 772.25($C_{55}H_{36}N_2OS$ = 772.97) |
| P-230 | m/z = 983.39($C_{73}H_{49}N_3O$ = 984.22) |
| P-231 | m/z = 908.34($C_{67}H_{44}N_2O_2$ = 909.10) |
| P-232 | m/z = 772.25($C_{55}H_{36}N_2OS$ = 772.97) |
| P-233 | m/z = 831.32($C_{61}H_{41}N_3O$ = 832.02) |
| P-234 | m/z = 826.23($C_{55}H_{33}F_3N_2OS$ = 826.94) |
| P-235 | m/z = 756.28($C_{55}H_{36}N_2O_2$ = 756.91) |
| P-236 | m/z = 772.25($C_{55}H_{36}N_2OS$ = 772.97) |
| P-237 | m/z = 844.31($C_{59}H_{44}N_2O_2S$ = 845.07) |
| P-238 | m/z = 849.32($C_{61}H_{40}FN_3O$ = 850.01) |
| P-239 | m/z = 908.34($C_{67}H_{44}N_2O_2$ = 909.10) |
| P-240 | m/z = 829.31($C_{61}H_{39}N_3O$ = 830.00) |
| P-241 | m/z = 772.25($C_{55}H_{36}N_2OS$ = 772.97) |
| P-242 | m/z = 756.28($C_{55}H_{36}N_2O_2$ = 756.91) |
| P-243 | m/z = 772.25($C_{55}H_{36}N_2OS$ = 772.97) |
| P-244 | m/z = 881.34($C_{65}H_{43}N_3O$ = 882.08) |
| P-245 | m/z = 848.29($C_{61}H_{40}N_2OS$ = 849.06) |
| P-246 | m/z = 923.33($C_{67}H_{45}N_3S$ = 924.18) |
| P-247 | m/z = 848.29($C_{61}H_{40}N_2OS$ = 849.06) |
| P-248 | m/z = 832.31($C_{61}H_{40}N_2O_2$ = 833.00) |
| P-249 | m/z = 864.26($C_{61}H_{40}N_2S_2$ = 865.13) |
| P-250 | m/z = 832.31($C_{61}H_{40}N_2O_2$ = 833.00) |
| P-251 | m/z = 907.36($C_{67}H_{45}N_3O$ = 908.12) |
| P-252 | m/z = 864.26($C_{61}H_{40}N_2S_2$ = 865.13) |
| P-253 | m/z = 923.33($C_{67}H_{45}N_3S$ = 924.18) |
| P-254 | m/z = 848.29($C_{61}H_{40}N_2OS$ = 849.06) |
| P-255 | m/z = 907.36($C_{67}H_{45}N_3O$ = 908.12) |
| P-256 | m/z = 848.29($C_{61}H_{40}N_2OS$ = 849.06) |
| P-257 | m/z = 848.29($C_{61}H_{40}N_2OS$ = 849.06) |
| P-258 | m/z = 848.29($C_{61}H_{40}N_2OS$ = 849.06) |
| P-259 | m/z = 939.33($C_{67}H_{45}N_3OS$ = 940.18) |
| P-260 | m/z = 939.33($C_{67}H_{45}N_3OS$ = 940.18) |
| P-261 | m/z = 838.25($C_{59}H_{38}N_2S_2$ = 839.09) |
| P-262 | m/z = 806.29($C_{59}H_{38}N_2O_2$ = 806.97) |
| P-263 | m/z = 822.27($C_{59}H_{38}N_2OS$ = 823.03) |
| P-264 | m/z = 822.27($C_{59}H_{38}N_2OS$ = 823.03) |
| P-265 | m/z = 973.35($C_{71}H_{47}N_3S$ = 974.24) |
| P-266 | m/z = 882.32($C_{65}H_{42}N_2O_2$ = 883.06) |

Fabrication and Evaluation of Organic Electric Element

[Example 1] Red Organic Electroluminescent Element (an Emission-Auxiliary Layer)

After vacuum-depositing 4,4',4"-Tris[2-naphthyl(phenyl) amino]triphenylamine (hereinafter, "2-TNATA") on an ITO layer (anode) formed on a glass substrate to form a hole injection layer with a thickness of 60 nm, a hole transport layer with a thickness of 60 nm was formed by vacuum-depositing N,N'-bis(1-naphthalenyl)-N,N'-bis-phenyl-(1,1'-biphenyl)-4,4'-diamine (hereinafter, "NPB") on the hole injection layer.

Subsequently, an emission-auxiliary layer with a thickness of 20 nm was formed by vacuum-depositing the compound P-1 of the present invention on the hole transport layer and 4,4'-N,N'-dicarbazole-biphenyl (hereinafter, "CBP") as a host material and bis-(1-phenylisoquinolyl) iridium(III)acetylacetonate (hereinafter, "(piq)$_2$Ir(acac)") as a dopant material in a weight ratio of 95:5 were deposited on the emission-auxiliary layer to form a light emitting layer with a thickness of 30 nm.

Subsequently, (1,1'-bisphenyl-4-olato)bis(2-methyl-8-quinolinolato)aluminum (hereinafter, "BAlq") was vacuum-deposited to a thickness of 10 nm on the light emitting layer to form a hole blocking layer, and tris-(8-hydroxyquinoline) aluminum (hereinafter, "Alq3") was vacuum-deposited to a thickness of 40 nm on the hole blocking layer to form a an electron transport layer.

Thereafter, LiF was deposited to a thickness of 0.2 nm to form an electron injection layer, and then Al was deposited to a thickness of 150 nm to form a cathode.

[Example 2] to [Example 44]

The organic electroluminescent elements were fabricated in the same manner as described in Example 1 except that the compounds of the present invention described in the following Table 4, instead of compound P-1 of the present invention, were used as material of an emission-auxiliary layer.

Comparative Example 1

The organic electroluminescent element was fabricated in the same manner as in Example 1, except that an emission-auxiliary layer was not formed.

[Comparative Example 2] and [Comparative Example 3]

The organic electroluminescent elements were fabricated in the same manner as described in Example 1 except that Comparative Compound A or B were used as material of an emission-auxiliary layer.

<Comparative Compound A>

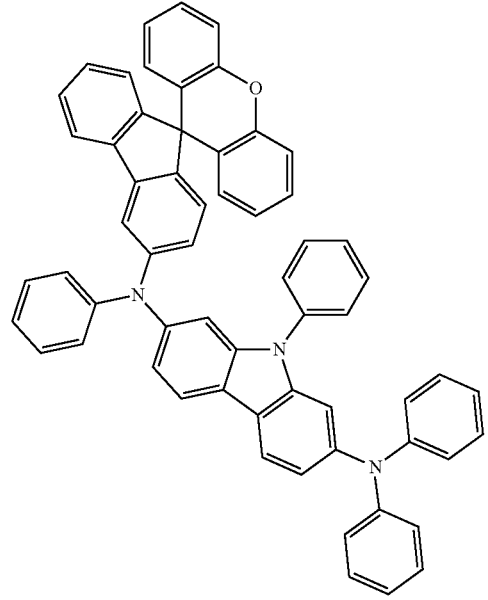

\<Comparative Compound B\>

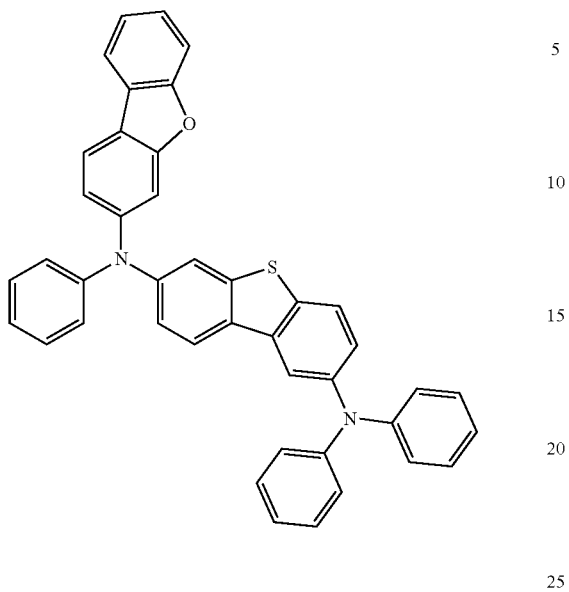

Electroluminescence (EL) characteristics were measured with PR-650 (Photoresearch) by applying a forward bias DC voltage to the organic electroluminescent elements prepared in Examples 1 to 44 of the present invention and Comparative Examples 1 to 3. And, the T95 life time was measured using a life time measuring apparatus manufactured by Mcscience Inc. at reference brightness of 2500 cd/m². The measurement results are shown in Tables 4 below.

TABLE 4

| | Compound | Voltage (V) | Current Density (mA/cm²) | Brightness (cd/m²) | Efficiency (cd/A) | Lifetime T (95) | CIE x | CIE y |
|---|---|---|---|---|---|---|---|---|
| comp. Ex (1) | — | 6.7 | 34.2 | 2500 | 7.3 | 62.9 | 0.61 | 0.31 |
| comp. Ex (2) | comp. Com A | 5.8 | 14.5 | 2500 | 17.2 | 85.0 | 0.60 | 0.34 |
| comp. Ex (3) | comp. Com B | 5.0 | 10.4 | 2500 | 24.0 | 113.2 | 0.61 | 0.30 |
| Ex. (1) | Com. (P-1) | 4.8 | 10.1 | 2500 | 24.8 | 151.4 | 0.62 | 0.33 |
| Ex. (2) | Com. (P-2) | 4.8 | 9.7 | 2500 | 25.8 | 163.0 | 0.62 | 0.33 |
| Ex. (3) | Com. (P-4) | 4.8 | 10.6 | 2500 | 23.5 | 131.6 | 0.63 | 0.33 |
| Ex. (4) | Com. (P-9) | 5.1 | 10.5 | 2500 | 23.7 | 131.8 | 0.63 | 0.31 |
| Ex. (5) | Com. (P-21) | 4.9 | 10.3 | 2500 | 24.2 | 148.6 | 0.61 | 0.33 |
| Ex. (6) | Com. (P-31) | 5.1 | 10.6 | 2500 | 23.6 | 131.7 | 0.61 | 0.35 |
| Ex. (7) | Com. (P-33) | 4.8 | 10.2 | 2500 | 24.5 | 149.9 | 0.64 | 0.34 |
| Ex. (8) | Com. (P-41) | 4.8 | 8.9 | 2500 | 28.0 | 177.7 | 0.64 | 0.32 |
| Ex. (9) | Com. (P-42) | 4.8 | 9.5 | 2500 | 26.4 | 161.9 | 0.61 | 0.35 |
| Ex. (10) | Com. (P-44) | 4.9 | 9.1 | 2500 | 27.4 | 174.4 | 0.60 | 0.32 |
| Ex. (11) | Com. (P-45) | 4.8 | 9.2 | 2500 | 27.2 | 172.7 | 0.61 | 0.34 |
| Ex. (12) | Com. (P-50) | 4.9 | 9.1 | 2500 | 27.5 | 174.4 | 0.65 | 0.34 |
| Ex. (13) | Com. (P-59) | 4.9 | 10.8 | 2500 | 23.1 | 129.2 | 0.62 | 0.32 |
| Ex. (14) | Com. (P-64) | 4.8 | 11.0 | 2500 | 22.8 | 127.9 | 0.63 | 0.31 |
| Ex. (15) | Com. (P-70) | 4.9 | 9.6 | 2500 | 25.9 | 164.7 | 0.65 | 0.32 |
| Ex. (16) | Com. (P-83) | 5.0 | 10.9 | 2500 | 22.9 | 134.3 | 0.63 | 0.33 |
| Ex. (17) | Com. (P-89) | 5.3 | 10.7 | 2500 | 23.4 | 151.5 | 0.63 | 0.31 |
| Ex. (18) | Com. (P-106) | 5.1 | 10.2 | 2500 | 24.4 | 157.6 | 0.62 | 0.34 |
| Ex. (19) | Com. (P-112) | 5.1 | 9.7 | 2500 | 25.7 | 171.1 | 0.63 | 0.33 |
| Ex. (20) | Com. (P-117) | 5.1 | 9.8 | 2500 | 25.4 | 149.2 | 0.61 | 0.34 |
| Ex. (21) | Com. (P-118) | 5.2 | 10.0 | 2500 | 25.0 | 147.9 | 0.64 | 0.34 |
| Ex. (22) | Com. (P-131) | 5.1 | 10.3 | 2500 | 24.3 | 142.4 | 0.61 | 0.31 |
| Ex. (23) | Com. (P-132) | 5.2 | 9.9 | 2500 | 25.1 | 167.7 | 0.63 | 0.31 |
| Ex. (24) | Com. (P-138) | 5.0 | 9.9 | 2500 | 25.3 | 167.9 | 0.60 | 0.32 |
| Ex. (25) | Com. (P-141) | 5.1 | 9.7 | 2500 | 25.7 | 165.3 | 0.61 | 0.34 |
| Ex. (26) | Com. (P-145) | 5.1 | 10.1 | 2500 | 24.7 | 159.1 | 0.61 | 0.30 |

TABLE 4-continued

| | Compound | Voltage (V) | Current Density (mA/cm$^2$) | Brightness (cd/m$^2$) | Efficiency (cd/A) | Lifetime T (95) | CIE x | CIE y |
|---|---|---|---|---|---|---|---|---|
| Ex. (27) | Com. (P-148) | 5.2 | 10.6 | 2500 | 23.6 | 138.3 | 0.61 | 0.31 |
| Ex. (28) | Com. (P-162) | 4.8 | 9.2 | 2500 | 27.1 | 172.5 | 0.63 | 0.34 |
| Ex. (29) | Com. (P-192) | 5.0 | 9.9 | 2500 | 25.2 | 140.9 | 0.61 | 0.34 |
| Ex. (30) | Com. (P-195) | 5.3 | 9.3 | 2500 | 27.0 | 181.4 | 0.61 | 0.30 |
| Ex. (31) | Com. (P-196) | 5.0 | 10.2 | 2500 | 24.6 | 156.0 | 0.62 | 0.31 |
| Ex. (32) | Com. (P-204) | 4.9 | 9.8 | 2500 | 25.6 | 148.8 | 0.61 | 0.31 |
| Ex. (33) | Com. (P-208) | 4.9 | 10.0 | 2500 | 25.1 | 148.5 | 0.63 | 0.31 |
| Ex. (34) | Com. (P-211) | 5.0 | 9.7 | 2500 | 25.9 | 164.5 | 0.62 | 0.33 |
| Ex. (35) | Com. (P-216) | 4.9 | 9.0 | 2500 | 27.7 | 166.3 | 0.60 | 0.34 |
| Ex. (36) | Com. (P-220) | 5.0 | 11.0 | 2500 | 22.8 | 127.8 | 0.61 | 0.34 |
| Ex. (37) | Com. (P-223) | 5.2 | 10.9 | 2500 | 22.9 | 134.4 | 0.63 | 0.34 |
| Ex. (38) | Com. (P-226) | 5.1 | 9.2 | 2500 | 27.3 | 171.1 | 0.63 | 0.33 |
| Ex. (39) | Com. (P-243) | 5.2 | 10.6 | 2500 | 23.6 | 151.4 | 0.61 | 0.31 |
| Ex. (40) | Com. (P-248) | 5.2 | 9.1 | 2500 | 27.5 | 173.0 | 0.65 | 0.31 |
| Ex. (41) | Com. (P-250) | 5.3 | 9.5 | 2500 | 26.4 | 171.3 | 0.64 | 0.31 |
| Ex. (42) | Com. (P-251) | 5.3 | 10.6 | 2500 | 23.5 | 138.3 | 0.63 | 0.32 |
| Ex. (43) | Com. (P-254) | 5.0 | 8.9 | 2500 | 28.1 | 168.0 | 0.62 | 0.32 |
| Ex. (44) | Com. (P-262) | 5.1 | 9.4 | 2500 | 26.6 | 167.8 | 0.61 | 0.34 |

As can be seen from the results of Table 4, when a red organic electroluminescent device was manufactured with the compounds of the present invention as material for an emission-auxiliary layer, lifetime can be improved, compared to Comparative Example 1 having no emission-auxiliary layer, or Comparative Examples 2 and 3 prepared with Comparative Compound A or Comparative Compound B as material for an emission-auxiliary layer.

The results from Comparative Example 2 or Comparative Example 3 prepared with Comparative Compound A or Comparative Compound B are superior to Comparative Example 1 having no emission-auxiliary layer, and it can be seen that Example 1 to Example 44 of the present invention are remarkably superior in lifetime.

Table 5 below shows the physical property values of Compound P-45 of the present invention, Comparative Compound A, Comparative Compound B, and NPB.

TABLE 5

| Compound | Compound P-45 | comp. ComA | comp. ComB | NPB |
|---|---|---|---|---|
| G. HOMO | −4.84 | −4.67 | −4.87 | −4.71 |
| G. LUMO | −1.00 | −0.99 | −1.14 | −1.12 |
| G. Band Gap | 3.84 | 3.68 | 3.73 | 3.59 |

Comparing the compound of the present invention with Comparative Compound A, the linking group between the amino groups is carbazole in Comparative Compound A, while dibenzofuran and dibenzothiophene are introduced as the linking group in the compound of the present invention.

As can be seen in Table 5, where carbazole is introduced as a linker (Comparative Compound A), the HOMO value is higher than that of the compound of the present invention in which dibenzofuran or dibenzothiophene is introduced, and has a higher HOMO value than the NPB used as a material for the hole transport layer in Example 1.

Therefore, in the case of Comparative Compound A, the hole is not easily moved to the host, compared to the compound of the present invention, and the hole is accumulated. As a result, the charge balance in the light emitting layer is decreased, so that the efficiency and lifetime are significantly lower than the compound of the present invention.

Comparing the compound of the present invention with Comparative Compound B, Comparative compound B has the structure in which dibenzofuran is introduced as a substituent of an amino group, while spiro[fluorene-9,9'-xanthene], spiro[fluorene-9,9'-thioxanthene], spiro[acridine-9,9'-fluorene], etc. are introduced as substituents in the compound of the present invention.

As can be seen from Table 5, the compound of the present invention has a higher LUMO value than Comparative Compound B in which dibenzofuran is substituted, so that electrons moving from the host to the hole transport layer can be more effectively blocked. Therefore, damage to the hole transport layer or the emission-auxiliary layer can be minimized, and as a result the lifetime seems significantly improved.

In the case of the emission-auxiliary layer, it will be very difficult for a person of ordinary skill in the art to infer/expect the characteristics exhibited in the case where the compound of the present invention is used for the emission-auxiliary layer, even from the case where a similar core compound is used, because the relationship between the hole transport layer and the light-emitting layer (host) needs to be understood.

In addition, in the evaluation results of the above-mentioned element fabrication, although the characteristics of the element are described with the case where the compound of the present invention is applied for an emission-auxiliary layer, the compound of the present invention can be also applied to a hole transport layer or to both a hole transport layer and an emission-auxiliary layer.

Although the exemplary embodiments of the present invention have been described for illustrative purposes, those skilled in the art to which the present invention pertains will be capable of various modifications without departing from the essential characteristics of the present invention. Therefore, the embodiment disclosed herein is intended to illustrate the scope of the technical idea of the present invention, and the spirit and scope of the present invention are not limited by the embodiments. The scope of the present invention shall be construed on the basis of the accompanying claims, and it shall be construed that all of the technical ideas included within the scope equivalent to the claims belong to the present invention.

The invention claimed is:
1. A compound of Formula 1:

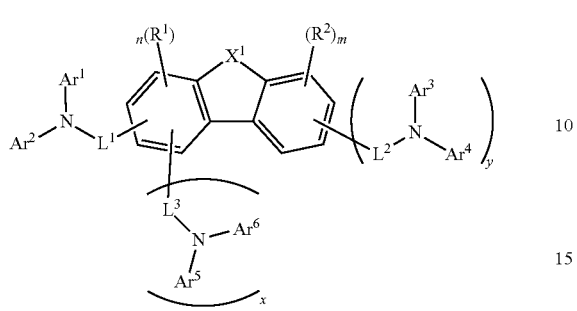

<Formula 1> wherein:
Ar$^1$ to Ar$^6$ are each independently selected from the group consisting of a C$_6$-C$_{60}$ aryl group, a fluorenyl group, a C$_2$-C$_{60}$ heterocyclic group containing at least one heteroatom of O, N, S, Si, and P, a C$_3$-C$_{60}$ aliphatic ring group, -L'-N(R$_a$)(R$_b$), Formula A-1 and Formula A-2, and at least one of Ar$^1$ to Ar$^6$ is Formula A-1 or Formula A-2,

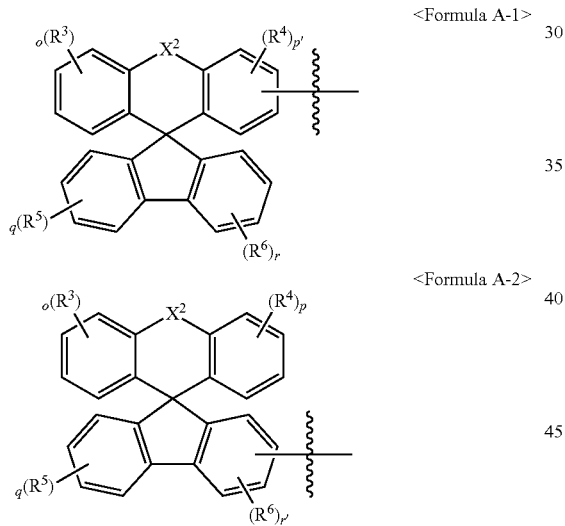

<Formula A-1>

<Formula A-2>

X$^1$ is O or S,
X$^2$ is N(R'), O or S,
R$^1$ to R$^6$ are each independently selected from the group consisting of hydrogen, deuterium, halogen, cyano group, nitro group, a C$_6$-C$_{60}$ aryl group, a fluorenyl group, a C$_2$-C$_{60}$ heterocyclic group containing at least one heteroatom of O, N, S, Si, and P, a C$_3$-C$_{60}$ aliphatic ring group, a C$_1$-C$_{30}$ alkyl group, a C$_2$-C$_{30}$ alkenyl group, a C$_2$-C$_{30}$ alkynyl group, a C$_1$-C$_{30}$ alkoxyl group, a C$_6$-C$_{30}$ aryloxy group and -L'-N(R$_a$)(R$_b$), and adjacent groups together may be bonded to each other to form a ring,
n, p' and r' are each an integer of 0 to 3, m, o, p, q and r are each an integer of 0 to 4, and where they are each an integer of 2 to 4, each of R$^1$s, each of R$^2$s, each of R$^3$s, each of R$^4$s, each of R$^5$s, or each of R$^6$s is the same or different from each other, x and y are each an integer of 0 to 2, and x+y is an integer greater than or equal to 1,
L$^1$ to L$^3$ and L' are each independently selected from the group consisting of a single bond, a C$_6$-C$_{60}$ arylene group, a fluorenylene group, a C$_3$-C$_{60}$ aliphatic ring group and a C$_2$-C$_{60}$ heterocyclic group containing at least one heteroatom of O, N, S, Si, and P,
R', R$_a$ and R$_b$ are each independently selected from the group consisting of a C$_6$-C$_{60}$ aryl group, a fluorenyl group, a C$_2$-C$_{60}$ heterocyclic group containing at least one heteroatom of O, N, S, Si, and P and a C$_3$-C$_{60}$ aliphatic ring group,
with the proviso that, in the case where L$^1$ and L$^2$ are each a single bond, X$^2$ is O or S, and y is an integer of 1, at least one of R$^1$ to R$^6$ forms an aromatic hydrocarbon ring with an adjacent group, and
Ar$^1$ to Ar$^6$, R$^1$ to R$^6$, L$^1$ to L$^3$, R' and the ring formed by adjacent groups may be each optionally substituted with one or more substituents selected from the group consisting of deuterium, halogen, a silane group unsubstituted or substituted with a C$_1$-C$_{20}$ alkyl group or a C$_6$-C$_{20}$ aryl group, a siloxane group, a boron group, a germanium group, a cyano group, a nitro group, a C$_1$-C$_{20}$ alkylthio group, a C$_1$-C$_{20}$ alkoxyl group, a C$_6$-C$_{20}$ aryloxy group, a C$_6$-C$_{20}$ arylthio group, a C$_1$-C$_{20}$ alkyl group, a C$_2$-C$_{20}$ alkenyl group, a C$_2$-C$_{20}$ alkynyl group, a C$_6$-C$_{20}$ aryl group, a fluorenyl group, a C$_2$-C$_{20}$ heterocyclic group containing at least one heteroatom of O, N, S, Si, and P, a C$_3$-C$_{20}$ aliphatic ring group, a C$_7$-C$_{20}$ arylalkyl group, and C$_8$-C$_{20}$ arylalkenyl group,
with the proviso that Formula 20 is excluded from Formula 1:

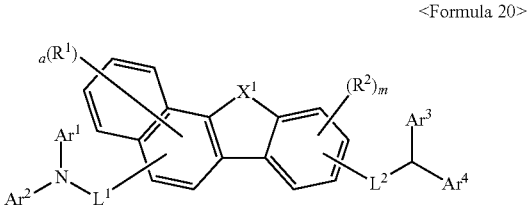

<Formula 20> wherein X$^1$, L$^1$-L$^2$, Ar$^1$-Ar$^4$, R$^1$, and R$^2$ are the same as defined for Formula 1, and a is an integer of 0 to 5 and m is an integer of 0 to 3.

2. The compound of claim 1, wherein Formula 1 is represented by Formula 2 or Formula 3:

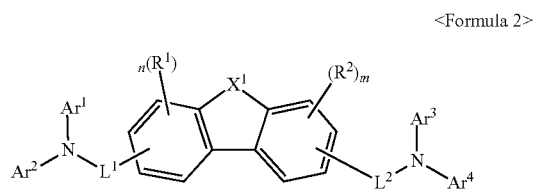

<Formula 2>

<Formula 3>

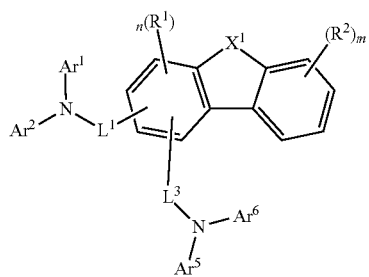

wherein $X^1$, $L^1$-$L^3$, $Ar^1$-$Ar^6$, $R^1$, $R^2$, n and m are the same as defined in claim 1, and n is an integer of 0 to 3 in Formula 2 and an integer of 0 to 2 in Formula 3.

3. The compound of claim 1, wherein Formula 1 is represented by one of Formula 4 to Formula 6, Formula 8, Formula 9, Formula 11 and Formula 14 to Formula 19:

<Formula 4>

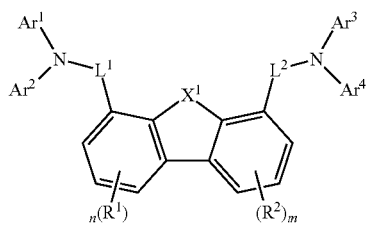

<Formula 5>

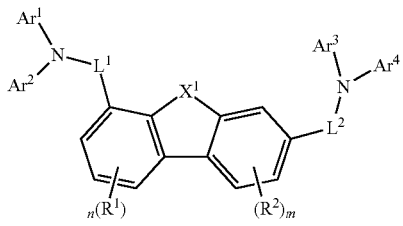

<Formula 6>

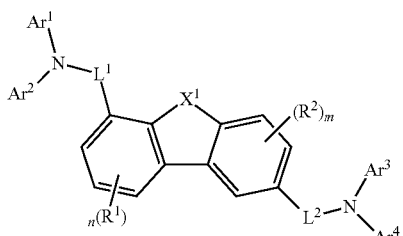

<Formula 7>

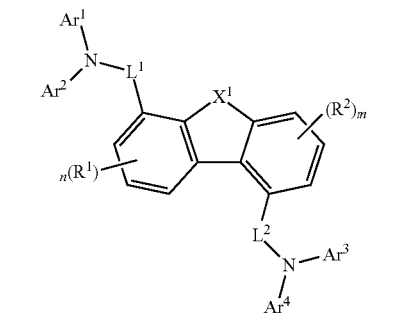

<Formula 8>

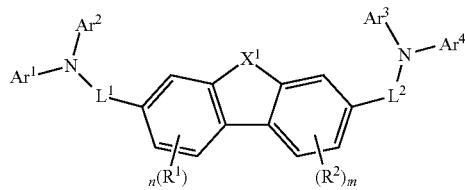

<Formula 9>

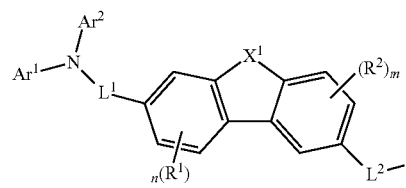

<Formula 10>

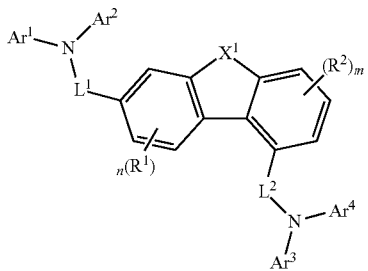

<Formula 11>

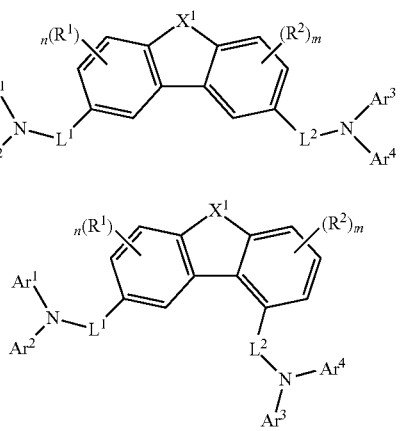

<Formula 12>

<Formula 13>

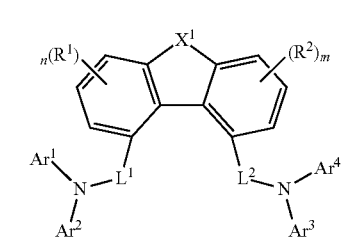

<Formula 14>

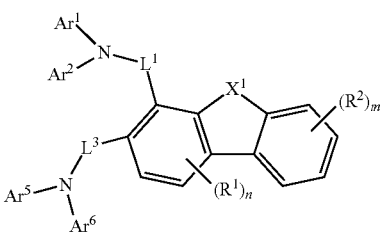

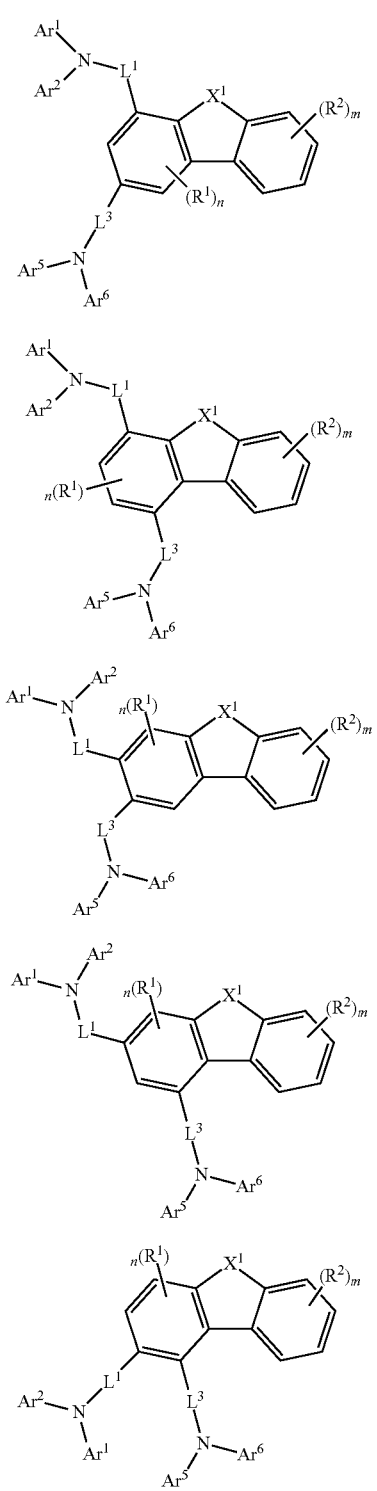
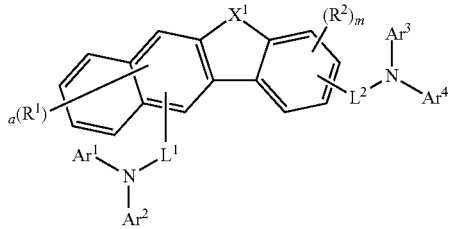
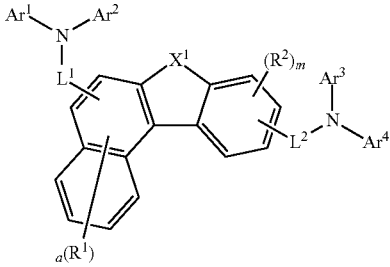
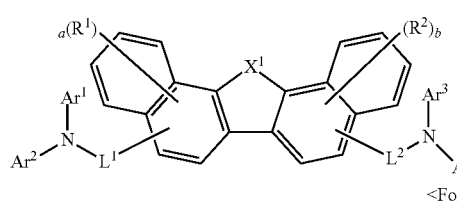
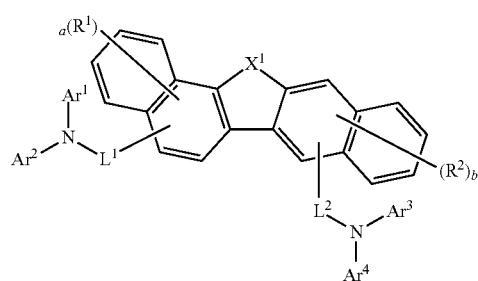
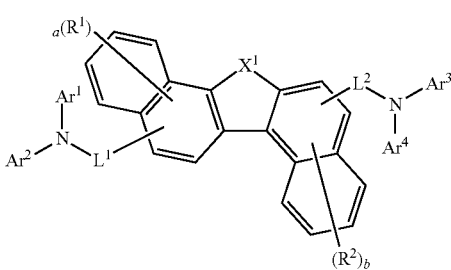
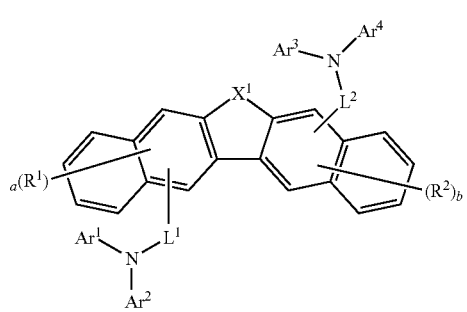
wherein $X^1$, $L^1$-$L^3$, $Ar^1$-$Ar^6$, $R^1$, and $R^2$, n and m are the same as defined in claim 1, n is an integer of 0 to 3 in Formulas 4 to 6, 8, 9 and 11 and an integer of 0 to 2 in Formulas 14 to 19, and m is an integer of 0 to 3 in Formulas 4 to 6, 8, 9 and 11 and an integer of 0 to 4 in Formulas 14 to 19.
4. The compound of claim 1, wherein Formula 1 is represented by one of Formula 21 to Formula 34:

<Formula 27>
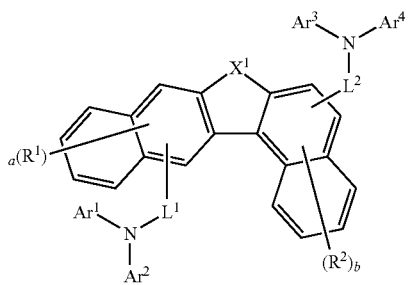
<Formula 28>
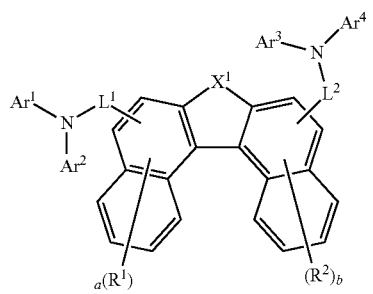
<Formula 29>
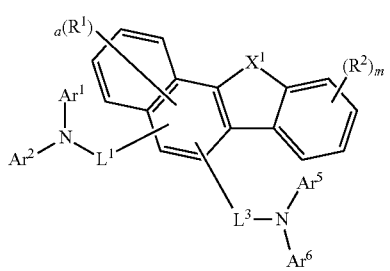
<Formula 30>
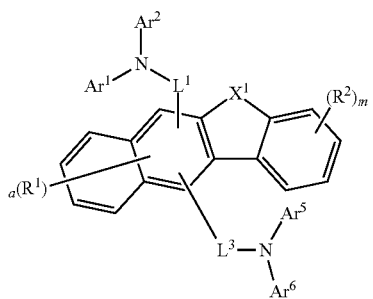
<Formula 31>
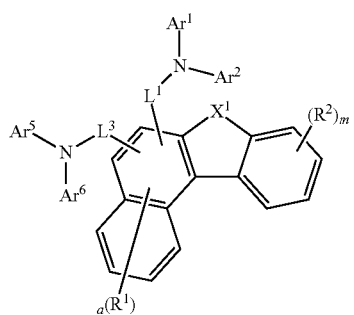
<Formula 32>
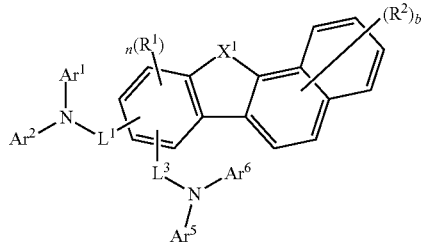
<Formula 33>
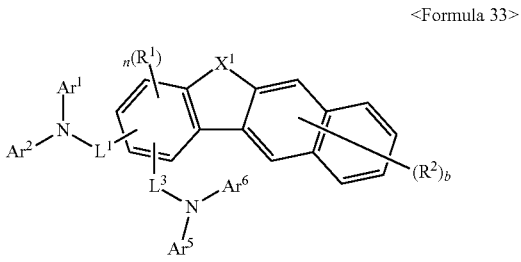
<Formula 34>
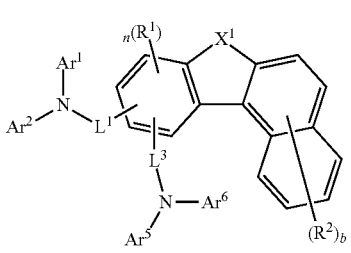
wherein $X^1$, $L^1$-$L^3$, $Ar^1$-$Ar^6$, $R^1$, and $R^2$, n and m are the same as defined in claim 1, and a and b are each an integer of 0 to 6.
5. The compound of claim 1, wherein at least one of $L^1$ to $L^3$ is a single bond.
6. A compound selected from the group consisting of the following compounds:
P-4
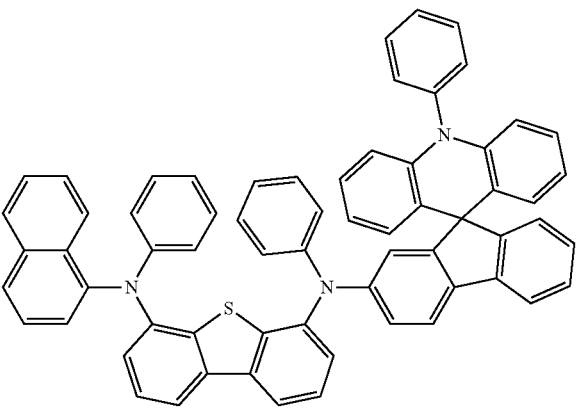

P-6
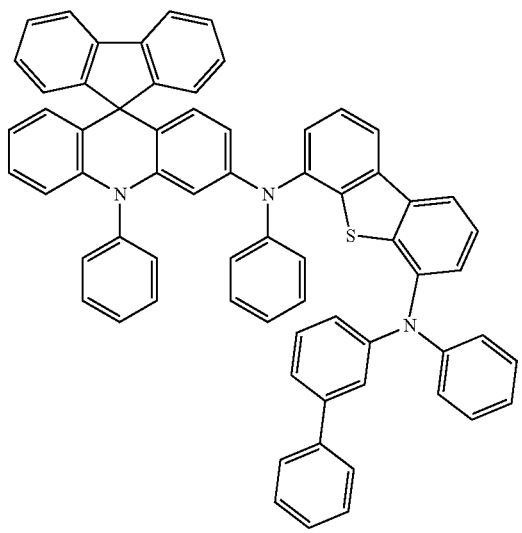
P-7
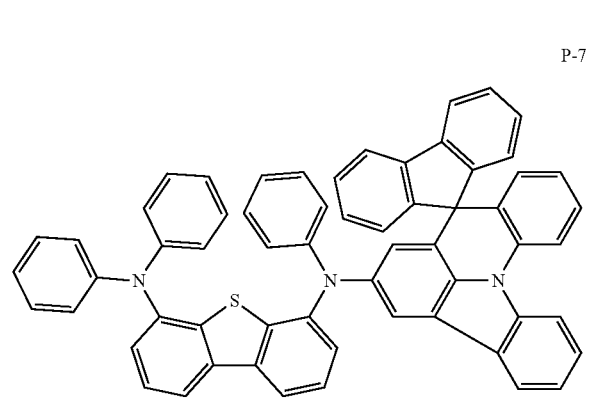
P-8
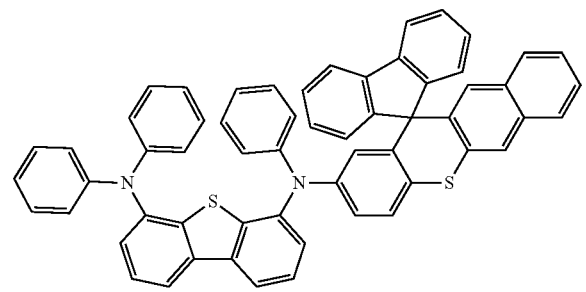
P-9
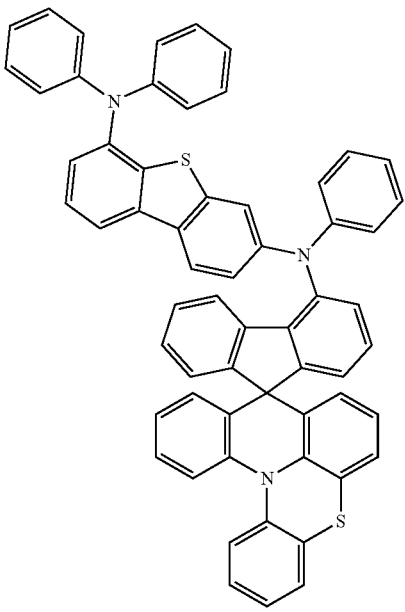
P-10
P-11
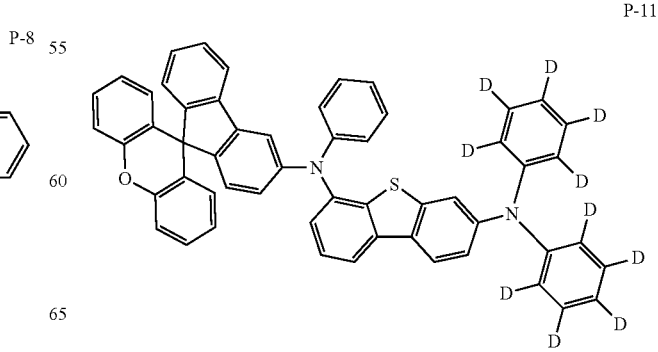

-continued
P-12
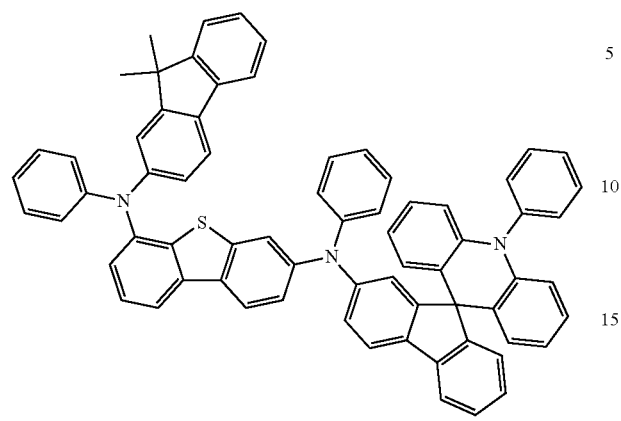
P-15
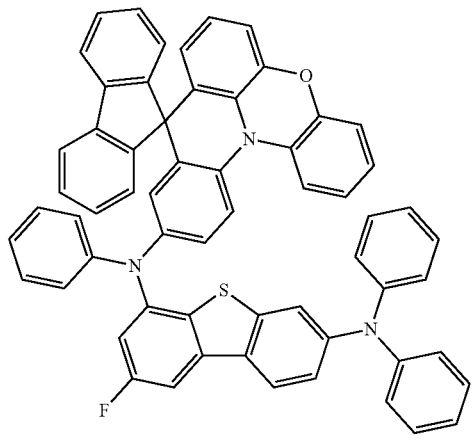
P-13
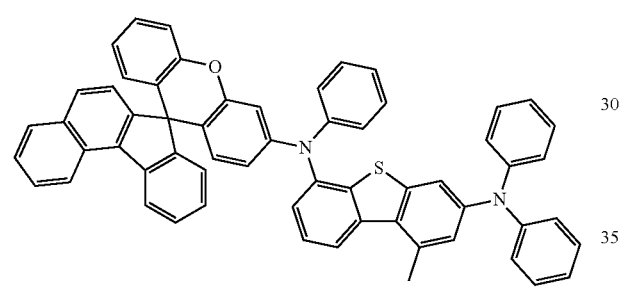
P-16
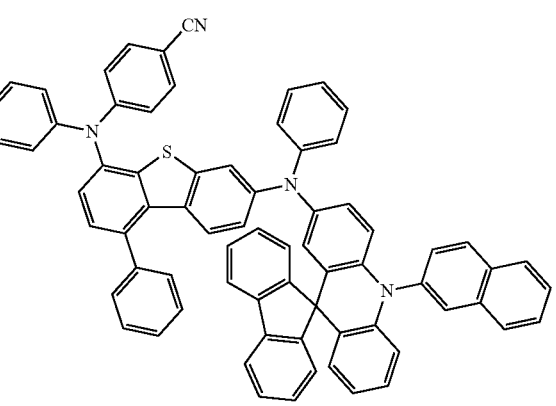
P-14
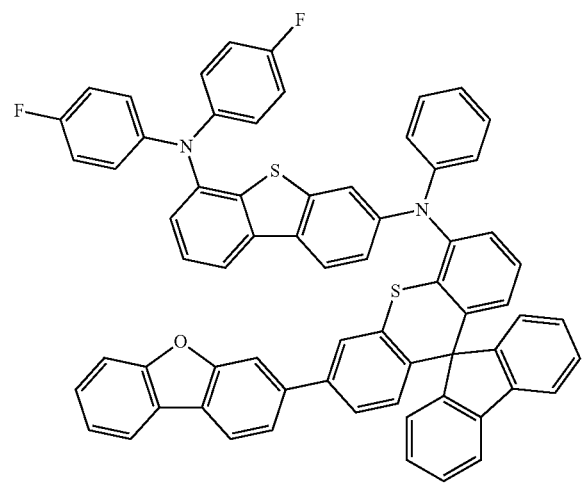
P-18
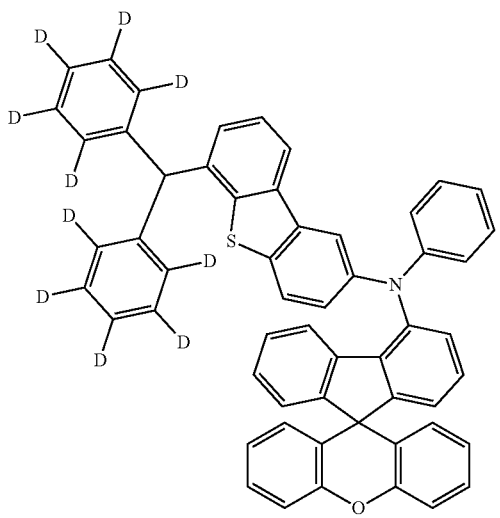

P-19
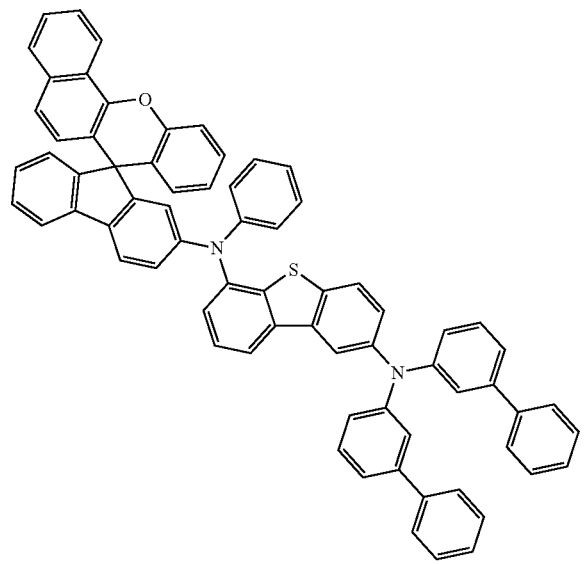
P-23
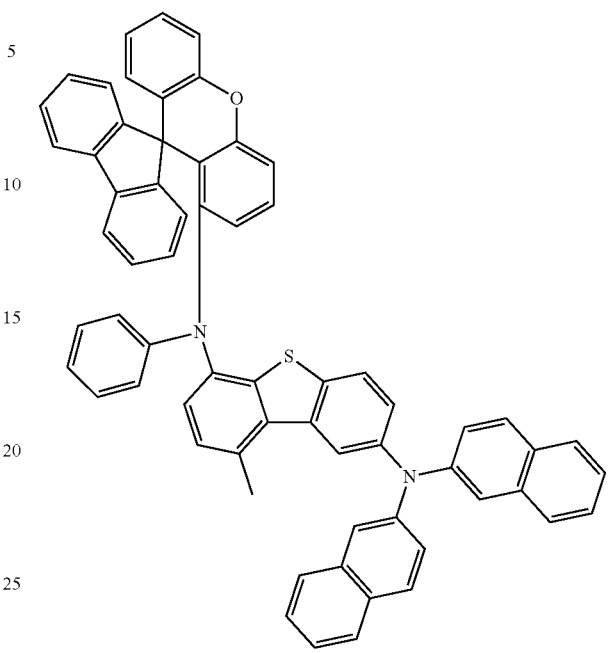
P-20
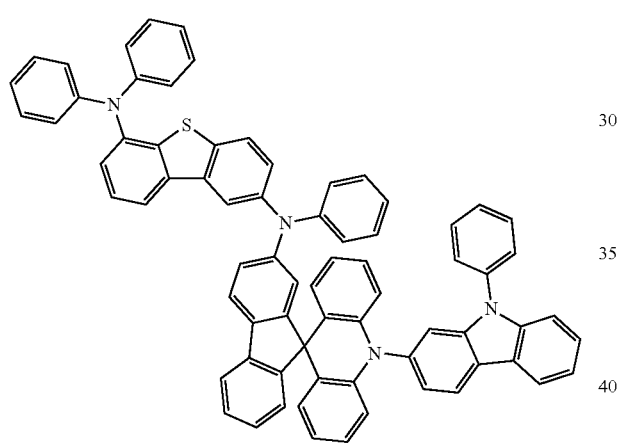
P-22
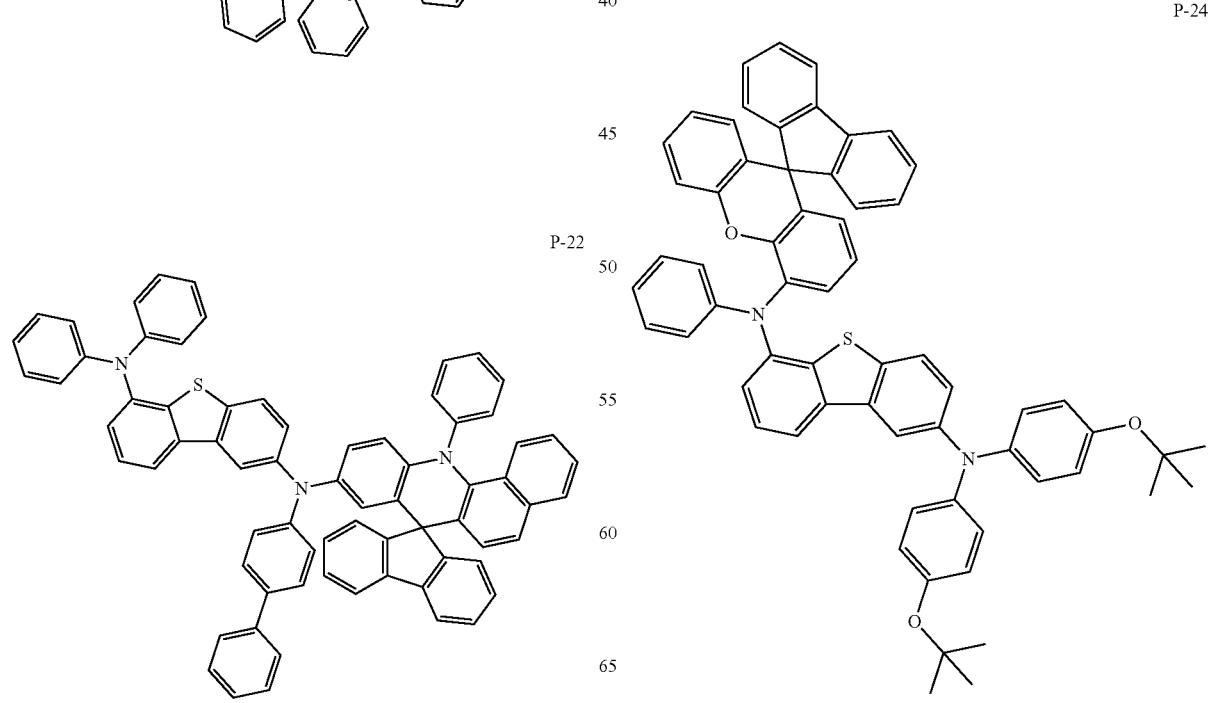
P-24

P-35
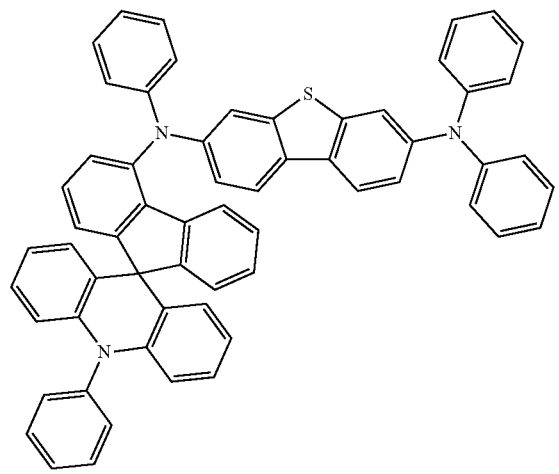
P-36
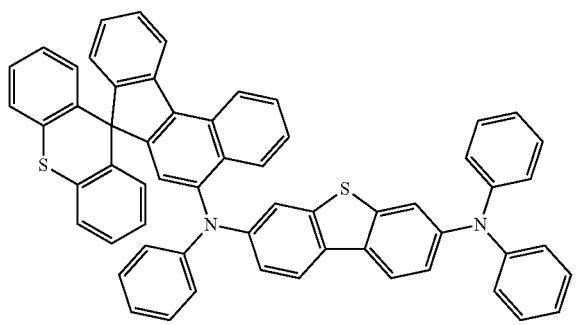
P-38
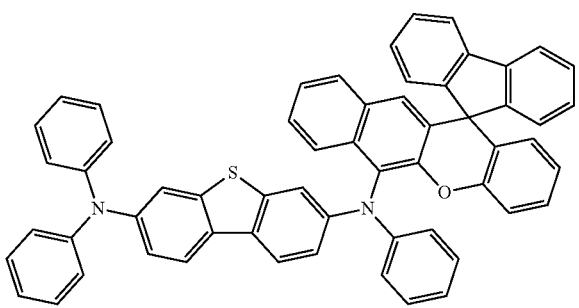
P-39
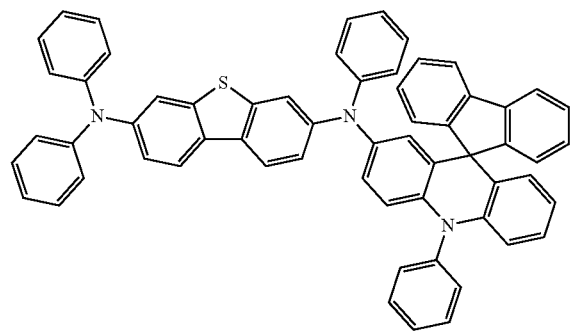
P-40
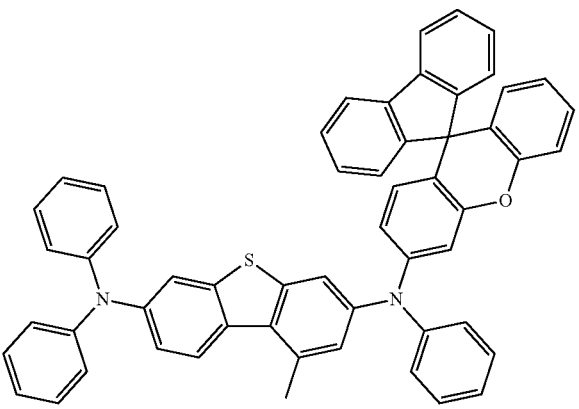
P-43
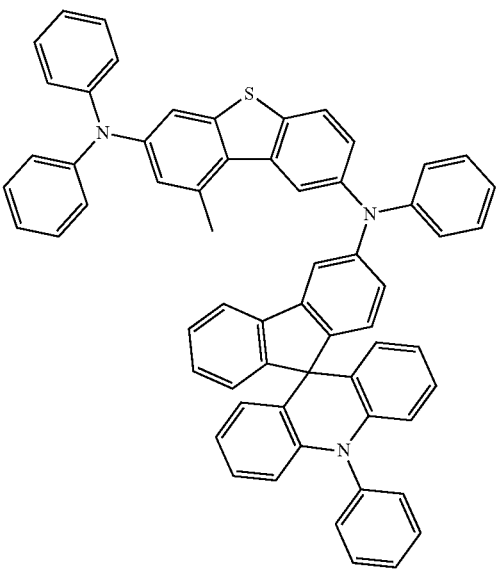
P-47
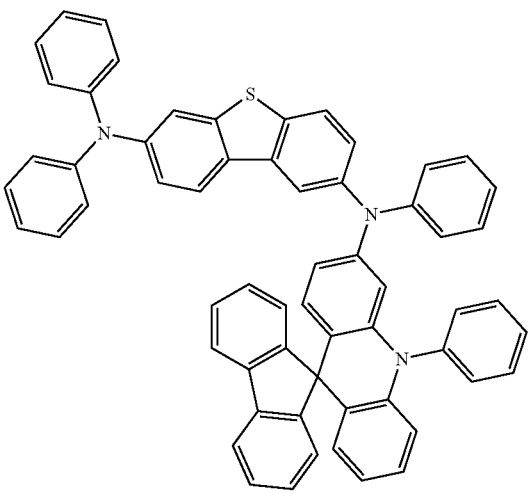

P-48
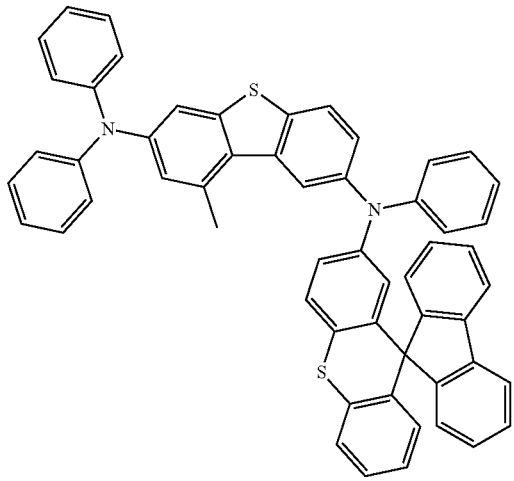
P-57
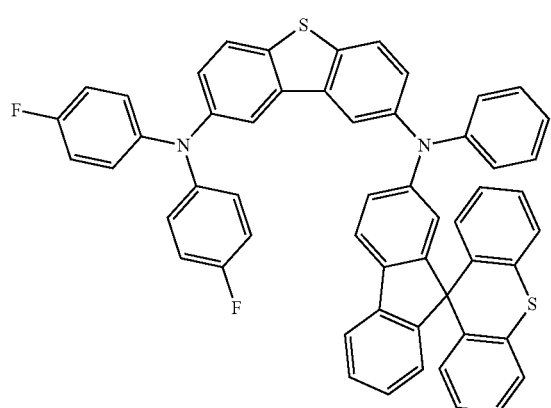
P-59
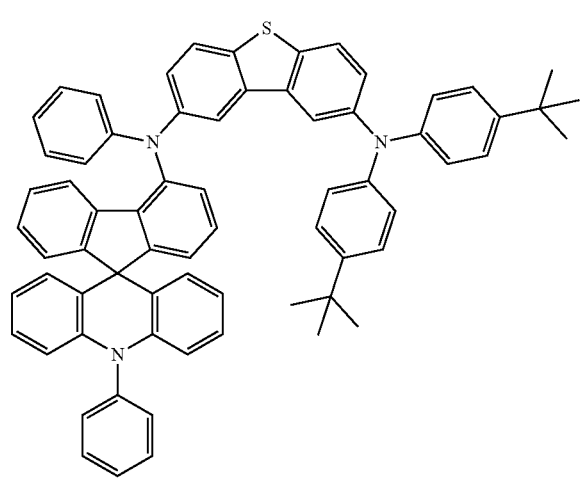
P-60
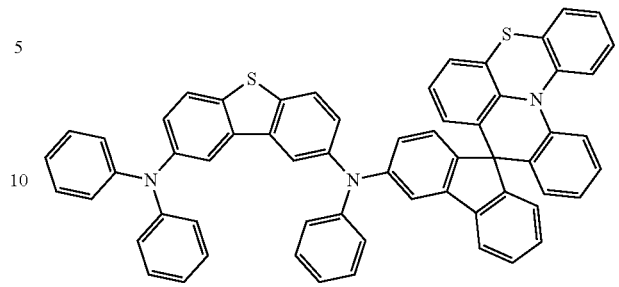
P-62
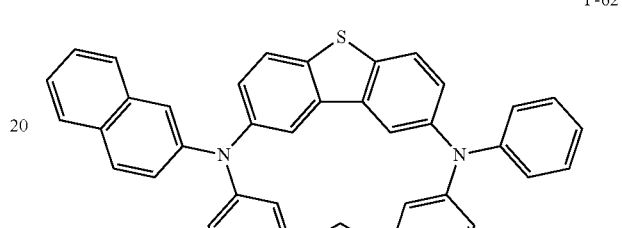
P-64
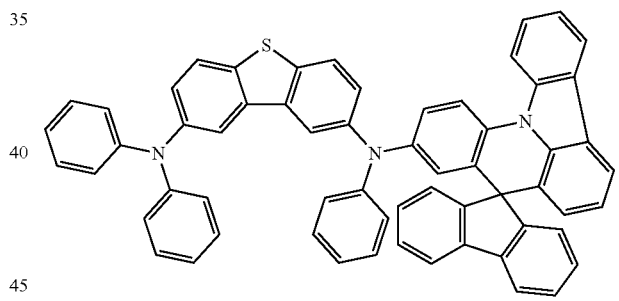
P-78
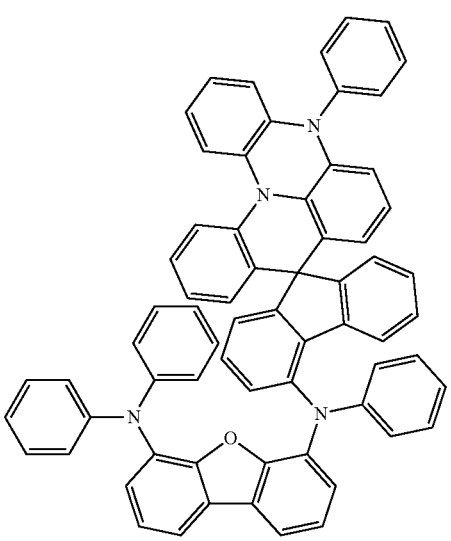

P-80
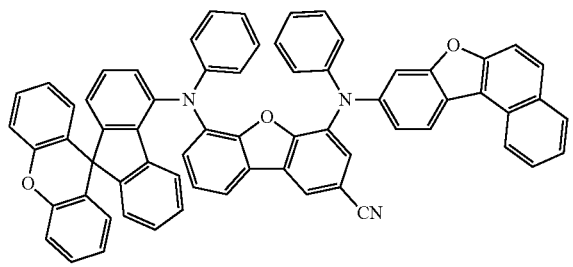
P-81
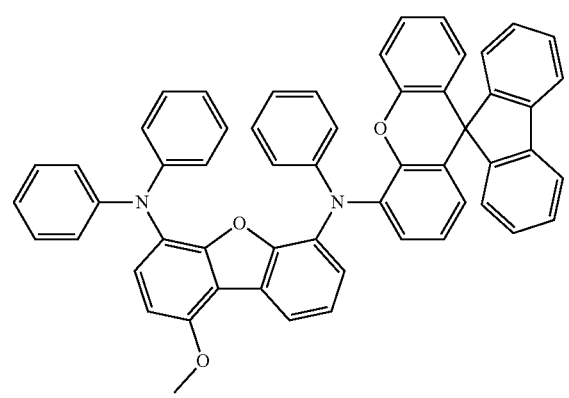
P-83
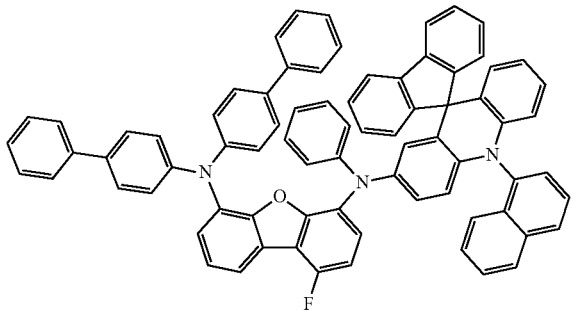
P-84
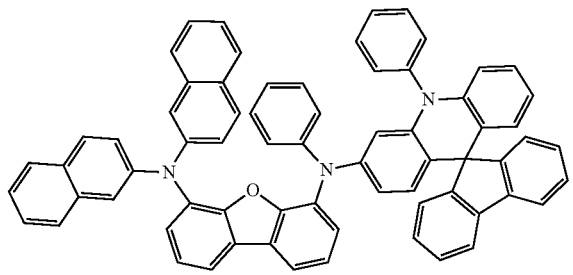
P-85
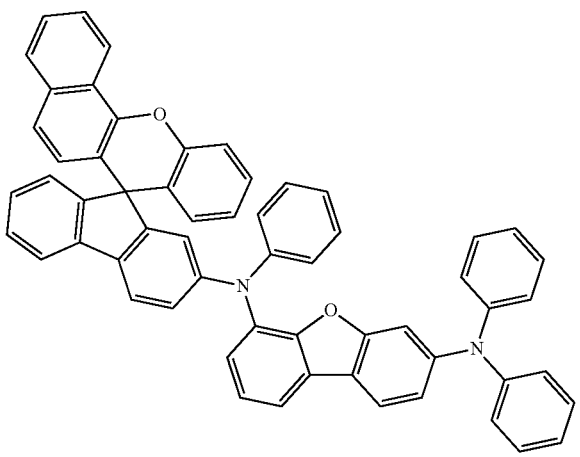
P-87
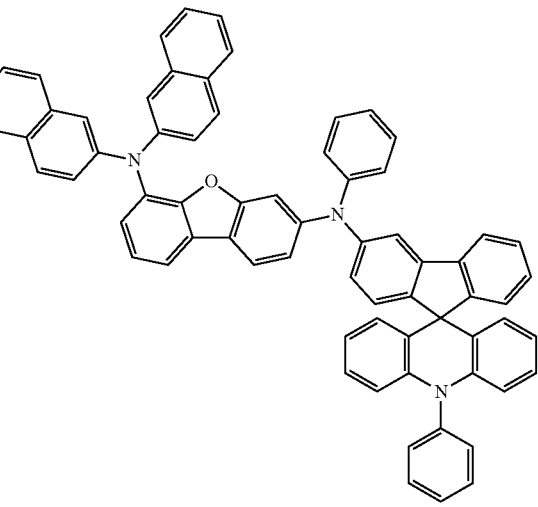
P-90
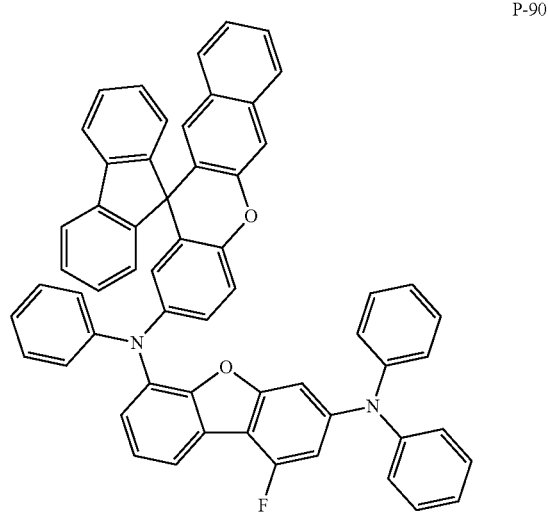

P-92
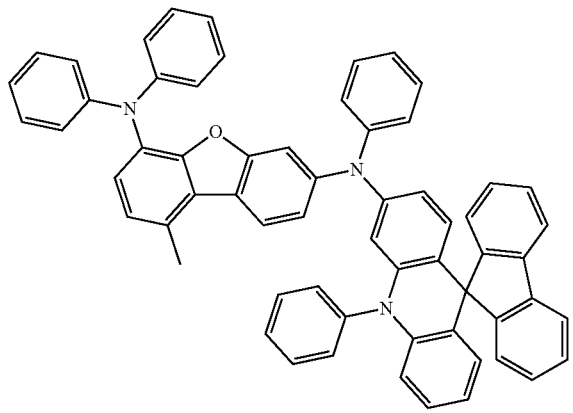
P-98
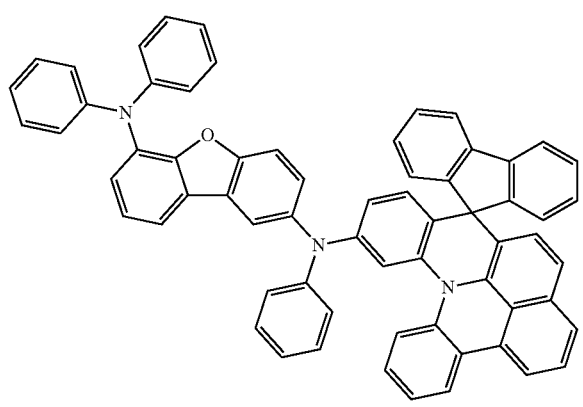
P-94
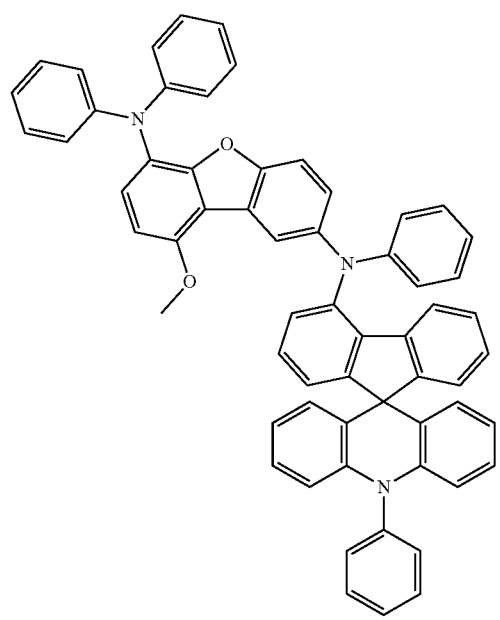
P-100
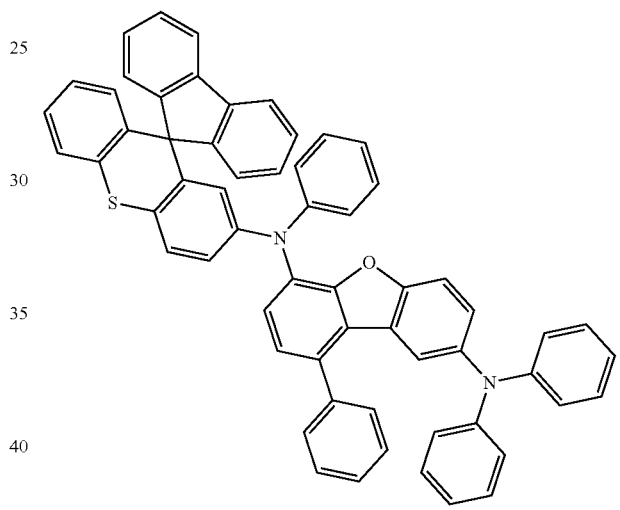
P-96
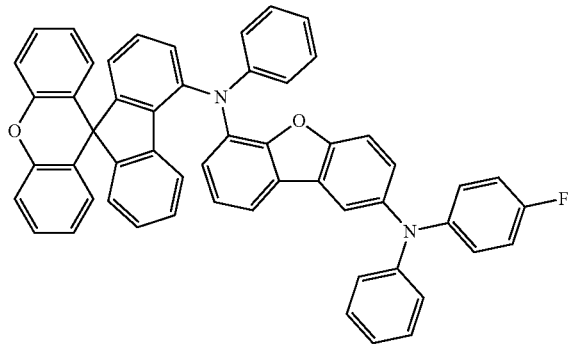
P-110
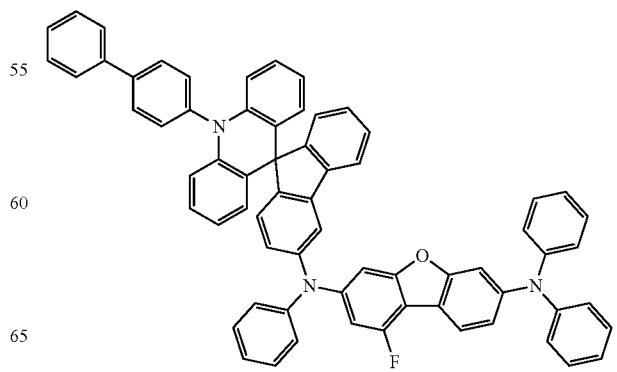

P-112
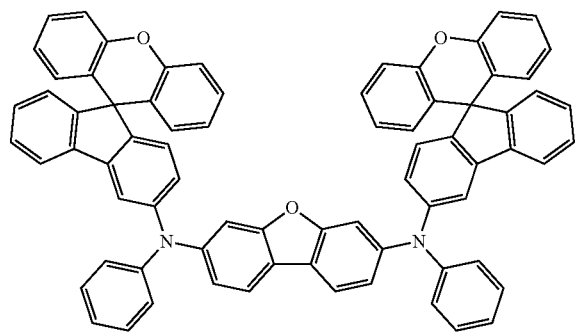
P-113
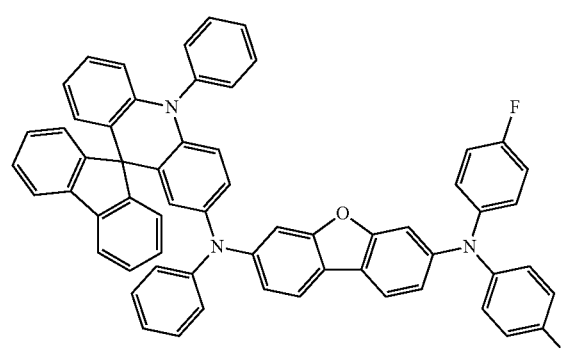
P-114
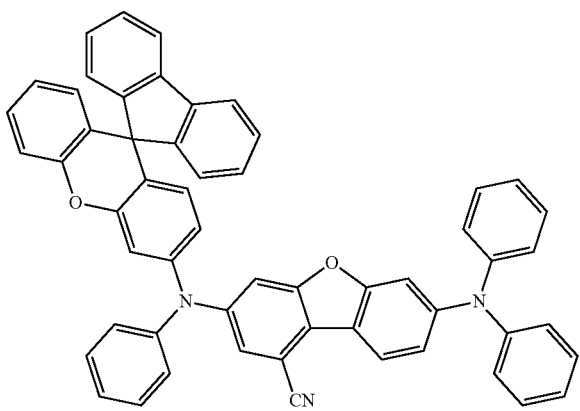
P-115
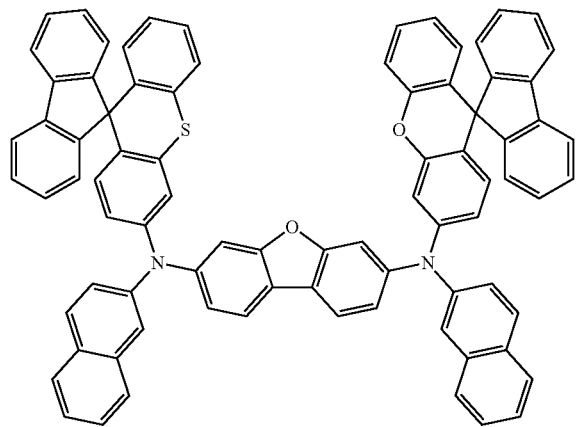
P-116
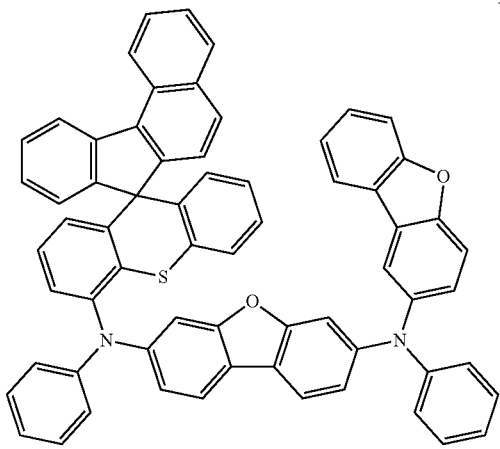
P-118
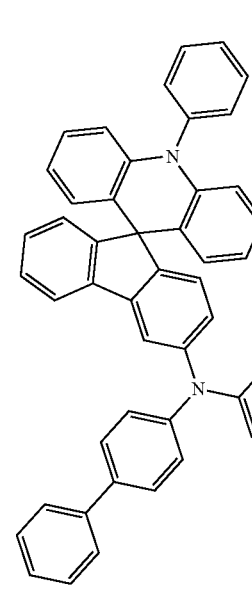
P-122
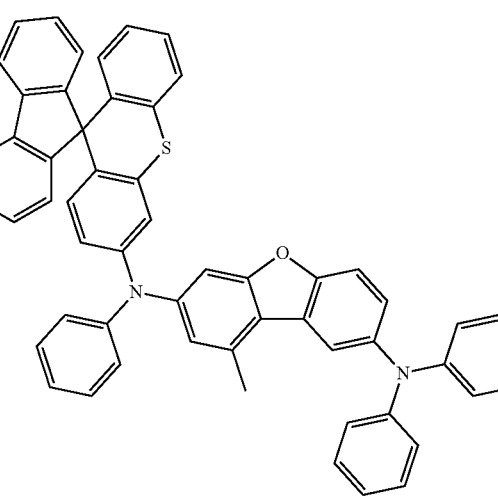

P-123
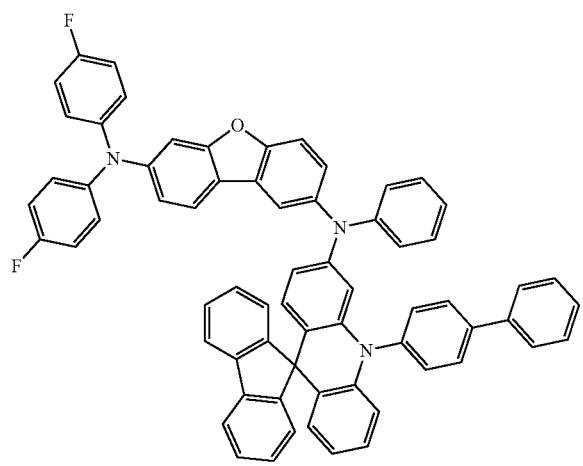
P-135
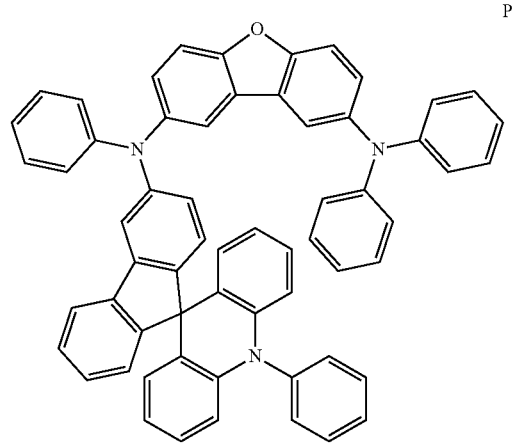
P-136
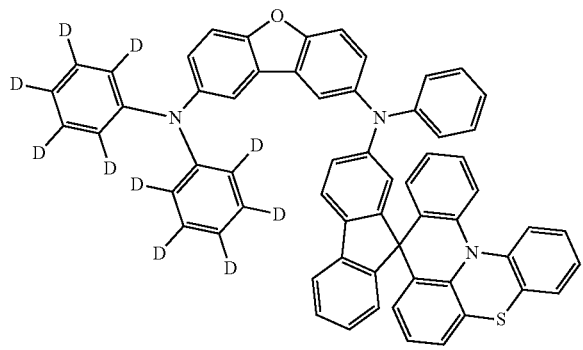
P-137
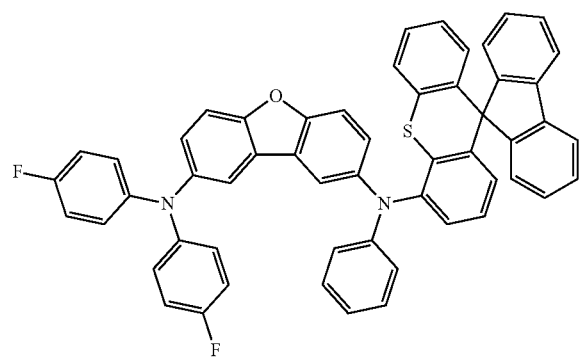
P-139
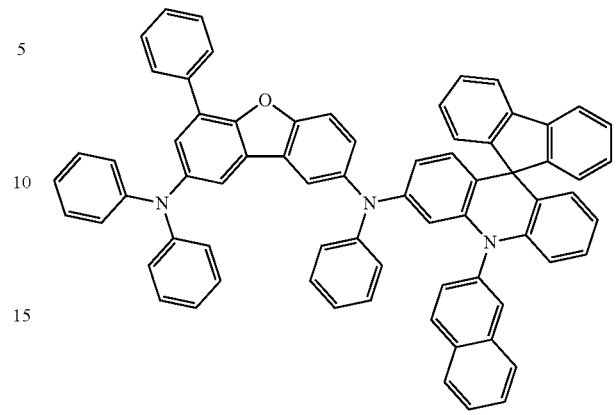
P-157
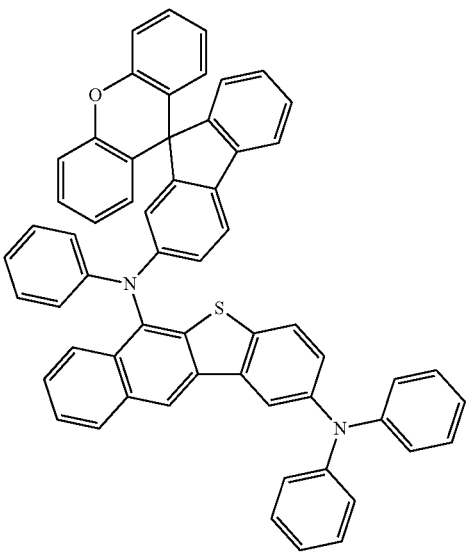
P-160
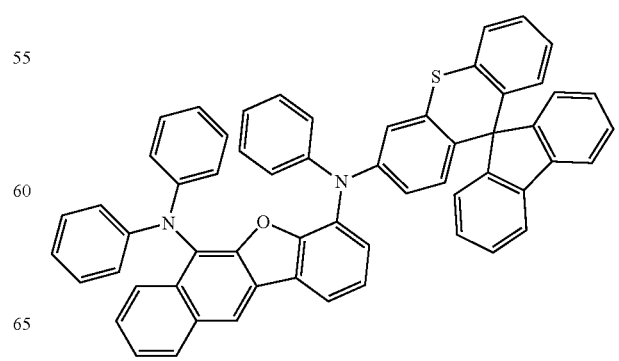

-continued
P-161
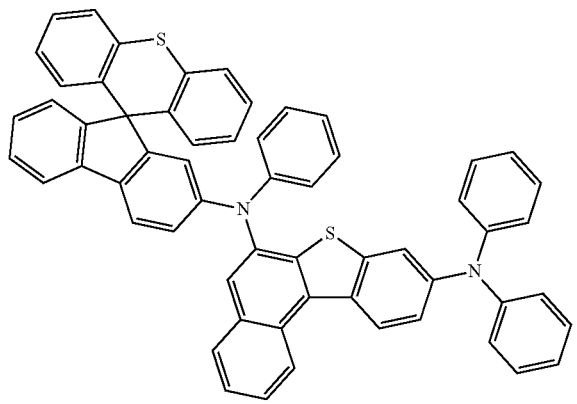
P-162
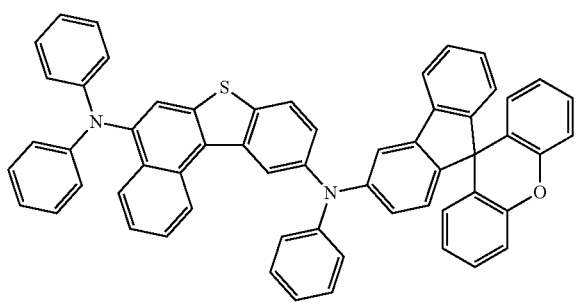
P-163
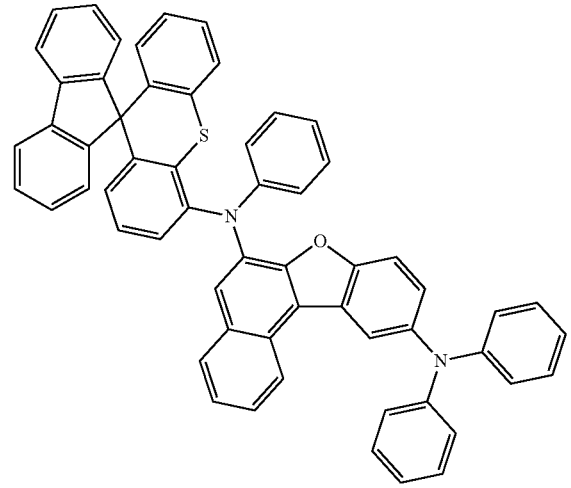
P-164
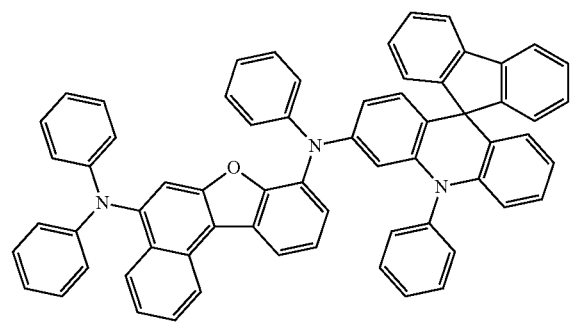
-continued
P-165
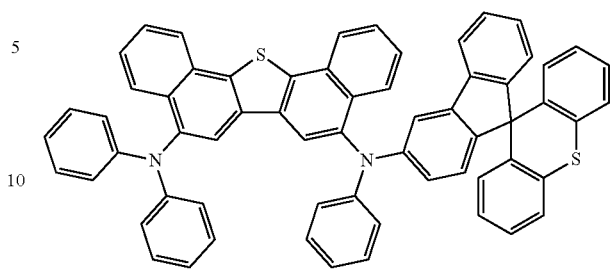
P-167
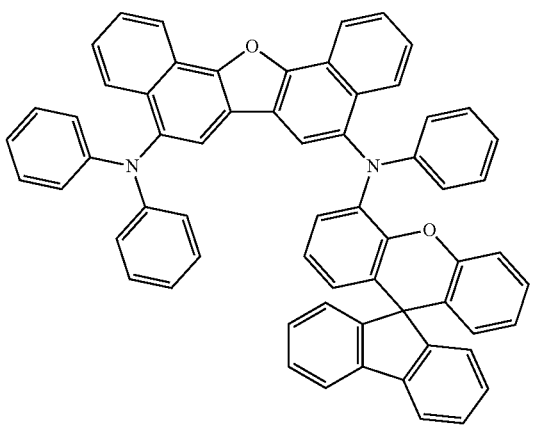
P-173
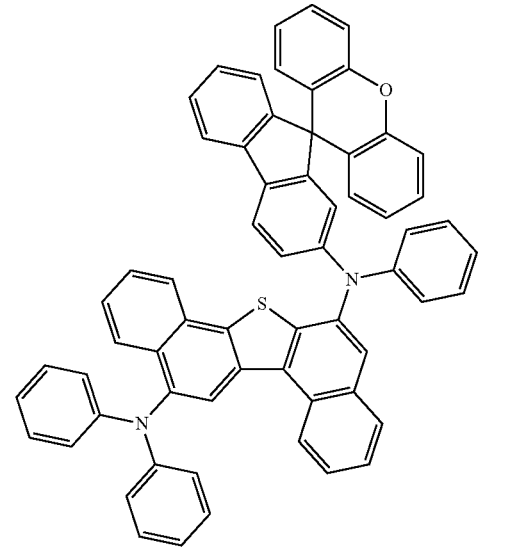
P-174
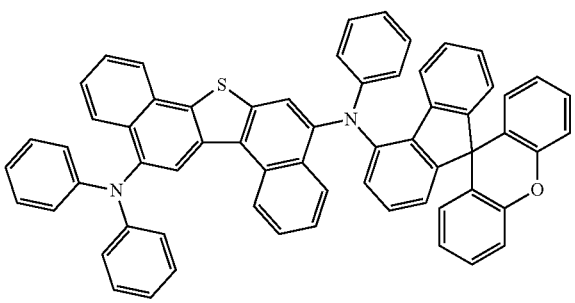

-continued
P-175
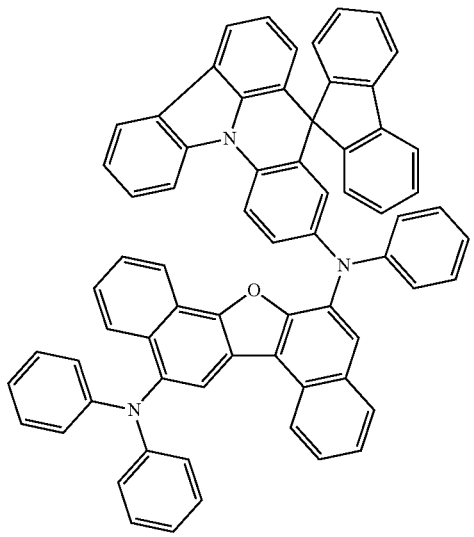
P-176
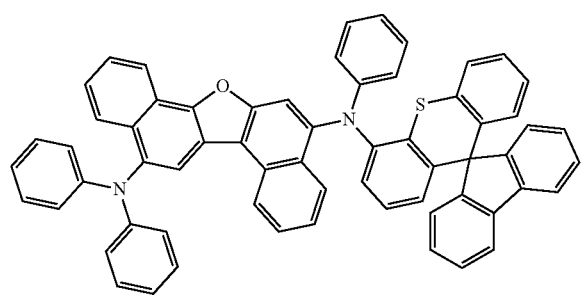
P-177
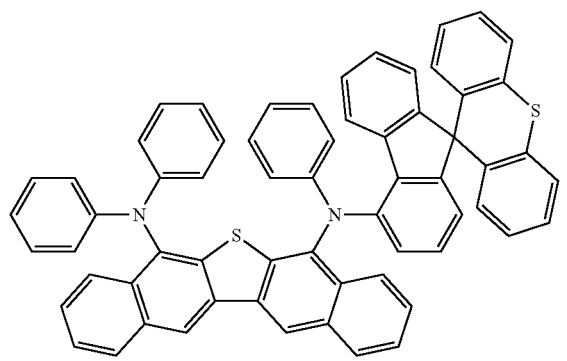
P-179
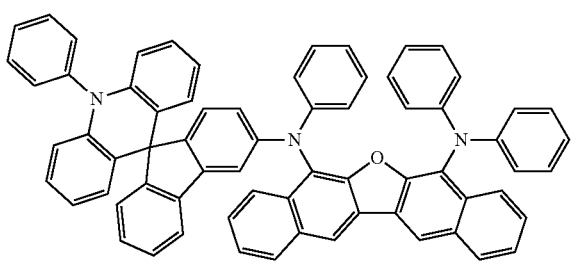
-continued
P-181
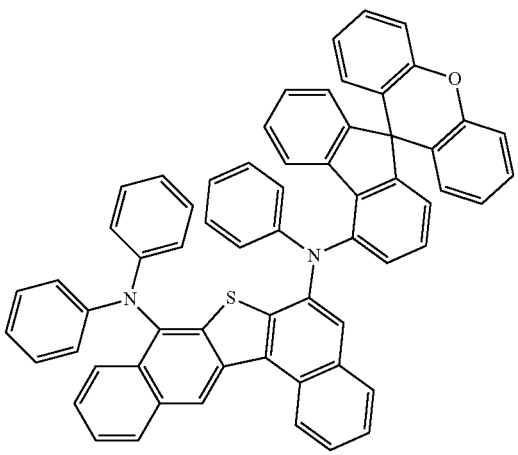
P-182
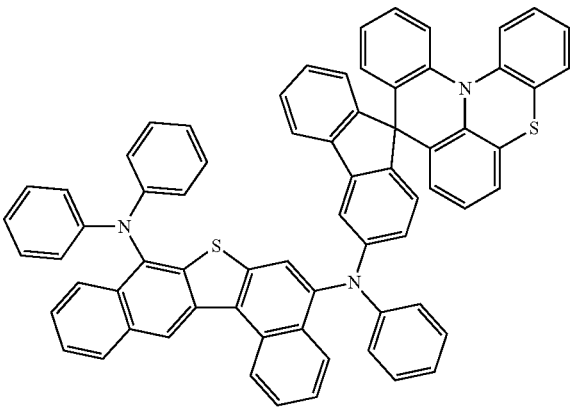
P-183
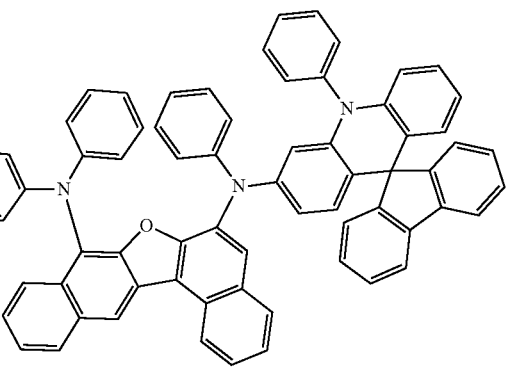

P-184
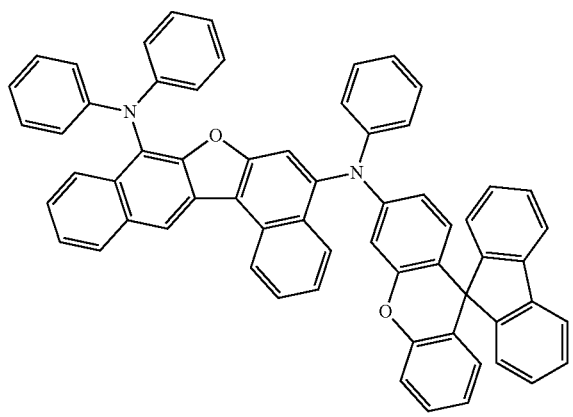
P-188
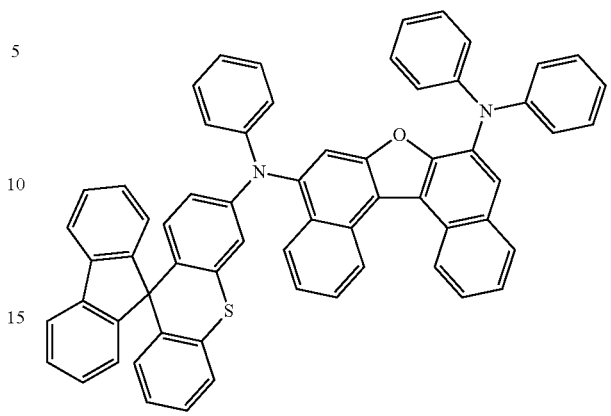
P-185
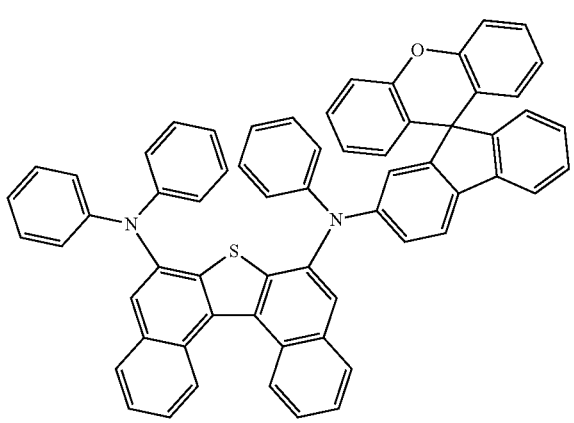
P-189
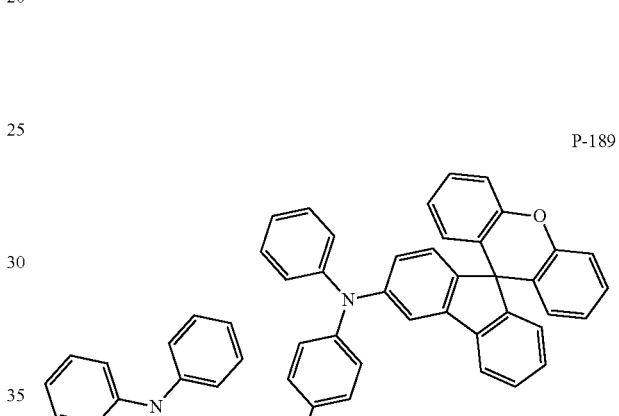
P-186
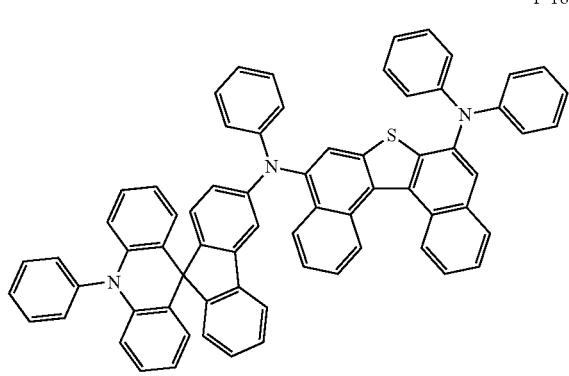
P-187
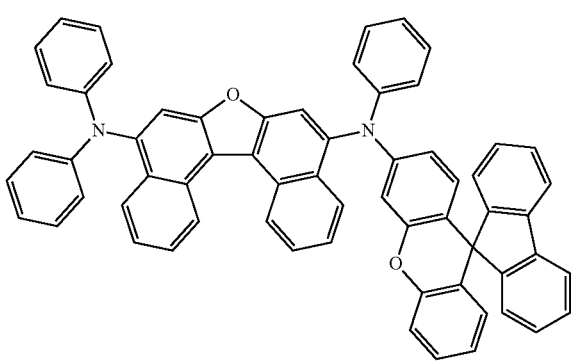
P-190
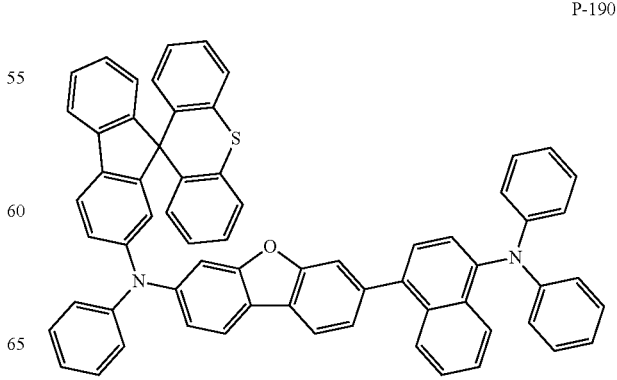

P-191
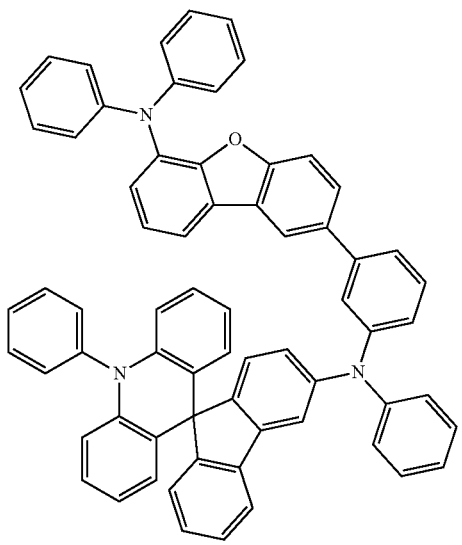
P-194
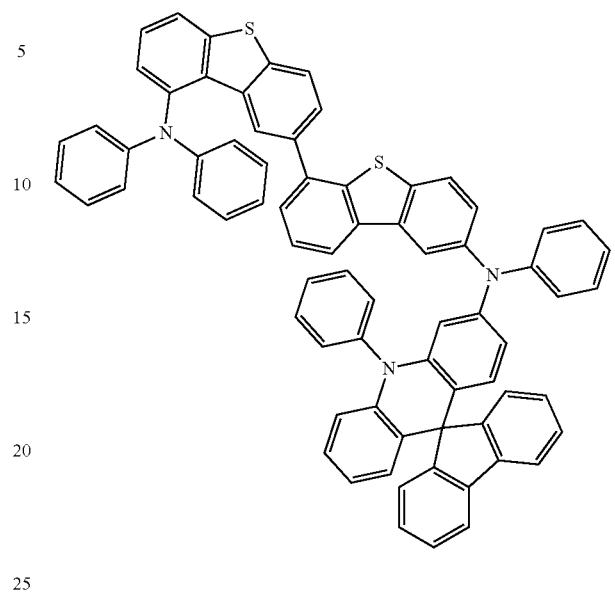
P-192
P-195
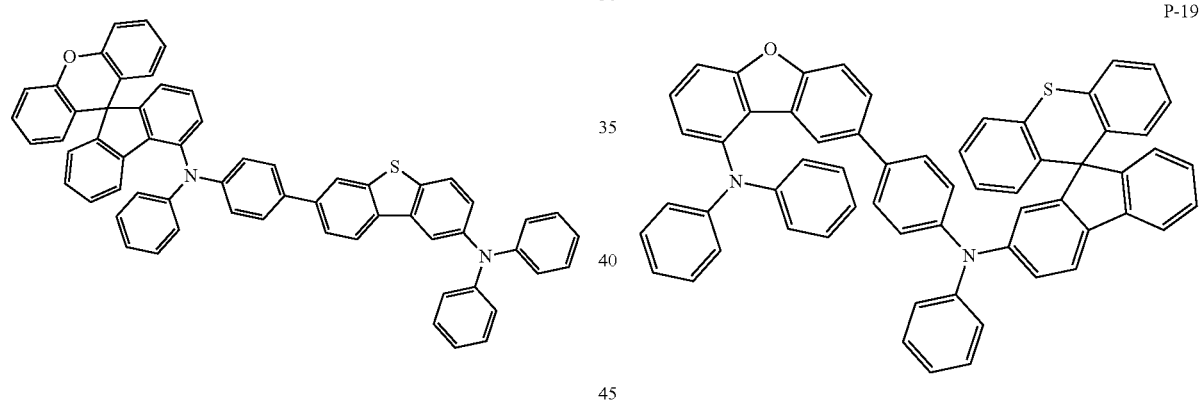
P-193
P-196
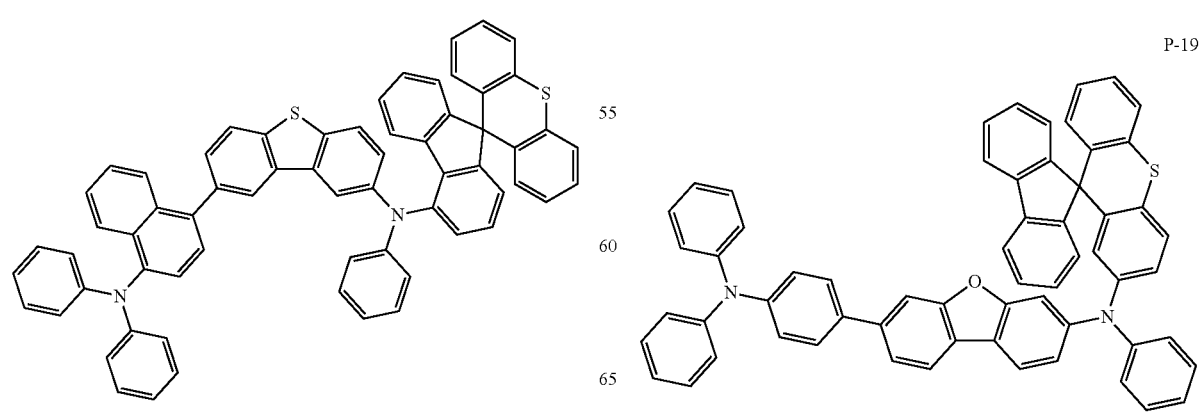

P-197
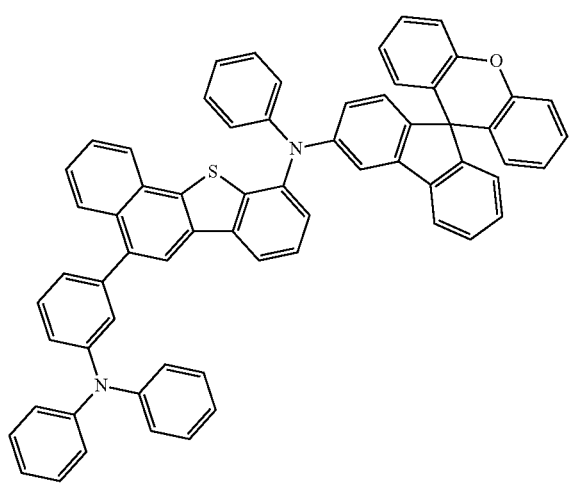
P-199
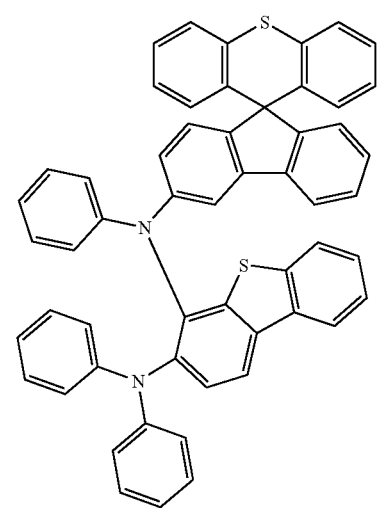
P-200
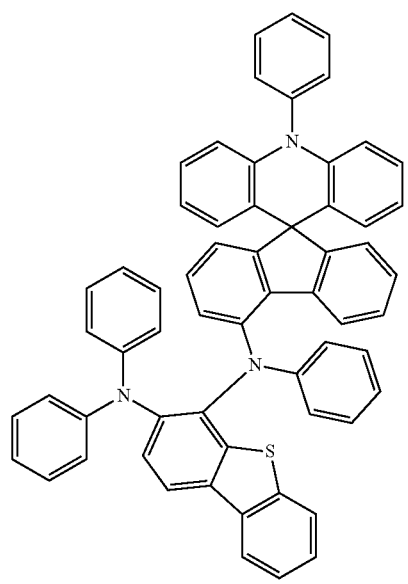
P-201
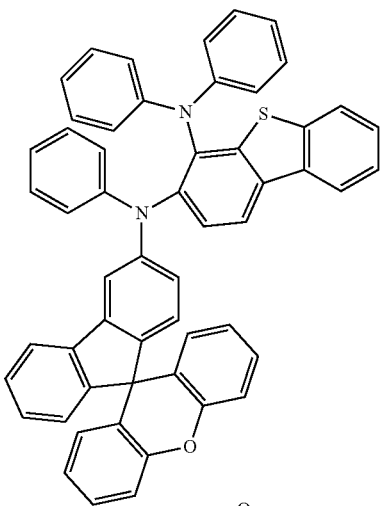
P-202
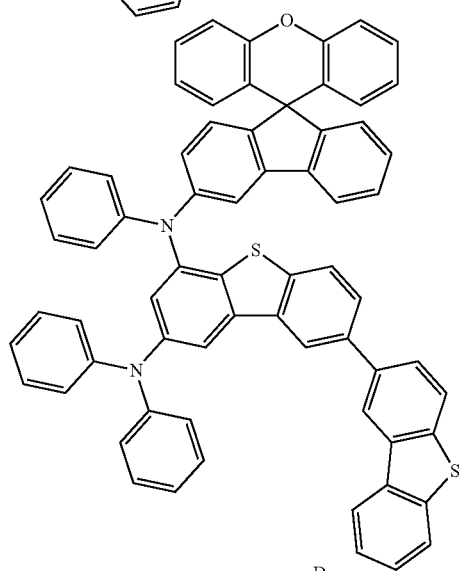
P-203
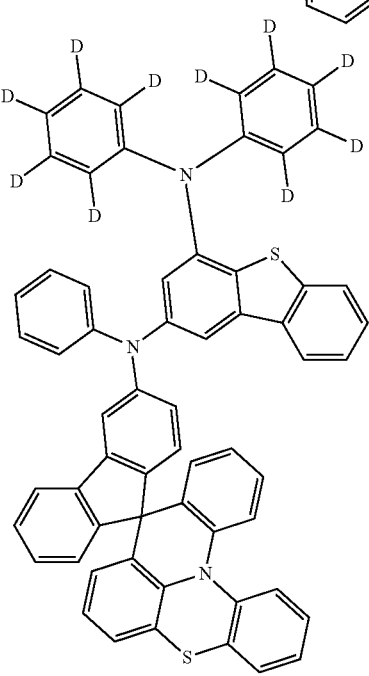

P-204
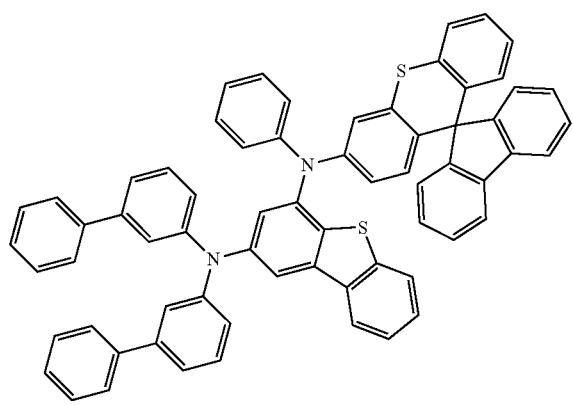
P-205
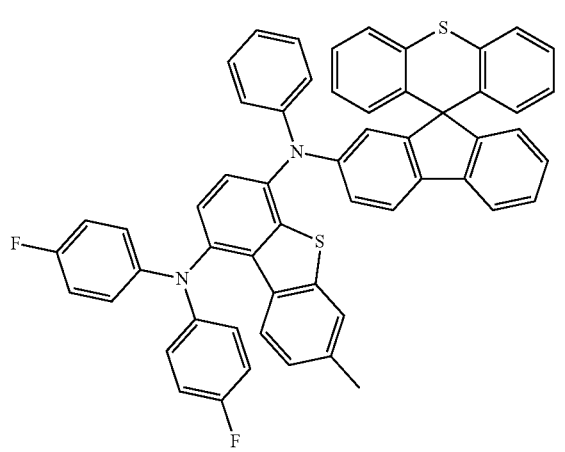
P-206
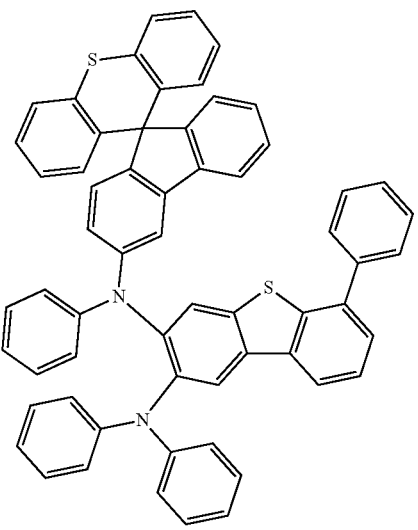
P-207
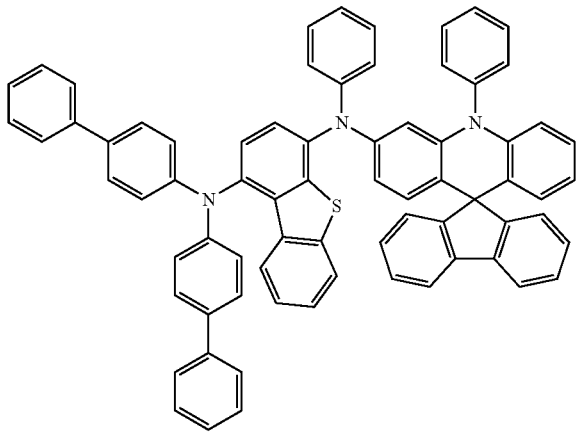
P-208
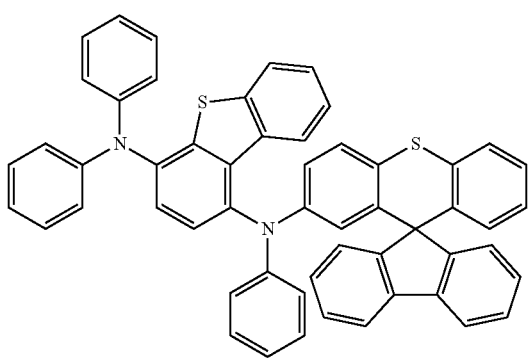
P-209

P-210
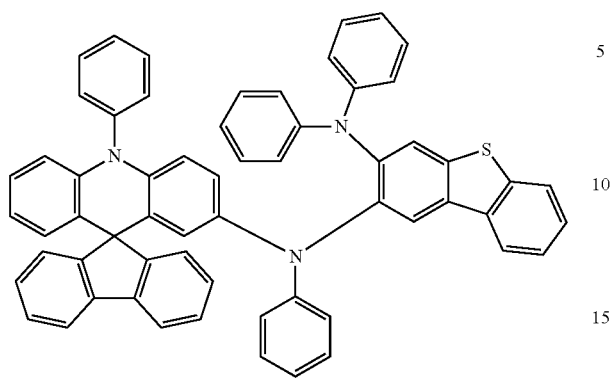
P-211
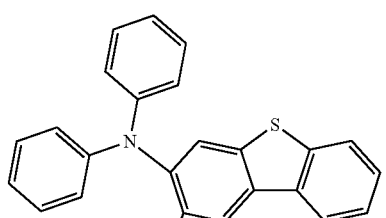
P-213
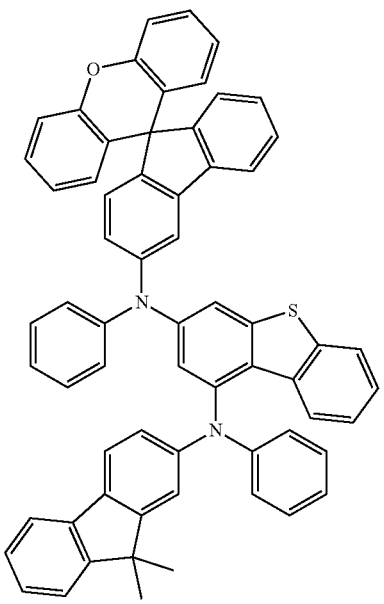
P-212
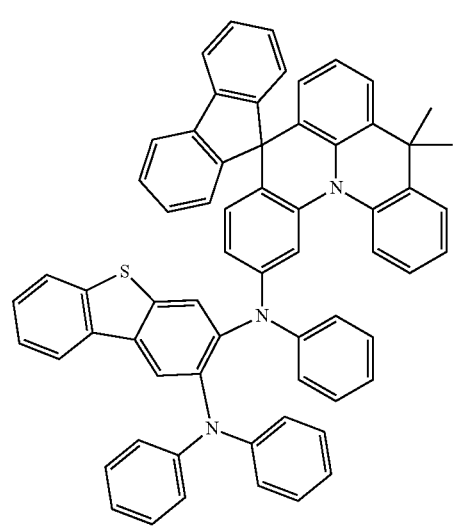
P-214
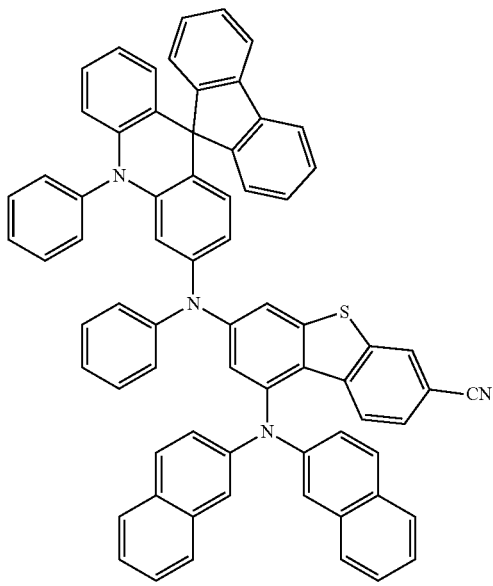

P-215
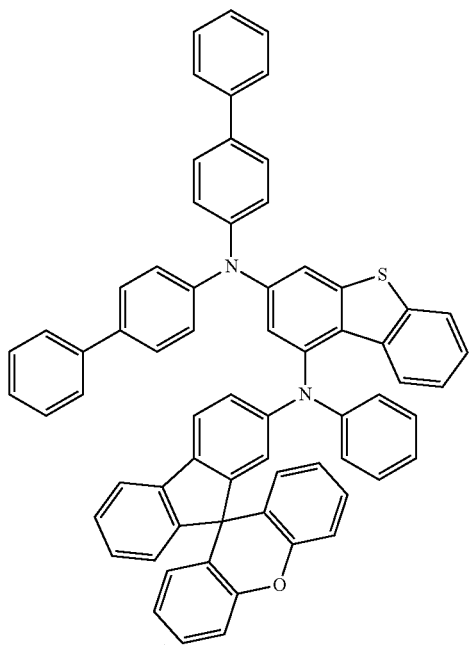
P-216
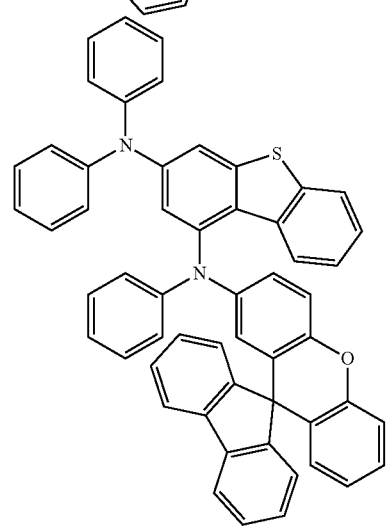
P-217
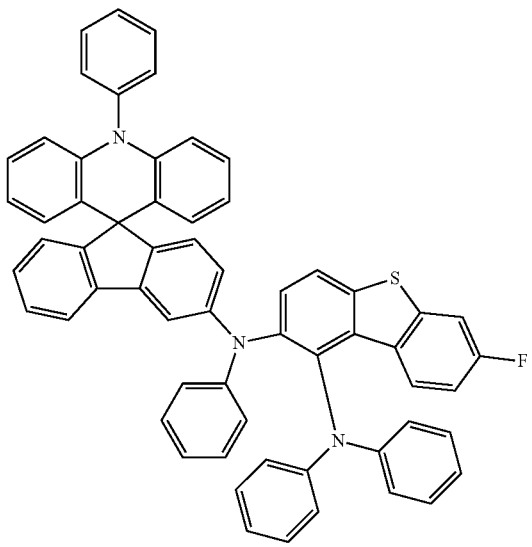
P-218
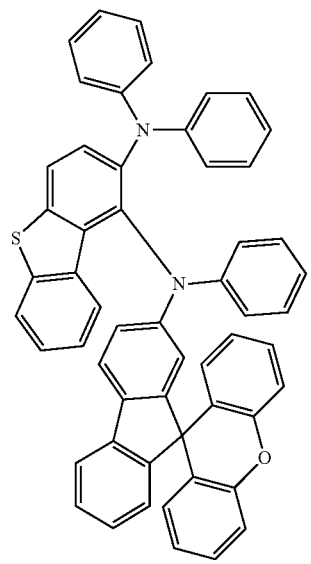
P-219
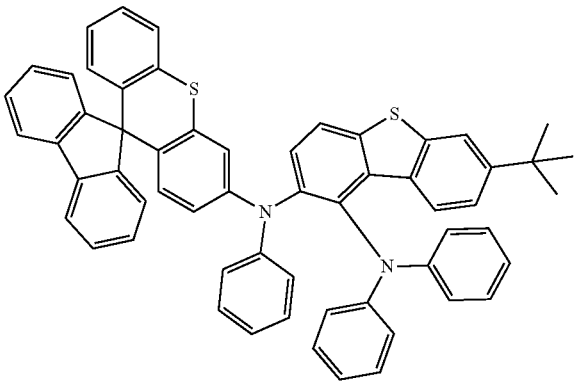
P-220
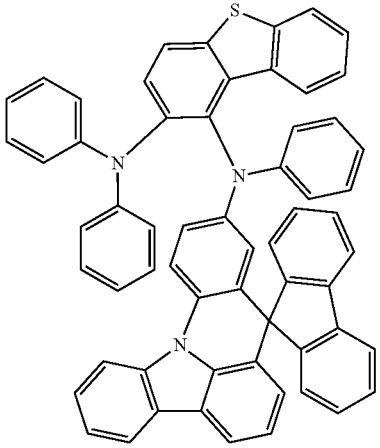

P-221
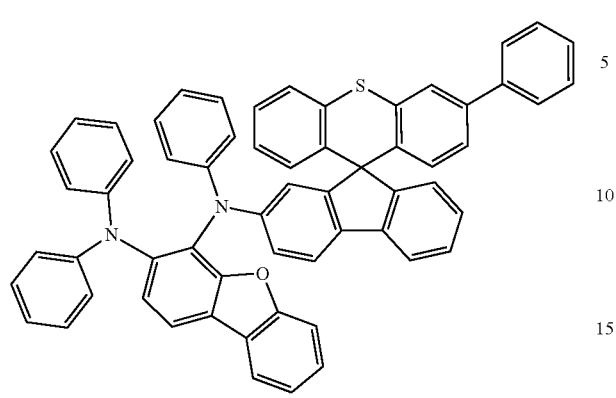
P-222
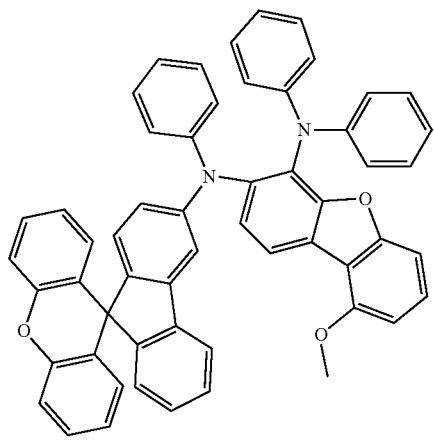
P-223
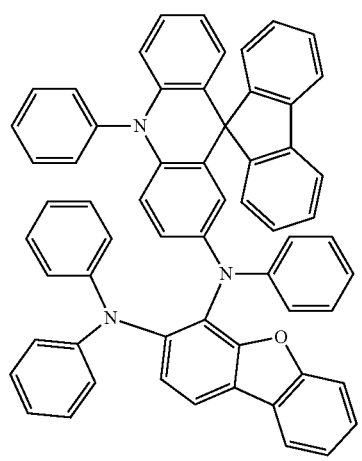
P-224
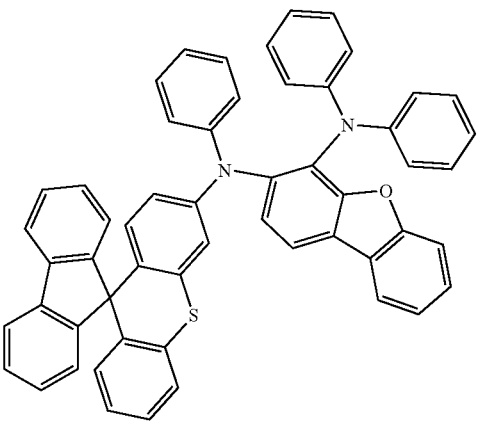
P-225
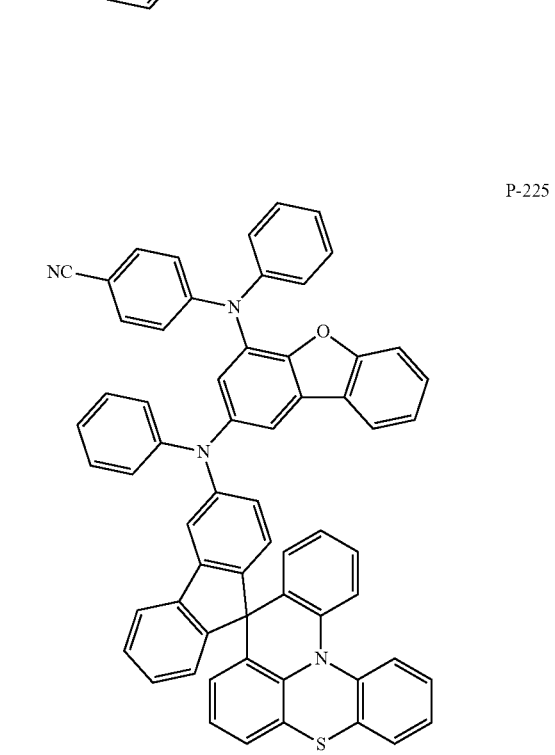
P-226
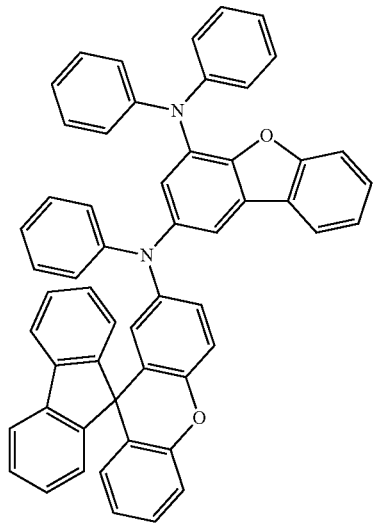

P-227
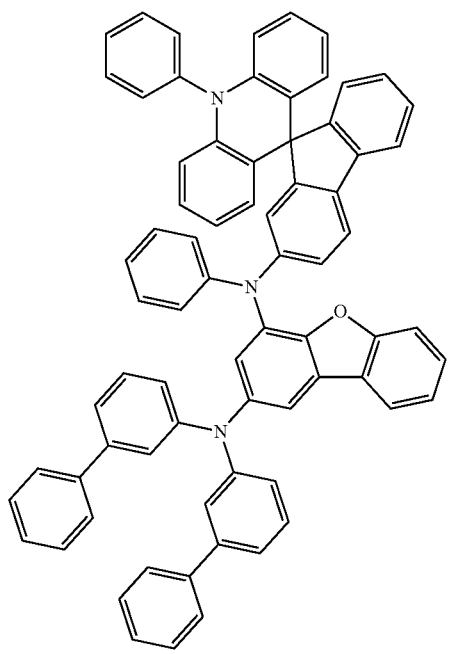
P-228
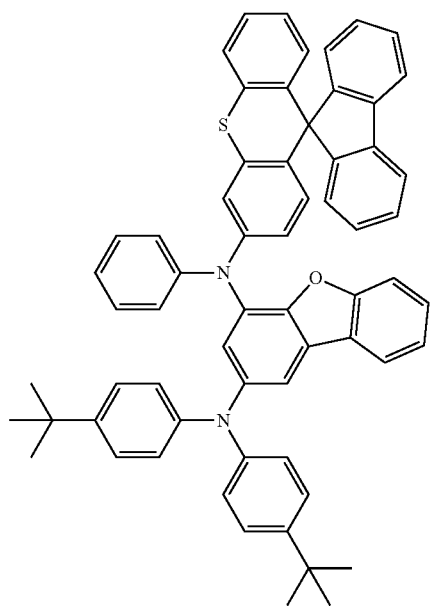
P-229
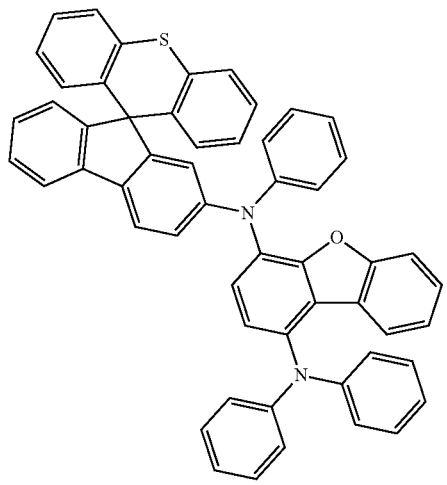
P-230
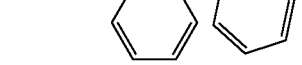

P-231
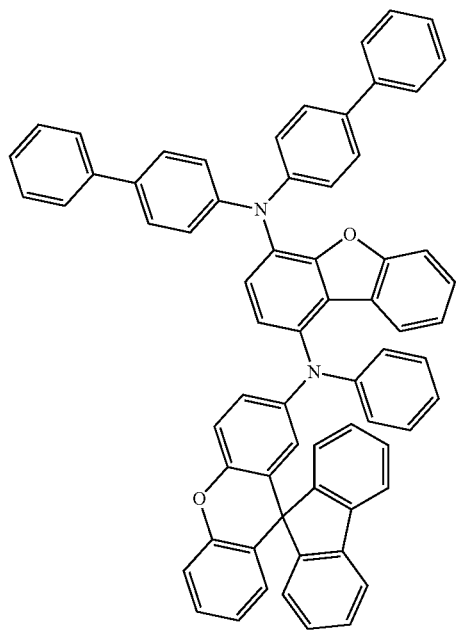
P-232
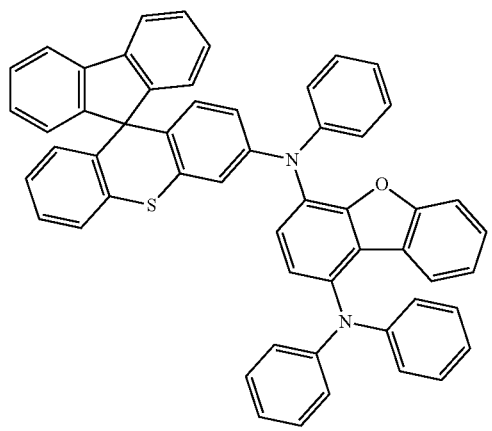
P-233
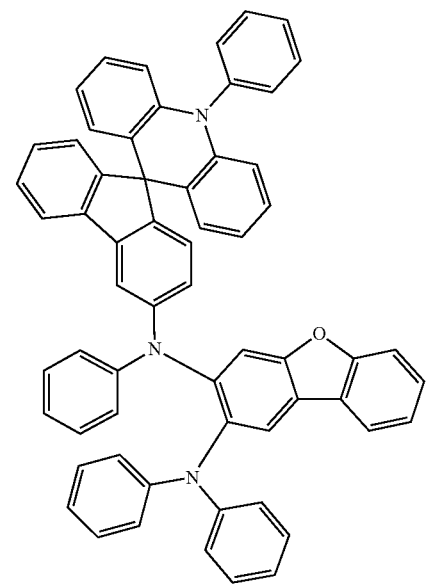
P-234
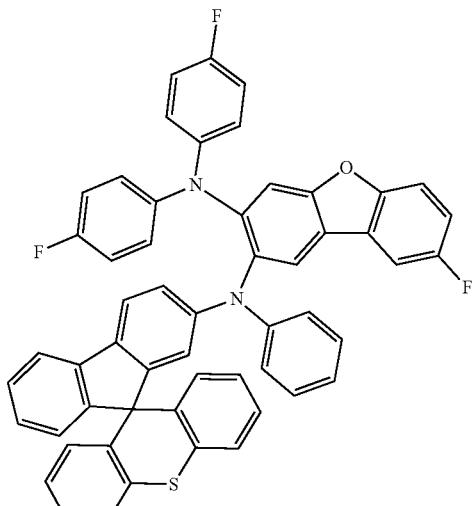
P-235
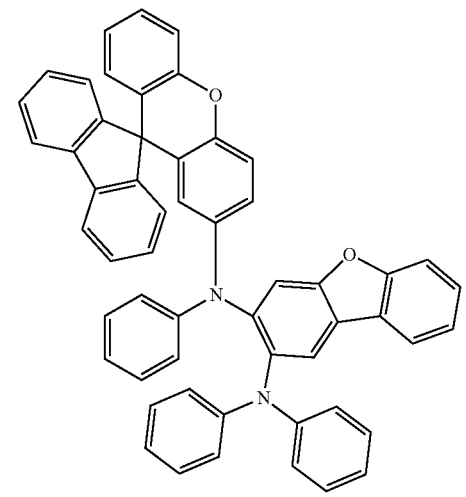
P-236
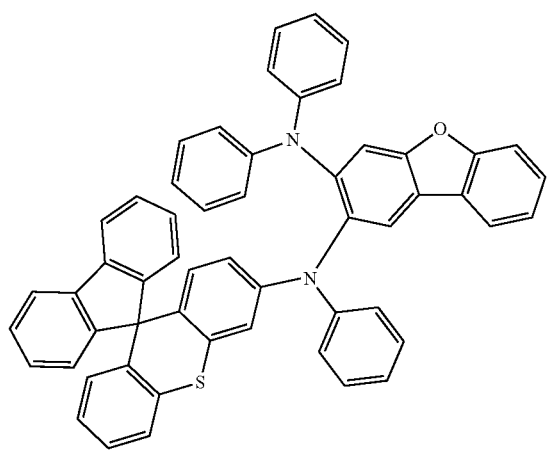

P-237
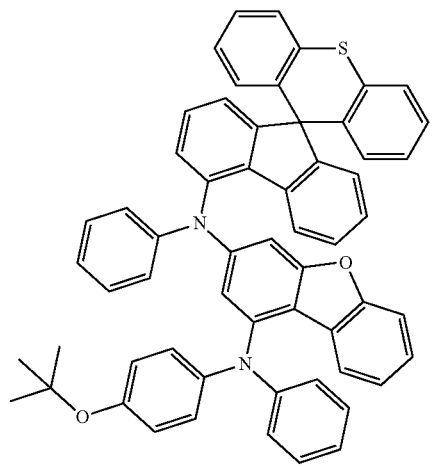
P-238
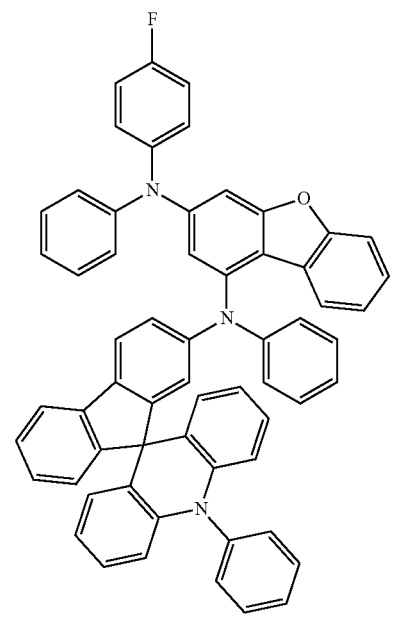
P-239
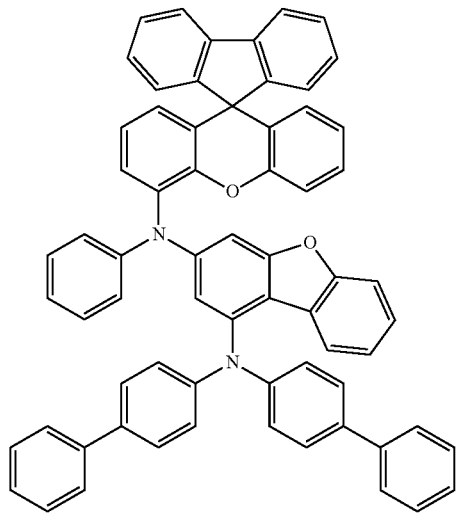
P-240
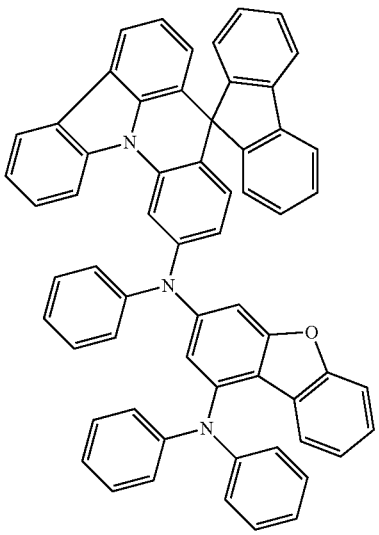
P-241
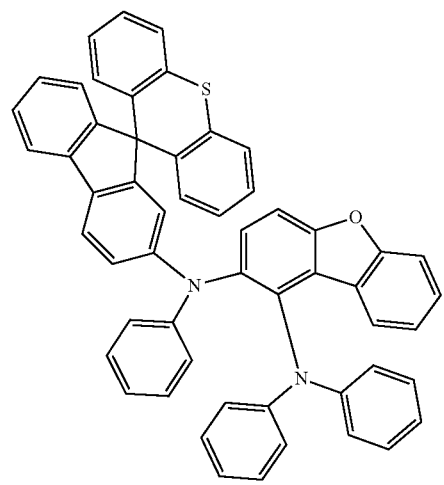
P-242
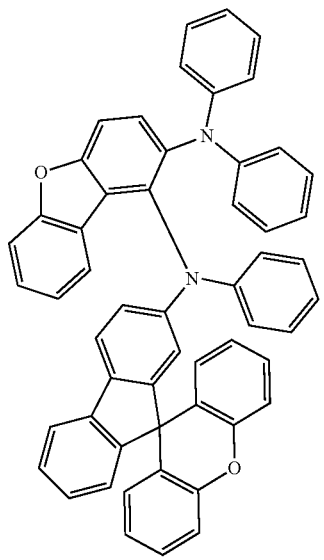

P-243
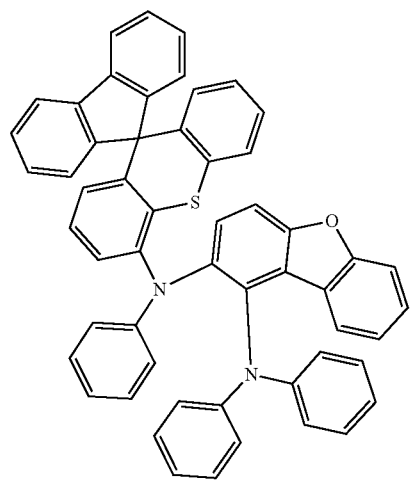
P-244
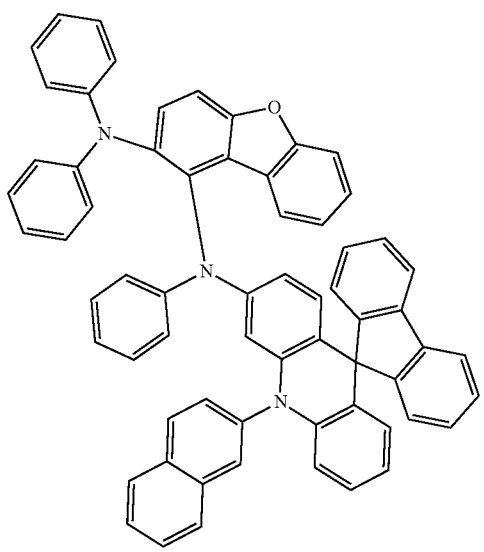
P-245
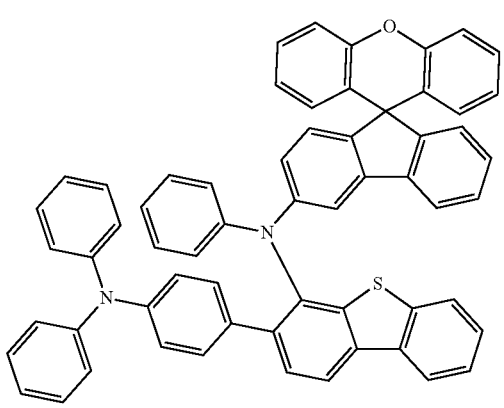
P-246
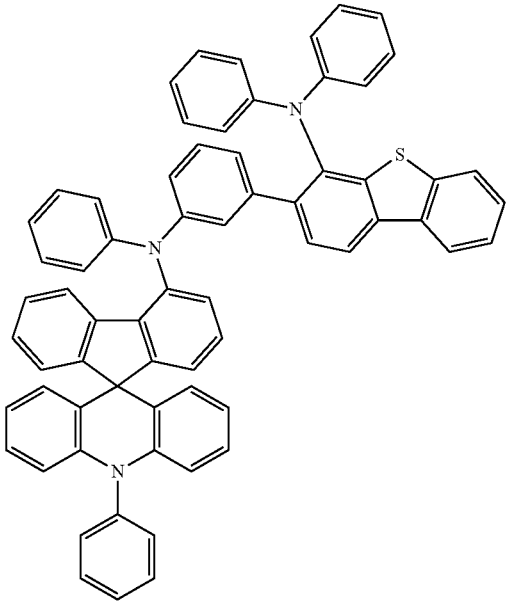
P-247
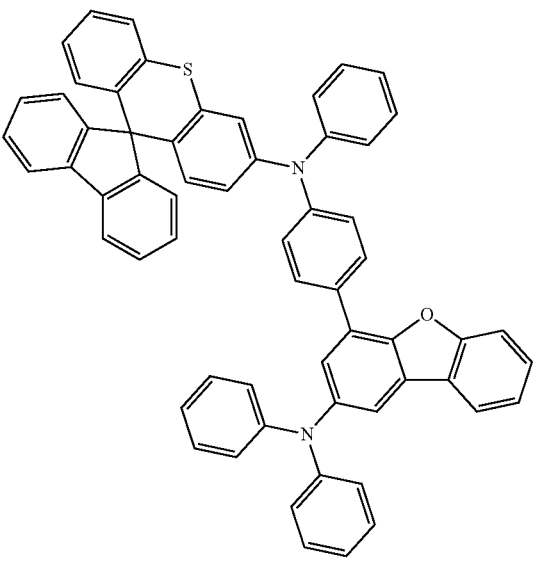

P-248
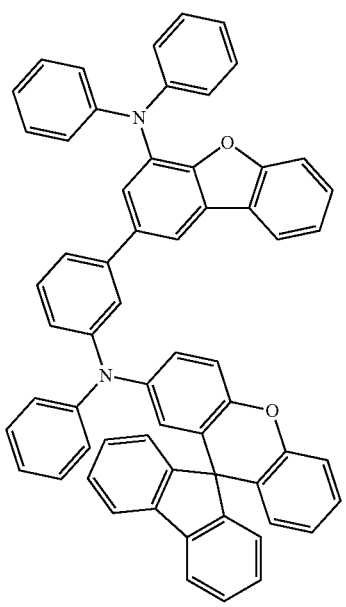
P-250
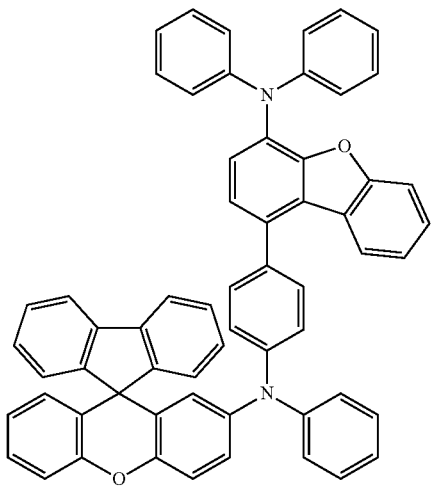
P-249
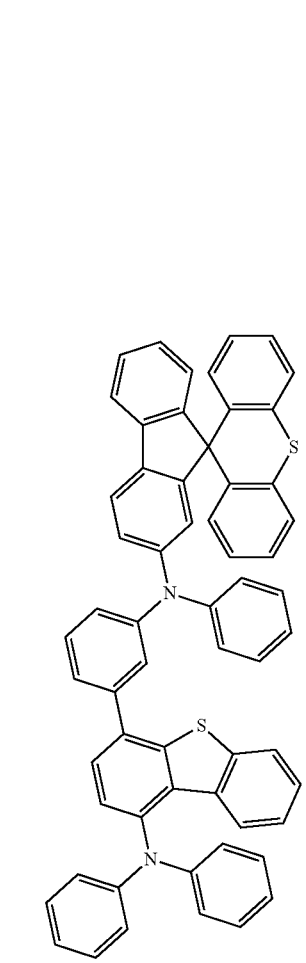
P-251
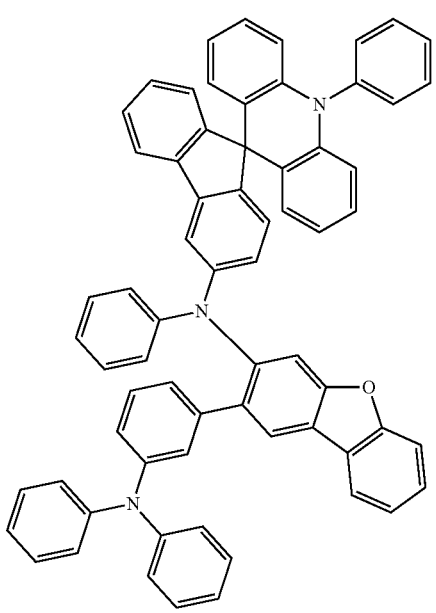

-continued
P-252
P-253
P-254
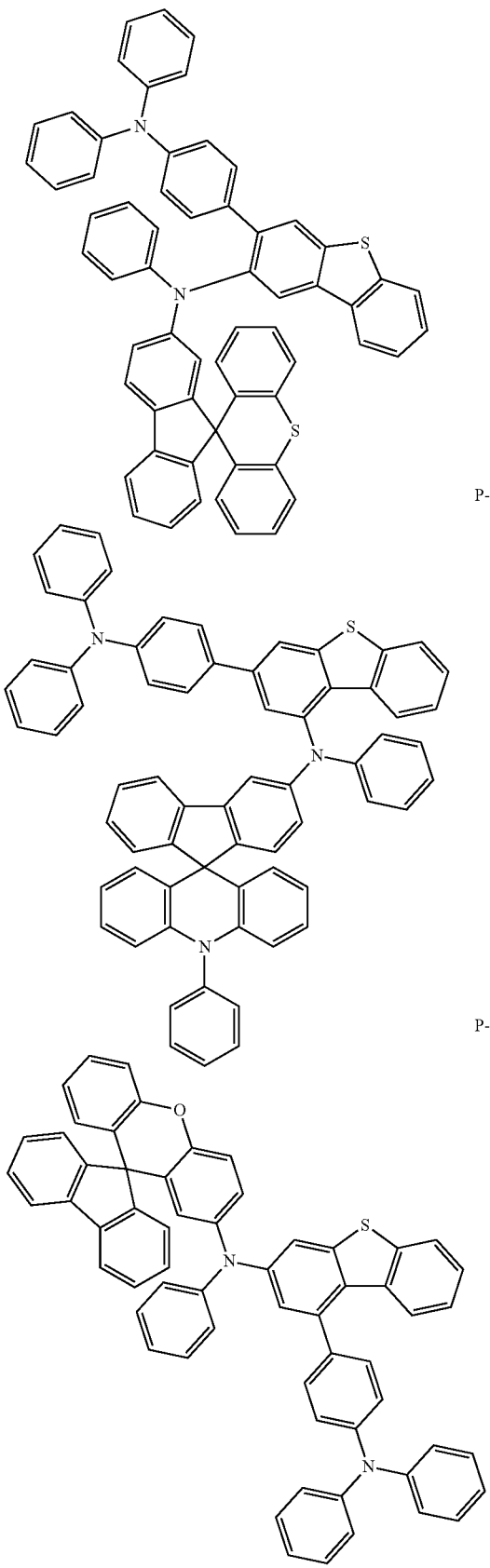
-continued
P-255
P-256
P-257
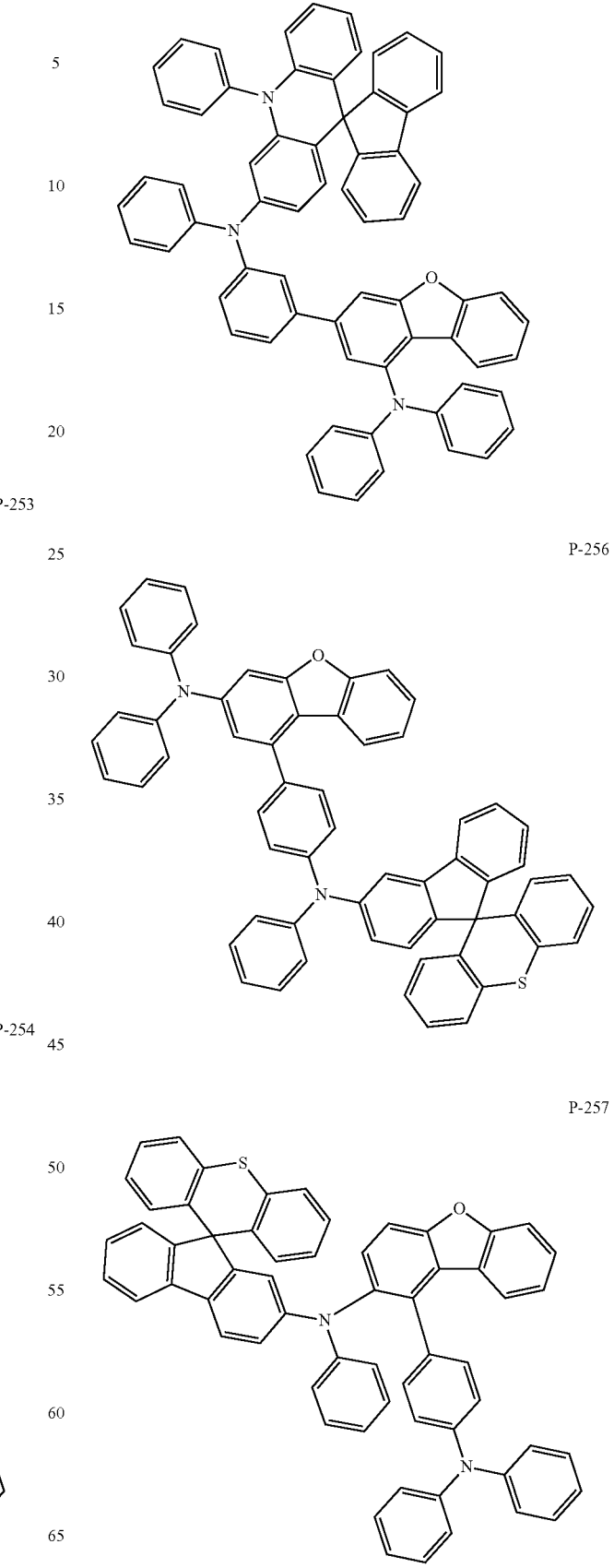

-continued
P-258
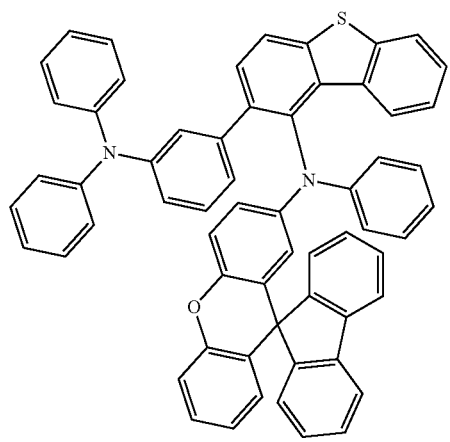
P-262
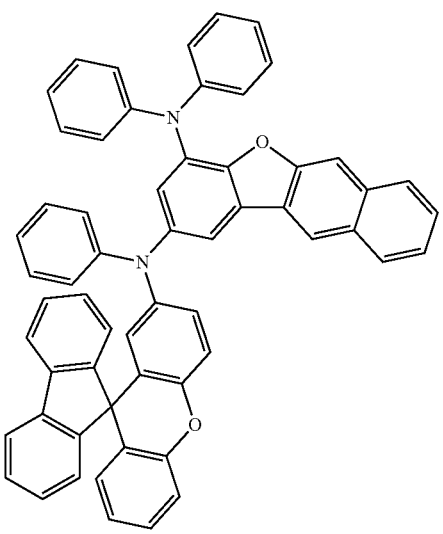
P-260
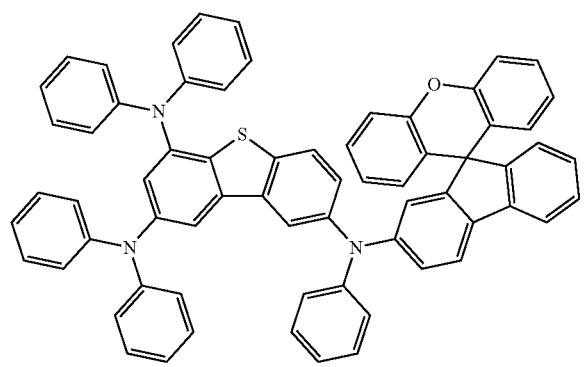
P-263
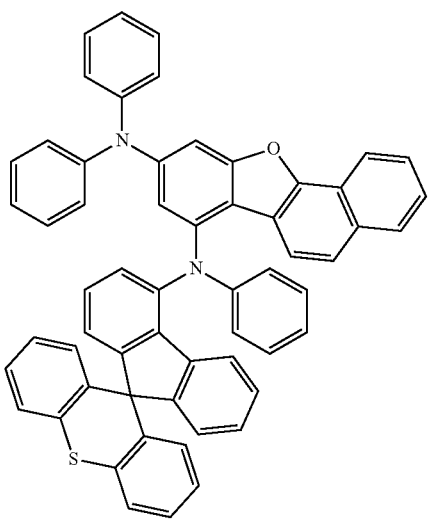
P-261
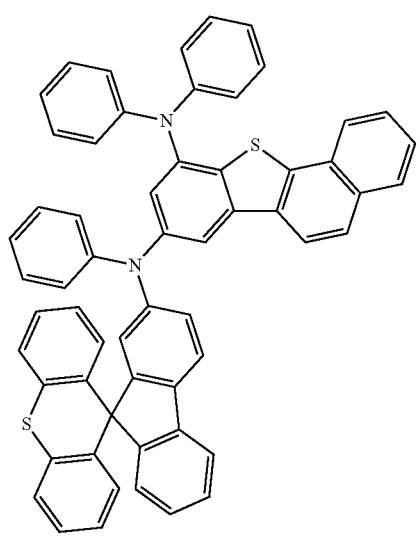
P-264
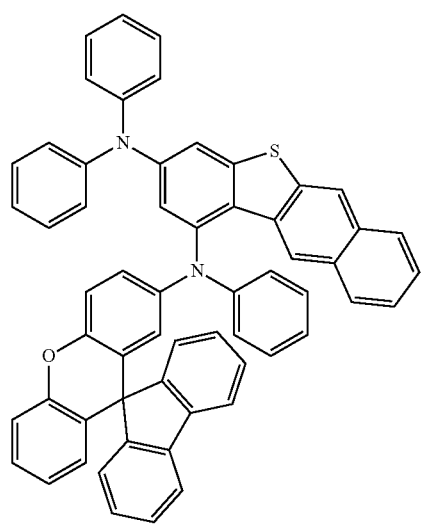

-continued

P-265
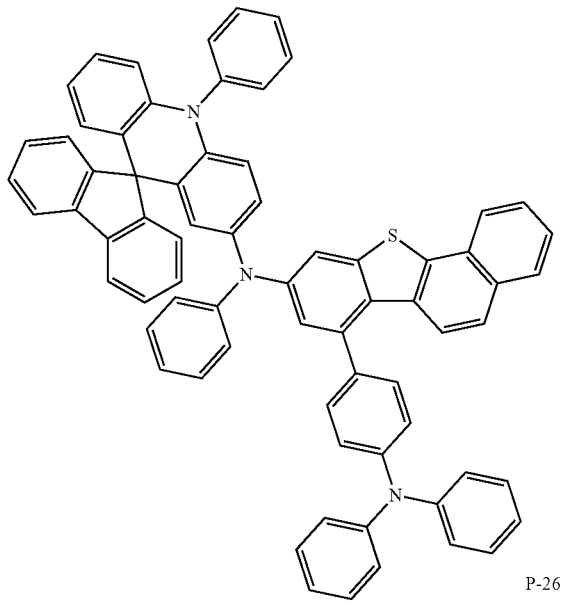

P-266
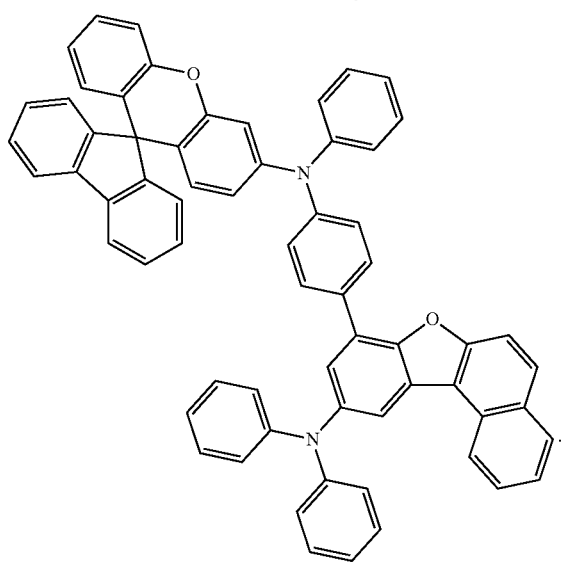

7. An organic electric element comprising an anode, a cathode, and an organic material layer formed between the anode and the cathode, wherein the organic material layer comprises an emission-auxiliary layer, and wherein the emission-auxiliary layer comprises a single compound or a mixture of two or more compounds represented by Formula 1 of claim 1.

8. The organic electric element of claim 7 further comprising a layer for improving luminous efficiency formed on one side of the anode and/or the cathode, the one side not facing the organic material layer.

9. The organic electric element of claim 7, wherein the organic material layer further comprises at least one of a hole injection layer, a hole transport layer, a light emitting layer, an electron transport-auxiliary layer, an electron transport layer and an electron injection layer.

10. The organic electric element of claim 7, wherein the organic material layer comprises two or more stacks and each of the stacks comprises a hole transport layer, the emission-auxiliary layer, a light emitting layer and an electron transport layer formed sequentially on the anode.

11. The organic electric element of claim 10, wherein the organic electric element further comprises a charge generation layer formed between the stacks.

12. An electronic device comprising a display device and a control unit for driving the display device, wherein the display device comprises the organic electric element of claim 7.

13. The electronic device of claim 12, wherein the organic electric element is selected from the group consisting of an organic electroluminescent element, an organic solar cell, an organic photo conductor, an organic transistor, an element for monochromatic illumination and an element for quantum dot display.

* * * * *